United States Patent
Zoghbi et al.

(10) Patent No.: US 6,709,817 B1
(45) Date of Patent: Mar. 23, 2004

(54) METHOD OF SCREENING RETT SYNDROME BY DETECTING A MUTATION IN MECP2

(75) Inventors: Huda Y. Zoghbi, Houston, TX (US); Ignatia B. Van den Veyver, Bellaire, TX (US); Ruthie Amir, Haifa (IL); Uta Francke, Los Altos Hills, CA (US)

(73) Assignee: Baylor College of Medicine, Houston, TX (US)

(*) Notice: Subject to any disclaimer, the term of this patent is extended or adjusted under 35 U.S.C. 154(b) by 351 days.

(21) Appl. No.: 09/657,013

(22) Filed: Sep. 7, 2000

Related U.S. Application Data
(60) Provisional application No. 60/152,778, filed on Sep. 7, 1999.

(51) Int. Cl.[7] ................................................. C12Q 1/68
(52) U.S. Cl. .................................................. 435/6
(58) Field of Search ............................... 435/6, 7.1, 29

(56) References Cited

PUBLICATIONS

Amir, RE, et al., *Influence of mutation type and X chromosome inactivation on Rett syndrome phenotypes*. Annals of Neurology. vol. 47(5) pp. 670–679 (2000).
Amir, RE, et al. *Rett syndrome is caused by mutations in X–linked MECP2, encoding methyl–CpG–binding protein2*. Nat Genet. vol. 23 pp. 185–188 (1999).
Bienvenu, T. et al. *MECP2 mutations account for most cases of typical forms of Rett syndrome*. Hum Mol Genet vol. 9(9), pp. 1377–1384 (2000).
Cameron, E.E., et al., Synergy of demethylation and histone deacetylase inhibition in the re–expression of genes silenced in cancer. Nature Genet. vol. 21, pp. 103–107 (1999).
Buyse I.M., et al., Diagnostic Testing for Rett Syndrome by DHPLC and direct Sequencing Analysis of the MECP2 Gene: Identification of Several Novel Mutations and Polymorphisms. Am. J. Hum. Genet. vol. 67 pp. 1426–1428 (2000).
Cheadle JP, et al., Long–read sequence analysis of the MECP2 gene in Rett syndrome patients: correlation of disease severity with mutation type and location. Hum Mol Genet vol. 9(7) pp. 1119–1129 (2000).
Coy JF, et al., A complex pattern of evolutionary conservation and alternative polyadenylation within the long 3'–untranslated region of the methyl–CpG–binding protein 2 gene (MeCP2) suggests a regulatory role in gene expression. Hum Mol Genet vol. 8 pp. 1253–1262 (1999).
Hagberg B, et al., A progressive syndrome of autism, dementia, ataxia, and loss of purposeful hand use in girls: Rett's syndrome: report of 35 cases. Ann Neurol vol. 14 pp. 471–479 (1983).
Hendrich, B., et al., Identification and characterization of a family of mammalian methyl–CpG binding proteins. Mol. Cell Biol. vol. 18, pp. 6538–6547 (1998).

Huppke P, et al., Rett syndrome: analysis of MECP2 and clinical characterization of 31 patients. Hum Mol Genet vol. 9(9), pp. 1369–1375 (2000).
Jones PL, et al., Methylated DNA and MeCP2 recruit histone deacetylase to repress transcription. Nat Genet vol. 19, pp. 187–191 (1998).
Nan X, et al., MeCP2 is a transcriptional repressor with abundant binding sites in genomic chromatin. Cell vol. 88, pp. 471–481 (1997).
Nan X, et al., Transcriptional repression by the methylCpG––binding protein MeCP2 involves a histone deacetylase complex. Nature vol. 393, pp. 386–389. (1998).
Orrico, A., et al., MECP2 mutation in male patients with non–specific X–linked mental retardation. FEBS Letters 24106, 1–4 (2000).
Wan M, et al., Rett syndrome and beyond: recurrent spontaneous and familial MECP2 mutations at CpG hotspots. Am J Hum Genet vol. 65, pp. 1520–1529 (1999).
Wolff, G.L., et al., Maternal epigenetics and methyl supplements affect agouti gene expression in $A^{vy}$/a mice. FASEB vol. 12, pp. 949–957 (1998).
Xiang, F., et al., Mutation screening in Rett syndrome patients. J Med Genet vol. 37, pp. 250–255 (2000).
Zappella M, et al., The preserved speech variant: a subgroup of the Rett complex: a clinical report of 30 cases. J Autism Dev Disord vol. 28, pp. 519–526. (1998).
Ng, Huck–Hui, et al.; Active Repression of Methylated Genes by the Chromosomal Protein MBD1; Molecular and Cellular Biology, vol. 20 (4), pp. 1394–1406, Feb. 2000.
Carney, R. J., et al.; Abstract—Screening for MECP2 Mutations in Females with Autistic Disorder; Presented at the International Congress of Genetics, Dec. 19, 2000.
Pericak–Vance, Margaret, et al.; Study Finds Link Between Patients with Autistic Disorder and Patients with Rett Syndrome; News Update, Duke University Medical Center, May 22, 2001.
Hoffbuhr, K., et al.; MeCP2 mutations in children with and without the phenotype of Rett syndrome; Neurology 2001; 56:1486–1495.
Amir, Ruthie, et al.; Candidate Gene Analysis in Rett Syndrome and the Identification of 21 SNPs in Xq; American Journal of Medical Genetics 90:69–71 (2000).
Battistini, S., et al.; A new CACNA1A gene mutation in acetazolamide–responsive familial hemiplegic migraine and ataxia; Neurology 1999; 53:38–43.

(List continued on next page.)

*Primary Examiner*—Terry McKelvey
(74) *Attorney, Agent, or Firm*—Fulbright & Jaworski, LLP

(57) ABSTRACT

The present invention relates to the identification of mutations in a gene encoding a methyl-CpG-binding domain containing protein or alterations in its corresponding protein in neurodevelopmental disease. The protein acts in a complex to regulate transcriptional repression through methylated CpG dinucleotides. Methods to screen mutations in said gene or alterations in said protein related to neurodevelopmental disease are provided. Methods to treat a vertebrate with said disease are also provided.

10 Claims, 5 Drawing Sheets

OTHER PUBLICATIONS

Shahbazian, Mona D., et al.; Molecular genetics of Rett syndrome and clinical spectrum of MECP2 mutations; Current Opinion in Neurology 2001, 14:171–176.

Shahbazian, Mona D., et al.; Review Article: Rett Syndrome and MeCP2: Linking Epigenetics and Neuronal Function; Am. J. Hum. Genet. 71:000–000, 2002.

Yntema, Helger G., et al.; Research Letter: In–Frame Deletion in MECP2 Causes Mild Nonspecific Mental Retardation; American Journal of Medical Genetics 107:81–83 (2002).

Yntema, Helger G., et al.; Short Report: Low frequency of MECP2 mutations in mentally retarded males; European Journal of Human Genetics (2002) 10, 487–490.

Imessaoudene, Belaid, et al.; MECP2 mutation in non–fatal, non–progressive encephalopathy in a male; J Med Genet 2001; 38:171–174.

Geerdink, N., et al.; MECP2 Mutation in a Boy with Severe Neonatal Encephalopathy: Clinical, Neuropathological and Molecular Findings; Neuropediatrics 2002; 33:33–36.

Hammer, Sara, et al.; The Phenotypic Consequences of MECP2 Mutations Extend Beyond Rett Syndrome; Mental Retardation and Developmental Disabilities Research Reviews 8:94–98 (2002).

Meloni, Ilaria, et al.; A Mutation in the Rett Syndrome Gene, MECP2, Causes X–Linked Mental Retardation and Progressive Spasticity in Males; Am. J. Hum. Genet. 67:982–985, 2000.

Couvert, Philippe, et al.; MECP2 is highly mutated in X–linked mental retardation; Human Molecular Genetics, vol. 10 (9), pp. 941–946, 2001.

Orrico, Alfredo, et al.; MECP2 mutation in male patients with non–specific X–linked mental retardation; FEBS Letters 481, pp. 285–288, 2000.

Winnepennickx, Birgitta, et al.; Rapid Communication—Identification of a Family with Nonspecific Mental Retardation (MRX79) with the A140V Mutation in the MECP2 Gene: Is There a Need for Routine Screening?, Human Mutation 20:249–252 (2002).

Dotti, M.T., et al.; A Rett syndrome MECP2 mutation that causes mental retardation in men; Neurology 2002; 58:226–230.

Klauck, Sabine M., et al.; A Mutation Hot Spot for Non-specific X–Linked Mental Retardation in the MECP2 Gene Causes the PPM–X Syndrome; Am. J. Hum. Genet. 70:1034–1037, 2002.

Cohen, David, et al.; Letters to the Editor—MECP2 Mutation in a Boy with Language Disorder and Schizophrenia; Am J. Psychiatry 159, pp. 148–149, Jan. 1, 2002.

Heilstedt, Heidi A., et al.; Infantile Hypotonia as a Presentation of Rett Syndrome; American Journal of Medical Genetics, 111:238–242 (2002).

Watson, Pamela, et al.; Original articles—Angelman syndrome phenotype associated with mutations in MECP2, a gene encoding a methyl CpG binding protein; J Med Genet 2001; 38:224–228.

Kleefstra, T., et al.; Short Report—De novo MECP2 frameshift mutation in a boy with moderate mental retardation, obesity and gynaecomastia; Clin Genet 2002: 61:359–362.

Lam, Ching–Wan, et al.; Electronic Letter—Spectrum of mutations in the MECP2 gene in patients with infantile autism and Rett syndrome; J Med Genet 2000; 37 (http://jmedgenet.com/cgi/content/full/37/12/e41).

Vourc'h, Patrick, et al.; Short Report—No mutations in the coding region of the Rett syndrome gene MECP2 in 59 autistic patients; European Journal of Human Genetics (2001) 9, pp. 556–558.

Beyer, Kim S., et al.; Original Investigation—Mutation analysis of the coding sequence of the MECP2 gene in infantile autism; Hum Genet (2002) 111:305–309.

Clayton–Smith, J., et al.; Somatic mutatino in MECP2 as a non–fatal neurodevelopmental disorder in males; The Lancet, vol. 356, pp. 830–832, Sep. 2, 2000.

Villard, L., et al.; Two affected boys in a Rett syndrome family; Neurology 2000; 55:1188–1193.

Millat, Gilles, et al.; Niemann–Pick C1 Disease: The L1061T Substitution is a Frequent Mutant Allele in Patients of Western European Descent and Correlates with a Classic Juvenile :Phenotype; Am. J. Hum. Genet. 65:1321–1329, 1999.

Ng, Huck–Hui, et al.; MBD2 is a transcriptional repressor belonging to the MeCP1 histone deacetylase complex; Nature Genetics, vol. 23, pp. 58–61, Sep. 1999.

Wan, Minghong, et al.; Brief Research Communication—Evaluation of Two X Chromosomal Candidate Genes for Rett Syndrome: Glutamate Dehydrogenase–2 (GLUD2) and Rab GDP–Dissociation Inhibitor (GDI1); Am. J. Med. Genet. 78:169–172, 1998.

Hendrich, Brian, et al.; Genomic structure and chromosomal mapping of the muring and human *Mbd1, Mbd2, Mbd3,* and *Mbd4* genes; Mammalian Genome 10, pp. 906–912, 1999.

FIG. 4

PANEL A

PANEL B

METHOD OF SCREENING RETT SYNDROME BY DETECTING A MUTATION IN MECP2

This application claims priority to U.S. Provisional Patent Application 60/152,778 filed Sep. 7, 1999.

The work herein was supported by grants from the United States Government. The Government may have certain rights in the invention.

FIELD OF THE INVENTION

The invention relates to detection of mutations in a methyl-CpG-binding domain-containing protein. More particularly it relates to detecting mutations in MECP2, MECP1, MBD1, MBD2, MBD3, and MBD4. It further relates to detection and treatment of neurodevelopmental disease.

BACKGROUND OF THE INVENTION

Rett syndrome (herein used interchangeably with the term "RTT"), first described by Andreas Rett (1966), is a progressive neurodevelopmental disorder and one of the most common causes of mental retardation in females, with an incidence of 1 in 10–15,000 (Hagberg, 1985). Patients with classic Rett syndrome appear to develop normally until 6–18 months of age, then gradually lose speech and purposeful hand use, and develop microcephaly, seizures, autism, ataxia, intermittent hyperventilation and stereotypic hand movements (Hagberg et al., 1983). After initial regression, patients stabilize and usually survive into adulthood. Since Rett syndrome occurs almost exclusively in females, it was proposed that RTT is caused by an X-linked dominant mutation with lethality in hemizygous males (Hagberg et al., 1983, Zoghbi 1988, Zoghbi et al., 1990, Ellison et al., 1992 and Schanen et al., 1997). Other hypotheses—such as an autosomal dominant mutation with sex-limited expression or two mutations, one autosomal and one X-linked—remained theoretical possibilities (Behler et al., 1990 and Migeon et al., 1995). Although most cases are sporadic, there have been a few familial occurrences of Rett syndrome with evidence for inheritance through the maternal germline. Further support for the X-linked inheritance model came from three families in which a non-random pattern of X-inactivation was confirmed in the obligate carrier females (Zoghbi et al., 1990, Schanen et al., 1997 and Sirianni et al., 1998). In two of these families, a male sibling with a severe neonatal encephalopathy died within a few months of birth (Schanen et al., 1998). Because of the very few familial cases, investigators favoring the X-linkage hypothesis pursued exclusion mapping on the X-chromosome to define the smallest region shared amongst affected kindred cases (Ellison et al., 1992, Schanen et al., 1997, Sirianni et al., 1998, Schanen et al., 1998, Archidiacono et al., 1991 and Curtis et al., 1993). These analyses eventually mapped the RTT gene telomeric to DXS998 in a 10 Mb gene-rich region in distal Xq.

In pursuit of the Rett gene, a systematic mutational analysis of genes located in Xq28 in Rett syndrome patients was performed. This region harbors a number of good candidate genes. Several were selected for mutation analysis because of their known function and expression patterns, but recently were excluded (Amir et al., 1999, incorporated by reference herein). The gene encoding methyl-CpG-binding protein 2 (MECP2), which maps to Xq28 between L1CAM and the RCP/GCP loci and undergoes X-inactivation was then analyzed (D'Esposito et al., 1996). MeCP2 is an abundant chromosome-binding protein that selectively binds 5-methyl cytosine residues in symmetrically positioned CpG dinucleotides in mammalian genomes (Lewis et al., 1992). These residues are preferentially located in the promoter regions of genes that are subject to transcriptional silencing after DNA methylation. Recent studies established that MeCP2 is the molecular link between DNA methylation and transcriptional silencing by histone deacetylation (Nan et al., 1998 and Jones et al., 1988). It contains at least two functional domains: an 85 amino acid (aa) methyl-CpG-binding domain (MBD), essential for its binding to 5-methyl cytosine (Nan et al., 1993), and a 104 aa transcriptional repression domain (TRD) that interacts with histone deacetylase and the transcriptional corepressor Sin3A. Interactions between this transcription repressor complex and chromatin-bound MeCP2 leads to deacetylation of core histones, which in turn leads to transcriptional repression (Nan et al., 1998 and Jones et al., 1988). Furthermore, this complex can inhibit transcription from a promoter at a distance (Nan et al., 1997). The surprising discovery of the present invention regards mutations in Rett syndrome of a member of a family of genes encoding methyl-CpG-binding domain proteins. This discovery facilitates development of a test for early diagnosis and prenatal detection of neurodevelopmental diseases. More importantly, the finding that epigenetic regulation plays a role in the pathogenesis of Rett syndrome provides opportunities for therapy.

SUMMARY OF THE INVENTION

In one embodiment of the present invention there is a method of screening a vertebrate for neurodevelopmental disease comprising the step of detecting a mutation in the nucleic acid sequence of a gene encoding a methyl-CpG-binding domain containing protein. In a specific embodiment, the neurodevelopmental disease is selected from the group consisting of Rett syndrome, autism, non-syndromic mental retardation, idiopathic neonatal encephalopathy, idiopathic infantile spasms, idiopathic cerebral palsy, Angelman syndrome, and schizophrenia.

In a specific embodiment said mutation is found in the sequences selected from the group consisting of a regulatory sequence, an exon, an intron, an exon/intron junction, and a 3' untranslated region.

A further embodiment of the present invention is the method wherein said mutation is detected by sequencing, a probe, electrophoretic mobility, nucleic acid hybridization, fluorescent in situ hybridization, nucleic acid-chip technology, polymerase chain reaction or reverse transcription-polymerase chain reaction.

Another embodiment of the present invention is a method of screening a vertebrate for neurodevelopmental disease comprising the step of detecting an alteration in the amino acid sequence of a methyl-CpG-binding domain containing protein. In a specific embodiment of the present invention said alteration is detected by electrophoresis, through chromosomal binding pattern analysis, by the methylation pattern of genomic DNA, by measuring upregulation of expression of a target gene, by measuring increased production of a protein encoded by a target gene, by measuring increased production of a protein encoded by a target gene wherein said protein is secreted from the cell, by antibodies, by amino acid sequencing, and by determining the molecular weight.

Another embodiment of the present invention is the method of screening a vertebrate for neurodevelopmental disease comprising the step of detecting a mutation in a nucleic acid sequence or in the corresponding amino acid sequence of a protein wherein said protein is present in a MECP2/complex and said mutation disrupts function of a protein present in said MECP2/complex. A specific embodiment of the present invention is the method wherein said nucleic acid sequence or corresponding amino acid sequence is selected from the group consisting of Sin3A, HDAC1, HDAC2, and RbAp48.

An additional embodiment of the present invention is a method of screening a vertebrate for neurodevelopmental disease comprising the step of detecting a mutation in a first gene involved in regulation of expression of a second gene encoding a methyl-CpG-binding domain containing protein. Said first gene may encode a transcription factor or a gene associated with X-inactivation. In a further embodiment the gene associated with X-inactivation is MECP2.

In another embodiment said gene involved in regulation of expression is associated with localization patterns of RNAs transcribed from said gene encoding a methyl-CpG-binding domain containing protein wherein said RNAs vary in length.

In an additional embodiment is the method of treating a vertebrate with a neurodevelopmental disease wherein a mutation in a first gene encoding a methyl-CpG-binding domain containing protein causes upregulation of expression of said second gene comprising the step of administering into said vertebrate a therapeutically effective amount of a compound to enhance methylation of said second gene or to enhance the function of the MECP2/complex. In a specific embodiment said compound to enhance methylation is selected from the group consisting of folic acid, vitamin B12, methionine, zinc, choline, betaine and combination thereof In another embodiment of the present invention is a method of treating a vertebrate with a neurodevelopmental disease wherein a mutation in a first gene encoding a methyl-CpG-binding domain containing protein which is present in a complex causes upregulation of expression of a second gene comprising the step of in vivo introduction into said vertebrate a therapeutically effective amount of an antisense sequence of said second gene. An alternative embodiment is the steps of introducing ex vivo into a cell a therapeutically effective amount of an antisense sequence of said second gene and introducing said transformed cell into said vertebrate. In a specific embodiment said complex is the MECP2/complex.

A further embodiment is the method of treating a vertebrate with a neurodevelopmental disease wherein a mutation in a methyl-CpG-binding domain containing protein causes an increase in methylation of a gene leading to a decrease in expression of said gene comprising the step of administering to said vertebrate a therapeutically effective amount of a compound that decreases methylation or interferes with a function of a component of a complex containing said methyl-CpG-binding domain containing protein. In specific embodiments, said compound is selected from the group consisting of 5-aza 2' deoxycytidine, Trichostatin A, phenylbutyrate, sodium butyrate, trapoxin and a folate depleting agent; said folate depleting agent is methotrexate or any agent which directly or indirectly inhibits dihydrofolate reductase; or said complex is the MECP2/complex.

Another embodiment of the present invention is a method of treating a vertebrate with a neurodevelopmental disease comprising the step of in vivo introduction into said vertebrate a therapeutically effective amount of a gene encoding a methyl-CpG-binding domain containing protein. An alternative method of the present invention is treating a vertebrate with a neurodevelopmental disease comprising the steps of introducing ex vivo into a cell a therapeutically effective amount of a gene encoding a methyl-CpG-binding domain containing protein and introducing said transformed cell into said vertebrate. In a specific embodiment said introduction also includes introduction of a suicide gene.

An additional embodiment of the present invention is a method of treating a vertebrate with a neurodevelopmental disease comprising the step of introducing into said vertebrate a cell containing a gene encoding a methyl-CpG-binding domain-containing protein. In a specific embodiment said gene and corresponding protein are of a methyl-CpG-binding domain containing protein selected from the group consisting of MECP2, MECP1, MBD1, MBD2, MBD3, and MBD4.

In another specific embodiment said neurodevelopmental disease is selected from the group consisting of Rett syndrome, autism, non-syndromic mental retardation, idiopathic neonatal encephalopathy, idiopathic infantile spasms, idiopathic cerebral palsy, Angelman syndrome, and schizophrenia.

An additional embodiment of the present invention is a kit for the detection of a neurodevelopmental disease, wherein said disease is selected from the group consisting of Rett syndrome, autism, non-syndromic mental retardation, neonatal encephalopathy, infantile spasms, idiopathic cerebral palsy, Angelman syndrome, and schizophrenia, comprising a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, and SEQ ID NO:89.

Other and further objects, features and advantages would be apparent and eventually more readily understood by reading the following specification and by reference to the company drawing forming a part thereof, or any examples of the presently preferred embodiments of the invention are given for the purpose of the disclosure.

DESCRIPTION OF DRAWINGS

Figure 4:
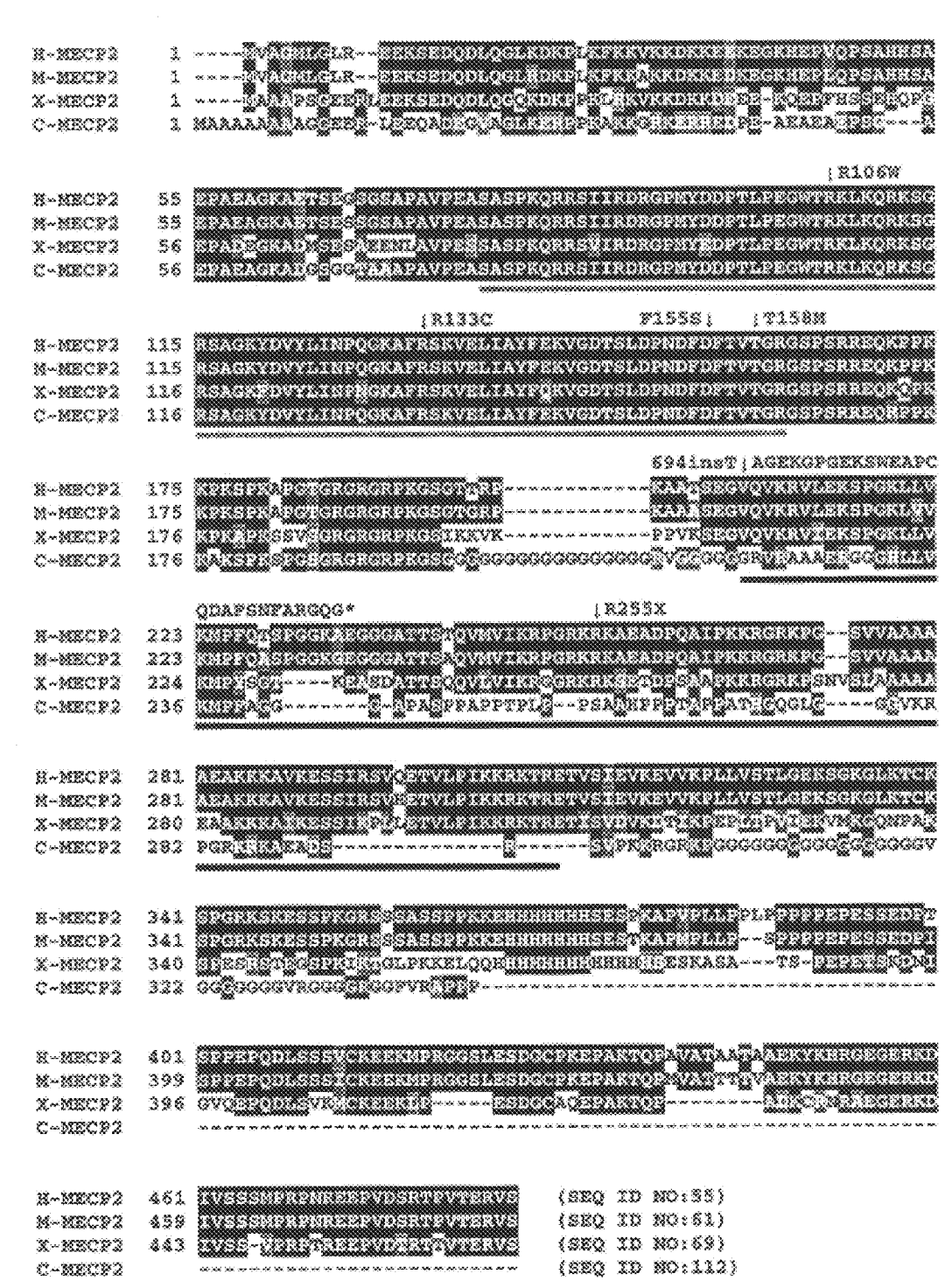

FIG. 4 shows alignment of MeCP2 sequences from different species with the positions of the mutations in Rett syndrome. Identical amino acids between species are boxed in black, similar amino acids are boxed in grey; the conserved methyl-cytosine-binding domain is underlined in grey, the transcription repression domain is underlined in black. Arrows show the precise positions of the mutations. The 694insT mutation leads to 27 out-of-frame amino acids and a stop codon (*). The protein sequence alignment allows comparison of human (H-MECP2), mouse (M-MECP2), chicken (G-MECP2) and *Xenopus laevis* (X-MECP2) proteins.

DESCRIPTION OF THE INVENTION

Figure 1:
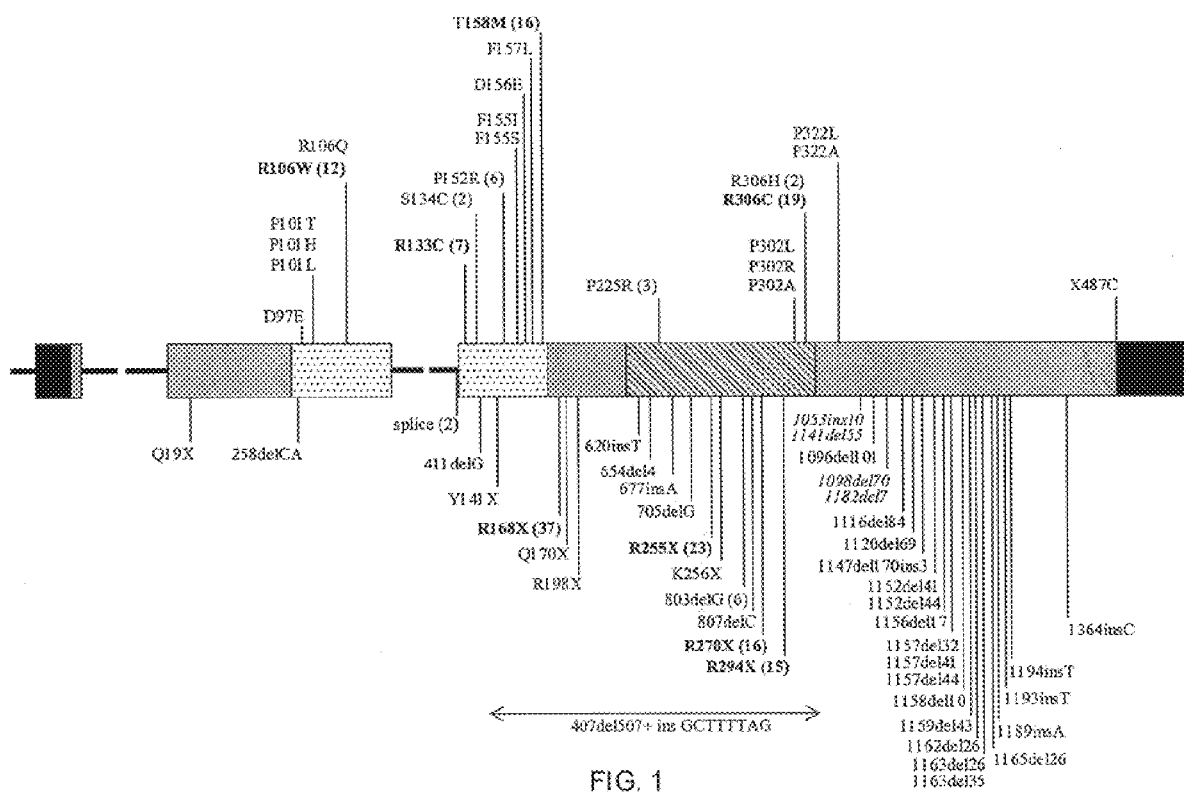
FIG. 1 illustrates the positions of mutations within the coding region of MECP2

It is readily apparent to one skilled in the art that various embodiments and modifications may be made to the invention disclosed in this Application without departing from the scope and spirit of the invention.

The term "antisense" as used herein is defined as the sequence of a gene which is complementary to the sequence of the gene which encodes the gene product.

The term "disrupts function" as used herein is defined as prohibits or interferes with normal function of a member of a complex of proteins. In another embodiment, the term refers to prohibiting or interfering with normal function of a complex of proteins. In preferred embodiments, the complex is the MECP2/complex.

The term "DNA" as used herein is defined as deoxyribonucleic acid.

The term "exon" as used herein is defined as a transcribed segment of a gene that is present in a mature messenger RNA molecule.

The term "exon/intron junction" as used herein is defined as two specific nucleotide locations at which point an intronic sequence is spliced from an RNA transcript.

The term "idiopathic" as used herein is defined as of unknown cause.

The term "intron" as used herein is defined as a region of a gene transcribed from a DNA template but subsequently removed by splicing together the segments (exons) which flank it.

The term "MECP2/complex" as used herein is defined as the complex of proteins, wherein said complex contains MECP2 and other proteins are selected from the group consisting of Sin3A, HDAC1, HDAC2, and RbAp48.

The term "methyl-CpG-binding domain containing protein" as used herein is defined as a protein which selectively binds methylated CpG dinucleotides in vertebrate genomic DNA. Examples include MECP2, MECP1, MBD1 (formerly known as PCM1), MBD2, MBD3, and MBD4.

The term "neurodevelopmental disease" as used herein is defined as a disease which affects neurological development. Examples included Rett syndrome, autism, non-syndromic mental retardation, idiopathic neonatal encephalopathy, idiopathic infantile spasms, idiopathic cerebral palsy and schizophrenia.

The term "nucleic acid chip technology" as used herein is defined as the method of immobilizing nucleic acid on a microchip for subsequent hybridization analysis.

The term "pharmacologically effective dose" is the amount of an agent administered to be physiologically significant. An agent is physiologically significant if its presence results in a positive or negative change in the physiology of a recipient mammal.

The term "polymerase chain reaction" (PCR) is well known in the art and includes the method of amplifying a nucleic acid sequence utilizing two oligonucleotide primers and a thermolabile nucleic acid polymerase.

The term "reverse transcription-polymerase chain reaction" as used herein is defined as the polymerization of a DNA molecule using an RNA molecule as a template for the purpose of utilizing said DNA molecule as a template for PCR.

The term "RNA" as used herein is defined as ribonucleic acid.

The term "splicing" as used herein is defined as a means of removing intron sequences within a primary RNA transcript in processing of said transcript to a mature messenger RNA.

The term "suicide gene" as used herein is defined as a gene whose gene product is lethal to a cell upon exposure to a prodrug.

The term "target gene" as used herein is defined as a gene in which the methyl-CpG-binding domain containing protein of the invention binds to CpG of said gene to modulate transcriptional repression. Genes subjected to transcriptional silencing following DNA methylation are candidates for target genes for methyl-CpG-binding domain containing protein. Potential candidates include leukosialin (CD43) and FMR1.

The term "therapeutically effective" as used herein is defined as the amount of a compound required to improve some symptom associated with a disease. For example, in the treatment of neurodevelopmental disease, a compound which decreases, prevents, delays, or arrests any symptom of the disease would be therapeutically effective. A therapeutically effective amount of a compound is not required to cure a disease but will provide a treatment for a disease.

The term 3' untranslated region (3' UTR) as used herein is defined as the sequence at the 3' end of a messenger RNA which does not become translated into protein and can include regulatory sequences and sequences important for posttranscriptional processing.

The term "transcribe" as used herein is defined as the process of generating an RNA transcript molecule using DNA as a template.

The term "transcript" as used herein is defined as an RNA molecule which has been transcribed from DNA.

The term "upregulation of expression" as used herein is defined as an increase in expression of a specific nucleic acid sequence relative to its basal endogenous levels. In a specific embodiment, the expression of a particular nucleic acid sequence is significantly reduced or suppressed, or completely suppressed, due to a silenced state of expression, such as that normally present when MECP2 is functional.

The term "X-linked inactivation" as used herein is defined as the inactivation through repression of genes located on the X chromosome in somatic cells of female mammals.

In one embodiment of the present invention there is a method of screening a vertebrate for neurodevelopmental disease comprising the step of detecting a mutation in the nucleic acid sequence encoding a methyl-CpG-binding domain containing protein.

Another embodiment of the present invention is the method of screening a vertebrate for neurodevelopmental disease comprising the step of detecting a mutation in a nucleic acid sequence or in the corresponding amino acid sequence of a protein wherein said protein is present in a MECP2/complex and said mutation disrupts function of a protein present in said MECP2/complex. A specific embodiment of the present invention is the method wherein said nucleic acid sequence or corresponding amino acid sequence is selected from the group consisting of Sin3A, HDAC1, HDAC2, and RbAp48.

An additional embodiment of the present invention is a method of screening a vertebrate for neurodevelopmental disease comprising the step of detecting a mutation in a first gene involved in regulation of expression of a second gene encoding a methyl-CpG-binding domain containing protein. Said first gene may encode a transcription factor or a gene product associated with X-inactivation. In one specific embodiment the gene is associated with X-inactivation is MECP2.

In another specific embodiment said gene involved in regulation of expression is associated with localization patterns of RNAs transcribed from said gene encoding a methyl-CpG-binding domain containing protein wherein said RNAs vary in length.

In an additional embodiment the method involves treating a vertebrate with a neurodevelopmental disease wherein a mutation in a first gene encoding a methyl-CpG-binding domain containing protein causes upregulation of expression of said second gene comprising the step of administering into said vertebrate a therapeutically effective amount of a compound to enhance methylation of said second gene or to enhance the function of the MECP2/complex. In a specific embodiment said compound to enhance methylation is selected from the group consisting of folic acid, vitamin B12, methionine, zinc, choline, betaine and combination thereof.

In another embodiment of the present invention is a method of treating a vertebrate with a neurodevelopmental disease wherein a mutation in a first gene encoding a methyl-CpG-binding domain containing protein which is present in a complex causes upregulation of expression of a second gene comprising the step of in vivo introduction into said vertebrate a therapeutically effective amount of an antisense sequence of said second gene. An alternative embodiment is the steps of introducing ex vivo into a cell a therapeutically effective amount of an antisense sequence of said second gene and introducing said transformed cell into said vertebrate. In a specific embodiment said complex is the MECP2/complex.

A further embodiment is the method of treating a vertebrate with a neurodevelopmental disease wherein a mutation in a methyl-CpG-binding domain containing protein causes an increase in methylation of a gene leading to a decrease in expression of said gene comprising the step of administering to said vertebrate a therapeutically effective amount of a compound that decreases methylation or interferes with a function of a component of a complex containing said methyl-CpG-binding domain containing protein. In specific embodiments, said compound is selected from the group consisting of 5-aza 2' deoxycytidine, Trichostatin A, phenylbutyrate, sodium butyrate, trapoxin and a folate depleting agent; an example of a folate depleting agent is methotrexate or any agent which directly or indirectly inhibits dihydrofolate reductase; or said complex is the MECP2/complex.

Another embodiment of the present invention is a method of treating a vertebrate with a neurodevelopmental disease comprising the step of in vivo introduction into said vertebrate a therapeutically effective amount of a gene encoding a methyl-CpG-binding domain containing protein. An alternative method of the present invention is treating a vertebrate with a neurodevelopmental disease comprising the steps of introducing ex vivo into a cell a therapeutically effective amount of a gene encoding a methyl-CpG-binding domain containing protein and introducing said transformed cell into said vertebrate. In a specific embodiment said introduction also includes introduction of a suicide gene.

An additional embodiment of the present invention is a method of treating a vertebrate with a neurodevelopmental disease comprising the step of introducing into said vertebrate a cell containing a gene encoding a methyl-CpG-binding domain-containing protein.

Rett Syndrome: The Classic Phenotype

As described above, Rett syndrome (RTT, MIM 312750 is an X-linked dominant neurodevelopmental disorder of early childhood that is one of the leading causes of mental retardation in females. Affected girls may appear to develop normally until some point between 6 and 18 months of life, when they suddenly begin to regress. They lose purposeful hand use and whatever language skills they have acquired (both receptive and expressive), their cranial growth slows, and they develop repetitive hand movements, ataxia and gait apraxia, seizures, breathing dysrhythmias (apnea or hyperpnea), and autistic behavior (Glaze et al., 1987; Hagberg et al., 1983; Rett, 1966c; Trevathan, 1988). They also suffer decreased somatic growth and wasting (Budden, 1997; Motil et al., 1998). Following this period of rapid deterioration, patients stabilize, may recover some skills and usually survive into adulthood (Budden, 1997; Hagberg et al., 1983; Motil et al., 1998). Additional neurologic abnormalities such as dystonia, parkinsonism, spasticity and kyphoscoliosis may develop (Al-Mateen et al., 1986; FitzGerald et al., 1990; Hagberg et al., 1983; Naidu, 1997). RTT patients can be susceptible to sudden death (Kerr and Julu, 1999), perhaps due to longer corrected QT intervals and abnormalities in T-wave and heart rate variability (Guideri et al., 1999; Sekul et al., 1994). The recent discovery that mutations in the gene encoding methyl-CpG-binding protein 2 (MECP2) cause up to 80% of Rett cases provides some insight into the developmental nature of the disorder. MECP2 is involved in transcriptional silencing through DNA methylation; misexpression of genes during development may account for some features of Rett syndrome, but the predominantly neurological phenotype and often grossly normal early development have yet to be understood.

Atypical RTT

The clinical variability of RTT is fairly broad and includes so-called atypical forms that may be either more mild or more severe than the classic RTT phenotype (Hagberg, 1995). The more severe atypical RTT appears early, without the period of apparently normal development, and involves congenital hypotonia and infantile spasm. Patients with a milder "forme fruste" phenotype usually experience less severe regression, milder mental retardation, and do not have seizures (Hagberg, 1989). Other patients experience a more gradual regression that begins after the third year, retain some speech and the ability to walk, but do lose hand use and develop seizures (Zappella et al., 1998).

Three males born into RTT families had encephalopathies with neonatal onset, and all died in infancy (Schanen et al., 1998b; Sirianni et al., 1998). Two of the males presented with congenital hypotonia, respiratory distress requiring mechanical ventilation, seizures and severe intestinal dysfunction (Schanen et al., 1998b). A MECP2 mutation was found in the only one of these males for whom DNA was available. Despite the lack of proof that the other two infants also had MECP2 mutations, the similarity of these cases is compelling enough to infer that MeCP2 dysfunction causes a distinct and especially severe phenotype in males.

Neuropathology and Laboratory Findings

There are no consistent laboratory findings in RTT. Neuropathology and imaging studies reveal prefrontal cortical atrophy and occasional narrowing of the brain stem (Nihei and Naitoh, 1990). Reduced cerebral blood flow in the prefrontal and temporoparietal association regions is similar to that observed in infants. Overall brain size can be reduced by as much as 34% (Jellinger and Seitelberger, 1986), with most of the reduction taking place in the prefrontal, posterior frontal and anterior temporal cortex and caudate nucleus. Neurons of the cerebral cortex, thalamus, basal ganglia, amygdala, hippocampus and entorhinal cortex tend be smaller and more densely packed (Bauman et al., 1995); this density may be a compensation for the reduced dendritic arborization observed in these areas (Armstrong et al., 1995; Armstrong et al., 1998; Belichenko and Dahlstrom, 1995). Young RTT patients have increased GABA receptor density in the caudate which diminishes with age; ionotropic glutamate receptors (e.g., AMPA and NMDA) are markedly reduced in the basal ganglia of patients over eight years old (Blue et al., 1999).

Identification of the RTT Gene

Since 99.5% of RTT cases are sporadic, the etiology of the syndrome was difficult to establish (Hagberg et al., 1983; Martinho et al., 1990; Migeon et al., 1995). The almost exclusive occurrence of the syndrome in females, the high concordance rate among monozygotic twins, and the rare familial cases all were consistent with a genetic origin (Comings, 1986; Ellison et al., 1992; Engerström and Forslund, 1992; Zoghbi, 1988; Zoghbi et al., 1990). More importantly, the inheritance through maternal lines and the findings of non-random patterns of XCI in obligate carrier females suggested that RTT is an X-linked dominant disorder caused by mutations in a gene that undergoes X-inactivation (Schanen et al., 1997; Sirianni et al., 1998; Zoghbi et al., 1990). The discovery that a few males born into RTT kindreds suffered from neonatal encephalopathy and death provided further support for this model (Schanen and Francke, 1998a; Schanen et al., 1998b; Sirianni et al., 1998). Because of the rarity of familial RTT, an exclusion mapping strategy comparing X-chromosome haplotypes among affected and unaffected individuals of four RTT families had to be used. This limited the candidate region to Xq27.3-Xqter, distal to the marker DXS998 (Ellison et al., 1992; Schanen and Francke, 1998a; Schanen et al., 1997; Sirianni et al., 1998; Webb et al., 1998). Systematic analysis of genes in Xq28 excluded several candidates (Amir et al., 2000a; Wan and Francke, 1998; both incorporated by reference herein), and led to the discovery of disease-causing mutations in MECP2 (Amir et al., 1999). This gene maps to Xq28 between L1CAM and RCP/GCP loci and does indeed undergo X-inactivation (D'Esposito et al., 1996; Vilain et al., 1996).

MeCP2 Structure and Function

MeCP2 is an abundantly expressed DNA-binding protein, located in the nucleus and associated with 5-methylcytosine (5-mC)-rich heterochromatin (Nan et al., 1997; Tate et al., 1996). Its 486 amino acids (aa) contain two known functional domains: an 84 aa methyl-CpG-binding domain (MBD) and a 104 aa transcriptional repression domain (TRD). The MBD binds to symmetrically methylated CpG dinucleotides; the TRD interacts with the corepressor Sin3A, and together they recruit histone deacetylases (Jones et al., 1998; Nan et al., 1998a; Ng and Bird, 1999). The resultant deacetylation of core histones H3 and H4 compresses the chromatin, rendering it inaccessible to the transcriptional machinery. DNA-methylation dependent repression is important for X chromosome inactivation (XCI) and genomic imprinting. MeCP2 is expressed in all tissues and is believed to act as a global transcriptional repressor (Coy et al., 1999; D'Esposito et al., 1996; Nan et al., 1997).

MeCP2 Mutations in RTT

To date, MECP2 mutations have been documented in up to 80% of the sporadic patients and approximately 50% of the familial cases (Amir et al., 2000b; Amir et al., 1999; Wan et al., 1999; Bienvenu et al., 2000; Cheadle et al., 2000; Huppke et al., 2000; all incorporated by reference herein). (The term "up to 80%" is stated herein because of different studies which achieved different mutation rates; patient selection criteria and methods of mutation analysis differed slightly from one study to the next, so a truly representative figure is not possible.) The majority of classic RTT patients with documented MECP2 mutations (91%) have random XCI in their peripheral blood leukocyte DNA (Amir et al., 2000b). To date, disease-causing mutations have been reported in 216 independent cases (i.e., counting mutations in twins or familial cases only once) (Amir 1999; Amir, 2000; Bienvenu, 2000; Cheadle, 2000; Huppke, 2000; Kim, 2000; Wan, 2000; Xiang, 2000). FIG. 1 illustrates the positions of these mutations within the coding region of MECP2; there are 64 different mutations, of which 23 are missense and 41 are truncating mutations. The diagram depicts exons 2–4 of MECP2 and mutations found in this region. The non-coding region is in black, the methyl-CpG-binding domain is dotted, and the transcription repression domain is hatched. Missense mutations are listed above the exons, whereas truncating mutations are shown below; mutations at CpG dinucleotides are shown in bold. The numbers in parentheses represent the number of occurrences for that mutation. Two individuals bore two distinct mutations; these are shown in italics. Nucleotide numbering begins with the first nucleotide in the start ATG. These data were compiled from the following sources: Amir (1999); Amir (2000); Bienvenu (2000); Cheadle (2000); Huppke (2000); Kim (2000); Wan (2000); Xiang (2000).

Consistent with the sporadic occurrence of RTT, most mutations occur de novo. The missense mutations all involve evolutionarily conserved amino acids in functional domains of the protein; some mutations affect residues that are important for DNA binding whereas others may disrupt the native structure of the protein and/or its interactions with other proteins. The nonsense, frameshift and splicing mutations likely result in premature termination of the protein, and most of these (35) are distal to the MBD. One hypothesis holds that the truncated proteins still bind methylated DNA but cannot interact with the corepressor Sin3A, although it is possible that mutations in the carboxy terminus of the protein may disable DNA binding (Chandler et al., 1999). This would prevent proper assembly of the silencing complex. Among the rare (6) early truncating mutations, two (Y141X, 411delG) are distal to the DNA binding surface of the MBD and are in patients that show non-random XCI. The third, a splicing mutation predicted to cause an early truncation interrupting the MBD, was observed in two patients (Amir et al., 2000; Huppke et al., 2000); the XCI patterns in these cases are unknown. The fourth and most severely truncated protein results from a de novo nonsense mutation, 129 C>T (Q19X) (Kim and Cook, 2000); the XCI pattern in this patient is moderately skewed. The remaining two mutations that are predicted to cause premature truncation are 258delCA and 407del507+insertionGCTTTTAG (Huppke, 2000; Cheadle, 2000). There are no data as to the XCI patterns in the patients with these two mutations.

A high proportion (67%) of mutations involved C→T transitions at CpG mutation hotspots; all of these recurred in unrelated patients, reflecting the hypermutability of these sites (Bird, 1980). The most common mutation thus far is R168X. The frameshift mutations usually involve a single nucleotide insertion or deletion at runs of the same nucleotide, but some patients have larger deletions (7–170 nucleotides) in the region encoding the C-terminus of the protein. A number of palindromic and quasipalindromic sequences contained in this region may lead to secondary structures that facilitate such deletions (Cooper and Krawczak, 1993). Deletions and insertions of multiple nucleotides in the C-terminus of MECP2 account for 8% of disease-causing mutations. Three of the four X-linked RTT families are reported to have MECP2 mutations. In two families, the obligate carrier female transmitted a truncating mutation to her affected offspring while remaining non- or mildly symptomatic (Wan et al., 1999). The transmitting females in both families have favorable non-random XCI that protected them from the effects of their MECP2 mutations (Wan et al., 1999). In one family the 803delG mutation was detected in a male who suffered from neonatal encephalopathy and died in infancy, indicating that hemizygous males with MECP2 mutations can survive past birth (Wan et al., 1999). In the third known X-linked family (two affected half-sisters) (Zoghbi, 1988) the mother is germline mosaic for the missense mutation R106W. It is noteworthy that a maternal germline origin was identified for another sporadic patient as well (Amir et al., 2000b). The identification of mutations in three out of four of the RTT families that were used in the exclusion mapping studies and up to 80% of the sporadic patients suggest that MECP2 is the major locus for RTT. In a specific embodiment, the remaining patients have mutations in the untranslated.

Influence of Mutation Type

Forty-eight classic RTT patients were recently evaluated for disease-causing mutations and there was a correlation of the mutation type with 13 clinical features, electrophysiologic findings and cerebrospinal fluid (CSF) neurochemistry (Amir et al., 2000b). A positive correlation was found between truncating mutations and two parameters: breathing abnormalities and low levels of CSF homovanillic acid (HVA). Scoliosis was more common in patients with missense mutations. The most striking finding was that neither the overall severity score nor any of the other parameters (age of onset, mortality, seizures and somatic growth failure) correlated with the type of mutation. Interestingly, another study evaluated phenotype-genotype correlations and found that patients with missense mutations tend to have significantly milder disease than patients with truncating mutations ($p=0.0023$); they also found that late truncating mutations produced milder phenotypes than early truncating mutations ($p=0.0190$) (Cheadle et al., 2000). Huppke et al. did not find statistically significant differences in the clinical severity score between patients with truncating and those with non-truncating mutations (Huppke et al., 2000). Cheadle et al. and Huppke et al. both report that several patients with the same mutation manifest different phenotypes, clearly indicating that factors other than mutation type influence the severity of disease (Cheadle et al., 2000; Huppke et al., 2000). The pattern of X chromosome inactivation is clearly one important modulator of the phenotype, as evidenced by females that carry the mutation but have either very mild symptoms or none at all (Wan et al., 1999; Amir et al., 2000).

Pathogenesis

The pathways leading from MeCP2 loss of function to the neuronal dysfunction in RTT are unclear. The phenotype seems primarily neurological, even though the gene is ubiquitously expressed during organogenesis and in postnatal life (Coy et al., 1999). In a specific embodiment, the brain is more vulnerable to the effects of MeCP2 inactivation. In an alternative embodiment, there is tissue-specific difference in the expression levels of MECP2. MECP2 does have multiple alternate transcripts that are differentially expressed in the human brain during development. MECP2 is highly expressed in fetal brain, with the largest (10.1 kb) transcript predominating; the 1.8 and 5 kb transcripts are more abundant in fetal liver (Coy et al., 1999; D'Esposito et al., 1996). The 10.1 kb transcript contains the longest 3'UTR, which may play a role in transcriptional or posttranscriptional regulation of the gene in brain tissue. Such regulation may affect the stability of the RNA and thereby contribute to the dependence of neurons on MECP2. In addition, MeCP2 is a member of a family of methyl-CpG-binding proteins (Hendrich et al., 1999), at least three of which (MBD1, MBD2a, and MBD3) have transcriptional repression activity or are members of repressor complexes (Ng and Bird, 1999; Wade et al., 1999; Bird and Wolffe, 1999). It is possible that these related proteins compensate for MeCP2 dysfunction in some tissues, and that in brain tissue this is less effective. Alternatively, neuronal genes may depend more on the activity of MeCP2 than other genes. Finally, it is possible that MeCP2 functions similarly in neuronal and nonneuronal tissues, but that the postmitotic nature of neurons renders them more susceptible to the alterations induced by compromised MeCP2 function.

MeCP2 acts as a global transcriptional repressor, and in specific embodiments it is involved in silencing specific genes, transposable repetitive sequences, or both (Nan et al., 1997; Bird and Wolffe, 1999). In one embodiment, loss of function of MeCP2 allows excessive transcriptional "noise" from repetitive sequences or misexpression of specific genes. The constellation of features seen in Rett syndrome and the consistency of the phenotype among classic Rett patients suggests that the disorder may be due to the dysfunction of a small number of genes. Functional studies of the various mutations and analysis of animal models for RTT should clarify the pathogenic mechanism and establish how DNA-methylation dependent processes are disrupted.

Finally, Rett is the first ICD-10 pervasive developmental disorder found to be caused by mutations in a single gene. That the peculiar neurologic features of Rett syndrome arise from mutations in a gene encoding a component of an epigenetic silencing complex raises the possibility that mutations in other components of the complex or other methyl-CpG-binding proteins may be responsible for some subtypes of autistic disorders. It is also possible that, among the genes affected by loss of normal MECP2 function, some are responsible for the autistic features in Rett syndrome. Such genes could prove to be involved in other pervasive developmental disorders.

MECP2 Mutation in Neurodevelopmental Diseases

In specific embodiments, defects in MECP2 are related to Rett syndrome, autism, non-syndromic mental retardation, idiopathic neonatal encephalopathy, idiopathic infantile spasms, idiopathic cerebral palsy, Angelman syndrome, and schizophrenia. Although MECP2 is clearly involved in Rett syndrome and its related features, recent evidence indicates that mutations in MECP2 are associated with mental retardation, including non-specific X-linked mental retardation and autism (Orrico et al., 2000; incorporated by reference herein). In another embodiment, MECP2 mutations are related to Angelman syndrome, which is an inherited disorder with multiple phenotypes including mental retardation (for reviews see Rougeulle and Lalande, 1998; Laan et al., 1999; Lalande et al., 1999; Mann and Bartolomei, 1999, each of which is incorporated by reference herein). The syndrome is the result of a deletion or mutation within maternal chromosome 15q11–q13. Methylation imprinting abnormalities occur (Laan et al., 1999), and furthermore there is evidence that multiple genes are involved in AS (Rougeulle and Lalande, 1998). In a specific embodiment, loss of MECP2 affects imprinting of a gene or genes involved in Angelman syndrome.

One skilled in the art in light of the present invention is made aware of the relationship between neurodevelopmental disease and a mutation or mutations in a methyl-CpG-binding domain containing protein which are responsible for said disease. Furthermore, a skilled artisan is aware that the invention addresses a mutation which is deleterious to the function of the methyl-CpG-binding domain containing protein.

A skilled artisan is aware that in the scope of the present invention there are multiple MECP2, MECP1, MBD1, MBD2, MBD3 and/or MBD4 sequences which are available to a skilled artisan through sequence repositories, such as GenBank or commercially available databases, such as Celera Genomics. These include human (H-MECP2), mouse (M-MECP2), chicken (G-MECP2) and Xenopus laevis (X-MECP2) proteins and nucleic acids. Specific examples of GenBank Accession Nos. for nucleic acid sequences are as follows: BE557079 (SEQ ID NO:17); BE201625 (SEQ ID NO:18); BE201619 (SEQ ID NO:19); L37298 (SEQ ID NO:20); X99686 (SEQ ID NO:21); X99687 (SEQ ID NO:22); X89430 (SEQ ID NO:23); AJ132917 (SEQ ID NO:24); NM_004992 (SEQ ID NO:25); Y12643 (SEQ ID NO:26); AF158180 (SEQ ID NO:27); AF158181 (SEQ ID NO:28); AJ132922 (SEQ ID NO:29); AF072257 (SEQ ID NO:30); AJ132915 (SEQ ID NO:31); AJ132923 (SEQ ID NO:32); AJ132921 (SEQ ID NO:33); AJ132924 (SEQ ID NO:34); AJ132920 (SEQ ID NO:35); AJ132919 (SEQ ID NO:36); AJ132918 (SEQ ID NO:37); AJ132916 (SEQ ID NO:38); AJ132914 (SEQ ID NO:39); NM_003926 (SEQ ID NO:40); NM_015832 (SEQ ID NO:41); NM_002384 (SEQ ID NO:42); NM_015847 (SEQ ID NO:43); NM_015846 (SEQ ID NO:44); NM_015845 (SEQ ID NO:45); NM_015844 (SEQ ID NO:46); and NM_003925 (SEQ ID NO:47). Specific examples of GenBank Accession Nos. for amino acid sequences are as follows: NP_003917 (SEQ ID NO:48); NP_056647 (SEQ ID NO:49); NP_002375 (SEQ ID NO:50); NP_056723 (SEQ ID NO:51); NP_056671 (SEQ ID NO:52); NP_056670 (SEQ ID NO:53); NP_056669 (SEQ ID NO:54); NP_004983 (SEQ ID NO:55); NP_003916 (SEQ ID NO:56); NP_003918 (SEQ ID NO:57); AAF22116 (SEQ ID NO:58); AAC08757 (SEQ ID NO:59); CAA73190 (SEQ ID NO:60); AAF33024 (SEQ ID NO:61); AAF33023 (SEQ ID NO:62); AAF21637 (SEQ ID NO:63); 1QK9A (SEQ ID NO:64); P51608 (SEQ ID NO:65); Q00566 (SEQ ID NO:66); CAB46495 (SEQ ID NO:67); CAB46446 (SEQ ID NO:68); AAD03736 (SEQ ID NO:69); AAD02651 (SEQ ID NO:70); AAC68880 (SEQ ID NO:71); AAC32737 (SEQ ID NO:72); AAC08758 (SEQ ID NO:73); CAA68001 (SEQ ID NO:74); CAA61599 (SEQ ID NO:75).

Multiple mutations in a relevant sequence may be present or may be required to be deleterious. A mutation can reside in the regulatory sequence of a gene, which can include an enhancer sequence, promoter sequences or cis sequences which bind transacting factors. Transacting factors for said regulatory sequences may be of a general nature in function or may be specific to said gene. Many types of transacting factors may be associated, including transcriptional factors or repressors. A mutation in the regulatory region of a gene might affect post-transcriptional processing. For example, incorrect capping of the transcript could lead to aberrant subcellular localization. In a specific embodiment, another mutation, which might affect regulation of the MECP2 gene, is through X-linked inactivation in which the normal pattern of repression in transcription of the gene on the X chromosome has been disrupted, either partially or completely. A mutation may also occur in an exon, an intron, an exon/intron junction or a 3' untranslated region (UTR). A mutation occurring in an exon/intron junction could affect either the donor site or the acceptor site, or multiple mutations can affect both. A skilled artisan would be aware that a deficiency in splicing could cause retention of intronic sequences in the mature messenger RNA allowing translation to proceed into intron sequences and likely leading to a nonsense condon which would generate a truncated protein. Furthermore, one skilled in the art would be aware of a variety of diseases caused by defects in splicing including Tay-Sachs disease, PKU, hemophilia B, and α thalassemia. A mutation in a 3' UTR could affect regulatory sequences present which could be associated with mRNA degradation, mRNA stability, subcellular localization, post-transcriptional processing or translation. Said mutation could also affect poly-(A) adenylation sites leading to a loss of polyadenylation or ectopic polyadenylation sites. Alternative polyadenylation in the 3' UTR of MECP2 results in a variety of transcripts, some of which are differentially expressed in the human brain (D'Esposito et al., 1996 and Coy et al., 1999). Mutations could affect localization of the different sized transcripts and could lead to aberrant phenotypes.

Mutations of nucleic acid sequence can be nonsense, missense, frameshift, insertion or deletion of one or more base pairs. Mutations could lead to a truncated protein, could alter the conformation of the protein or could directly affect an amino acid required for function of the protein. An alteration which produces no deleterious effects on the function or structure of the protein and produces no detectable phenotype is not the focus of the present invention.

Mutations in nucleic acid sequences which encode methyl-CpG-binding domain containing proteins can be detected in a variety of methods known to those in the art including by sequencing, probe, nucleic acid hybridization, PCR, nucleic acid chip hybridization, electrophoresis, or fluorescent in situ hybridization (FISH). Sequencing methods are common laboratory procedures known to many in the art and would be able to detect the exact nature of the mutation. In addition, mutation could be detected by probe. For instance, one skilled in the art would be aware that a fluorescent tag could be specific for binding of a mutation and could be exposed to, for instance, glass beads coated with nucleic acids containing potential mutations. Upon binding of the tag to the mutation in question, a change in fluorescence (such as creation of fluorescence, increase in intensity, or partial or complete quenching) could be indicative of the presence of that mutation. Nucleic acid hybridization including Southerns or northerns could be utilized to detect mutations such as those involved in alteration of large regions of the sequence or of those involved in alteration of a sequence containing a restriction endonuclease site. Hybridization is detected by a variety of ways including radioactivity, color change, light emission, or fluorescence. PCR could also be used to amplify a region suspected to contain a mutation and the resulting amplified region could either be subjected to sequencing or to restriction digestion analysis in the event that mutation was responsible for creating or removing a restriction endonuclease site. The mutation could be identified through an RNA species from the gene by RT-PCR methods which are well known in the art. One skilled in the art would also know that a specific method of nucleic acid hybridization could be utilized in the form of nucleic acid chip hybridization in which nucleic acids are present on a immobilized surface such as a microchip or microchips and are subjected to hybridization techniques sensitive enough to detect minor changes in sequences; a variety of detection methods could be used including light emission, fluorescence, color change, or radioactivity. Electrophoresis could detect mutations of the sequence either by mobility changes or in conjunction with another method of detecting a mutation such as with sequencing or by PCR. Finally, one skilled in the art would be aware that FISH is a proficient technique of detecting large regions of sequences on chromosomes which have been deleted or rearranged.

One skilled in the art is aware that alterations can be detected in the methyl-CpG-binding domain containing protein through the following methods: sequencing, mass spectrometry, by molecular weight, with antibodies, through increased expression of a target gene, by chromosomal coating or by alterations in methylation of DNA patterns. Examples of alterations include a change, loss, or addition of an amino acid, truncation or fragmentation of the protein. Alterations can increase degradation of the protein, can change conformation of the protein, or can be present in a hydrophobic or hydrophilic domain of the protein. The alteration need not be in an active site of the protein to have a deleterious effect on its function or structure, or both. Alteration can include modifications to the protein such as phosphorylation, myristilation, acetylation, or methylation. Sequencing of the protein or a fragment thereof directly by methods well known in the art would identify specific amino acid alterations. Alterations in protein sequences can be detected by analyzing either the entire protein or fragments of the protein and subjecting them to mass spectrometry, which would be able to detect even minor changes in molecular weight. Additionally, antibodies can be used to detect mutations in said proteins if the epitope includes the particular site which has been mutated. Antibodies can be used to detect mutations in the protein by immunoblotting, with in situ methods, or by immunoprecipitation. Antibodies to the methyl-CpG-binding domain containing protein on immunoblots may alternatively recognize any epitope of the protein and could detect truncations or modifications of the protein which would affect electrophoretic mobility, including phosphorylation or myristilation. Analysis of interactions among components of the MECP2 complex can also utilize antibodies. For instance, an antibody to a protein in the MECP2/complex may be utilized to immunoprecipitate another protein in the complex, either of which may contain a mutation.

The presence of a mutation in a methyl-CpG-binding domain containing protein may be inferred by the phenotype (s) which occurs either directly or indirectly as a result of such a mutation. For instance, an increase in expression of a target gene of a methyl-CpG-binding domain containing protein would be suggestive that a mutation exists which has rendered the protein at least partly defective. Potential target genes of MECP2 are the leukosialin (CD43) and FMR1 genes. Mutations in MECP2 would be expected to affect target genes which are either directly or indirectly responsible for the phenotypes present in the neurodevelopmental diseases described herein. A skilled artisan is aware of various methods to determine target genes of MECP2, including assaying for altered expression following mutation or alteration in MECP2, particularly by comparing the expression in an individual with the mutation to an individual with no MECP2 mutation.

Another method of identifying a mutation in a methyl-CpG-binding domain containing protein is through the analysis of the coating phenotype on the chromosome. That is, MECP2 has been shown to be present throughout entire chromosomes in a particular coating pattern. One skilled in the art recognizes that a mutation in the MECP2 protein can alter the pattern of chromosomal coating. One method to characterize a change in a pattern is with antibodies, which could be detected by color change, light emission or fluorescence. Finally, a mutation in the methyl-CpG-binding domain containing protein can be identified through the pattern of methylation of DNA. It is known that methyl-CpG-binding domain containing proteins such as MECP2 bind methylated CpG dinucleotides to mediate transcriptional repression, and loss of function of said protein affects the methylation pattern of the DNA. One method to characterize a methylation pattern is to utilize an endonuclease whose action or lack of action is indicative of a particular methylation state.

In a specific embodiment of the present invention, at least one component of a MECP2/complex is defective and renders the complex ineffectual in its function. One skilled in the art is aware that multiple components make up said complex and that a defect or a disruption of the stoichiometry within the complex results in defective function of the complex. A mutation in a gene encoding a component of said complex or an alteration of a component of said complex could also affect association or disassociation of said complex components leading to partial or complete loss of complex function.

Interaction between two or more components of the MECP2/complex is characterized in a variety of ways to determine the presence of a defect in a component of the complex. One method to investigate such interaction is the purification of the complex and subsequent analysis of the identity of the purified products. Immunoprecipitation with antibodies to one of the components of the complex followed by analysis of the immunoprecipitated components is employed. For instance, immunoprecipitation followed by analysis of the immunoprecipitated components with different antibodies identifies alterations in the quantity or identity of the components.

Methods to treat a vertebrate with a neurodevelopmental disease with a mutation in a methyl-CpG-binding domain containing protein which causes loss of transcriptional repression of a target gene can include administration of a therapeutically effective amount of a compound to enhance methylation. Hypermethylation of the promoter region of a target gene can reduce the expression level by another mechanism. Cameron et al. (1999) have shown in cancer cells that DNA methylation, although generally thought to work synergistically with histone deacetylation to induce transcriptional repression, may in certain situations be dominant over and independent of histone deacetylation for stable maintenance of transcriptional silencing of genes. Dietary methyl supplementation may be a good therapeutic option; it has been shown recently that such diets can alter epigenetic regulation of agouti expression in mice (Wolff et al., 1998). Examples of said compound to enhance methylation are selected from the group consisting of folic acid, vitamin B12, methionine, zinc, choline, betaine and combinations thereof. In addition, a compound may be administered to enhance the function of complex. Such a compound could be a cofactor for catalysis, an analog of a required component, or a compound which enhances the complex function in any manner.

One of the effects of loss of function of a methyl-CpG-binding domain-containing protein can be an indirect or direct increase in methylation. Methods to treat a vertebrate with a neurodevelopmental disease with a mutation in a methyl-CpG-binding domain containing protein which results in an increase in methylation leading to a decrease in expression of a target gene include administration of a therapeutically effective amount of a compound that decreased methylation. Examples of said compound may be selected from the group consisting of 5-aza 2' deoxycytidine, Trichostatin A, phenyl-butyrate, sodium butyrate, trapoxin and a folate depleting agent. An example of a folate depleting agent is methotrexate or any agent that directly or indirectly inhibits dihydrofolate reductase.

A skilled artisan is aware that ideally a routine method for detection of a mutation in a nucleic acid or an alteration of an amino acid in neurodevelopmental disease is preferably rapid, repeatable, and/or easy to perform.

NUCLEIC ACID-BASED EXPRESSION SYSTEMS

1. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCRTM, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

e. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

f. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

g. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

2. Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

3. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cellibaculovirus system can produce a high level of protein expression of a heterologous nucleic acid segment, such as described in U.S. Pat. NoS. 5,871,986, 4,879,236, both herein incorporated by reference, and which can be bought, for example, under the name MAxBAc® 2.0 from INVITROGEN® and BACPACK™ BACULOVIRUS EXPRESSION SYSTEM FROM CLONTECH®.

Other examples of expression systems include STRATAGENE®'S COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

Nucleic Acid Detection

In addition to their use in monitoring the expression of MECP2, MECP1, MBD1, MBD2, MBD3 and/or MBD4 proteins, polypeptides and/or peptides, the nucleic acid sequences disclosed herein have a variety of other uses. For example, they have utility as probes or primers for embodiments involving nucleic acid hybridization.

1. Hybridization

The use of a probe or primer of between 13 and 100 nucleotides, preferably between 17 and 100 nucleotides in length, or in some aspects of the invention up to 1–2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM MgCl$_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl$_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to MECP2, MECP1, MBD1, MBD2, MBD3 and/or MBD4 are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety.

A reverse transcriptase PCR™ amplification procedure may be performed to quantify the amount of MRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assy (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alphathio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). Davey et al., European Application No. 329 822 disclose a nucleic acid amplification process involving cyclically synthesizing single-stranded RNA ("ssRNA"), ssDNA, and double-stranded DNA (dsDNA), which may be used in accordance with the present invention.

Miller et al., PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art. See Sambrook et al., 1989. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substititution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

5. Kits

All the essential materials and/or reagents required for detecting MECP2, MECP1, MBD1, MBD2, MBD3 and/or MBD4 in a sample may be assembled together in a kit. This generally will comprise a probe or primers designed to hybridize specifically to individual nucleic acids of interest in the practice of the present invention, including MECP2, MECP1, MBD1, MBD2, MBD3 and/or MBD4, respectively. Also included may be enzymes suitable for amplifying nucleic acids, including various polymerases (reverse transcriptase, Taq, etc.), deoxynucleotides and buffers to provide the necessary reaction mixture for amplification. Such kits may also include enzymes and other reagents suitable for detection of specific nucleic acids or amplification products. Such kits generally will comprise, in suitable means, distinct containers for each individual reagent or enzyme as well as for each probe or primer pair.

MECP2, MECP1, MBD1, MBD2, MBD3 and MBD4 Nucleic Acids

A. Nucleic Acids and Uses Thereof

Certain aspects of the present invention concern at least one MECP2, MECP1, MBD1, MBD2, MBD3 or MBD4 nucleic acid. In certain aspects, the at least one MECP2, MECP1, MBD1, MBD2, MBD3 or MBD4 nucleic acid comprises a wild-type or mutant MECP2, MECP1, MBD1, MBD2, MBD3 or MBD4 nucleic acid, respectively. In particular aspects, the MECP2, MECP1, MBD1, MBD2, MBD3 or MBD4 nucleic acid encodes for at least one transcribed nucleic acid. In certain aspects, the MECP2, MECP1, MBD1, MBD2, MBD3 or MBD4 nucleic acid comprises at least one transcribed nucleic acid. In particular aspects, the MECP2, MECP1, MBD1, MBD2, MBD3 or MBD4 nucleic acid encodes at least one MECP2, MECP1, MBD1, MBD2, MBD3 and/or MBD4 protein, polypeptide or peptide, respectively, or biologically functional equivalent thereof. In other aspects, the MECP2, MECP1, MBD1, MBD2, MBD3 or MBD4 nucleic acid comprises at least one nucleic acid segment of SEQ ID NO: 17 through SEQ ID NO:47, or at least one biologically functional equivalent thereof.

The present invention also concerns the isolation or creation of at least one recombinant construct or at least one recombinant host cell through the application of recombinant nucleic acid technology known to those of skill in the art or as described herein. The recombinant construct or host cell may comprise at least one MECP2, MECP1, MBD1, MBD2, MBD3 and/or MBD4 nucleic acid, and may express at least one MECP2, MECP1, MBD1, MBD2, MBD3 and/or MBD4 protein, peptide or peptide, or at least one biologically functional equivalent thereof.

As used herein "wild-type" refers to the naturally occurring sequence of a nucleic acid at a genetic locus in the genome of an organism, and sequences transcribed or translated from such a nucleic acid. Thus, the term "wild-type" also may refer to the amino acid sequence encoded by the nucleic acid. As a genetic locus may have more than one sequence or alleles in a population of individuals, the term "wild-type" encompasses all such naturally occurring alleles. As used herein the term "polymorphic" means that variation exists (i.e. two or more alleles exist) at a genetic locus in the individuals of a population. As used herein "mutant" refers to a change in the sequence of a nucleic acid or its encoded protein, polypeptide or peptide that is the result of the hand of man.

A nucleic acid may be made by any technique known to one of ordinary skill in the art. Non-limiting examples of synthetic nucleic acid, particularly a synthetic oligonucleotide, include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. patent application Ser. No. 5,705,629, each incorporated herein by reference. A non-limiting example of enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells, such as recombinant DNA vector production in bacteria (see for example, Sambrook et al. 1989, incorporated herein by reference).

A nucleic acid may be purified on polyacrylamide gels, cesium chloride centrifugation gradients, or by any other means known to one of ordinary skill in the art (see for example, Sambrook et al. 1989, incorporated herein by reference).

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g. adenine "A," guanine "G," thymine "T" and cytosine "C") or RNA (e.g. A, G, uracil "U" and C). The term "nucleic acid" encompass the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss", a double stranded nucleic acid by the prefix "ds", and a triple stranded nucleic acid by the prefix "ts."

Thus, the present invention also encompasses at least one nucleic acid that is complementary to a MECP2, MECP1, MBD1, MBD2, MBD3 or MBD4 nucleic acid. In particular embodiments the invention encompasses at least one nucleic acid or nucleic acid segment complementary to the sequence set forth in SEQ ID NO: 17 through SEQ ID NO:47. Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" also refers to nucleic acid(s) that are substantially complementary, as may be assessed by the same nucleotide comparison set forth above. The term "substantially complementary" refers to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 75%, about 80%, about 85%, about 90%, about 95%, about 98%, about 99%, to about 100%, and any range therein, of the nucleobase sequence is capable of base-pairing with at least one single or double stranded nucleic acid molecule during hybridization. In certain embodiments, the term "substantially complementary" refers to at least one nucleic acid that may hybridize to at least one nucleic acid strand or duplex in stringent conditions. In certain embodiments, a "partly complementary" nucleic acid comprises at least one sequence that may hybridize in low stringency conditions to at least one single or double stranded nucleic acid, or contains at least one sequence in which less than about 70% of the nucleobase sequence is capable of base-pairing with at least one single or double stranded nucleic acid molecule during hybridization.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating at least one nucleic acid, such as a gene or nucleic acid segment thereof, or detecting at least one specific mRNA transcript or nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence of formamide, tetramethylammonium chloride or other solvent (s) in the hybridization mixture. It is generally appreciated that conditions may be rendered more stringent, such as, for example, the addition of increasing amounts of formamide.

It is also understood that these ranges, compositions and conditions for hybridization are mentioned by way of non-limiting example only, and that the desired stringency for a particular hybridization reaction is often determined empirically by comparison to one or more positive or negative controls. Depending on the application envisioned it is preferred to employ varying conditions of hybridization to achieve varying degrees of selectivity of the nucleic acid(s) towards target sequence(s). In a non-limiting example, identification or isolation of related target nucleic acid(s) that do not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

One or more nucleic acid(s) may comprise, or be composed entirely of, at least one derivative or mimic of at least one nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refers to a molecule that may or may not structurally resemble a naturally occurring molecule, but functions similarly to the naturally occurring molecule. As used herein, a "moiety" generally refers to a smaller chemical or molecular component of a larger chemical or molecular structure, and is encompassed by the term "molecule."

As used herein a "nucleobase" refers to a naturally occurring heterocyclic base, such as A, T, G, C or U ("naturally occurring nucleobase(s)"), found in at least one naturally occurring nucleic acid (i.e. DNA and RNA), and their naturally or non-naturally occurring derivatives and mimics. Non-limiting examples of nucleobases include purines and pyrimidines, as well as derivatives and mimics thereof, which generally can form one or more hydrogen bonds ("anneal" or "hybridize") with at least one naturally occurring nucleobase in manner that may substitute for naturally occurring nucleobase pairing (e.g. the hydrogen bonding between A and T, G and C, and A and U).

Nucleobase, nucleoside and nucleotide mimics or derivatives are well known in the art, and have been described in exemplary references such as, for example, Scheit, Nucleotide Analogs (John Wiley, New York, 1980), incorporated herein by reference. "Purine" and "pyrimidine" nucleobases encompass naturally occurring purine and pyrimidine nucleobases and also derivatives and mimics thereof, including but not limited to, those purines and pyrimidines substituted by one or more of alkyl, caboxyalkyl, amino, hydroxyl, halogen (i.e. fluoro, chloro, bromo, or iodo), thiol, or alkylthiol wherein the alkyl group comprises of from about 1, about 2, about 3, about 4, about 5, to about 6 carbon atoms. Non-limiting examples of purines and pyrimidines include deazapurines, 2,6-diaminopurine, 5-fluorouracil, xanthine, hypoxanthine, 8-bromoguanine, 8-chloroguanine, bromothymine, 8-aminoguanine, 8-hydroxyguanine, 8-methylguanine, 8-thioguanine, azaguanines, 2-aminopurine, 5-ethylcytosine, 5-methylcyosine, 5-bromouracil, 5-ethyluracil, 5-iodouracil, 5-chlorouracil, 5-propyluracil, thiouracil, 2-methyladenine, methylthioadenine, N,N-diemethyladenine, azaadenines, 8-bromoadenine, 8-hydroxyadenine, 6-hydroxyaminopurine, 6-thiopurine, 4-(6-aminohexyl/cytosine), and the like. Examples of purine and pyrimidine derivatives and mimics are well known in the art.

As used herein, "nucleoside" refers to an individual chemical unit comprising a nucleobase covalently attached to a nucleobase linker moiety. A non-limiting example of a "nucleobase linker moiety" is a sugar comprising 5-carbon atoms (a "5-carbon sugar"), including but not limited to deoxyribose, ribose or arabinose, and derivatives or mimics of 5-carbon sugars. Non-limiting examples of derivatives or mimics of 5-carbon sugars include 2'-fluoro-2'-deoxyribose or carbocyclic sugars where a carbon is substituted for the oxygen atom in the sugar ring. By way of non-limiting example, nucleosides comprising purine (i.e. A and G) or 7-deazapurine nucleobases typically covalently attach the 9 position of the purine or 7-deazapurine to the 1'-position of a 5-carbon sugar. In another non-limiting example, nucleosides comprising pyrimidine nucleobases (i.e. C, T or U) typically covalently attach the 1 position of the pyrimidine to 1'-position of a 5-carbon sugar (Kornberg and Baker, DNA Replication, 2nd Ed. (Freeman, San Francisco, 1992). However, other types of covalent attachments of a nucleobase to a nucleobase linker moiety are known in the art, and non-limiting examples are described herein.

As used herein, a "nucleotide" refers to a nucleoside further comprising a "backbone moiety" generally used for the covalent attachment of one or more nucleotides to another molecule or to each other to form one or more nucleic acids. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or mimics of a naturally occurring 5-carbon sugar or phosphorus moiety, and non-limiting examples are described herein.

A non-limiting example of a nucleic acid comprising such nucleoside or nucleotide derivatives and mimics is a "polyether nucleic acid", described in U.S. patent application Ser. No. 5,908,845, incorporated herein by reference, wherein one or more nucleobases are linked to chiral carbon atoms in a polyether backbone. Another example of a nucleic acid comprising nucleoside or nucleotide derivatives or mimics is a "peptide nucleic acid", also known as a "PNA", "peptide-based nucleic acid mimics" or "PENAMs", described in U.S. patent application Ser. Nos. 5,786,461, 5891,625, 5,773,571, 5,766,855, 5,736,336, 5,719,262, 5,714,331, 5,539,082, and WO 92/20702, each of which is incorporated herein by reference. A peptide nucleic acid generally comprises at least one nucleobase and at least one nucleobase linker moiety that is either not a 5-carbon sugar and/or at least one backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

Peptide nucleic acids generally have enhanced sequence specificity, binding properties, and resistance to enzymatic degradation in comparison to molecules such as DNA and RNA (Egholm et al., Nature 1993, 365, 566; PCT/EP/01219). In addition, U.S. Pat. Nos. 5,766,855, 5,719,262, 5,714,331 and 5,736,336 describe PNAs comprising naturally and non-naturally occurring nucleobases and alkylamine side chains with further improvements in sequence specificity, solubility and binding affinity. These properties promote double or triple helix formation between a target nucleic acid and the PNA.

U.S. Pat. No. 5,641,625 describes that the binding of a PNA may to a target sequence has applications the creation of PNA probes to nucleotide sequences, modulating (i.e. enhancing or reducing) gene expression by binding of a PNA to an expressed nucleotide sequence, and cleavage of specific dsDNA molecules. In certain embodiments, nucleic acid analogues such as one or more peptide nucleic acids may be used to inhibit nucleic acid amplification, such as in PCR, to reduce false positives and discriminate between single base mutants, as described in U.S. patent application Ser. No. 5891,625.

U.S. Pat. No. 5,786,461 describes PNAs with amino acid side chains attached to the PNA backbone to enhance solubility. The neutrality of the PNA backbone may contribute to the thermal stability of PNA/DNA and PNA/RNA duplexes by reducing charge repulsion. The melting temperature of PNA containing duplexes, or temperature at which the strands of the duplex release into single stranded molecules, has been described as less dependent upon salt concentration.

One method for increasing amount of cellular uptake property of PNAs is to attach a lipophilic group. U.S. application Ser. No. 117,363, filed Sep. 3, 1993, describes several alkylamino functionalities and their use in the attachment of such pendant groups to oligonucleosides. U.S. application Ser. No. 07/943,516, filed Sep. 11, 1992, and its corresponding published PCT application WO 94/06815, describe other novel amine-containing compounds and their incorporation into oligonucleotides for, inter alia, the purposes of enhancing cellular uptake, increasing lipophilicity, causing greater cellular retention and increasing the distribution of the compound within the cell.

Additional non-limiting examples of nucleosides, nucleotides or nucleic acids comprising 5-carbon sugar and/or backbone moiety derivatives or mimics are well known in the art.

In certain aspects, the present invention concerns at least one nucleic acid that is an isolated nucleic acid. As used herein, the term "isolated nucleic acid" refers to at least one nucleic acid molecule that has been isolated free of, or is otherwise free of, the bulk of the total genomic and transcribed nucleic acids of one or more cells, particularly mammalian cells, and more particularly human, mouse and rat cells. In certain embodiments, "isolated nucleic acid" refers to a nucleic acid that has been isolated free of, or is otherwise free of, bulk of cellular components and macromolecules such as lipids, proteins, small biological molecules, and the like. As different species may have a RNA or a DNA containing genome, the term "isolated nucleic acid" encompasses both the terms "isolated DNA" and "isolated RNA". Thus, the isolated nucleic acid may comprise a RNA or DNA molecule isolated from, or otherwise free of, the bulk of total RNA, DNA or other nucleic acids of a particular species. As used herein, an isolated nucleic acid isolated from a particular species is referred to as a "species specific nucleic acid." When designating a nucleic acid isolated from a particular species, such as human, such a type of nucleic acid may be identified by the name of the species. For example, a nucleic acid isolated from one or more humans would be an "isolated human nucleic acid", a nucleic acid isolated from mouse would be an "isolated mouse nucleic acid", etc.

Of course, more than one copy of an isolated nucleic acid may be isolated from biological material, or produced in vitro, using standard techniques that are known to those of skill in the art. In particular embodiments, the isolated nucleic acid is capable of expressing a protein, polypeptide or peptide that has MECP2, MECP1, MBD1, MBD2, MBD3 or MBD4 activity. In other embodiments, the isolated nucleic acid comprises an isolated MECP2, MECP1, MBD1, MBD2, MBD3 or MBD4 gene.

Herein certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In other particular aspects, the gene comprises a MECP2, MECP1, MBD1, MBD2, MBD3 or MBD4 nucleic acid, and/or encodes a MECP2, MECP1, MBD1, MBD2, MBD3 or MBD4 polypeptide or peptide coding sequences, respectively. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit. As will be understood by those in the art, this function term "gene"

includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

"Isolated substantially away from other coding sequences" means that the gene of interest, in this case the MECP2, MECP1, MBD1, MBD2, MBD3 or MBD4 gene(s), forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

In certain embodiments, the nucleic acid is a nucleic acid segment. As used herein, the term "nucleic acid segment", are smaller fragments of a nucleic acid, such as for non-limiting example, those that encode only part of the MECP2, MECP1, MBD1, MBD2, MBD3 or MBD4 peptide or polypeptide sequence. Thus, a "nucleic acid segment" may comprise any part of the MECP2, MECP1, MBD1, MBD2, MBD3 or MBD4 gene sequence(s), of from about 2 nucleotides to the full length of the MECP2, MECP1, MBD1, MBD2, MBD3 and/or MBD4 peptide- or polypeptide-encoding region. In certain embodiments, the "nucleic acid segment" encompasses the full length MECP2, MECP1, MBD1, MBD2, MBD3 or MBD4 gene(s) sequence. In particular embodiments, the nucleic acid comprises any part of the SEQ ID NO: 17 through SEQ ID NO:47 sequence(s), of from about 2 nucleotides to the full length of the sequence disclosed in SEQ ID NO:17 through SEQ ID NO:47.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on. In certain embodiments, the nucleic acid segment may be a probe or primer. As used herein, a "probe" is a relatively short nucleic acid, such as an oligonucleotide, used to identify sequences to which it hybridizes, such as nucleic acid hybridization. As used herein, a "primer" is a relatively short nucleic acid, such as an oligonucleotide, used to prime polymerization from a template nucleic acid, such as in polymerase chain reaction in the presence of a polymerase and dNTPs. A non-limiting example of this would be the creation of nucleic acid segments of various lengths and sequence composition for probes and primers based on the sequences disclosed in SEQ ID NO: 17 through SEQ ID NO:47.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). As used herein, a "nucleic acid construct" is a nucleic acid molecule comprising a sequence of interest and affiliated nucleic acid segments, such as regulatory sequences, replicatory sequences, restriction enzyme sites and the like. In a specific embodiment the nucleic acid construct is borne on a vector, such as a plasmid. The overall length may vary considerably between nucleic acid constructs. Thus, a nucleic acid segment of almost any length may be employed, with the total length preferably being limited by the ease of preparation or use in the intended recombinant nucleic acid protocol.

In a non-limiting example, one or more nucleic acid constructs may be prepared that include a contiguous stretch of nucleotides identical to or complementary to SEQ ID NO: 17 through SEQ ID NO:47. A nucleic acid construct may be about 3, about 5, about 8, about 10 to about 14, or about 15, about 20, about 30, about 40, about 50, about 100, about 200, about 500, about 1,000, about 2,000, about 3,000, about 5,000, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges", as used herein, means any length or range including or between the quoted values (i.e. all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.; about 1,001, about 1002, etc,; about 50,001, about 50,002, etc; about 750,001, about 750,002, etc.; about 1,000,001, about 1,000,002, etc. Non-limiting examples of intermediate ranges include about 3 to about 32, about 150 to about 500,001, about 3,032 to about 7,145, about 5,000 to about 15,000, about 20,007 to about 1,000,003, etc.

In certain embodiments, the nucleic acid construct is a recombinant vector. As used herein, a "recombinant vector" is a nucleic acid molecule comprising different nucleic acid segments including at least one sequence of interest, wherein the vector is utilized for transmittal of the sequence of interest between biological entities, such as between cells, between tissues, or even between laboratory container, such as an eppendorf tube or test tube, and a cell. In particular embodiments, the invention concerns one or more recombinant vector(s) comprising nucleic acid sequences that encode an MECP2, MECP 1, MBD1, MBD2, MBD3 or MBD4 protein, polypeptide or peptide that includes within its amino acid sequence a contiguous amino acid sequence in accordance with, or essentially as set forth in, SEQ ID NO:48 through SEQ ID NO:75, corresponding to different species' MECP2, MECP1, MBD1, MBD2, MBD3 or MBD4. In other embodiments, the invention concerns recombinant vector(s) comprising nucleic acid sequences that encode a human or mouse MECP2, MECP1, MBD1, MBD2, MBD3 or MBD4 protein, polypeptide or peptide that includes within its amino acid sequence a contiguous amino acid sequence in accordance with, or essentially as set forth in SEQ ID NO:48 through SEQ ID NO:75. In particular aspects, the recombinant vectors are DNA vectors.

The term "a sequence essentially as set forth in SEQ ID NO:48 through SEQ ID NO:75" means that the sequence substantially corresponds to a portion of SEQ ID NO:48 through SEQ ID NO:75, respectively, and has relatively few amino acids that are not identical to, or a biologically functional equivalent of, the amino acids of SEQ ID NO:48 through SEQ ID NO:75. Thus, "a sequence essentially as set forth in SEQ ID NO:48 through SEQ ID NO:75" encompasses nucleic acids, nucleic acid segments, and genes that comprise part or all of the nucleic acid sequences as set forth in SEQ ID NO:17 through SEQ ID NO:47.

The term "biologically functional equivalent" is well understood in the art and is further defined in detail herein. Accordingly, a sequence that has between about 70% and about 80%; or more preferably, between about 81% and about 90%; or even more preferably, between about 91% and about 99%; of amino acids that are identical or functionally equivalent to the amino acids of SEQ ID NO:48 through SEQ ID NO:75 will be a sequence that is "essentially as set forth in SEQ ID NO:48 through SEQ ID NO:75", provided the biological activity of the respective protein, polypeptide or peptide is maintained.

In certain other embodiments, the invention concerns at least one recombinant vector that include within its sequence a nucleic acid sequence essentially as set forth in SEQ ID NO: 17 through SEQ ID NO:47. In particular embodiments, the recombinant vector comprises DNA sequences that encode protein(s), polypeptide(s) or peptide(s) exhibiting MECP2, MECP1, MBD1, MBD2, MBD3 or MBD4 activity.

The term "functionally equivalent codon" is used herein to refer to codons that encode the same amino acid, such as the six codons for arginine and serine, and also refers to codons that encode biologically equivalent amino acids. For optimization of expression of MECP2, MECP1, MBD1, MBD2, MBD3 or MBD4 in human cells, the preferred human DNA codons are known in the art.

It will also be understood that amino acid sequences or nucleic acid sequences may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

Excepting intronic and flanking regions, and allowing for the degeneracy of the genetic code, nucleic acid sequences that have between about 70% and about 79%; or more preferably, between about 80% and about 89%; or even more particularly, between about 90% and about 99%; of nucleotides that are identical to the nucleotides of SEQ ID NO:17 through SEQ ID NO:47 will be nucleic acid sequences that are "essentially as set forth in SEQ ID NO:17 through SEQ ID NO:47".

It will also be understood that this invention is not limited to the particular nucleic acid or amino acid sequences of SEQ ID NO:17 through SEQ ID NO:75. Recombinant vectors and isolated nucleic acid segments may therefore variously include these coding regions themselves, coding regions bearing selected alterations or modifications in the basic coding region, and they may encode larger polypeptides or peptides that nevertheless include such coding regions or may encode biologically functional equivalent proteins, polypeptide or peptides that have variant amino acids sequences.

The nucleic acids of the present invention encompass biologically functional equivalent MECP2, MECP1, MBD1, MBD2, MBD3 or MBD4 proteins, polypeptides, or peptides, respectively. Such sequences may arise as a consequence of codon redundancy or functional equivalency that are known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes designed by man may be introduced, for example, through the application of site-directed mutagenesis techniques as discussed herein below, e.g., to introduce improvements or alterations to the antigenicity of the protein, polypeptide or peptide, or to test mutants in order to examine MECP2, MECP1, MBD1, MBD2, MBD3 and/or MBD4 protein, polypeptide or peptide activity at the molecular level.

Fusion proteins, polypeptides or peptides may be prepared, e.g., where the MECP2, MECP1, MBD1, MBD2, MBD3 and/or MBD4 coding regions are aligned within the same expression unit with other proteins, polypeptides or peptides having desired functions. Non-limiting examples of such desired functions of expression sequences include purification or immunodetection purposes for the added expression sequences, e.g., proteinaceous compositions that may be purified by affinity chromatography or the enzyme labeling of coding regions, respectively. (EP 266,032, or via deoxynucleoside H-phosphonate intermediates as described by Froehler et al., Nucl. Acids Res., 14:5399–5407, 1986)

Encompassed by the invention are nucleic acid sequences encoding relatively small peptides or fusion peptides, such as, for example, peptides of from about 3, about 4, about 5, about 10, about 15, about 20, about 25, about 30, about 35, about 40, about 45, about 50, about 55, about 60, about 65, about 70, about 75, about 80, about 85, about 90, about 95, about 100 amino acids in length, or more preferably, of from about 15 to about 30 amino acids in length; as set forth in SEQ ID NO:48 through SEQ ID NO:75 and also larger polypeptides up to and including proteins corresponding to the full-length sequences set forth in SEQ ID NO:48 through SEQ ID NO:75.

As used herein an "organism" may be a prokaryote, eukaryote, virus and the like. As used herein the term "sequence" encompasses both the terms "nucleic acid" and "proteancecous" or "proteanaceous composition." As used herein, the term "proteinaceous composition" encompasses the terms "protein", "polypeptide" and "peptide." As used herein "artificial sequence" refers to a sequence of a nucleic acid not derived from sequence naturally occurring at a genetic locus, as well as the sequence of any proteins, polypeptides or peptides encoded by such a nucleic acid. A "synthetic sequence", refers to a nucleic acid or proteinaceous composition produced by chemical synthesis in vitro, rather than enzymatic production in vitro (i.e. an "enzymatically produced" sequence) or biological production in vivo (i.e. a "biologically produced" sequence).

Dosage and Formulation

The compounds (active ingredients) of this invention can be formulated and administered to treat neurodevelopmental disease by any means that produces contact of the active ingredient with the agent's site of action in the body of a vertebrate. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a therapeutically effective amount of active ingredient and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

The active ingredient can be administered orally in solid dosage forms such as capsules, tablets and powders, or in liquid dosage forms such as elixirs, syrups, emulsions and suspensions. The active ingredient can also be formulated for administration parenterally by injection, rapid infusion, nasopharyngeal absorption or dermoabsorption. The agent may be administered intramuscularly, intravenously, subcutaneously, transdermally or as a suppository. In administering a compound for methyl supplementation, the compound may be given systematically. For compounds which decrease methylation, a preferred embodiment is intrathecal administration which avoids systemic effects.

Gelatin capsules contain the active ingredient and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Useful pharmaceutical dosage forms for administration of the compounds of this invention can be illustrated as follows. Pharmacological ranges for the active ingredients can be determined by the skilled artisan using methods well known in the art. Example ranges for active ingredients are as follows: folate ranges between 400 micrograms and 4 milligrams/day; methionine ranges between 250 mg(total) and as high as 100 mg/kg/day daily, up to 2–3 g; choline ranges between 100 mg and 2 grams; Vitamin B12 at approximately 100 micrograms orally or 1 mg intramuscularly per month; betaine ranges up to 6 grams per day; zinc ranges between 25 and 50 mg; and sodium phenylbutyrate ranges up to 20 grams per day.

Capsules: Capsules are prepared by filling standard two-piece hard gelatin capsulates each with powdered active ingredient, 175 milligrams of lactose, 24 milligrams of talc and 6 milligrams magnesium stearate.

Soft Gelatin Capsules: A mixture of active ingredient in soybean oil is prepared and injected by means of a positive displacement pump into gelatin to form soft gelatin capsules containing the active ingredient. The capsules are then washed and dried.

Tablets: Tablets are prepared by conventional procedures so that the dosage unit contains the suggested amount of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 millileters contains the suggested amount of finely divided active ingredient, 200 milligrams of sodium carboxymethyl cellulose, 5 milligrams of sodium benzoate, 1.0 grams of sorbitol solution U.S.P. and 0.025 millileters of vanillin.

Accordingly, the pharmaceutical composition of the present invention may be delivered via various routes and to various sites in an animal body to achieve a particular effect. One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The composition of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

Gene Therapy Administration

The relatively normal development during the first 6–18 months of life of a patient with Rett syndrome will provide an opportunity for presymptomatic therapeutic intervention, especially if newborn screening programs can identify affected females. For gene therapy, a skilled artisan would be cognizant that the vector to be utilized must contain the gene of interest operatively limited to a promoter. For antisense gene therapy, the antisense sequence of the gene of interest would be operatively linked to a promoter. One skilled in the art recognizes that in certain instances other sequences such as a 3' UTR regulatory sequences are useful in expressing the gene of interest. Where appropriate, the gene therapy vectors can be formulated into preparations in solid, semisolid, liquid or gaseous forms in the ways known in the art for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds. A sufficient amount of vector containing the therapeutics nucleic acid sequence must be administered to provide a pharmacologically effective dose of the gene product.

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome or transporter molecule.

Accordingly, the present invention provides a method of transferring a therapeutic gene to a host, which comprises administering the vector of the present invention, preferably as part of a composition, using any of the aforementioned routes of administration or alternative routes known to those skilled in the art and appropriate for a particular application. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

It is possible that cells containing the therapeutic gene may also contain a suicide gene (i.e., a gene which encodes a product that can be used to destroy the cell, such as herpes simplex virus thymidine kinase). In many gene therapy situations, it is desirable to be able to express a gene for therapeutic purposes in a host cell but also to have the capacity to destroy the host cell once the therapy is completed, becomes uncontrollable, or does not lead to a predictable or desirable result. Thus, expression of the therapeutic gene in a host cell can be driven by a promoter, although the product of said suicide gene remains harmless in the absence of a prodrug. Once the therapy is complete or no longer desired or needed, administration of a prodrug causes the suicide gene product to become lethal to the cell. Examples of suicide gene/prodrug combinations which may be used are Herpes Simplex Virus-thymidine kinase (HSV-tk) and ganciclovir, acyclovir or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

The method of cell therapy may be employed by methods known in the art wherein a cultured cell containing a non-defective copy of a gene encoding a methyl-CpG-binding domain containing protein is introduced.

One skilled in the art is taught by the present invention that methods to screen for mutations in methyl-CpG-binding domain containing protein in neurodevelopmental disease and methods to treat said disease may be appropriate regardless of whether the consequences of the mutation are direct or indirect. That is, the mutation may produce a phenotype which is a direct cause of the disease, or the mutation may indirectly affect a disease state through a secondary gene or gene product. In either case, the methods to screen and the methods to treat as claimed are applicable.

The following examples are offered by way of example and are not intended to limit the scope of the invention in any manner.

EXAMPLE 1

Analysis of MeCP2 by Conformation-Sensitive Gel Electrophoresis

Using published genomic sequence from the human MECP2 locus, primers which were complementary to intronic sequences were used for PCR amplification of all MECP2 coding exons, including the splice junctions. Genomic DNA was screened from 21 sporadic and 8 familial Rett syndrome patients using conformation-sensitive gel electrophoresis (CSGE) to look for heteroduplexes and by direct sequencing. Total genomic DNA was isolated from peripheral blood leucocytes or from lymphoblastoid cell lines using standard protocols known in the art (Zoghbi et al 1990). The following primer pairs were designed using the available genomic sequence of the MECP2 locus (GenBank accession number AF030876) and were used for amplifying the coding exons and portions of the 3' UTR: exon 1 forward 5'-GTTATGTCTTTAGTCTTTGG-3' (SEQ. ID NO. 1) and reverse 5'-TGTGTTTATCTTCAAAATGT-3' (SEQ. ID NO. 2); exon 2 forward 5'-CCTGCCTCTGCTCACTTGTT-3' (SEQ. ID. NO. 3) and reverse 5'-GGGGTCATCATACATGGGTC-3' (SEQ. ID. NO. 4), forward 5'-AGCCCGTGCAGCCATCAGCC-3' (SEQ. ID. NO. 5) and reverse 5'-GTTCCCCCCGACCCCACCCT-3' (SEQ. ID. NO. 6); exon 3 forward 5'-TTTGTCAGAGCGTTGTCACC-3' (SEQ. ID. NO. 7) and reverse 5'-CTTCCCAGGACTTTTCTCCA-3' (SEQ. ID. NO. 8); forward 5'-AACCACCTAAGAAGCCCAAA-3' (SEQ. ID NO. 9) and reverse 5'-CTGCACAGATCGGATAGAAGAC-3 (SEQ. ID. NO. 10); forward 5'-GGCAGGAAGCGAAAAGCTGAG-3' (SEQ. ID. NO. 11) and reverse 5'-TGAGTGGTGGTGATGGTGGTGG-3' (SEQ. ID. NO. 12); forward 5'-TGGTGAAGCCCCTGCTGGT-3' (SEQ. ID. NO. 13) and reverse 5'-CTCCCTCCCCTCGGTGTTTG-3' (SEQ. ID. NO. 14); forward 5'-GGAGAAGATGCCCAGAGGAG-3' (SEQ. ID. NO. 15) and reverse 5'-CGGTAAGAAAAACATCCCCAA-3' (SEQ. ID. NO. 16).

PCR amplification was performed in a 25–50 il final volume with IX PCR buffer (50 mM KCL, 10 mM Tris-HCL, 1.5 mM MgCl2, 0.1% w/v gelatin), 0.25 mM dNTPs, 0.625 units of Taq polymerase (Cetus), and 1 im concentration of each primer. PCR conditions were as follows: initial denaturation at 95° C. for 5 min followed by 35 cycles of denaturation at 95° C., annealing at (Tm), and extension at 72° C. for 1 min each. The Tm was 58–62° C. for exon 2 and exon 3 and 50° C. for exon 1. The amplified products were denatured at 95° C. for 5 min, allowed to reanneal at 68° C. for 60 min, and electrophoresed at 450–500 V for 16 h on conformation-sensitive polyacrylamide gels to resolve heteroduplexes according to the manufacturer's specifications (Bio-Rad) (Ganguly et al., 1993).

PCR products were purified using a Qiagen PCR purification kit and sequenced directly using the ABI PRISM dye terminator cycle sequencing ready reaction kit (Perkin-Elmer). An ABI 377 DNA sequencer (Applied Biosystems) performed automated sequencing. GCG software, Wisconsin package version 10.0-unix, was used to analyze sequences.

EXAMPLE 2

Mutations Identified in the MECP2 Gene of Rett Syndrome Patients

All sporadic patients screened in this analysis had classic Rett syndrome. The familial cases included 5 pairs of full sisters, two pairs of half-sisters and a pair of second half-cousins (Ellison et al., 1992). Among the sporadic patients three missense mutations, one frameshift mutation, and a nonsense mutation were identified (Table 1; FIG. 1).

TABLE 1

MECP2 mutations in Rett Syndrome

| Patient | Nucleotide[a] | Protein[a] | Parents |
|---|---|---|---|
| sporadic-39 | 471C→T | R133C | de novo |
| sporadic-24 | 538T→C | F155S | de novo |
| sporadic-6 | 547C→T | T158M | de novo |
| sporadic-22 | 837C→T | Nonsense | de novo |
| sporadic-29 | 694insT | Frameshift[b] | not present in the mother[c] |
| familial: C2[d], C3[d] | 390C→T | R106W | not present in the mother[c] |
| Benign variants | | | |
| familial: F3[e], F4[e] | 656C T | None | present in sibs and father |
| sporadic-10 | 1307C T | None | not present in the mother[c] |

[a]Nucleotide and amino acid numbering according to GenBank accession no. X99686.
[b]Stop codon after 27 out-of-frame amino acids.
[c]Father is unavailable.
[d]Two affected half-sisters.
[e]Two affected full-sisters.

Figure 2:
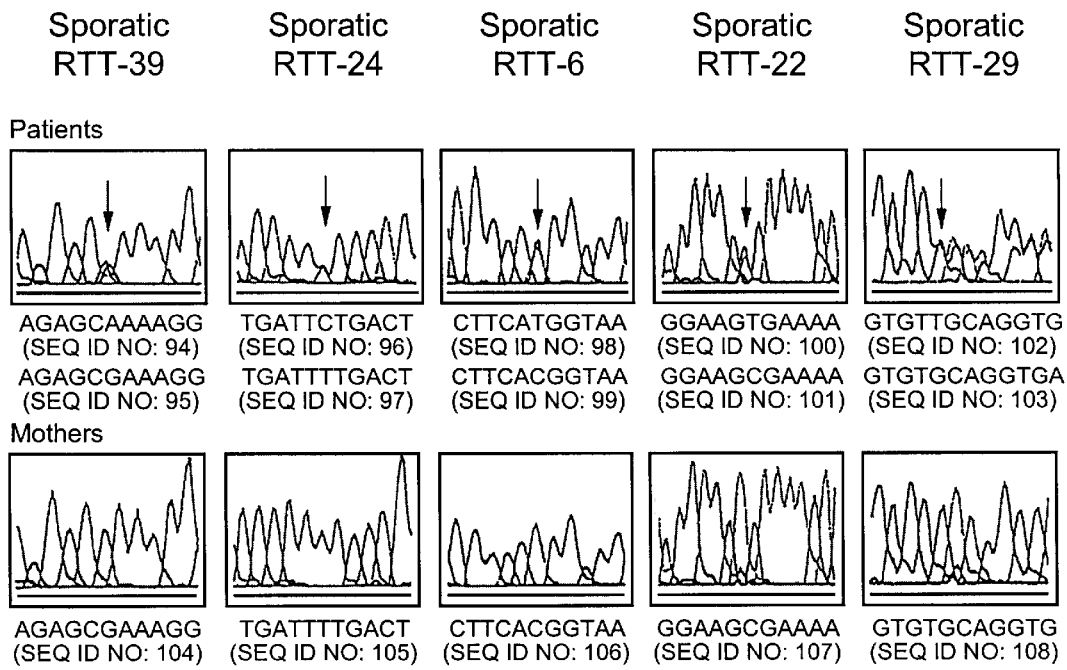
FIG. 2 demonstrates a subset of MECP2 mutations in sporadic Rett syndrome patients. Portions of the electropherograms illustrating 5 mutations found in sporadic patients 6, 22, 24, 29 and 39 are shown. The top panels represent the mutated sequences in the patients, the bottom panels represent the normal sequence from each patient's mother. The boxed nucleotides and arrows point out the mutated nucleotides for each patient in panels 39 (A), 24 (C), 6 (T) and 22 (T), and the inserted nucleotide (T) in panel 29. The two sequences under the chromatogram of patient 29 represent the superimposed sequences caused by the frameshift. All sequences are in the sense orientation except for that of patient 39.
Figure 3:
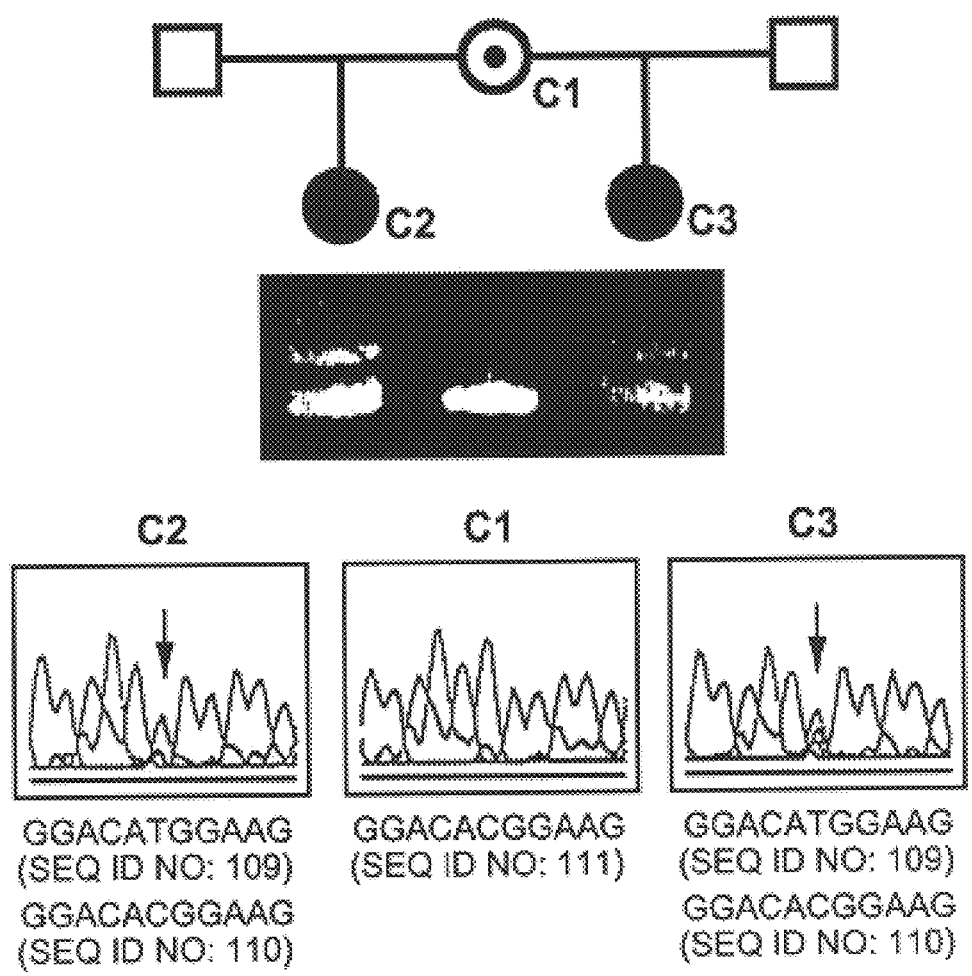
FIG. 3 demonstrates mutations in the family of affected half-sisters. The pedigree is shown on top. The gel picture in the middle presents the result of the heteroduplex analysis: no heteroduplex was found in the mother (C1), but both affected daughters (C2, C3) show clear double bands representing heteroduplexes. The electropherograms of tested individuals are below their respective pedigree symbols. The affected half-sisters share the same mutation (C→T) while their mother, who is their common parent, has a C at this position.

The R133C mutation in patient 39 replaces the basic amino acid arginine with cysteine. The F155S and the T158M mutations in patients 24 and 6, respectively, substitute a hydrophobic amino acid with a polar amino acid. These changes disrupt the structure of the methyl-CpG-binding domain, thereby interfering with its function. The nonsense mutation in patient 22 is a C to T (bp 837) substitution, which converts a CGA to a TGA (R255X) that truncates the MeCP2 protein at residue 255 of 486. In patient 29, an insertion (694insT) at codon 208 shifts the reading frame and introduces a stop codon after 27 amino acids. In these last two cases, the truncated proteins lack an intact transcription repression domain. DNA samples from both parents for all patients were analyzed except 29 (frameshift mutation), whose father's DNA was not available for study. None of the parents' samples showed any abnormalities by CSGE or sequence analysis, demonstrating that these are de novo mutations (FIG. 1). Since DNA was analyzed from only the mother of patient 29, mosaicism in the father cannot be excluded. A missense mutation (R106W) changing a conserved aa in the MBD of the protein in a family with two affected half-sisters who have the same mother was also identified (FIG. 2). Because the half-sisters carry the identical mutation, their mother must be an obligate carrier. This obligate carrier female is completely normal and is known to have a random X-inactivation pattern in her peripheral blood leukocytes, in contrast to the several carrier females who have skewed X-inactivation patterns (Zoghbi et al., 1990, Schanen et al., 1997 and Sirianni et al., 1998). Neither sequence nor heteroduplex analysis detected the mutation in her genomic DNA. A skilled artisan is aware that mutations other than those listed herein may be discovered by the same methods. One skilled in the art recognizes that these findings suggest that germline mosaicism is likely to be the mechanism by which she transmitted the disease to both daughters, but it is formally possible that she has low-level somatic mosaicism in other tissues. All four of the missense mutations change amino acids in the methyl-CpG-binding domain that are completely conserved in human, mouse, chicken and Xenopus (FIG. 3). None of these mutations were detected in 96 non-Rett chromosomes. Two silent single-nucleotide polymorphisms (SNPs) were identified: a 656C→T substitution that occurred in two affected sisters and was inherited from the normal father, and a 1307C→T substitution in a sporadic patient whose mother's DNA does not have the polymorphism and whose father's DNA is not available. These SNPs were not detected in the 96 non-Rett chromosomes; the presence of the 656C→T SNP in the normal father, together with the finding that these nucleotide substitutions do not alter the respective codons, suggests that they are benign.

EXAMPLE 4

Diagnostic Testing for Rett Syndrome by DHPLC and Direct Sequencing Analysis of MECP2

Many methods for detecting mutations have been described, and strengths and limitations inhere in each technique (Cotton, 1997; herein incorporated by reference). DNA sequence analysis is considered to be a preferred method for the identification of point mutations or deletion/insertion mutations that involve a few bases, and in a specific embodiment DNA diagnostic testing is performed by PCR-based direct sequencing of the MECP2 coding region using automated fluorescence methods. However, in a more preferred embodiment, an RTT diagnosis utilizes a robust method to scan patient samples for sequence variations/mutations prior to targeted sequence analysis. Denaturing high-performance liquid chromatography (DHPLC) is such a method. A highly sensitive PCR-based method for nucleotide variant detection, DHPLC relies on the principle of heteroduplex analysis by ion-pair reverse-phase liquid chromatography under partially denaturing conditions (Oefner and Underhill, 1995, Liu et al., 1998, Oefner and Underhill, 1998, O'Donovan et al., 1998; each incorporated by reference herein). Thus, a two-tiered molecular diagnostic approach for Rett syndrome is utilized in order to increase test efficiency while maintaining the sensitivity provided by sequence analysis.

Patient material

Genomic DNA from Rett syndrome patients with a previously identified mutation in the MECP2 coding region was used as positive control material for the development of DNA diagnostic tests (Amir et al., 1999, Amir et al., 2000). Greater than 200 females with possible Rett syndrome and 19 females with a diagnosis of classic RTT were tested, whose blood samples were submitted to the Baylor College of Medicine DNA Diagnostic laboratory.

Genomic DNA was extracted from blood leukocytes using the Puregene DNA isolation kit (Gentra Systems Inc.) or the QIAamp DNA Blood kit (Qiagen Inc.), following the manufacturer's instructions.

PCR Amplification

PCR primers (Table 2) were designed to amplify three MECP2 coding exons 2, 3 and 4 using a total of 6 reactions. (These were exons 1, 2, and 3 before the recent discovery of a new 5' UTR exon. (Reichwald et al., 2000; incorporated by reference herein)

TABLE 2

Primer sequences used for PCR and dye-terminator sequencing

A. PCR primers.

| | | |
|---|---|---|
| Exon 2-For | U-TAA GCT GGG AAA TAG CCT AGT AC | (SEQ ID NO: 76) |
| Exon 2-Rev | R-TTA TAT GGC ACA GTT TGG CAC AG | (SEQ ID NO: 77) |
| Exon 3-For | U-AGG ACA TCA AGA TCT GAG TGT AT | (SEQ ID NO: 78) |
| Exon 3-Rev | R-GGT CAT TTC AAG CAC ACC TG | (SEQ ID NO: 79) |
| Exon 4a-For | U-CGA GTG AGT GGC TTT GGT GA | (SEQ ID NO: 80) |
| Exon 4a-For.2 | U-CGC TCT GCC CTA TCT CTG A | (SEQ ID NO: 81) |
| Exon 4-Rev | R-ACA GAT CGG ATA GAA GAC TCC TT | (SEQ ID NO: 82) |
| Exon 4b-For.3 | U-GGC AGG AAG CGA AAA GCT GAG | (SEQ ID NO: 83) |
| Exon 4b-Rev.3 | R- TGA GTG GTG GTG ATG GTG GTG G | (SEQ ID NO: 84) |
| Exon 4c/d-cFor | U-GGA AAG GAC TGA AGA CCT GTA AG | (SEQ ID NO: 85) |
| Exon 4-dRev | R-CTC CCT CCC CTC GGT GTT TG | (SEQ ID NO: 86) |
| Exon 4e-For | U-GGA GAA GAT GCC CAG AGG AG | (SEQ ID NO: 87) |
| Exon 4-Rev | R-CGG TAA GAA AAA CAT CCC CAA | (SEQ ID NO: 88) |
| U (−21 M13 primertail) | TGT AAA ACG ACG GCC AGT | (SEQ ID NO: 89) |
| R (M13 reverse tail) | CAG GAA ACA GCT ATG ACC | (SEQ ID NO: 90) |

B. Dye-terminator sequencing primers

| | | |
|---|---|---|
| Exon 2-Rev.2 | CTA AAA AAA AAA AAA GGA AGG TTA C | (SEQ ID NO: 91) |
| Exon 4c-For.S | AGC CCT GGG CGG AAA AGC | (SEQ ID NO: 92) |
| Exon 4d-Rev.S | TAC TTT TCT GCG GCC GTG | (SEQ ID NO: 93) |

Primers for coding exons 2 and 3 correspond to flanking intron sequences. Exon 4 was amplified as four overlapping fragments (4a, 4b, 4cd, 4e) that collectively span the 5' intronic sequence and 3' UTR sequences. Two forward primers were used to amplify exon 4a: exon 4a-For primer (used for sequencing) was redesigned as exon 4a-For.2 (used for DHPLC) to prevent upstream polymorphisms from interfering with DHPLC analysis. Both primers are used in combination with the exon 4a-Rev primer. Primers (GibcoBRL) were synthesized with universal M13 tails (−21M13 or M13 reverse) to facilitate direct sequencing using Dye-primer chemistry (see Table 2). PCR reactions were carried out in 50pl reaction volumes, containing 100 ng genomic DNA, 1×PCR buffer (50 mM KCl, 10 mM Tris HCl, pH 8.3, 1.5 mM $MgCl_2$, 0.001% w/v gelatin, Perkin Elmer), 0.05 mM dNTP, 1.88 pmol of each primer and 1.25 U Taq Polymerase (Perkin Elmer). The exon 3cd PCR reaction mix contained 1 mM $MgCl_2$ and 4.69pmol of each primer. PCR conditions included an initial denaturation at 94° C. for 2 min 30 sec, followed by 10 "step-down" cycles of 30 sec at 94° C., 30 sec at 65° C. (decreasing 1.5° C. per cycle) and 1 min 45 sec at 72° C., followed by 28 cycles of 30 sec at 94° C., 30 sec at 51° C. and 1 min 30 sec at 72° C., and a final extension step at 72° C. for 5 min.

DHPLC Analysis

Heteroduplex formation was induced by heat denaturation of PCR products at 94° C. for 5 min, followed by gradual reannealing from 94° C. to 25° C. over 45 min. DHPLC analysis was performed with the WAVE DNA Fragment analysis system (Transgenomic Inc.). PCR products (10 μl per sample) were eluted at a flow rate of 0.9 ml/min with a linear acetonitrile gradient. The values of the buffer gradients (Buffer A: 0.1M triethylammoniumacetate, Buffer B: 0.1M triethylammoniumacetate/25% acetonitrile), start and end points of the gradient, and melting temperature predictions were determined by the WaveMaker software (Transgenomic Inc.). Analysis per sample took ~7.5 min including regeneration and re-equilibration to the starting conditions. Optimal run temperatures were empirically determined; mobile phase temperatures were assessed within a 5° C. window above and below the suggested run temperature, based on each fragment's characteristic melting profile. Run temperatures that allowed detection of all tested sequence variants were 59° C. for exon 2; 61, 63, 66 and 67° C. for exon 3; 61, 64 and 66° C. for exon 4a; 64 and 65° C. for exon 4b; 65 and 66° C. for exon 4c/d; and 60, 63 and 65° C. for exon 4e. Data analysis was based on visual inspection of the chromatograms and comparison to normal controls included in each run. Heterozygous profiles were detected as distinct elution peaks from homozygous wild-type peaks.

Direct Sequencing Analysis

PCR products used for sequencing analysis were purified using the QlAquick PCR purification kit (Qiagen inc.) and bi-directionally sequenced using the ABI Prism BigDye Primer Cycle Sequencing Ready Reaction kit (PE Applied Biosystems). The BigDye Terminator Cycle Sequencing Ready Reaction kit (PE Applied Biosystems) was used to sequence the exon 2 reverse and the exon 4c/d forward and reverse reactions (primers listed in Table 2). Samples were analyzed on an ABI 377 DNA sequencer according to the manufacturer's instructions (PE Applied Biosystems). Patient sequence data from both orientations were aligned for comparison with corresponding wild-type sequence using the Sequencher 3.0 analysis software.

MECP2 Mutation Detection by Direct Sequence Analysis

Mutation analysis for Rett syndrome was initially set up using bi-directional sequencing of PCR products corresponding to the MECP2 coding region. Dye-primer sequencing chemistry was used, except for several dye-terminator sequencing reactions required for technical reasons (exon 2 reverse, and exon 4c/d forward and reverse reactions). Control samples used in an assay validation included 11 previously characterized DNA samples from patients with a diagnosis Qf classic Rett syndrome and from unaffected family members (Amir et al, 1999, Amir et al., 2000). Sequence analysis according to our protocol was performed in a blinded manner, and 11 out of 11 control samples were correctly identified as mutant, polymorphic, or negative.

Diagnostic sequencing was performed on the first 143 patients referred to the Baylor DNA Diagnostic laboratory with a definite or possible diagnosis of Rett syndrome. Sequence variations were observed in a total of 66 out of 143 patients. Of these, 63 (44%) were heterozygous for a disease-causing MECP2 mutation. A mutation was considered disease-causing under either of the following conditions: (1) it had already been reported in the literature or (2) it was a truncating mutation that disrupted gene function (nonsense, insertion, or deletion frameshift). In three individuals (2%) who were heterozygous for an unclassified sequence variant, analysis of both parents was recommended to define each variant as either a de novo mutation or a benign polymorphism. The remaining 77 cases (54%) were negative by sequencing.

MECP2 Mutation Detection by DHPLC Analysis

Figure 5:
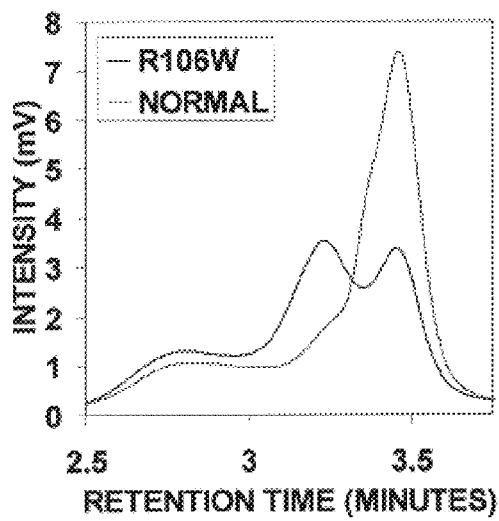
FIG. 5 demonstrates DHPLC elution profiles for two MECP2 coding region mutations detected in two sporadic RTT patients. Panel A shows relevant exon 3 elution profiles (63° C.) for a normal individual and a patient carrying the R106W mutation. The direct sequencing result illustrates the corresponding 316 C-T nucleotide substitution. Panel B shows relevant exon 4b elution profiles (64° C.) for a normal individual and a patient carrying the S360X mutation. The direct sequencing result illustrates the corresponding 1079 C-A nucleotide substitution.
Figure 5:
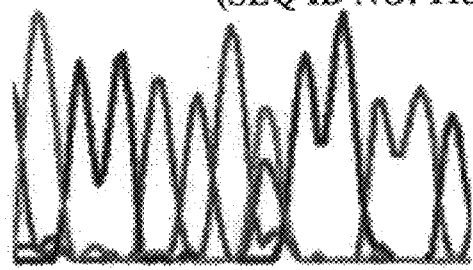
Figure 5:
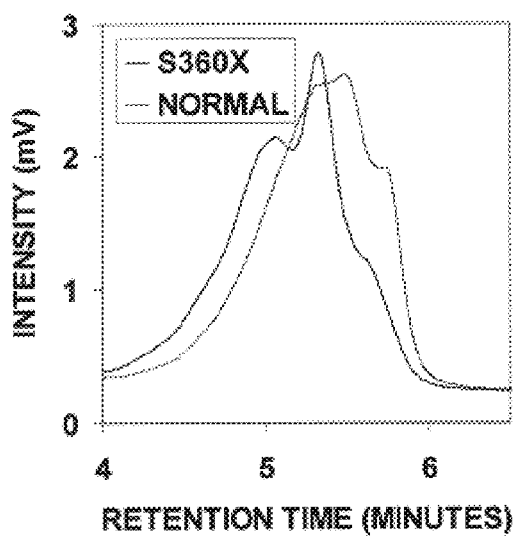
Figure 5:
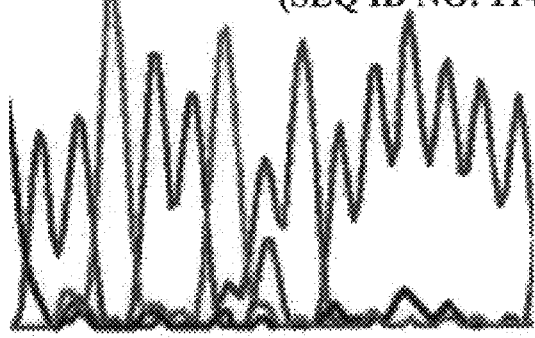

DHPLC was evaluated for its potential as a screening method to reduce the need for sequencing the complete coding region in almost half of laboratory caseload. PCR heteroduplexes are resolved from homoduplexes on a DHPLC column via differential elution profiles under partially denaturating conditions. DHPLC run conditions were optimized with the aid of WaveMaker software and by empiric determination using 50 positive control samples (see Methods) that included mutations (base substitutions/insertions/deletions), polymorphisms, and unclassified missense variants in exons 3 and 4. Because no exon 2 mutations have been identified to date, exon 2 run conditions were based on software prediction. Exons 3 and 4 contain multiple melting domains, so multiple run temperatures were used to analyze PCR fragments in these regions. All 50 sequence variants were identified under one or more run conditions as unique elution profiles. Examples of variant DHPLC chromatograms are shown in FIG. 5.

Validation of MECP2 coding region analysis by DHPLC consisted of two phases. For the first phase, a set of 15 samples that were previously tested by sequence analysis were analyzed by DHPLC in a blinded manner. DHPLC analysis of the entire MECP2 coding yielded 100% concordance with prior sequencing data (10 positives, 5 negatives; see Table 3).

TABLE 3

Different phases involved in the development of a two-step protocol for RTT testing by DHPLC and bi-directional direct sequencing analysis.

1. Bi-directional direct sequencing 143 cases  63 positive (44%)  3 unclassified (2.1%)  77 negative (53.8%)
2. DHPLC analysis validation
1. Validation phase 1

15 samples tested blindly  10 positive  5 negative
100% concordance
2. Validation phase 2

36 cases tested in parallel  19 positive  17 negative
100% concordance
3. DHPLC and bi-directional direct sequencing 86 cases  39 positive (43%)  2 unclassified (2.3%)  47 negative (54.6%)
98.8% concordance  1 case DHPLC negative and sequencing positive In the second phase of DHPLC validation, 36 samples that were being examined by sequence analysis in our laboratory were tested in parallel by DHPLC. Nineteen samples were found to carry one or more sequence variations and 17 were negative, which yielded 100% concordance between both methods (Table 3).

Based on these results, a two-tiered molecular diagnostic strategy was adopted. In a specific embodiment, all MECP2 coding exons are first analyzed by DHPLC. PCR fragments encoding a sequence variant are further analyzed by bidirectional sequencing. For samples that are negative by initial DHPLC analysis or found to carry a polymorphism or unclassified sequence variant, the entire MECP2 coding region is analyzed by bi-directional sequencing. This strategy proved to be both efficient and robust. Eighty-six cases have been analyzed using this strategy (see Table 3). Mutations were identified in 37 cases (43%), 2 had unclassified variants (2.3%), and 47 (54.7%) were negative. The DHPLC results were consistent with sequencing analysis in 98.8% of these cases. One patient was initially negative by DHPLC analysis, but direct sequencing of the complete MECP2 coding region of this patient revealed an unclassified missense substitution in exon 2 (S86C). This substitution was missed by DHPLC despite the use of three different temperatures (61, 63 and 66° C.), causing a false negative rate of 1.2%. The region encoding amino acids 85–90 is very GC-rich, but was anticipated to melt at 66° C. Reanalysis by DHPLC allowed detection of this specific variant at 67° C. (but not at 66° C.). This temperature was subsequently added to the current set of running conditions (see methods).

MECP2 Sequence Variations Detected

A total of 229 unrelated female patients with a diagnosis of possible Rett (210) or classic Rett (19) were tested for MECP2 mutations. Table 4 lists all the identified mutations, and Table 5 lists the polymorphic and unclassified sequence variations detected in this group of patients.

TABLE 4

MECP2 mutations detected by DHPLC and direct sequencing analysis.

| Variant | Exon | Nucleotide change | Amino acid change | Domain | Times Recurring | Original reference |
|---|---|---|---|---|---|---|
| Missense | 3 | 317 C-A | R106Q | MBD | 2 | Bienvenu et al., 2000 |
| | 3 | 316 C-T | R106W | MBD | 3 | Amir et al., 1999 |
| | 4 | 397 C-T | R133C | MBD | — | Amir et al., 1999 |
| | 4 | 455 C-G | P152R | MBD | — | Cheadle et al., 2000 |
| | 4 | 464 T-C | F155S | MBD | — | Amir et al., 1999 |
| | 4 | 473 C-T | T158M | MBD | 21 | Amir et al., 1999 |
| | 4 | 916 C-T | R306C | TRD | 8 | Wan et al., 1999 |
| | 4 | 917 G-A | R306H | TRD | — | Cheadle et al., 2000 |
| Nonsense | 4 | 423 C-G | Y141X | MBD | — | Amir et al., 2000 |
| | 4 | 430 A-T | K144X | MBD | — | herein |
| | 4 | 502 C-T | R168X | | 13 | Wan et al., 199 |
| | 4 | 508 C-T | Q170X | | — | herein |
| | 4 | 613 G-T | S204X | | — | herein |
| | 4 | 763 C-T | R255X | TRD | 12 | Amir et al., 1999 |
| | 4 | 808 C-T | R270X | TRD | 8 | Cheadle et al., 2000 |
| | 4 | 880 C-T | R294X | TRD | 7 | Cheadle et al., 2000 |
| | 4 | 1079 C-A | S360X | | — | herein |
| Splicing | | IVS2-2 A-G | | | — | Huppke et al., 2000 |
| Frameshift | 3 | 90insA | | | — | herein |
| | 4 | 554delG | | | — | herein |
| | 4 | 710delG | | TRD | — | herein |
| | 4 | 753delC | | TRD | — | herein |
| | 4 | 753insCC | | TRD | — | herein |
| | 4 | 806delG | | TRD | 2 | Wan et al., 1999 |
| | 4 | 808delC | | TRD | — | herein |
| | 4 | 965del6 + 1027insG + 1138del71 | | | — | herein |
| | 4 | 1118del122 | | | — | herein |

TABLE 4-continued

MECP2 mutations detected by DHPLC and direct sequencing analysis.

| Variant | Exon | Nucleotide change | Amino acid change | Domain | Times Recurring | Original reference |
|---|---|---|---|---|---|---|
| | 4 | 1157del41 | | | — | herein |
| | 4 | 1161del6 + 1177del26 | | | — | herein |
| | 4 | 1163del26 | | | — | Bienvenu et al., 2000 |
| | 4 | 1162del29 | | | — | herein |
| | 4 | 1164del44 | | | — | herein |
| | 4 | 1308delTC | | | — | herein |

TABLE 5

MECP2 polymorphisms and unclassified sequence variants detected by DHPLC and direct sequencing analysis.

| Variant | Exon | Nucleotide change | Amino acid change | Domain | Times Recurring | Original reference |
|---|---|---|---|---|---|---|
| polymorphism | 3 | 375 C-A | 1125 | MBD | — | Cheadle et al., 2000 |
| | 4 | 582 C-T | S194 | MBD | 2 | Cheadle et al., 2000 |
| | 4 | 608 C-T | T203M | | — | herein |
| | 4 | 843 C-T | A281 | TRD | — | herein |
| | 4 | 984 C-T | L328 | | — | herein |
| | 4 | 1189 G-A | E397K | | — | Wan et al., 1999 |
| | 4 | 1233 C-T | S411 | | 6 | Amir et al., 1999 |
| | 4 | 1330 C-T | A444T | | 2 | herein |
| unclassified | 3 | 257 C-G | S86C | MBD | — | herein |
| | 3 | 298 C-G | L100V | MBD | — | herein |
| | 4 | 857 A-G | K286R | TRD | — | herein |
| | 4 | 859 G-C | A287P | TRD | — | herein |
| | 4 | 871 T-G | S291A | TRD | — | herein |
| | 4 | 914 A-G | K305R | TRD | — | herein |
| | 4 | 1234 G-A | V412I | | — | herein |
| | 4 | 1164del9 (in-frame del) | | | — | herein |

Disease-causing mutations were detected in 84/210 (40%) and 16/19 (84.2%) of possible and classic sporadic RTT patients, respectively. A total of 33 different mutations are reported, of which 17 are novel (4 nonsense and 13 frameshift mutations—see Table 4). Nine recurrent mutations accounted for 77% of the subjects bearing a MECP2 mutation.

A total of 8 polymorphisms (5 silent, 3 missense) were detected in 15 patients (Table 5). The S194, S411 and A444T appear to be more common, recurring 2, 6 and 2 times, respectively. Parental analysis enabled classification of two newly identified missense polymorphisms, T203M and A444T. In both cases, the normal father of the affected patient encoded the amino acid substitution. Twelve of the 15 cases also encoded a mutation in addition to the polymorphism, although the chromosomal phase was not identified. Eight unclassified sequence variants were found. Parental analysis was recommended to determine whether these substitutions are de novo mutations or polymorphisms. Of these, the K286R, S291A and V412I variants are likely be polymorphisms because they were identified in subjects that also encoded a classified MECP2 mutation.

Prenatal Diagnosis

To date, four prenatal tests have been performed. A familial mutation (R106W, P152R, R168X and R294X) was identified in the index case for each family. Subsequent analysis of maternal DNA by DHPLC and direct sequencing of the PCR fragment of interest suggested that the familial mutations arose de novo in each case, although germline mosaicism was not excluded. Prenatal diagnosis by DHPLC and direct sequencing performed on amniotic fluid and cultured amniocytes was negative for the familial mutation in all 4 cases. Maternal cell contamination was ruled out by PCR analysis of short tandem repeats at other loci.

Significance of DHPLC Analysis in RTT Diagnosis

The data provided herein represents the mutation data accumulated from a diagnostic laboratory, which includes testing of 229 unrelated patients with a diagnosis of possible (210) or classic (19) Rett syndrome. Disease-causing mutations were detected in 84% of classical sporadic RTT patients, which is consistent with the estimate reported in the literature. That only 40% of the suggestive RTT patients were positive for MECP2 mutations reflects the clinical heterogeneity of these patients referred from different sources. We found a total of 33 different mutations (Table 4), including 17 novel MECP2 coding region mutations. Thirteen of these are novel frameshift mutations, with the majority located in the last exon. These findings are consistent with the region being a recombinational hotspot, containing palindromic and quasi-palindromic sequences (Cheadle et al., 2000, Bienvenu et al., 2000, Huppke et al., 2000, Amir et al., 2000). Nine recurrent mutations were identified that account for 77% of the disease-causing mutations (Table 3). Seven of these recurrent mutations (R106W, T158M, R306C, R168X, R255X, R270X, R294X) involve C-T transitions at CpG dinucleotides (Wan et al., 2000, Cheadle et al., 2000, Bienvenu et al., 2000, Huppke et al., 2000, Amir et al., 2000). In addition, eight MECP2 sequence polymorphisms were identified, including 2 novel missense polymorphisms that were classified by parental analysis (T203M, A444T; Table 5). Finally, there were 8 unclassified MECP2 missense variants, for which parental analyses were recommended (Table 5).

The diagnostic testing strategy combining DHPLC and direct sequencing has proven to be a sensitive and efficient method for MECP2 mutation analysis. This two-tiered approach presents a number of advantages over a sequencing protocol. It is less labor- and reagent-intensive than fluorescent gel sequencing, and testing efficiency is increased by pre-screening patient samples by DHPLC prior to targeted sequence analysis. (The amount of sequencing was reduced by a factor of six for the 40% of cases in which mutations were detected.) At the same time, the combined sensitivity of this approach is at least equal to or greater than that of sequencing. Mutation-positive samples were initially identified by DHPLC in all but one case (see Table 3). Any variants that could be missed by DHPLC would be identified by sequence analysis of the complete MECP2 coding region, which is prescribed for all samples that test negative by DHPLC. Likewise, samples that test positive by DHPLC and are found to have a polymorphism or unclassified variant by targeted sequencing are subsequently sequenced for the complete coding region, further reducing the risk for false negatives. It can be argued that negative samples benefit from routine analysis by two sensitive and independent methods in contrast to sequencing alone. The collective data from the first 86 cases demonstrate the strength of this approach.

Further advantages of DHPLC include computer-assisted determination of analytical conditions and automated sample handling features. Nevertheless, mutation detection is dependent on the complexity of each fragment's sequence-specific melting profile and the optimization of DHPLC analytical conditions for each specific fragment. This fact was highlighted regarding one patient who tested negative by DHPLC analysis but was positive for a novel missense variant (S86C) by sequencing - despite the use of three different DHPLC temperature conditions for that fragment. Temperature conditions had been determined by a combination of computer software predictions and empirical data using available positive controls. Although four different variants were tested during development of the DHPLC run conditions for exon 2 (L100V, R106W, R106Q, 1125), these were located slightly downstream of S86C. Nevertheless, software predictions suggested that sequence alterations in this region would be detected. When repeat analysis of this patient's sample revealed that 67° C. rather than 66° C. allowed detection of the S86C variant, this temperature was added to the DHPLC run conditions.

Improvements in the melting profile software, in a specific embodiment, increase sensitivity and facilitate the use of DHPLC for diagnostic testing of unknown mutations in any given region of interest. DHPLC analysis may not detect homozygous or hemizygous point mutations without mixing equal amounts of test and control samples to induce heteroduplex formation. This would mean that samples from males with possible atypical Rett syndrome should be sequenced entirely. In summary, the use of DHPLC as an initial screening tool is ideal for MECP2 mutation analysis. The two-tiered strategy combining DHPLC with direct sequence analysis provides a robust and efficient means of Rett syndrome molecular diagnostic testing, and in another embodiment is used to screen patients with mental retardation or autism for MECP2 mutations.

EXAMPLE 4

Model for Effect of Disease

Given that all mutations identified are de novo in sporadic cases, one mutation segregates in familial Rett syndrome, all missense mutations change conserved amino acids in the MBD, and both truncating mutations disrupt the TRD of MeCP2, it can be concluded that mutations in MECP2 are the cause of Rett syndrome in these individuals. The nature of these mutations makes it likely that they lead to either partial or complete loss of function of MeCP2. The random pattern of X-inactivation in the majority of Rett syndrome patients according to PGK, HPRT, and AR methylation assays (Zoghbi et al., 1990 and Allen et al., 1992) ensures expression of the normal allele in some cells. The normal allele probably enables survival of affected females but does not protect them from major neurodevelopmental abnormalities. It is unlikely that the mutations found were normal polymorphisms because the mutations are heterogeneous, there are at least two highly deleterious mutations (a nonsense mutation and a frame-shift mutation leading to premature termination), missense mutations are present in conserved residues, and most of the mutations are clearly not present in either parent while the remainder are absent from at least the mother.

Rett syndrome is the first human disease found to be caused by mutations in a gene encoding a transacting factor that plays a role in the epigenetic regulation of gene expression. The Rett phenotype is likely limited for the most part to the nervous system for the following reasons. MeCP2 is widely expressed, and is abundant in the brain; alternative polyadenylation in the 3' untranslated region (UTR) results in a variety of transcripts, some of which are differentially expressed in human brain (D'Esposito et al., 1996 and Coy et al., 1999). The longest 10.1-kb transcript is most highly expressed in fetal brain, whereas the 5-kb transcript is enriched in adult brain (Coy et al., 1999). It is conceivable that loss of function of this protein in some cells, especially differentiated and postmitotic neurons, would lead to overexpression of some genes which in turn may be detrimental during nervous system maturation. Mutations have been found in only five out of twenty-one sporadic and one familial patient, upon scrutiny of only the coding region. However, the high degree of conservation across species of several regions in the 3'UTR suggests that these sequences are under evolutionary selection and that they are important for post-transcriptional regulation of MECP2 (Coy et al., 1999). This, together with the abundance of the longer transcript during human fetal development, makes the 3'UTR a likely site for mutations. Another possibility is that some cases of Rett syndrome might be caused by autosomal mutations in related proteins. For example, MeCP2 belongs to a family of MBD-containing proteins that mediate transcriptional regulation (Hendrich et al., 1998). Hendrich et al, recently described the genomic structure and mapping data of four additional members of this family (Hendrich et al., 1999); mutations in any of these proteins and/or their interactors may cause Rett syndrome or related phenotypes such as autism and non-syndromic mental retardation.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

PATENTS

U.S. Pat. No. 5,840,873, issued Nov. 24, 1998
U.S. Pat. No. 5,843,640, issued Dec. 1, 1998
U.S. Pat. No. 5,843,650, issued Dec. 1, 1998
U.S. Pat. No. 5,843,651, issued Dec. 1, 1998
U.S. Pat. No. 5,843,663, issued Dec. 1, 1998
U.S. Pat. No. 5,846,708, issued Dec. 8, 1998
U.S. Pat. No. 5,846,709, issued Dec. 8, 1998
U.S. Pat. No. 5,846,717, issued Dec. 8, 1998
U.S. Pat. No. 5,846,726, issued Dec. 8, 1998
U.S. Pat. No. 5,846,729, issued Dec. 8, 1998
U.S. Pat. No. 5,846,783, issued Dec. 8, 1998
U.S. Pat. No. 5,849,481, issued Dec. 15, 1998
U.S. Pat. No. 5,849,483, issued Dec. 15, 1998
U.S. Pat. No. 5,849,486, issued Dec. 15, 1998
U.S. Pat. No. 5,849,487, issued Dec. 15, 1998
U.S. Pat. No. 5,849,497, issued Dec. 15, 1998
U.S. Pat. No. 5,849,546, issued Dec. 15, 1998
U.S. Pat. No. 5,849,547, issued Dec. 15, 1998
U.S. Pat. No. 5,851,770, issued Dec. 22, 1998
U.S. Pat. No. 5,851,772, issued Dec. 22, 1988
U.S. Pat. No. 5,853,990, issued Dec. 29, 1998
U.S. Pat. No. 5,853, 993, issued Dec. 29, 1998
U.S. Pat. No. 5,853,992, issued Dec. 29, 1998
U.S. Pat. No. 5,856,092, issued Jan. 5, 1999
U.S. Pat. No. 5,858,652, issued Jan. 12, 1999
U.S. Pat. No. 5,861,244, issued Jan. 19, 1999
U.S. Pat. No. 5,863,732, issued Jan. 26, 1999
U.S. Pat. No. 5,863,753, issued Jan. 26, 1999
U.S. Pat. No. 5,866,331, issued Feb. 2, 1999
U.S. Pat. No. 5,866,336, issued Feb. 2, 1999
U.S. Pat. No. 5,866,337, issued Feb. 2, 1999
U.S. Pat. No. 5,900,48 1, issued May 4, 1999
U.S. Pat. No. 5,905,024, issued May 18, 1999
U.S. Pat. No. 5,910,407, issued Jun. 8, 1999
U.S. Pat. No. 5,912,124, issued Jun. 15, 1999
U.S. Pat. No. 5,912,145, issued Jun. 15, 1999
U.S. Pat. No. 5,912,148, issued Jun. 15, 1999
U.S. Pat. No. 5,916,776, issued Jun. 29, 1999
U.S. Pat. No. 5,916,779, issued Jun. 29, 1999
U.S. Pat. No. 5,919,626, issued Jul. 6, 1999
U.S. Pat. No. 5,919,630, issued Jul. 6, 1999
U.S. Pat. No. 5,922,574, issued Jul. 13, 1999
U.S. Pat. No. 5,925,517, issued Jul. 20, 1999
U.S. Pat. No. 5,925,525, issued Jul. 20, 1999
U.S. Pat. No. 5,928,862, issued Jul. 27, 1999
U.S. Pat. No. 5,928,869, issued Jul. 27, 1999
U.S. Pat. No. 5,928,870, issued, Jul. 27, 1999
U.S. Pat. No. 5,928,905, issued Jul. 27, 1999
U.S. Pat. No. 5,928,906, issued Jul. 27, 1999
U.S. Pat. No. 5,929,227, issued Jul. 27, 1999
U.S. Pat. No. 5,932,413, issued Aug. 3, 1999
U.S. Pat. No. 5,932,451, issued Aug. 3, 1999
U.S. Pat. No. 5,935,951, issued Aug. 10, 1999
U.S. Pat. No. 5,935,825, issued Aug. 10, 1999
U.S. Pat. No. 5,939,291, issued Aug. 17, 1999
U.S. Pat. No. 5,942,391, issued Aug. 24, 1999
European Application No. 320 308
European Application No. 329 822
GB Application No. 2 202 328
PCT Application No. PCT/US87/00880
PCT Application No. PCT/US89/01025
PCT Application WO 88/10315
PCT Application WO 89/06700
PCT Application WO 90/07641

PUBLICATIONS

Al-Mateen M, Philippart M, Shields W D. 1986. Rett syndrome. A commonly overlooked progressive encephalopathy in girls. Am J Dis Child 140:761–5.

Allen, R. C., Zoghbi, H. Y., Moseley, A. B., Rosenblatt, H. M. & Belmont, J. W. Methylation of HpaII and HhaI sites near the polymorphic CAG repeat in the human androgen-receptor gene correlates with X chromosome inactivation. Am. J. Hum. Genet. 51, 1229–1239 (1992).

Amir R, Dahle E J, Toriolo D, Zoghbi H Y. 2000a. Candidate gene analysis in Rett syndrome and the identification of 21 SNPs in Xq. Am J Med Genet 90:69–71.

Amir R E, Van den Veyver I B, Schultz R, Malicki D M, Tran C Q, Dahle J E, Philippi A, Timar L, Percy A K, Motil K J, Lichtarge O, O'Brian Smith E, Glaze D G, Zoghbi H Y. 2000b. Influence of mutation type and X chromosome inactivation on Rett syndrome phenotypes. Annals of Neurology 47(5):670–9.

Amir R E, Van den Veyver I B, Wan M, Tran C Q, Francke U, Zoghbi H Y. 1999. Rett syndrome is caused by mutations in X-linked MECP2, encoding methyl- CpG-binding protein 2. Nat Genet 23:185–8.

Archidiacono, N. et al. Rett syndrome: exclusion mapping following the hypothesis of germinal mosaicism for new X-linked mutations. Hum. Genet. 86, 604–606 (1991).

Armstrong D, Dunn J K, Antalffy B, Trivedi R. 1995. Selective dendritic alterations in the cortex of Rett syndrome. J Neuropathol Exp Neurol 54:195–201.

Armstrong D D, Dunn K, Antalffy B. 1998. Decreased dendritic branching in frontal, motor and limbic cortex in Rett syndrome compared with trisomy 21. J Neuropathol Exp Neurol 57:1013–7.

Bauman M L, Kemper T L, Arin D M. 1995. Microscopic observations of the brain in Rett syndrome. Neuropediatrics 26:105–8.

Belichenko P V, Dahlstrom A. 1995. Studies on the 3-dimensional architecture of dendritic spines and varicosities in human cortex by confocal laser scanning microscopy and Lucifer yellow microinjections. J Neurosci Methods 57:55–61.

Bienvenu T, Carrie A, de Roux N, Vinet M C, Jonveaux P, Couvert P, Villard L, Arzimanoglou A, Beldjord C, Fontes M, Tardieu M, Chelly J. 2000. MECP2 mutations account for most cases of typical forms of Rett syndrome. Hum Mol Genet 9(9):1377–84.

Bird A P. 1980. DNA methylation and the frequency of CpG in animal DNA. Nucleic Acids Res 8:7 1499–504.

Bird, A P and Wolffe, A P. 1999 Methylation-induced repression: belts, braces, and chromatin. Cell 99:451–54.

Blue M E, Naidu S, Johnston M V. 1999. Altered development of glutamate and GABA receptors in the basal ganglia of girls with Rett syndrome. Exp Neurol 156:345–52.

Budden S S. 1997. Rett syndrome: habilitation and management reviewed. Eur Child Adolesc Psychiatry 6:103–7.

Buhler, E. M., Malik, N. J. & Alkan, M. Another model for the inheritance of Rett syndrome. Am. J. Med. Genet. 36, 126–131 (1990).

Cameron, E. E., Bachman, K. E., Myohanen, S., Herman, J. G. & Baylin, S. B. Synergy of demethylation and histone deacetylase inhibition in the re-expression of genes silenced in cancer. Nature Genet. 21, 103–107 (1999).

Chandler S P, Guschin D, Landsberger N, Wolffe A P. 1999. The methyl-CpG binding transcriptional repressor MeCP2 stably associates with nucleosomal DNA. Biochemistry 38(22):7008–18.

Cheadle J P, Gill H, Glemong N, Maynard J, Kerr A, Leonard H, Krawczak M, Cooper D N, Lynch S, Thomas N, Hughes H, Hulten M, Ravine D, Sampson J R, Clarke A. 2000. Long-read sequence analysis of the MECP2 gene in Rett syndrome patients: correlation of disease severity with mutation type and location. Hum Mol Genet 9(7):1119–29.

Comings D E. 1986. The genetics of Rett syndrome: the consequences of a disorder where every case is a new mutation. Am J Med Genet Suppl 1:383–8.

Cooper D N, Krawczak M, 1993, Human Gene Mutation, BIOS Scientific Publishers Limited, Oxford.

Cotton, R. G. H. (1997) Slowly but surely towards better scanning for mutations. Trends Genet. 13, 43–46.

Coy J F, Sedlacek Z, Bachner D, Delius H, Poustka A. 1999. A complex pattern of evolutionary conservation and alternative polyadenylation within the long 3'-untranslated region of the methyl-CpG-binding protein 2 gene (MeCP2) suggests a regulatory role in gene expression. Hum Mol Genet 8:1253–62.

Curtis, A. R. et al. X chromosome linkage studies in familial Rett syndrome. Hum. Genet. 90, 551–555 (1993).

D'Esposito M, Quaderi NA, Ciccodicola A, Bruni P, Esposito T, D'Urso M, Brown SD. 1996. Isolation, physical mapping, and northern analysis of the X-linked human gene encoding methyl CpG-binding protein, MECP2. Mamm Genome 7:533–5.

Ellison K A, Fill C P, Terwilliger J, DeGennaro L J, Martin-Gallardo A, Anvret M, Percy A K, Ott J, Zoghbi H. 1992. Examination of X chromosome markers in Rett syndrome: exclusion mapping with a novel variation on multilocus linkage analysis. Am J Hum Genet 50:278–87.

Engerström I W, Forslund M. 1992. Mother and daughter with Rett syndrome. Dev Med Child Neurol 34:1022–3.

FitzGerald P M, Jankovic J, Glaze D G, Schultz R, Percy A K. 1990. Extrapyramidal involvement in Rett's syndrome. Neurology 40:293–5.

Ganguly, A., Rock, M. J. & Prockop, D. J. Conformation-sensitive gel electrophoresis for rapid detection of single-base differences in double-stranded PCR products and DNA fragments: evidence for solvent-induced bends in DNA heteroduplexes (published erratum appears in Proc. Natl. Acad. Sci. U.S.A. 1994 May 24;91(11):5217). Proc. Natl. Acad. Sci. U.S.A. 90, 10325–10329 (1993).

Glaze D G, Frost J D, Jr., Zoghbi H Y, Percy A K. 1987. Rett's syndrome: characterization of respiratory patterns and sleep. Ann Neurol 21:377–82.

Guideri F, Acampa M, Hayek G, Zappella M, Di Perri T. 1999. Reduced heart rate variability in patients affected with Rett syndrome. A possible explanation for sudden death. Neuropediatrics 30:146–8.

Hagberg B. 1995. Clinical delineation of Rett syndrome variants. Neuropediatrics 26:62.

Hagberg B, Aicardi J, Dias K, Ramos O. 1983. A progressive syndrome of autism, dementia, ataxia, and loss of purposeful hand use in girls: Rett's syndrome: report of 35 cases. Ann Neurol 14:471–9.

Hagberg B A. 1989. Rett syndrome: clinical peculiarities, diagnostic approach, and possible cause. Pediatr Neurol 5:75–83.

Hagberg, G. (1985) Rett's syndrome: prevalence and impact on progressive severe mental retardation in girls. Acta Paediatr. Scand. 74, 405–408.

Hendrich, B. & Bird, A. Identification and characterization of a family of mammalian methyl-CpG binding proteins. Mol. Cell Biol. 18, 6538–6547 (1998).

Hendrich B, Abbott C, McQueen H, Chambers D, Cross S, Bird A. 1999. Genomic structure and chromosomal mapping of the murine and human mbd1, mbd2, mbd3, and mbd4 genes. Mamm Genome 10:906–12.

Huppke P, Laccone F, Kramer N, Engel W, Hanefeld F. 2000. Rett syndrome: analysis of MECP2 and clinical characterization of 31 patients. Hum Mol Genet 9(9):1369–75.

Jellinger K, Seitelberger F. 1986. Neuropathology of Rett syndrome. Am J Med Genet Suppl 1:259–88.

Jones P L, Veenstra G J, Wade P A, Vermaak D, Kass S U, Landsberger N, Strouboulis J, Wolffe AP. 1998. Methylated DNA and MeCP2 recruit histone deacetylase to repress transcription. Nat Genet 19:187–91.

Kerr A M, Julu P O. 1999. Recent insights into hyperventilation from the study of Rett syndrome. Arch Dis Child 80:384–7.

Kim S J, Cook E H Jr. 2000. Novel de novo nonsense mutation of MECP2 in a patient with Rett syndrome. Hum Mutat 15(4):382–3.

Laan, L. A., Haeringen, A., Brouwer, O. F. Angelman syndrome: a review of clinical and genetic aspects. Clin Neurol Neurosurg 101(3), 161–170 (1999).

Lalande, M., Minassian, B. A., DeLorey, T. M., Olsen, R. W. Parental imprinting and Angelman syndrome. Adv Neurol 79, 421–429 (1999).

Lewis, J. D. et al. Purification, sequence, and cellular localization of a novel chromosomal protein that binds to methylated DNA. Cell 69, 905–914 (1992).

Liu, W., Smith, D. I., Rechtzigel, K. J., Thibodeau, S. N., James, C. D. (1998) Denaturing high performance liquid chromatography (DHPLC) used in the detection of germline and somatic mutations. Nucleic Acids Res. 26, 1396–1400.

Mann, M. R., Bartolomei, M. S. Towards a molecular understanding of Prader-Willi and Angelman syndromes. Hum Mol Genet 8(10), 1867–1873 (1999).

Martinho P S, Otto P G, Kok F, Diament A, Marques-Dias M J, Gonzalez C H. 1990. In search of a genetic basis for the Rett syndrome. Hum Genet 86:131–4.

Migeon B R, Dunn M A, Thomas G, Schmeckpeper B J, Naidu S. 1995. Studies of X inactivation and isodisomy in twins provide further evidence that the X chromosome is not involved in Rett syndrome. Am J Hum Genet 56:647–53.

Motil K J, Schultz R J, Wong W W, Glaze D G. 1998. Increased energy expenditure associated with repetitive involuntary movement does not contribute to growth failure in girls with Rett syndrome. J Pediatr 132:228–33.

Naidu S. 1997. Rett syndrome: a disorder affecting early brain growth [published erratum appears in Ann Neurol 1997 Nov;42(5):816]. Ann Neurol 42:3–10.

Nan X, Campoy F J, Bird A. 1997. MeCP2 is a transcriptional repressor with abundant binding sites in genomic chromatin. Cell 88:471–81.

Nan X, Ng H H, Johnson C A, Laherty C D, Turner B M, Eisenman R N, Bird A. 1998a. Transcriptional repression by the methyl-CpG-binding protein MeCP2 involves a histone deacetylase complex. Nature 393:386–9.

Nan, X., Meehan, R. R. & Bird, A. Dissection of the methyl-CpG binding domain from the chromosomal protein MeCP2. Nucleic Acids Res. 21, 4886–4892 (1993).

Ng H H, Bird A. 1999. DNA methylation and chromatin modification. Curr Opin Genet Dev 9:158–63.

Nihei K, Naitoh H. 1990. Cranial computed tomographic and magnetic resonance imaging studies on the Rett syndrome. Brain Dev 12:101–5.

O'Donovan, M. C., Oefner, P. J., Roberts, S. C., Ausin, J., Hoogendoorn, B., Guy, C., Speight, G., Upadhyaya, M., Sommer, S., McMuffin, P (1998) Blind analysis of denaturing high-performance liquid chromatography as a tool for mutation detection. Genomics, 52, 44–49.

Oefner, P. J. and Underhill, P. A. (1995) Comparative DNA sequencing by denaturing high-performance liquid chromatography (DHPLC). Am. J. Hum. Genet. 57S, A266.

Oefner, P. J. and Underhill, P. A. (1998) DNA mutation detection using denaturing high performance liquid chromatography (DHPLC). In "Current Protocols in Human Genetics" (N. C. Dracopoli, J. Haines, B. R. Korf, C. Morton, C. E. Seidman, J. G. Seidman, D. T. Moir and D. R. Smith, Eds.), Suppl. 19, 7.10.1–7.10.12, Wiley, New York.

Orrico, A., Lam, C-W., Galli, L., Dotti, M. T., Hayek, G., Tong, S.-F., Poon, P. M. K., Zappella, M., Federico, A., Sorrentino, V. MECP2 mutation in male patients with non-specific X-linked mental retardation. FEBS Letters 24106, 1–4 (2000).

Reichwald, K., Thiesen, J., Wiehe, T., Weitzel, J., Strätling, W. H., Kioschis, P., Poutska, A., Rosenthal, A., Platzer, M. (2000) Comparative sequence analysis of the MECP2-locus in human and mouse reveals new transcribed regions. Mammalian Genome 11, 182–190.

Rett A. 1966. Über ein zerebral-atrophisches Syndrome bei Hyperammonemie. Vienna: Bruder Hollinek .

Rougeulle, C., Lalande, M. Angelman syndrome: how many genes to remain silent? Neurogenetics 1(4), 229–237 (1998).

Sambrook, Fritsch, Maniatis, In: Molecular Cloning: A Laboratory Manual, Vol. 1, Cold Spring Harbor Laboratory Press, Cold Spring Harbor, N.Y., Ch. 7,7.19–17.29, 1989.

Schanen C, Francke U. 1998a. A severely affected male born into a Rett syndrome kindred supports X-linked inheritance and allows extension of the exclusion map. Am J Hum Genet 63:267–9.

Schanen N C, Dahle E J, Capozzoli F, Holm V A, Zoghbi H Y, Francke U. 1997. A new Rett syndrome family consistent with X-linked inheritance expands the X chromosome exclusion map. Am J Hum Genet 61:634–41.

Schanen, N. C., and Francke, U. (1998) A severely affected male born into a Rett syndrome kindred supports X-linked inheritance and allows extension of the exclusion map. Am. J. Hum. Genet. 63, 267–269.

Schanen N C, Kurczynski T W, Brunelle D, Woodcock M M, Dure L St, Percy A K. 1998b. Neonatal encephalopathy in two boys in families with recurrent Rett syndrome. J Child Neurol 13:229–31.

Sekul E A, Moak J P, Schultz R J, Glaze D G, Dunn J K, Percy A K. 1994. Electrocardiographic findings in Rett syndrome: an explanation for sudden death? J Pediatr 125:80–2.

Sirianni N, Naidu S, Pereira J, Pillotto R F, Hoffman E P. 1998. Rett syndrome: confirmation of X-linked dominant inheritance, and localization of the gene to Xq28. Am J Hum Genet 63:1552–8.

Tate, P., Skarnes, W. & Bird, A. The methyl-CpG binding protein MeCP2 is essential for embryonic development in the mouse. Nature Genet. 12, 205–208 (1996).

Trevathan E, et al. 1988. Diagnostic criteria for Rett syndrome. The Rett Syndrome Diagnostic Criteria Work Group. Ann Neurol 23:425–8.

Vilain A, Apiou F, Vogt N, Dutrillaux B, Malfoy B. 1996. Assignment of the gene for methyl-CpG-binding protein 2 (MECP2) to human chromosome band Xq28 by in situ hybridization. Cytogenet Cell Genet 74:293–4.

Wade P A, Gegonne A, Jones P L, Ballestar E, Aubry F, Wolffe A P. 1999. Mi-2 complex couples DNA methylation to chromatin remodeling and histone deacetylation. Nat Genet 23:62–6.

Wan M, Francke U. 1998. Evaluation of two X chromosomal candidate genes for Rett syndrome: glutamate dehydrogenase-2 (GLUD2) and rab GDP-dissociation inhibitor (GDI1). Am J Med Genet 78:169–72.

Wan M, Lee S S, Zhang X, Houwink-Manville I, Song H R, Amir R E, Budden S, Naidu S, Pereira J L, Lo I F, Zoghbi H Y, Schanen N C, Francke U. 1999. Rett syndrome and beyond: recurrent spontaneous and familial MECP2 mutations at CpG hotspots. Am J Hum Genet 65:1520–1529.

Webb T, Clarke A, Hanefeld F, Pereira J L, Rosenbloom L, Woods CG. 1998. Linkage analysis in Rett syndrome families suggests that there may be a critical region at Xq28. J Med Genet 35:997–1003.

Wolff, G. L., Kodell, R. L., Moore, S. R. & Cooney, C. A. Maternal epigenetics and methyl supplements affect agouti gene expression in Avy/a mice. FASEB 12, 949–957 (1998).

Xiang, F., Buervenich, S., Nicolao, P., Bailey, M., Zhang, Z., Anvret, M. 2000. Mutation screening in Rett syndrome patients. *J Med Genet* 37:250–255.

Zappella M, Gillberg C, Ehlers S. 1998. The preserved speech variant: a subgroup of the Rett complex: a clinical report of 30 cases. J Autism Dev Disord 28:519–26.

Zoghbi H. 1988. Genetic aspects of Rett syndrome. J Child Neurol 3:S76–8.

Zoghbi H Y, Percy A K, Schultz R J, Fill C. 1990. Patterns of X chromosome inactivation in the Rett syndrome. Brain Dev 12:131–5.

One skilled in the art readily appreciates that the present invention is well adapted to carry out the objectives and obtain the ends and advantages mentioned as well as those inherent therein. Sequences, mutations, complexes, methods, treatments, pharmaceutical compositions, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

We claim:

1. A method of screening a human for Rett syndrome comprising the step of detecting a mutation in a nucleic acid sequence encoding MECP2.

2. The method of claim 1, wherein said detecting step is further defined as amplification of SEQ ID NO:20, SEQ ID NO:21, SEQ ID NO:22, SEQ ID NO:23, SEQ ID NO:24, SEQ ID NO:25, SEQ ID NO:26, or SEQ ID NO:27.

3. The method of claim 1, wherein said detecting step is further defined as amplification with at least one primer selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, and SEQ ID NO:89.

4. The method of claim 1, wherein said mutation is a nonsense mutation, missense mutation, frameshift mutation, rearrangement, insertion or deletion.

5. The method of claim 1, wherein said mutation is selected from the group consisting of 430 A-T, 508 C-T, 613 G-T, 1079 C-A, 90insA, 554delG, 710delG, 753delC, 753insCC, 808delC, 965del6+1027insG+1138del71, 1118del122, 1157del41, 1161del6+1177del26, 1162del29, 1164del44, 1308delTC, and a combination thereof.

6. The method of claim 1, wherein said mutation is detected by a method selected from the group consisting of sequencing, electrophoretic mobility, nucleic acid hybridization, fluorescent in situ hybridization, polymerase chain reaction, reverse transcription-polymerase chain reaction, and denaturing high-performance liquid chromatography.

7. The method of claim 1, wherein said mutation is detected by denaturing high-performance liquid chromatography.

8. The method of claim 1, wherein said mutation is detected by a method selected from the group consisting of denaturing high-performance liquid chromatography, sequencing, and a combination thereof.

9. The method of claim 1, wherein said nucleic acid hybridization comprises a tagged probe that binds the mutation, wherein upon binding of the tag to the mutation, a change in the tag indicates the presence or absence of said mutation.

10. The method of claim 1, wherein said nucleic acid hybridization comprises at least one nucleic acid present on an immobilized surface, wherein said nucleic acid is subjected to hybridization and whereupon said hybridization to the nucleic acid comprises detection of the presence or absence of said mutation.

* * * * *

```
                            SEQUENCE LISTING

<160> NUMBER OF SEQ ID NOS: 114

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
gttatgtctt tagtctttgg                                                  20

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
tgtgtttatc ttcaaaatgt                                                  20

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3
cctgcctctg ctcacttgtt                                                  20

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
ggggtcatca tacatgggtc                                                  20

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
agcccgtgca gccatcagcc                                                  20

<210> SEQ ID NO 6
<211> LENGTH: 20
<212> TYPE: DNA
<213> ORGANISM: Artificial sequence
<220> FEATURE:
```

```
<223> OTHER INFORMATION: Primer

<400> SEQUENCE: 6 gttcccccg accccaccct                                                    20

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
tttgtcagag cgttgtcacc                                                   20

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
cttcccagga cttttctcca                                                   20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
aaccacctaa gaagcccaaa                                                   20

<210> SEQ ID NO 10
<211> LENGTH: 22
<212> TYPE: DNA
<213> ORGANISM: Artificial sequence
<220> FEATURE:
<223> OTHER INFORMATION: Primer

<400> SEQUENCE: 10
ctgcacagat cggatagaag ac                                                22

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
ggcaggaagc gaaaagctga g                                                 21

<210> SEQ ID NO 12
<211> LENGTH: 22
<212> TYPE: DNA
<213> ORGANISM: Artificial sequence
<220> FEATURE:
<223> OTHER INFORMATION: Primer

<400> SEQUENCE: 12
tgagtggtgg tgatggtggt gg                                                22
```

```
<210> SEQ ID NO 13
<211> LENGTH: 19
<212> TYPE: DNA
<213> ORGANISM: Artificial sequence
<220> FEATURE:
<223> OTHER INFORMATION: Primer

<400> SEQUENCE: 13
tggtgaagcc cctgctggt                                                  19

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
ctccctcccc tcggtgtttg                                                 20

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
ggagaagatg cccagaggag                                                 20

<210> SEQ ID NO 16
<211> LENGTH: 21
<212> TYPE: DNA
<213> ORGANISM: Artificial sequence
<220> FEATURE:
<223> OTHER INFORMATION: Primer

<400> SEQUENCE: 16
cggtaagaaa aacatcccca a                                               21

<210> SEQ ID NO 17
<211> LENGTH: 554
<212> TYPE: DNA
<213> ORGANISM: Zebrafish

<400> SEQUENCE: 17
ctcttcggtg caactccgct ggctgtcgtc ccactgctgc tgcttcccgg atctgcctct     60
ttgtgcttcc ggctgggatg cttgtgaggc ttctgtcctg tttctgcctc ctccccggta    120
ggggtcacag ttgatgcagt cagtcgtttc tcaaaggtct ctgtcgctga ggtggtggat    180
gcctccagct cctctaaagt ctctcgggtt ttgcgttttt tgataggaag agccctctcc    240
tgaacaggct tagcggaaga ctccttcagg gcttttttct tggcttcggc ggtgagaatg    300
gctgcagcgg cgtatgcagc agcagacccc gtccccactg ttgactgtga aacagttgct    360
ggcttgcgtc cacgttttttt agggtgcttg gcggatcct gctctgattt cctcttacgt    420
cctcggcgtg ctttggcaac tggcgcttgc cctaaaggag cccctggttc agtattgggg    480
gccacaaagg gcatctttac taagagtatt cctggactct gttctatgac gcgtttcacc    540 ggcaccccttt ctgt                                                     554

<210> SEQ ID NO 18
<211> LENGTH: 310
<212> TYPE: DNA
```

<213> ORGANISM: Zebrafish

<400> SEQUENCE: 18

| gaaatctgaa cccattgacc ctgaagttgg agctgctctt atcgctccaa aatcttccgc | 60 |
|---|---|
| atcggccaag cagcggcggt ctgtcattcg ggacagaggc ccaatgtatg aagatccttc | 120 |
| gctgcctcat ggctggacac gcaagctgat acagcgcaaa tcagggcgct tcgctggcga | 180 |
| atttgacgtc taccttatca acccagaagg gaaagccttc cgttccaatg tggagctgat | 240 |
| ggcgtacttg catatggtgg gcgattccgt ttcagatccc aatgactttg acttcactgt | 300 |
| cacaggcagg | 310 |

<210> SEQ ID NO 19
<211> LENGTH: 560
<212> TYPE: DNA
<213> ORGANISM: Zebrafish

<400> SEQUENCE: 19

| aaataaaaat ggccgccgca gagagcggag aggagagact aggtgaggac aagaatgaag | 60 |
|---|---|
| accaggaggg ctcaaaagac aagacgcaga agcataagaa aagcaaaaag gaaaggcatg | 120 |
| atgtggaaaa actggagacc acagtctctg ttcctccgcc cccatctctc tttacgcaga | 180 |
| gggatgtcgg acagcaggca gaggcaggga agtctgaacc cattgaccct gaagttggag | 240 |
| ctgctctcag cgctccagaa tcttccgcat cggccaagca gcggcggtct gtcattcggg | 300 |
| acagaggccc aatgtatgaa gatccttcgc tgcctcaggc tggacacgc aagctgaaac | 360 |
| agcgcaaatc agggcgctcc gctggcaaat ttgacgtcta ccttatcaac ccagaaggga | 420 |
| aagccttccg ttccaaggtg gagctcatgg catacttcca aaaggttggc gataccatta | 480 |
| cagatcccaa tgactttgac ttcacggtca ccggcagggg aagcccgtct cgcagagaaa | 540 |
| aaagaccggc aaaaagccct | 560 |

<210> SEQ ID NO 20
<211> LENGTH: 1669
<212> TYPE: DNA
<213> ORGANISM: Human

<400> SEQUENCE: 20

| agactacagt tcctgctttg atgtgacatg tgactcccca gaatacacct tgcttctgta | 60 |
|---|---|
| gaccagctcc aacaggattc catggtagct gggatgttag ggctcaggga agaaaagtca | 120 |
| gaagaccagg acctccaggg cctcaaggac aaaccccttca gtttaaaaa ggtgaagaaa | 180 |
| gataagaaag aagagaaaga gggcaagcat gagcccgtgc agccatcagc ccaccactct | 240 |
| gctgagcccg cagaggcagg caaagcagag acatcagaag ggtcaggctc cgccccggct | 300 |
| gtgccggaag cttctgcctc ccccaaacag cggcgctcca tcatccgtga ccggggaccc | 360 |
| atgtatgatg accccaccct gcctgaaggc tggacacgga gcttaagca aggaaatct | 420 |
| ggccgctctg ctgggaagta tgatgtgtat ttgatcaatc cccagggaaa agcctttcgc | 480 |
| tctaaagtgg agttgattgc gtacttcgaa aaggtaggcg acacatccct ggaccctaat | 540 |
| gattttgact tcacggtaac tgggagaggg agccctccc ggcagagca gaaaccacct | 600 |
| aagaagccca atctcccaa agctccagga actggcagag gccgggacg ccccaaaggg | 660 |
| agcggcacca cgagacccaa ggcggccacg tcagagggtg tgcaggtgaa aagggtcctg | 720 |
| gagaaaagtc ctgggaagct ccttgtcaag atgccttttc aaacttcgcc aggggcaag | 780 |
| gctgagggg gtggggccac cacatccacc caggtcatgg tgatcaaacg ccccggcagg | 840 |

```
aagcgaaaag ctgaagctga ccctcaggcc attcccaaga acggggccg aaagccgggg      900 agtgtggtgg cagccgctgc cgccgaggcc aaaaagaaag ccgtgaagga gtcttctatc      960
cgatctgtgc aggagaccgt actccccatc aagaagcgca agacccggga gacggtcagc     1020
atcgaggtca aggaagtggt gaagcccctg ctggtgtcca ccctcggtga aagagcggg      1080 aaaggactga agacctgtaa gagccctggg cggaaaagca aggagagcag ccccaagggg     1140
cgcagcagca gcgcctcctc accccccaag aaggagcacc accaccatca ccaccactca     1200
gagtccccaa aggcccccgt gccactgctc caccctgc ccccctcc acctgagccc         1260 gagagctccg aggaccccac cagcccccct gagcccagg acttgagcag cagcgtctgc      1320
aaagaggaga agatgcccag aggaggctca ctggagagca cggctgccc caaggagcca     1380 gctaagactc agcccgcggt tgccaccgcc gccacggccg cagaaaagta caaacaccga     1440
ggggagggag agcgcaaaga cattgtttca tcctccatgc aaggccaaa cagagaggag      1500 cctgtggaca gccggacgcc cgtgaccgag agagttagct gactttacac ggagcggatt     1560
gcaaagcaaa ccaacaagaa taaaggcagc tgttgtctct tctccttatg ggtagggctc     1620
tgacaaagct tcccgattaa ctgaaataaa aatatttttt ttttctttc                 1669

<210> SEQ ID NO 21
<211> LENGTH: 1533
<212> TYPE: DNA
<213> ORGANISM: Human

<400> SEQUENCE: 21
agttcctgct ttgatgtgac ctgtgactcc ccagaataca ccttgcttct gtagaccagc       60
tccaacagga ttccatggta gctgggatgt tagggctcag ggaagaaaag tcagaagacc      120
aggacctcca gggcctcaag gacaaacccc tcaagtttaa aaaggtgaag aaagataaga      180
aagaagagaa agagggcaag catgagcccg tgcagccatc agcccaccac tctgctgagc      240
ccgcagaggc aggcaaagca gagacatcag aagggtcagg ctccgccccg gctgtgccgg      300
aagcttctgc ctcccccaaa cagcggcgct ccatcatccg tgaccgggga cccatgtatg      360
atgaccccac cctgcctgaa ggctggacac ggaagcttaa gcaaggaaa tctggccgct      420 ctgctgggaa gtatgatgtg tatttgatca atccccaggg aaaagccttt cgctctaaag      480
tggagttgat tgcgtacttc gaaaaggtag gcgacacatc cctggaccct aatgattttg      540
acttcacggt aactgggaga gggagcccct cccggcgaga gcagaaacca cctaagaagc      600
ccaaatctcc caaagctcca ggaactggca gaggccgggg acgccccaaa gggagcggca      660
ccacgagacc caaggcggcc acgtcagagg gtgtgcaggt gaaaagggtc ctggagaaaa      720
gtcctgggaa gctccttgtc aagatgcctt ttcaaacttc gccaggggc aaggctgagg      780 ggggtggggc caccacatcc acccaggtca tggtgatcaa cgccccggc aggaagcgaa      840 aagctgaggc cgaccctcag gccattccca agaaacgggg ccgaaagccg ggagtgtgg      900 tggcagccgc tgccgccgag gccaaaaaga agccgtgaa ggggtcttct atccgatctg      960
tgcaggagac cgtactcccc atcaagaagc gcaagacccg ggagacggtc agcatcgagg     1020
tcaaggaagt ggtgaagccc ctgctggtgt ccaccctcgg tgagagagc gggaaaggac     1080 tgaagacctg taagagccct gggcggaaaa gcaaggagag cagccccaag ggcgcagca     1140 gcagcgcctc tcacccccca agaaggagc accaccacca tcaccaccac tcagagtccc     1200
caaaggcccc cgtgccactg ctcccacccc tgcccccacc tccacctgag cccgagagct     1260
```

| | |
|---|---|
| ccgaggaccc caccagcccc cctgagcccc aggacttgag cagcagcgtc tgcaaagagg | 1320 |
| agaagatgcc cagaggaggc tcactggaga gcgacggctg ccccaaggag ccagctaaga | 1380 |
| ctcagcccgc ggttgccacc gccgccacgg ccgcagaaaa gtacaaacac cgaggggagg | 1440 |
| gagagcgcaa agacattgtt tcatcctcca tgccaaggcc aaacagagag gagcctgtgg | 1500 |
| acagccggac gcccgtgacc gagagagtta gct | 1533 |

<210> SEQ ID NO 22
<211> LENGTH: 756
<212> TYPE: DNA
<213> ORGANISM: Human

<400> SEQUENCE: 22

| | |
|---|---|
| gtaagtaaga gcaactccta tctctacagg gcagggaggg cagggacaag gatccctcat | 60 |
| ggagcaggaa aatgtatgtg cccagggtgg ggtcggggggg aacataaaca atgaacactg | 120 |
| agaccaggtg tgcttgaaat gaccgtgtac agaggtcgct gccctgagtg ggaagttctc | 180 |
| aaggtagcag gccctctatc ctctccacac ctcaagtctt tatctgggga tcgaatagct | 240 |
| gcggaacgaa ggaacttgca gagccagggg ttcagagggg tgaagaagca tgtttcagtt | 300 |
| ctgccttttta aatgatccca aaaggttag cagttttcaa atgacatttg cagacagcct | 360 |
| catttaattc catgagaagg gtgagcaaag gattatcttg ttgaaactga ttcctggaga | 420 |
| gactgagcac cgtacctgag ttcaaacttg ggaatgttct agatggtgac tcaggcccag | 480 |
| gcaccaacca gcagaatggg cctcagcctg acaacccttc tgtaccaggc ctgactcttt | 540 |
| ggttgctgaa ctttggagag gcctgggggg gtcagcggca ggcagacgag tgagtggctt | 600 |
| tggtgacagg tcctcagggg cagccaggca gtgtgactct cgttcaatag taacgtttgt | 660 |
| cagaggcgtt gtcaccacca tccgctctgc cctatctctg acattgctat ggagagcctc | 720 |
| taattgttcc ttgtgtcttt ctgtttgtcc ccacga | 756 |

<210> SEQ ID NO 23
<211> LENGTH: 2351
<212> TYPE: DNA
<213> ORGANISM: Human

<400> SEQUENCE: 23

| | |
|---|---|
| ggaagaaaag tcagaagacc aggacctcca gggcctcaag gacaaacccc tcaagtttaa | 60 |
| aaaggtgaag aaagataaga aagaagagaa agagggcaag catgagcccg tgcagccatc | 120 |
| agcccaccac tctgctgagc ccgcagaggc aggcaaagca gagacatcag aagggtcagg | 180 |
| ctccgcccgc ctgtgcgaag cttctgcctc ccccaaacag cggcgctcca tcatccgtga | 240 |
| ccgggggaccc atgtatgatg accccaccct gcctgaaggc tggacacgga agcttaagca | 300 |
| aaggaaatct ggccgctctg ctgggaagta tgatgtgtat ttgatcaatc cccagggaaa | 360 |
| agcctttcgc tctaaagtgg agttgattgc gtacttcgaa aaggtaggcg acacatccct | 420 |
| ggaccctaat gattttgact tcacggtaac tgggagaggg agccccctcc ggcgagagca | 480 |
| gaaaccacct aagaagccca atctcccaa agctccagga actggcagag gccggggacg | 540 |
| ccccaaaggg agcggcacca cgagacccaa ggcggccacg tcagagggtg tgcaggtgaa | 600 |
| aagggtcctg gagaaaagtc ctgggaagct ccttgtcaag atgccttttc aaacttcgcc | 660 |
| agggggcaag gctgaggggg gtggggccac cacatccacc caggtcatgg tgatcaaacg | 720 |
| ccccggcagg aagcgaaaag ctgaggccga ccctcaggcc attcccaaga acggggccg | 780 |
| aaagccgggg agtgtggtgg cagccgctgc cgccgaggcc aaaaagaaag ccgtgaagga | 840 |

```
gtcttctatc cgatctgtgc aggagaccgt actccccatc aagaagcgca agacccggga      900
gacggtcagc atcgaggtca aggaagtggt gaagcccctg ctggtgtcca ccctcggtga      960
gaagagcggg aaaggactga agacctgtaa gagccctggg cggaaaagca aggagagcag     1020
ccccaagggg cgcagcagca cgcctcctc accccccaag aaggagcacc accaccatca      1080
ccaccactca gagtccccaa aggcccccgt gccactgctc ccacccctgc ccccacctcc     1140
acctgagccc gagagctccg aggacccac cagccccct gagcccagg acttgagcag        1200
cagcgtctgc aaagaggaga agatgcccag aggaggctca ctggagagcg acggctgccc    1260
caaggagcca gctaagactc agcccgcggt tgccaccgcc gccacggccg cagaaaagta     1320
caaacaccga ggggagggag agcgcaaaga cattgtttca tcctccatgc caaggccaaa    1380
cagagaggag cctgtggaca gccggacgcc cgtgaccgag agagttagct gactttacac     1440
ggagcggatt gcaaagcaaa ccaacaagaa taaaggcagc tgttgtctct ctccttatg     1500
ggtagggctc tgacaaagct tcccgattaa ctgaaataaa aatatttt ttttctttc        1560
agtaaactta gagtttcgtg gcttcagggt gggagtagtt ggagcattgg ggatgttttt    1620
cttaccgaca agcacagtca ggttgaagac ctaaccaggg ccagaagtag ctttgcactt    1680
ttctaaacta ggctccttca acaaggcttg ctgcagatac tactgaccag acaagctgtt    1740
gaccaggcac ctcccctccc gcccaaacct ttcccccatg tggtcgttag agacagagcg   1800
acagagcagt tgagaggaca ctcccgtttt cggtgccatc agtgcccgt ctacagctcc     1860
ccaagctccc cccacctccc ccactcccaa ccacgttggg acaggcagtt gtgagccagg    1920
agagacagtt ggattcttta gagaagatgg atatgaccag tggctatggc ctgtgcgatc    1980
ccacccgtgg tggctcaagt ctggccccac accagcccca atccaaaact ggcaaggacg    2040
cttcacagga caggaaagtg gcacctgtct gctccagctc tggcatggct aggaggggg     2100
agtcccttga actactgggt gtagactggc ctgaaccaca ggagaggatg gcccagggtg    2160
aggtggcatg gtccattctc aagggacgtc ctccaacggg tggcgctaga ggccatggag    2220
gcagtaggac aagtgcagg caggctggcc tggggtcagg ccgggcagag catagcgggg    2280
tgagagggat tcctaatcac tcagagcagt ctgtgactta gtggacaggg gaggggcaa    2340
aggggcccg g                                                          2351
```

<210> SEQ ID NO 24
<211> LENGTH: 10091
<212> TYPE: DNA
<213> ORGANISM: Human

<400> SEQUENCE: 24

```
cagttcctgc tttgatgtga catgtgactc cccagaatac accttgcttc tgtagaccag       60
ctccaacagg attccatggt agctgggatg ttagggctca gggaagaaaa gtcagaagac      120
caggacctcc agggcctcaa ggacaaaccc ctcaagtta aaaggtgaa gaaagataag        180
aaagaagaga aagagggcaa gcatgagccc gtgcagccat cagcccacca ctctgctgag     240
cccgcagagg caggcaaagc agagacatca gaagggtcag gctccgcccc ggctgtgccg    300
gaagcttctg cctcccccaa acagcggcgc tccatcatcc gtgaccgggg acccatgtat     360
gatgacccca ccctgcctga aggctggaca cggaagctta gcaaaggaa atctggccgc      420
tctgctggga gtatgatgt gtatttgatc aatcccccagg gaaaagcctt tcgctctaaa    480
gtggagttga ttgcgtactt cgaaaaggta ggcgacacat ccctggaccc taatgatttt     540
```

-continued

```
gacttcacgg taactgggag agggagcccc tcccggcgag agcagaaacc acctaagaag    600
cccaaatctc ccaaagctcc aggaactggc agaggccggg gacgcccaa agggagcggc     660
accacgagac ccaaggcggc cacgtcagag ggtgtgcagg tgaaaagggt cctggagaaa    720
agtcctggga agctccttgt caagatgcct tttcaaactt cgccaggggg caaggctgag    780
gggggtgggg ccaccacatc cacccaggtc atggtgatca aacgccccgg caggaagcga    840
aaagctgagg ccgaccctca ggccattccc aagaaacggg gccgaaagcc ggggagtgtg    900
gtggcagccg ctgccgccga ggccaaaaag aaagccgtga aggagtcttc tatccgatct    960
gtgcaggaga ccgtactccc catcaagaag cgcaagaccc gggagacggt cagcatcgag   1020
gtcaaggaag tggtgaagcc cctgctggtg tccaccctcg gtgagaagag cgggaaagga   1080
ctgaagacct gtaagagccc tgggcggaaa agcaaggaga gcagcccaa ggggcgcagc    1140
agcagcgcct cctcacccc caagaaggag caccaccacc atcaccacca ctcagagtcc    1200
ccaaaggccc ccgtgccact gctcccaccc ctgcccccac ctccacctga gcccgagagc   1260
tccgaggacc ccaccagccc ccctgagccc caggacttga gcagcagcgt ctgcaaagag   1320
gagaagatgc ccagaggagg ctcactggag agcgacggct gccccaagga gccagctaag   1380
actcagcccg cggttgccac cgccgccacg gccgcagaaa agtacaaaca ccgaggggag   1440
ggagagcgca aagacattgt ttcatcctcc atgccaaggc caaacagaga ggagcctgtg   1500
gacagccgga cgcccgtgac cgagagagtt agctgacttt acacggagcg gattgcaaag   1560
caaaccaaca agaataaagg cagctgttgt ctcttctcct tatgggtagg gctctgacaa   1620
agcttcccga ttaactgaaa taaaaaatat ttttttttct ttcagtaaac ttagagtttc   1680
gtggcttcag ggtgggagta gttggagcat tggggatgtt tttcttaccg acaagcacag   1740
tcaggttgaa gacctaacca gggccagaag tagctttgca cttttctaaa ctaggctcct   1800
tcaacaaggc ttgctgcaga tactactgac cagacaagct gttgaccagg cacctccct    1860
cccgcccaaa cctttccccc atgtggtcgt tagagacaga gcgacagagc agttgagagg   1920
acactcccgt tttcggtgcc atcagtgccc cgtctacagc tcccccagct cccccccacct  1980
cccccactcc caaccacgtt gggacaggga ggtgtgaggc aggagagaca gttggattct   2040
ttagagaaga tggatatgac cagtggctat ggcctgtgcg atcccacccg tggtggctca   2100
agtctggccc cacaccagcc ccaatccaaa actggcaagg acgcttcaca ggacaggaaa   2160
gtggcacctg tctgctccag ctctggcatg ctaggaggg gggagtccct tgaactactg    2220
ggtgtagact ggcctgaacc acaggagagg atggcccagg gtgaggtggc atggtccatt   2280
ctcaagggac gtcctccaac gggtggcgct agaggccatg gaggcagtag acaaggtgc    2340
aggcaggctg gcctggggtc aggccgggca gagcacagcg gggtgagagg gattcctaat   2400
cactcagagc agtctgtgac ttagtggaca ggggaggggg caaaggggga ggagaagaaa   2460
atgttcttcc agttactttc caattctcct ttagggacag cttagaatta tttgcactat   2520
tgagtcttca tgttcccact tcaaaacaaa cagatgctct gagagcaaac tggcttgaat   2580
tggtgacatt tagtccctca agccaccaga tgtgacagtg ttgagaacta cctggatttg   2640
tatatatacc tgcgcttgtt ttaaagtggg ctcagcacat agggttccca cgaagctccg   2700
aaactctaag tgtttgctgc aattttataa ggacttcctg attggtttct cttctcccct   2760
tccatttctg cctttttgttc atttcatcct ttcacttctt tccttcctc cgtcctcctc    2820
cttcctagtt catcccttct cttccaggca gccgcggtgc ccaaccacac ttgtcggctc    2880
cagtccccag aactctgcct gcccctttgtc ctcctgctgc cagtaccagc cccaccctgt   2940
```

```
tttgagccct gaggaggcct tgggctctgc tgagtccaac ctggcctgtc tgtgaagagc      3000
aagagagcag caaggtcttg ctctcctagg tagcccctc ttccctggta agaaaaagca       3060
aaaggcattt cccaccctga caacgagcc ttttcacccct tctactctag agaagtggac      3120
tggaggagct gggcccgatt tggtagttga ggaaagcaca gaggcctcct gtggcctgcc      3180
agtcatcgag tggcccaaca ggggctccat gccagccgac cttgacctca ctcagaagtc      3240
cagagtctag cgtagtgcag cagggcagta gcggtaccaa tgcagaactc caagacccg      3300 agctgggacc agtacctggg tccccagccc ttcctctgct cccccttttc cctcggagtt      3360
cttcttgaat ggcaatgttt tgcttttgct cgatgcagac agggggccag aacaccacac      3420
atttcactgt ctgtctggtc catagctgtg gtgtaggggc ttagaggcat gggcttgctg      3480
tgggttttta attgatcagt tttcatgtgg gatcccatct ttttaacctc tgttcaggaa      3540
gtccttatct agctgcatat cttcatcata ttggtatatc cttttctgtg tttacagaga      3600
tgtctcttat atctaaatct gtccaactga gaagtacctt atcaaagtag caaatgagac      3660
agcagtctta tgcttccaga aacacccaca ggcatgtccc atgtgagctg ctgccatgaa      3720
ctgtcaagtg tgtgttgtct tgtgtatttc agttattgtc cctggcttcc ttactatggt      3780
gtaatcatga aggagtgaaa catcatagaa actgtctagc acttccttgc cagtcttag      3840 tgatcaggaa ccatagttga cagttccaat cagtagctta agaaaaaacc gtgtttgtct      3900
cttctggaat ggttagaagt gagggagttt gccccgttct gtttgtagag tctcatagtt      3960
ggactttcta gcatatatgt gtccatttcc ttatgctgta aaagcaagtc ctgcaaccaa      4020
actcccatca gcccaatccc tgatccctga tcccttccac ctgctctgct gatgaccccc      4080
ccagcttcac ttctgactct tccccaggaa gggaaggggg gtcagaagag agggtgagtc      4140
ctccagaact cttcctccaa ggacagaagg ctcctgcccc catagtggcc tcgaactcct      4200
ggcactacca aaggacactt atccacgaga gcgcagcatc cgaccaggtt gtcactgaga      4260
agatgtttat tttggtcagt tgggttttta tgtattatac ttagtcaaat gtaatgtggc      4320
ttctggaatc attgtccaga gctgcttccc cgtcacctgg gcgtcatctg gtcctggtaa      4380
gaggagtgcg tggcccacca ggcccccctg tcacccatga cagttcattc agggccgatg      4440
gggcagtcgt ggttgggaac acagcatttc aagcgtcact ttatttcatt cgggccccac      4500
ctgcagctcc ctcaaagagg cagttgccca gcctctttcc cttccagttt attccagagc      4560
tgccagtggg gcctgaggct ccttagggtt ttctctctat tttccccttt cttcctcatt      4620
ccctcgtctt tcccaaaggc atcacgagtc agtcgccttt cagcaggcag ccttggcggt      4680
ttatcgccct ggcaggcagg ggccctgcag ctctcatgct gcccctgcct tggggtcagg      4740
ttgacaggag gttggaggga aagccttaag ctgcaggatt ctcaccagct gtgtccggcc      4800
cagttttggg gtctgacctc aatttcaatt ttgtctgtac ttgaacatta tgaagatggg      4860
ggcctctttc agtgaatttg tgaacagcag aattgaccga cagctttcca gtacccatgg      4920
ggctaggtca ttaaggccac atccacagtc tcccccaccc ttgttccagt tgttagttac      4980
tacctcctct cctgacaata ctgtatgtcg tcgagctccc cccaggtcta cccctcccgg      5040
ccctgcctgc tggtgggctt gtcatagcca gtgggattgc cggtcttgac agctcagtga      5100
gctggagata cttggtcaca gccaggcgct agcacagctc ccttctgttg atgctgtatt      5160
cccatatcaa aaggcacagg ggacacccag aaacgccaca tcccccaatc catcagtgcc      5220
aaactagcca acggccccag cttctcagct cgctggatgg cggaagctgc tactcgtgag      5280
```

-continued

| | |
|---|---|
| cgccagtgcg ggtgcagaca atcttctgtt gggtggcatc attccaggcc cgaagcatga | 5340 |
| acagtgcacc tgggacaggg agcagcccca aattgtcacc tgcttctctg cccagctttt | 5400 |
| cattgctgtg acagtgatgg cgaaagaggg taataaccag acacaaactg ccaagttggg | 5460 |
| tggagaaagg agtttcttta gctgacagaa tctctgaatt ttaaatcact tagtaagcgg | 5520 |
| ctcaagccca ggagggagca gagggatacg agcggagtcc cctgcgcggg accatctgga | 5580 |
| attggtttag cccaagtgga gcctgacagc cagaactctg tgtcccccgt ctaaccacag | 5640 |
| ctccttttcc agagcattcc agtcaggctc tctgggctga ctgggccagg ggaggttaca | 5700 |
| ggtaccagtt ctttaagaag atctttgggc atatacattt ttagcctgtg tcattgcccc | 5760 |
| aaatggattc ctgtttcaag ttcacacctg cagattctag acctgtgtc ctagacttca | 5820 |
| gggagtcagc tgtttctaga gttcctacca tggagtgggt ctggaggacc tgcccggtgg | 5880 |
| gggggcagag ccctgctccc tccgggtctt cctactcttc tctctgctct gacgggattt | 5940 |
| gttgattctc tccatttggg tgtctttctc ttttagatat tgtatcaatc tttagaaaag | 6000 |
| gcatagtcta cttgttataa atcgttagga tactgcctcc cccagggtct aaaattacat | 6060 |
| attagagggg aaaagctgaa cactgaagtc agttctcaac aatttagaag gaaaacctag | 6120 |
| aaaacatttg gcagaaaatt acatttcgat gttttttgaat gaatacaagc aagcttttac | 6180 |
| aacagtgctg atctaaaaat acttagcact tggcctgaga tgcctggtga gcattacagg | 6240 |
| caagggaat ctggaggtag ccgacctgag gacatggctt ctgaacctgt cttttgggag | 6300 |
| tggtatggaa ggtggagcgt tcaccagtga cctggaaggc ccagcaccac cctccttccc | 6360 |
| actcttctca tcttgacaga gcctgcccca gcgctgacgt gtcaggaaaa cacccaggga | 6420 |
| actaggaagg cacttctgcc tgaggggcag cctgccttgc ccactcctgc tctgctcgcc | 6480 |
| tcggatcagc tgagccttct gagctggcct ctcactgcct ccccaaggcc cctgcctgc | 6540 |
| cctgtcagga ggcagaagga agcaggtgtg agggcagtgc aaggagggag cacaaccccc | 6600 |
| agctcccgct ccgggctccg acttgtgcac aggcagagcc cagaccctgg aggaaatcct | 6660 |
| acctttgaat tcaagaacat ttggggaatt tggaaatctc tttgccccca aaccccccatt | 6720 |
| ctgtcctacc tttaatcagg tcctgctcag cagtgagagc agatgaggtg aaaaggccaa | 6780 |
| gaggtttggc tcctgcccac tgatagcccc tctccccgca gtgtttgtgt gtcaagtggc | 6840 |
| aaagctgttc ttcctggtga ccctgattat atccagtaac acatagactg tgcgcatagg | 6900 |
| cctgcttgt ctcctctatc ctgggctttt gttttgcttt ttagttttgc ttttagtttt | 6960 |
| tctgtcccctt ttatttaacg caccgactag acacacaaag cagttgaatt tttatatata | 7020 |
| tatctgtata ttgcacaatt ataaactcat tttgcttgtg gctccacaca cacaaaaaaa | 7080 |
| gacctgttaa aattatacct gttgcttaat tacaatattt ctgataacca tagcatagga | 7140 |
| caagggaaaa taaaaaaaga aaaaaagaa aaaaaacga caaatctgtc tgctggtcac | 7200 |
| ttcttctgtc caagcagatt cgtggtcttt tcctcgcttc tttcaagggc tttcctgtgc | 7260 |
| caggtgaagg aggctccagg cagcacccag gttttgcact cttgttttctc ccgtgcttgt | 7320 |
| gaaagaggtc ccaaggttct gggtgcagga gcgctccctt gacctgctga agtccggaac | 7380 |
| gtagtcggca cagcctggtc gccttccacc tctgggagct ggagtccact ggggtggcct | 7440 |
| gactccccca gtccccttcc cgtgacctgg tcagggtgag cccatgtgga gtcagcctcg | 7500 |
| caggcctccc tgccagtagg gtccgagtgt gtttcatcct tcccactctg tcgagcctgg | 7560 |
| ttcttcgagc ggagacggga ggcctggcct gtctcggaac ctgtgagctg caccaggtag | 7620 |
| aacgccaggg accccagaat catgtgcgtc agtccaaggg gtcccctcca ggagtagtga | 7680 |

-continued

```
agactccaga aatgtcccttt tcttctcccc catcctacga gtaattgcat ttgcttttgt   7740
aattcttaat gagcaatatc tgctagagag tttagctgta acagttcttt ttgatcatct   7800
tttttaata attagaaaca ccaaaaaaat ccagaaactt gttcttccaa agcagagagc   7860
attataatca ccagggccaa aagcttccct ccctgctgtc attgcttctt ctgaggcctg   7920
aatccaaaag aaaaacagcc ataggccctt tcagtggccg ggctacccgt gagcccttcg   7980
gaggaccagg gctggggcag cctctgggcc cacatccggg gccagctccg gcgtgtgttc   8040
agtgttagca gtgggtcatg atgctctttc ccacccagcc tgggataggg gcagaggagg   8100
cgaggaggcc gttgccgctg atgtttggcc gtgaacaggt gggtgtctgc gtgcgtccac   8160
gtgcgtgttt tctgactgac atgaaatcga cgcccgagtt agcctcaccc ggtgacctct   8220
agccctgccc ggatggagcg gggcccaccc ggttcagtgt ttctggggag ctggacagtg   8280
gagtgcaaaa ggcttgcaga acttgaagcc tgctccttcc cttgctacca cggcctcctt   8340
tccgtttgat ttgtcactgc ttcaatcaat aacagccgct ccagagtcag tagtcaatga   8400
atatatgacc aaatatcacc aggactgtta ctcaatgtgt gccgagccct tgcccatgct   8460
gggctcccgt gtatctggac actgtaacgt gtgctgtgtt tgctccccttt cccttccttt   8520
ctttgccctt tacttgtctt tctggggttt ttctgttttgg gtttggtttg gttttattt   8580
ctccttttgt gttccaaaca tgaggttctc tctactggtc ctcttaactg tggtgttgag   8640
gcttatattt gtgtaatttt tggtgggtga aaggaatttt gctaagtaaa tctcttctgt   8700
gtttgaactg aagtctgtat tgtaactatg tttaaagtaa ttgttccaga gacaaatatt   8760
tctagacact ttttctttac aaacaaaagc attcggaggg aggggggatgg tgactgagat   8820
gagagggggag agctgaacag atgacccctg cccagatcag ccagaagcca cccaaagcag   8880
tggagcccag gagtcccact ccaagccagc aagccgaata gctgatgtgt tgccactttc   8940
caagtcactg caaaaccagg ttttgttccg cccagtggat tcttgttttg cttcccctcc   9000
ccccgagatt attaccacca tcccgtgctt ttaaggaaag gcaagattga tgtttccttg   9060
aggggagcca ggaggggatg tgtgtgtgca gagctgaaga gctggggaga atggggctgg   9120
gcccacccaa gcaggaggct gggacgctct gctgtgggca caggtcaggc taatgttggc   9180
agatgcagct cttcctggac aggccaggtg gtgggcattc tctctccaag gtgtgccccg   9240
tgggcattac tgtttaagac acttccgtca catcccaccc catcctccag ggctcaacac   9300
tgtgacatct ctattcccca ccctcccctt cccagggcaa taaaatgacc atggaggggg   9360
cttgcactct cttggctgtc acccgatcgc cagcaaaact tagatgtgag aaaacccctt   9420
cccattccat ggcgaaaaca tctccttaga aaagccatta ccctcattag gcatggtttt   9480
gggctcccaa aacacctgac agcccctccc tcctctgaga ggcggagagt gctgactgta   9540
gtgaccattg catgccgggt gcagcatctg gaagagctag gcagggtgtc tgccccctcc   9600
tgagttgaag tcatgctccc ctgtgccagc ccagaggccg agagctatgg acagcattgc   9660
cagtaacaca ggccaccctg tgcagaaggg agctggctcc agcctggaaa cctgtctgag   9720
gttgggagag gtgcacttgg ggcacaggga gaggccggga cacacttagc tggagatgtc   9780
tctaaaagcc ctgtatcgta ttcaccttca gttttttgtgt tttgggacaa ttactttaga   9840
aaataagtag gtcgttttaa aaacaaaaat tattgattgc ttttttgtag tgttcagaaa   9900
aaaggttctt tgtgtatagc caaatgactg aaagcactga tatatttaaa aacaaaaggc   9960
aatttattaa ggaaatttgt accatttcag taaacctgtc tgaatgtacc tgtatacgtt  10020
```

-continued

| | |
|---|---|
| tcaaaaacac cccccccca ctgaatccct gtaacctatt tattatataa agagtttgcc | 10080 |
| ttataaattt a | 10091 |

<210> SEQ ID NO 25
<211> LENGTH: 10182
<212> TYPE: DNA
<213> ORGANISM: Human

<400> SEQUENCE: 25

| | |
|---|---|
| ccggaaaatg gccgccgccg ccgccgccgc gccgagcgga ggaggaggag gaggcgagga | 60 |
| ggagagactg ctccataaaa atacagactc accagttcct gctttgatgt gacatgtgac | 120 |
| tccccagaat acaccttgct tctgtagacc agctccaaca ggattccatg gtagctggga | 180 |
| tgttagggct cagggaagaa aagtcagaag accaggacct ccagggcctc aaggacaaac | 240 |
| ccctcaagtt taaaaggtg aagaaagata agaaagaaga gaaagagggc aagcatgagc | 300 |
| ccgtgcagcc atcagcccac cactctgctg agcccgcaga ggcaggcaaa gcagagacat | 360 |
| cagaagggtc aggctccgcc ccggctgtgc cggaagcttc tgcctccccc aaacagcggc | 420 |
| gctccatcat ccgtgaccgg ggacccatgt atgatgaccc caccctgcct gaaggctgga | 480 |
| cacggaagct taagcaaagg aaatctggcc gctctgctgg gaagtatgat gtgtatttga | 540 |
| tcaatcccca gggaaaagcc tttcgctcta agtggagtt gattgcgtac ttcgaaaagg | 600 |
| taggcgacac atccctggac cctaatgatt ttgacttcac ggtaactggg agagggagcc | 660 |
| cctcccggcg agagcagaaa ccacctaaga agcccaaatc tcccaaagct ccaggaactg | 720 |
| gcagaggccg gggacgcccc aaagggagcg caccacgag acccaaggcg gccacgtcag | 780 |
| agggtgtgca ggtgaaaagg gtcctggaga aaagtcctgg gaagctcctt gtcaagatgc | 840 |
| cttttcaaac ttcgccaggg ggcaaggctg agggggtgg ggccaccaca tccacccagg | 900 |
| tcatggtgat caaacgcccc ggcaggaagc gaaaagctga ggccgaccct caggccattc | 960 |
| ccaagaaacg gggccgaaag ccggggagtg tggtggcagc cgctgccgcc gaggccaaaa | 1020 |
| agaaagccgt gaaggagtct tctatccgat ctgtgcagga gaccgtactc cccatcaaga | 1080 |
| agcgcaagac ccgggagacg gtcagcatcg aggtcaagga agtggtgaag ccctgctgg | 1140 |
| tgtccaccct cggtgagaag agcgggaaag gactgaagac ctgtaagagc cctgggcgga | 1200 |
| aaagcaagga gagcagcccc aaggggcgca gcagcagcgc ctcctcaccc cccaagaagg | 1260 |
| agcaccacca ccatcaccac cactcagagt ccccaaaggc cccgtgcca ctgctcccac | 1320 |
| ccctgccccc acctccacct gagcccgaga gctccgagga cccaccagc cccctgagc | 1380 |
| cccaggactt gagcagcagc gtctgcaaag aggagaagat gccagagga ggctcactgg | 1440 |
| agagcgacgg ctgccccaag gagccagcta agactcagcc cgcggttgcc accgccgcca | 1500 |
| cggccgcaga aaagtacaaa caccgagggg agggagagcg caaagacatt gtttcatcct | 1560 |
| ccatgccaag gccaaacaga gaggagcctg tggacagccg gacgcccgtg accgagagag | 1620 |
| ttagctgact ttacacggag cggattgcaa agcaaaccaa caagaataaa ggcagctgtt | 1680 |
| gtctcttctc cttatgggta gggctctgac aaagcttccc gattaactga aataaaaat | 1740 |
| atttttttt ctttcagtaa acttagagtt tcgtggcttc agggtgggag tagttggagc | 1800 |
| attgggatg ttttcttac cgacaagcac agtcaggttg aagacctaac cagggccaga | 1860 |
| agtagctttg cacttttcta aactaggctc cttcaacaag gcttgctgca gatactactg | 1920 |
| accagacaag ctgttgacca ggcacctccc ctcccgccca aacctttccc ccatgtggtc | 1980 |
| gttagagaca gagcgacaga gcagttgaga ggacactccc gttttcggtg ccatcagtgc | 2040 |

```
cccgtctaca gctcccccag ctcccccac  ctcccccact  cccaaccacg ttgggacagg  2100
gaggtgtgag gcaggagaga cagttggatt ctttagagaa gatggatatg accagtggct  2160
atggcctgtg cgatcccacc cgtggtggct caagtctggc cccacaccag ccccaatcca  2220
aaactggcaa ggacgcttca caggacagga aagtggcacc tgtctgctcc agctctggca  2280
tggctaggag gggggagtcc cttgaactac tgggtgtaga ctggcctgaa ccacaggaga  2340
ggatggccca gggtgaggtg gcatggtcca ttctcaaggg acgtcctcca acgggtggcg  2400
ctagaggcca tggaggcagt aggacaaggt gcaggcaggc tggcctgggg tcaggccggg  2460
cagagcacag cggggtgaga gggattccta atcactcaga gcagtctgtg acttagtgga  2520
caggggaggg ggcaaagggg gaggagaaga aaatgttctt ccagttactt tccaattctc  2580
ctttagggac agcttagaat tatttgcact attgagtctt catgttccca cttcaaaaca  2640
aacagatgct ctgagagcaa actggcttga attggtgaca tttagtccct caagccacca  2700
gatgtgacag tgttgagaac tacctggatt tgtatatata cctgcgcttg ttttaaagtg  2760
ggctcagcac atagggttcc cacgaagctc cgaaactcta agtgtttgct gcaattttat  2820
aaggacttcc tgattggttt ctcttctccc cttccatttc tgccttttgt tcatttcatc  2880
ctttcacttc tttcccttcc tccgtcctcc tccttcctag ttcatccctt ctcttccagg  2940
cagccgcggt gcccaaccac acttgtcggc tccagtcccc agaactctgc ctgccctttg  3000
tcctcctgct gccagtacca gccccaccct gttttgagcc ctgaggaggc cttgggctct  3060
gctgagtccg acctggcctg tctgtgaaga gcaagagagc agcaaggtct tgctctccta  3120
ggtagccccc tcttccctgg taagaaaaag caaaaggcat ttcccaccct gaacaacgag  3180 cctttttcacc cttctactct agagaagtgg actggaggag ctgggcccga tttggtagtt  3240
gaggaaagca cagaggcctc ctgtggcctg ccagtcatcg agtggcccaa cagggctcc   3300 atgccagccg accttgacct cactcagaag tccagagtct agcgtagtgc agcagggcag  3360
tagcggtacc aatgcagaac tcccaagacc cgagctggga ccagtacctg ggtccccagc  3420
ccttcctctg ctcccccttt tccctcggag ttcttcttga atggcaatgt tttgcttttg  3480
ctcgatgcag acagggggcc agaacaccac acatttcact gtctgtctgg tccatagctg  3540
tggtgtaggg gcttagaggc atgggcttgc tgtgggtttt taattgatca gttttcatgt  3600
gggatcccat cttttaacc  tctgttcagg aagtccttat ctagctgcat atcttcatca  3660
tattggtata tccttttctg tgtttacaga gatgtctctt atatctaaat ctgtccaact  3720
gagaagtacc ttatcaaagt agcaaatgag acagcagtct tatgcttcca gaaacaccca  3780
caggcatgtc ccatgtgagc tgctgccatg aactgtcaag tgtgtgttgt cttgtgtatt  3840
tcagttattg tccctggctt ccttactatg gtgtaatcat gaaggagtga aacatcatag  3900
aaactgtcta gcacttcctt gccagtcttt agtgatcagg aaccatagtt gacagttcca  3960
atcagtagct taagaaaaaa ccgtgttttgt ctcttctgga atggttagaa gtgagggagt  4020
ttgccccgtt ctgtttgtag agtctcatag ttggactttc tagcatatat gtgtccattt  4080
ccttatgctg taaaagcaag tcctgcaacc aaactcccat cagcccaatc cctgatccct  4140
gatcccttcc acctgctctg ctgatgaccc ccccagcttc acttctgact cttccccagg  4200
aagggaaggg gggtcagaag agagggtgag tcctccagaa ctcttcctcc aaggacagaa  4260
ggctcctgcc cccatagtgg cctcgaactc ctggcactac caaggacac ttatccacga  4320 gagcgcagca tccgaccagg ttgtcactga aagatgtttt attttggtca gttgggtttt  4380
```

```
tatgtattat acttagtcaa atgtaatgtg gcttctggaa tcattgtcca gagctgcttc    4440
cccgtcacct gggcgtcatc tggtcctggt aagaggagtg cgtggcccac caggcccccc    4500
tgtcacccat gacagttcat tcagggccga tggggcagtc gtggttggga acacagcatt    4560
tcaagcgtca ctttatttca ttcgggcccc acctgcagct ccctcaaaga ggcagttgcc    4620
cagcctcttt cccttccagt ttattccaga gctgccagtg gggcctgagg ctccttaggg    4680
ttttctctct atttccccct ttcttcctca ttccctcgtc tttcccaaag gcatcacgag    4740
tcagtcgcct ttcagcaggc agccttggcg gtttatcgcc ctggcaggca ggggccctgc    4800
agctctcatg ctgcccctgc cttggggtca ggttgacagg aggttggagg gaaagcctta    4860
agctgcagga ttctcaccag ctgtgtccgg cccagttttg gggtgtgacc tcaatttcaa    4920
ttttgtctgt acttgaacat tatgaagatg ggggcctctt tcagtgaatt tgtgaacagc    4980
agaattgacc gacagctttc cagtacccat ggggctaggt cattaaggcc acatccacag    5040
tctcccccac ccttgttcca gttgttagtt actacctcct ctcctgacaa tactgtatgt    5100
cgtcgagctc ccccccaggtc taccectccc ggccctgcct gctggtgggc ttgtcatagc    5160
cagtgggatt gccggtcttg acagctcagt gagctggaga tacttggtca cagccaggcg    5220
ctagcacagc tcccttctgt tgatgctgta ttcccatatc aaaagacaca ggggacaccc    5280
agaaacgcca catcccccaa tccatcagtg ccaaactagc caacggcccc agcttctcag    5340
ctcgctggat ggcggaagct gctactcgtg agcgccagtg cgggtgcaga caatcttctg    5400
ttgggtggca tcattccagg cccgaagcat gaacagtgca cctgggacag ggagcagccc    5460
caaattgtca cctgcttctc tgcccagctt tcattgctg tgacagtgat ggcgaaagag    5520
ggtaataacc agacacaaac tgccaagttg ggtggagaaa ggagtttctt tagctgacag    5580
aatctctgaa ttttaaatca cttagtaagc ggctcaagcc caggagggag cagagggata    5640
cgagcggagt cccctgcgcg ggaccatctg gaattggttt agcccaagtg gagcctgaca    5700
gccagaactc tgtgtccccc gtctaaccac agctcctttt ccagagcatt ccagtcaggc    5760
tctctgggct gactgggcca ggggaggtta caggtaccag ttctttaaga agatctttgg    5820
gcatatacat ttttagcctg tgtcattgcc ccaaatggat tcctgtttca agttcacacc    5880
tgcagattct aggacctgtg tcctagactt cagggagtca gctgtttcta gagttcctac    5940
catggagtgg gtctggagga cctgcccggt gggggggcag agccctgctc cctccgggtc    6000
ttcctactct tctctctgct ctgacgggat ttgttgattc tctccatttt ggtgtctttc    6060
tcttttagat attgtatcaa tctttagaaa aggcatagtc tacttgttat aaatcgttag    6120
gatactgcct cccccagggt ctaaaattac atattagagg ggaaaagctg aacactgaag    6180
tcagttctca acaatttaga aggaaaacct agaaaacatt tggcagaaaa ttacatttcg    6240
atgtttttga atgaatacga gcaagctttt acaacagtgc tgatctaaaa atacttagca    6300
cttggcctga gatgcctggt gagcattaca ggcaagggga atctggaggt agccgacctg    6360
aggacatggc ttctgaacct gtcttttggg agtggtatgg aagtggagc gttcaccagt    6420 gacctggaag gcccagcacc accctccttc ccactcttct catcttgaca gagcctgccc    6480
cagcgctgac gtgtcaggaa aacacccagg gaactaggaa ggcacttctg cctgaggggc    6540
agcctgcctt gcccactcct gctctgctcg cctcggatca gctgagcctt ctgagctggc    6600
ctctcactgc ctccccaagg ccccctgcct gccctgtcag gaggcagaag gaagcaggtg    6660
tgagggcagt gcaaggaggg agcacaaccc ccagctcccg ctccgggctc cgacttgtgc    6720
acaggcagag cccagaccct ggaggaaatc ctacctttga attcaagaac atttggggaa    6780
```

-continued

```
tttggaaatc tctttgcccc caaaccccca ttctgtccta cctttaatca ggtcctgctc    6840
agcagtgaga gcagatgagg tgaaaaggcc aagaggtttg gctcctgccc actgatagcc    6900
cctctccccg cagtgtttgt gtgtcaagtg gcaaagctgt tcttcctggt gaccctgatt    6960
atatccagta acacatagac tgtgcgcata ggcctgcttt gtctcctcta tcctgggctt    7020
ttgttttgct ttttagtttt gcttttagtt tttctgtccc ttttatttaa cgcaccgact    7080
agacacacaa agcagttgaa tttttatata tatatctgta tattgcacaa ttataaactc    7140
attttgcttg tggctccaca cacacaaaaa aagacctgtt aaaattatac ctgttgctta    7200
attacaatat ttctgataac catagcatag gacaagggaa aataaaaaaa gaaaaaaaag    7260
aaaaaaaaac gacaaatctg tctgctggtc acttcttctg tccaagcaga ttcgtggtct    7320
tttcctcgct tctttcaagg gctttcctgt gccaggtgaa ggaggctcca ggcagcaccc    7380
aggttttgca ctcttgtttc tcccgtgctt gtgaaagagg tcccaaggtt ctgggtgcag    7440
gagcgctccc ttgacctgct gaagtccgga acgtagtcgg cacagcctgg tcgccttcca    7500
cctctgggag ctggagtcca ctggggtggc ctgactcccc cagtccccctt cccgtgacct    7560 ggtcagggtg agcccatgtg gagtcagcct cgcaggcctc cctgccagta gggtccgagt    7620
gtgtttcatc cttcccactc tgtcgagcct ggggctgga gcggagacgg gaggcctggc    7680
ctgtctcgga acctgtgagc tgcaccaggt agaacgccag ggaccccaga atcatgtgcg    7740
tcagtccaag gggtcccctc caggagtagt gaagactcca gaaatgtccc tttcttctcc    7800
cccatcctac gagtaattgc atttgctttt gtaattctta atgagcaata tctgctagag    7860
agtttagctg taacagttct ttttgatcat ctttttttaa taattagaaa caccaaaaaa    7920
atccagaaac ttgttcttcc aaagcagaga gcattataat caccagggcc aaaagcttcc    7980
ctccctgctg tcattgcttc ttctgaggcc tgaatccaaa agaaaaacag ccataggccc    8040
tttcagtggc cgggctaccc gtgagccctt cggaggacca gggctggggc agcctctggg    8100
cccacatccg gggccagctc cggcgtgtgt tcagtgttag cagtgggtca tgatgctctt    8160
tcccacccag cctgggatag gggcagagga ggcgaggagg ccgttgccgc tgatgtttgg    8220
ccgtgaacag gtgggtgtct gcgtgcgtcc acgtgcgtgt tttctgactg acatgaaatc    8280
gacgcccgag ttagcctcac ccggtgacct ctagccctgc ccggatggag cggggcccac    8340
ccggttcagt gtttctgggg agctggacag tggagtgcaa aaggcttgca gaacttgaag    8400
cctgctcctt cccttgctac cacggcctcc tttccgtttg atttgtcact gcttcaatca    8460
ataacagccg ctccagagtc agtagtcaat gaatatatga ccaaatatca ccaggactgt    8520
tactcaatgt gtgccgagcc cttgcccatg ctgggctccc gtgtatctgg acactgtaac    8580
gtgtgctgtg tttgctcccc ttccccttcc ttctttgccc tttacttgtc tttctggggt    8640
ttttctgttt gggtttggtt tggtttttat ttctcctttt gtgttccaaa catgaggttc    8700
tctctactgg tcctcttaac tgtggtgttg aggcttatat ttgtgtaatt tttggtgggt    8760
gaaaggaatt ttgctaagta aatctcttct gtgtttgaac tgaagtctgt attgtaacta    8820
tgtttaaagt aattgttcca gagacaaata tttctagaca cttttttcttt acaaacaaaa    8880 gcattcggag ggagggggat ggtgactgag atgagagggg agagctgaac agatgacccc    8940
tgcccagatc agccagaagc cacccaaagc agtggagccc aggagtccca ctccaagcca    9000
gcaagccgaa tagctgatgt gttgccactt tccaagtcac tgcaaaacca ggttttgttc    9060
cgcccagtgg attcttgttt tgcttcccct cccccccgaga ttattaccac catcccgtgc    9120
```

-continued

```
ttttaaggaa aggcaagatt gatgtttcct tgaggggagc caggaggga  tgtgtgtgtg    9180
cagagctgaa gagctgggga gaatgggct  gggcccaccc aagcaggagg ctgggacgct    9240
ctgctgtggg cacaggtcag gctaatgttg gcagatgcag ctcttcctgg acaggccagg    9300
tggtgggcat tctctctcca aggtgtgccc cgtgggcatt actgtttaag acacttccgt    9360
cacatcccac cccatcctcc agggctcaac actgtgacat ctctattccc cacctcccc    9420
ttcccagggc aataaaatga ccatggaggg ggcttgcact ctcttggctg tcaccgatc    9480
gccagcaaaa cttagatgtg agaaaacccc ttcccattcc atggcgaaaa catctcctta    9540
gaaaagccat taccctcatt aggcatggtt ttgggctccc aaaacacctg acagcccctc    9600
cctcctctga gaggcggaga gtgctgactg tagtgaccat tgcatgccgg gtgcagcatc    9660
tggaagagct aggcagggtg tctgcccct  cctgagttga agtcatgctc ccctgtgcca    9720
gcccagaggc cgagagctat ggacagcatt gccagtaaca caggccaccc tgtgcagaag    9780
ggagctggct ccagcctgga aacctgtctg aggttgggag aggtgcactt ggggcacagg    9840
gagaggccgg gacacactta gctggagatg tctctaaaag ccctgtatcg tattcacctt    9900
cagtttttgt gttttgggac aattacttta gaaataagt  aggtcgtttt aaaaacaaaa    9960
attattgatt gctttttgt  agtgttcaga aaaaggttc  tttgtgtata gccaaatgac   10020
tgaaagcact gatatattta aaaacaaaag gcaatttatt aaggaaattt gtaccatttc   10080
agtaaacctg tctgaatgta cctgtatacg tttcaaaaac ccccccccc  cactgaatcc   10140
ctgtaaccta tttattatat aaagagtttg ccttataaat tt                      10182
```

<210> SEQ ID NO 26
<211> LENGTH: 1652
<212> TYPE: DNA
<213> ORGANISM: Human

<400> SEQUENCE: 26

```
ttgatgtgac atgtgactcc ccagaataca ccttgcttct gtagaccagc tccaacagga      60
ttccatggta gctgggatgt tagggctcag ggaagaaaag tcagaagacc aggacctcca     120
gggcctcaag gacaaacccc tcaagtttaa aaaggtgaag aaagataaga aagaagagaa     180
agagggcaag catgagcccg tgcagccatc agcccaccac tctgctgagc ccgcagaggc     240
aggcaaagca gagacatcag aagggtcagg ctccgccccg gctgtgccgg aagcttctgc     300
ctcccccaaa cagcggcgct ccatcatccg tgaccgggga cccatgtatg atgaccccac     360
cctgcctgaa ggctggacac ggaagcttaa gcaaaggaaa tctggccgct ctgctgggaa     420
gtatgatgtg tatttgatca atccccaggg aaaagccttt cgctctaaag tggagttgat     480
tgcgtacttc gaaaaggtag gcgacacatc cctggaccct aatgattttg acttcacggt     540
aactgggaga gggagcccct cccggcgaga gcagaaacca cctaagaagc ccaaatctcc     600
caaagctcca ggaactggca gaggccgggg acgcccaaa  gggagcggca ccacgagacc     660
caaggcggcc acgtcagagg gtgtgcaggt gaaaagggtc ctgagaaaaa gtcctgggaa     720
gctccttgtc aagatgcctt ttcaaacttc gccaggggc  aaggctgagg gggtggggc     780
caccacatcc acccaggtca tggtgatcaa acgcccggc  aggaagcgaa agctgaggc     840
cgaccctcag gccattccca agaaacgggg ccgaaagccg gggagtgtgg tggcagccgc     900
tgccgccgag gccaaaaaga agcgtgaag  ggagtcttct atccgatctg tgcaggagac     960
cgtactcccc atcaagaagc gcaagacccg ggagacggtc agcatcgagg tcaaggaagt    1020
ggtgaagccc ctgctggtgt ccaccctcgg tgagaagagc gggaaaggac tgaagacctg    1080
```

-continued

```
taagagccct gggcggaaaa gcaaggagag cagccccaag gggcgcagca gcagcgcctc      1140 ctcaccccc aagaaggagc accaccacca tcaccaccac tcagagtccc caaaggcccc       1200
cgtgccactg ctcccacccc tgcccccacc tccacctgag cccgagagct ccgaggaccc      1260
caccagcccc cctgagcccc aggacttgag cagcagcgtc tgcaaagagg agaagatgcc      1320
cagaggaggc tcactggaga gcgacggttg ccccaaggag ccagctaaga ctcagcccgc      1380
ggttgccacc gccgccacgg ccgcagaaaa gtacaaacac cgaggggagg gagagcgcaa      1440
agacattgtt tcatcctcca tgccaaggcc aaacagagag gagcctgtgg acagccggac      1500
gcccgtgacc gagagagtta gctgactta cacggagcgg attgcaaagc aaaccaacaa      1560
gaataaaggc agctgttgtc tcttctcctt acgggtaggg ctctgacaaa gcttcccgat      1620
taactgaaat aaaaaatatt ttttttcctt tc                                    1652
```

<210> SEQ ID NO 27
<211> LENGTH: 10182
<212> TYPE: DNA
<213> ORGANISM: Human

<400> SEQUENCE: 27

```
ccggaaaatg gccgccgccg ccgccgccgc gccgagcgga ggaggaggag gaggcgagga        60
ggagagactg ctccataaaa atacagactc accagttcct gctttgatgt gacatgtgac       120
tccccagaat acaccttgct tctgtagacc agctccaaca ggattccatg gtagctggga       180
tgttagggct cagggaagaa aagtcagaag accaggacct ccagggcctc aaggacaaac       240
ccctcaagtt taaaaggtg aagaaagata agaaagaaga gaaagagggc aagcatgagc       300
ccgtgcagcc atcagcccac cactctgctg agcccgcaga ggcaggcaaa gcagagacat       360
cagaagggtc aggctccgcc ccggctgtgc cggaagcttc tgcctccccc aaacagcggc       420
gctccatcat ccgtgaccgg ggacccatgt atgatgaccc caccctgcct gaaggctgga       480
cacggaagct taagcaaagg aaatctggcc gctctgctgg gaagtatgat gtgtatttga       540
tcaatcccca gggaaaagcc tttcgctcta agtggagtt gattgcgtac ttcgaaaagg       600
taggcgacac atccctggac cctaatgatt ttgacttcac ggtaactggg agagggagcc       660
cctcccggcg agagcagaaa ccacctaaga agcccaaatc tcccaaagct ccaggaactg       720
gcagaggccg gggacgcccc aaagggagcg gcaccacgag acccaaggcg ccacgtcag       780 agggtgtgca ggtgaaaagg gtcctggaga aaagtcctgg gaagctcctt gtcaagatgc       840
cttttcaaac ttcgccaggg ggcaaggctg aggggggtgg ggccaccaca tccacccagg       900
tcatggtgat caaacgcccc ggcaggaagc gaaaagctga ggccgaccct caggccattc       960
ccaagaaacg gggccgaaag ccggggagtg tggtggcagc cgctgccgcc gaggccaaaa      1020
agaaagccgt gaaggagtct tctatccgat ctgtgcagga gaccgtactc cccatcaaga      1080
agcgcaagac ccgggagacg gtcagcatcg aggtcaagga agtggtgaag ccctgctgg       1140 tgtccaccct cggtgagaag agcggaaag gactgaagac ctgtaagagc cctgggcgga      1200
aaagcaagga gagcagcccc aaggggcgca gcagcagcgc ctcctcaccc cccaagaagg      1260
agcaccacca ccatcaccac cactcagagt ccccaaaggc cccgtgcca ctgctcccac       1320 ccctgccccc acctccacct gagcccgaga gctccgagga cccaccagc cccctgagc       1380 cccaggactt gagcagcagc gtctgcaaag aggagaagat gccagagga ggctcactgg      1440 agagcgacgg ctgccccaag gagccagcta agactcagcc cgcggttgcc accgccgcca      1500
```

```
cggccgcaga aaagtacaaa caccgagggg agggagagcg caaagacatt gtttcatcct   1560
ccatgccaag gccaaacaga gaggagcctg tggacagccg gacgcccgtg accgagagag   1620
ttagctgact ttacacggag cggattgcaa agcaaaccaa caagaataaa ggcagctgtt   1680
gtctcttctc cttatgggta gggctctgac aaagcttccc gattaactga aataaaaaat   1740 atttttttt ctttcagtaa acttagagtt tcgtggcttc agggtgggag tagttggagc    1800
attggggatg tttttcttac cgacaagcac agtcaggttg aagacctaac cagggccaga   1860
agtagctttg cacttttcta aactaggctc cttcaacaag gcttgctgca gatactactg   1920
accagacaag ctgttgacca ggcacctccc ctcccgccca aacctttccc ccatgtggtc   1980
gttagagaca gagcgacaga gcagttgaga ggacactccc gttttcggtg ccatcagtgc   2040
cccgtctaca gctcccccag ctccccccac ctcccccact cccaaccacg ttgggacagg   2100
gaggtgtgag gcaggagaga cagttggatt ctttagagaa gatggatatg accagtggct   2160
atggcctgtg cgatcccacc cgtggtggct caagtctggc cccacaccag ccccaatcca   2220
aaactggcaa ggacgcttca caggacagga aagtggcacc tgtctgctcc agctctggca   2280
tggctaggag gggggagtcc cttgaactac tgggtgtaga ctggcctgaa ccacaggaga   2340
ggatggccca gggtgaggtg gcatggtcca ttctcaaggg acgtcctcca acgggtggcg   2400
ctagaggcca tggaggcagt aggacaaggt gcaggcaggc tggcctgggg tcaggccggg   2460
cagagcacag cggggtgaga gggattccta atcactcaga gcagtctgtg acttagtgga   2520
caggggaggg ggcaaagggg gaggagaaga aaatgttctt ccagttactt tccaattctc   2580
ctttagggac agcttagaat tatttgcact attgagtctt catgttccca cttcaaaaca   2640
aacagatgct ctgagagcaa actggcttga attggtgaca tttagtccct caagccacca   2700
gatgtgacag tgttgagaac tacctggatt tgtatatata cctgcgcttg ttttaaagtg   2760
ggctcagcac atagggttcc cacgaagctc cgaaactcta agtgtttgct gcaattttat   2820
aaggacttcc tgattggttt ctcttctccc cttccatttc tgccttttgt tcatttcatc   2880 cttttcacttc tttcccttcc tccgtcctcc tccttcctag ttcatccctt ctcttccagg   2940
cagccgcggt gcccaaccac acttgtcggc tccagtcccc agaactctgc ctgccctttg   3000
tcctcctgct gccagtacca gccccaccct gttttgagcc ctgaggaggc cttgggctct   3060
gctgagtccg acctggcctg tctgtgaaga gcaagagagc agcaaggtct tgctctccta   3120
ggtagccccc tcttccctgg taagaaaaag caaaaggcat ttcccaccct gaacaacgag   3180
ccttttcacc cttctactct agagaagtgg actggaggag ctgggcccga tttggtagtt   3240
gaggaaagca cagaggcctc ctgtggcctg ccagtcatcg agtggcccaa caggggctcc   3300
atgccagccg accttgacct cactcagaag tccagagtct agcgtagtgc agcagggcag   3360
tagcggtacc aatgcagaac tcccaagacc cgagctggga ccagtacctg ggtccccagc   3420
ccttcctctg ctccccctttt tccctcggag ttcttcttga atggcaatgt tttgcttttg   3480
ctcgatgcag acagggggcc agaacaccac acatttcact gtctgtctgg tccatagctg   3540
tggtgtaggg gcttagaggc atgggcttgc tgtgggtttt taattgatca gttttcatgt   3600
gggatcccat ctttttaacc tctgttcagg aagtccttat ctagctgcat atcttcatca   3660
tattggtata tccttttctg tgtttacaga gatgtctctt atatctaaat ctgtccaact   3720
gagaagtacc ttatcaaagt agcaaatgag acagcagtct tatgcttcca gaaacaccca   3780
ccttcctgtc ccatgtgagc tgctgccatg aactgtcaag tgtgtgttgt cttgtgtatt   3840
tcagttattg tccctggctt ccttactatg gtgtaatcat gaaggagtga acatcatag    3900
```

```
aaactgtcta gcacttcctt gccagtcttt agtgatcagg aaccatagtt gacagttcca    3960
atcagtagct taagaaaaaa ccgtgtttgt ctcttctgga atggttagaa gtgagggagt    4020
ttgccccgtt ctgtttgtag agtctcatag ttggactttc tagcatatat gtgtccattt    4080
ccttatgctg taaaagcaag tcctgcaacc aaactcccat cagcccaatc cctgatccct    4140
gatcccttcc acctgctctg ctgatgaccc ccccagcttc acttctgact cttccccagg    4200
aagggaaggg gggtcagaag agagggtgag tcctccagaa ctcttcctcc aaggacagaa    4260
ggctcctgcc cccatagtgg cctcgaactc ctggcactac caaaggacac ttatccacga    4320
gagcgcagca tccgaccagg ttgtcactga aagatgtttt attttggtca gttgggtttt    4380
tatgtattat acttagtcaa atgtaatgtg gcttctggaa tcattgtcca gagctgcttc    4440
cccgtcacct gggcgtcatc tggtcctggt aagaggagtg cgtggcccac caggcccccc    4500
tgtcacccat gacagttcat tcagggccga tggggcagtc gtggttggga acacagcatt    4560
tcaagcgtca ctttatttca ttcgggcccc acctgcagct ccctcaaaga ggcagttgcc    4620
cagcctcttt cccttccagt ttattccaga gctgccagtg gggcctgagg ctccttaggg    4680
ttttctctct atttccccct ttcttcctca ttccctcgtc tttcccaaag gcatcacgag    4740
tcagtcgcct ttcagcaggc agccttggcg gtttatcgcc ctggcaggca ggggccctgc    4800
agctctcatg ctgcccctgc cttggggtca ggttgacagg aggttggagg gaaagcctta    4860
agctgcagga ttctcaccag ctgtgtccgg cccagttttg gggtgtgacc tcaatttcaa    4920
ttttgtctgt acttgaacat tatgaagatg ggggcctctt tcagtgaatt tgtgaacagc    4980
agaattgacc gacagctttc cagtacccat ggggctaggt cattaaggcc acatccacag    5040
tctcccccac ccttgttcca gttgttagtt actacctcct ctcctgacaa tactgtatgt    5100
cgtcgagctc cccccaggtc taccectccc ggccctgcct gctggtgggc ttgtcatagc    5160
cagtgggatt gccggtcttg acagctcagt gagctggaga tacttggtca cagccaggcg    5220
ctagcacagc tcccttctgt tgatgctgta ttcccatatc aaaagacaca ggggacaccc    5280
agaaacgcca catcccccaa tccatcagtg ccaaactagc caacggcccc agcttctcag    5340
ctcgctggat ggcggaagct gctactcgta gcgccagtg cgggtgcaga caatcttctg     5400
ttgggtggca tcattccagg cccgaagcat gaacagtgca cctgggacag ggagcagccc    5460
caaattgtca cctgcttctc tgcccagctt ttcattgctg tgacagtgat ggcgaaagag    5520
ggtaataacc agacacaaac tgccaagttg ggtggagaaa ggagtttctt tagctgacag    5580
aatctctgaa ttttaaatca cttagtaagc ggctcaagcc caggagggag cagaggata    5640 cgagcggagt cccctgcgcg ggaccatctg gaattggttt agcccaagtg gagcctgaca    5700
gccagaactc tgtgtccccc gtctaaccac agctccttt ccagagcatt ccagtcaggc     5760
tctctgggct gactgggcca ggggaggtta caggtaccag ttctttaaga agatctttgg    5820
gcatatacat ttttagcctg tgtcattgcc ccaaatggat tcctgtttca agttcacacc    5880
tgcagattct aggacctgtg tcctagactt cagggagtca gctgtttcta gagttcctac    5940
catggagtgg gtctggagga cctgcccggt gggggggcag agccctgctc cctccgggtc    6000
ttcctactct tctctctgct ctgacgggat ttgttgattc tctccatttt ggtgtctttc    6060
tcttttagat attgtatcaa tctttagaaa aggcatagtc tacttgttat aaatcgttag    6120
gatactgcct ccccccaggg t ctaaaattac atattagagg ggaaaagctg aacactgaag   6180
tcagttctca acaatttaga aggaaaacct agaaaacatt tggcagaaaa ttacatttcg    6240
```

```
atgttttga atgaatacga gcaagctttt acaacagtgc tgatctaaaa atacttagca    6300
cttggcctga gatgcctggt gagcattaca ggcaagggga atctggaggt agccgacctg    6360
aggacatggc ttctgaacct gtcttttggg agtggtatgg aaggtggagc gttcaccagt    6420
gacctggaag gcccagcacc accctccttc ccactcttct catcttgaca gagcctgccc    6480
cagcgctgac gtgtcaggaa acacccagg gaactaggaa ggcacttctg cctgaggggc    6540
agcctgcctt gcccactcct gctctgctcg cctcggatca gctgagcctt ctgagctggc    6600
ctctcactgc ctccccaagg cccctgcct gccctgtcag gaggcagaag gaagcaggtg    6660
tgagggcagt gcaaggaggg agcacaaccc ccagctcccg ctccgggctc cgacttgtgc    6720
acaggcagag cccagaccct ggaggaaatc ctacctttga attcaagaac atttggggaa    6780
tttggaaatc tctttgcccc caaaccccca ttctgtccta cctttaatca ggtcctgctc    6840
agcagtgaga gcagatgagg tgaaaaggcc aagaggtttg gctcctgccc actgatagcc    6900
cctctccccg cagtgtttgt gtgtcaagtg gcaaagctgt tcttcctggt gaccctgatt    6960
atatccagta acacatagac tgtgcgcata ggcctgcttt gtctcctcta tcctgggctt    7020
ttgttttgct ttttagtttt gcttttagtt tttctgtccc ttttatttaa cgcaccgact    7080
agacacacaa agcagttgaa tttttatata tatatctgta tattgcacaa ttataaactc    7140
attttgcttg tggctccaca cacacaaaaa aagacctgtt aaaattatac ctgttgctta    7200
attacaatat ttctgataac catagcatag gacaagggaa aataaaaaaa gaaaaaaaag    7260
aaaaaaaaac gacaaatctg tctgctggtc acttcttctg tccaagcaga ttcgtggtct    7320
tttcctcgct tctttcaagg gctttcctgt gccaggtgaa ggaggctcca ggcagcaccc    7380
aggttttgca ctcttgtttc tcccgtgctt gtgaaagagg tcccaaggtt ctgggtgcag    7440
gagcgctccc ttgacctgct gaagtccgga acgtagtcgg cacagcctgg tcgccttcca    7500
cctctgggag ctggagtcca ctggggtggc ctgactcccc cagtccccctt cccgtgacct    7560 ggtcagggtg agcccatgtg gagtcagcct cgcaggcctc cctgccagta gggtccgagt    7620
gtgtttcatc cttcccactc tgtcgagcct gggggctgga gcggagacgg gaggcctggc    7680
ctgtctcgga acctgtgagc tgcaccaggt agaacgccag ggaccccaga atcatgtgcg    7740
tcagtccaag gggtcccctc caggagtagt gaagactcca gaaatgtccc tttcttctcc    7800
cccatcctac gagtaattgc atttgctttt gtaattctta atgagcaata tctgctagag    7860
agtttagctg taacagttct ttttgatcat ctttttttaa taattagaaa caccaaaaaa    7920
atccagaaac ttgttcttcc aaagcagaga gcattataat caccagggcc aaaagcttcc    7980
ctccctgctg tcattgcttc ttctgaggcc tgaatccaaa agaaaaacag ccataggccc    8040
tttcagtggc cgggctaccc gtgagccctt cggaggacca gggctggggc agcctctggg    8100
cccacatccg gggccagctc cggcgtgtgt tcagtgttag cagtgggtca tgatgctctt    8160
tcccacccag cctgggatag gggcagagga ggcgaggagg ccgttgccgc tgatgtttgg    8220
ccgtgaacag gtgggtgtct gcgtgcgtcc acgtgcgtgt tttctgactg acatgaaatc    8280
gacgcccgag ttagcctcac ccggtgacct ctagccctgc ccggatggag cggggcccac    8340
ccggttcagt gttctggggg agctggacag tggagtgcaa aaggcttgca gaacttgaag    8400
cctgctcctt cccttgctac cacggcctcc tttccgtttg atttgtcact gcttcaatca    8460
ataacagccg ctccagagtc agtagtcaat gaatatatga ccaaatatca ccaggactgt    8520
tactcaatgt gtgccgagcc cttgcccatg ctgggctccc gtgtatctgg acactgtaac    8580
gtgtgctgtg tttgctcccc ttccccttcc ttctttgccc tttacttgtc tttctgggt    8640
```

```
ttttctgttt gggtttggtt tggtttttat ttctccttt gtgttccaaa catgaggttc      8700
tctctactgg tcctcttaac tgtggtgttg aggcttatat ttgtgtaatt tttggtgggt      8760
gaaaggaatt ttgctaagta aatctcttct gtgtttgaac tgaagtctgt attgtaacta      8820
tgtttaaagt aattgttcca gagacaaata tttttctttt acaaacaaaa                8880
gcattcggag ggaggggat ggtgactgag atgagagggg agagctgaac agatgacccc      8940
tgcccagatc agccagaagc cacccaaagc agtggagccc aggagtccca ctccaagcca      9000
gcaagccgaa tagctgatgt gttgccactt tccaagtcac tgcaaaacca ggttttgttc      9060
cgcccagtgg attcttgttt tgcttcccct ccccccgaga ttattaccac catcccgtgc      9120
ttttaaggaa aggcaagatt gatgtttcct tgaggggagc caggagggga tgtgtgtgtg      9180
cagagctgaa gagctgggga gaatggggct gggcccaccc aagcaggagg ctgggacgct      9240
ctgctgtggg cacaggtcag gctaatgttg gcagatgcag ctcttcctgg acaggccagg      9300
tggtgggcat tctctctcca aggtgtgccc cgtgggcatt actgtttaag acacttccgt      9360
cacatcccac cccatcctcc agggctcaac actgtgacat ctctattccc caccctcccc      9420
ttcccagggc aataaaatga ccatggaggg ggcttgcact ctcttggctg tcacccgatc      9480
gccagcaaaa cttagatgtg agaaaacccc ttcccattcc atggcgaaaa catctcctta      9540
gaaaagccat taccctcatt aggcatggtt ttgggctccc aaaacacctg acagccctc      9600
cctcctctga gaggcggaga gtgctgactg tagtgaccat tgcatgccgg gtgcagcatc      9660
tggaagagct aggcagggtg tctgcccct cctgagttga agtcatgctc ccctgtgcca      9720
gcccagaggc cgagagctat ggacagcatt gccagtaaca caggccaccc tgtgcagaag      9780
ggagctggct ccagcctgga aacctgtctg aggttgggag aggtgcactt ggggcacagg      9840
gagaggccgg gacacactta gctggagatg tctctaaaag ccctgtatcg tattcaccttt     9900
cagtttttgt gttttgggac aattacttta gaaaataagt aggtcgtttt aaaaacaaaa      9960
attattgatt gcttttttgt agtgttcaga aaaaggttc tttgtgtata gccaaatgac      10020
tgaaagcact gatatattta aaacaaaag gcaatttatt aaggaaattt gtaccatttc      10080
agtaaacctg tctgaatgta cctgtatacg tttcaaaaac cccccccc cactgaatcc      10140
ctgtaaccta tttattatat aaagagttg ccttataaat tt                        10182
```

<210> SEQ ID NO 28
<211> LENGTH: 10182
<212> TYPE: DNA
<213> ORGANISM: Human

<400> SEQUENCE: 28

```
ccggaaaatg gccgccgccg ccgccgccgc gccgagcgga ggaggaggag gaggcgagga       60
ggagagactg ctccataaaa atacagactc accagttcct gctttgatgt gacatgtgac      120
tccccagaat acaccttgct tctgtagacc agctccaaca ggattccatg gtagctggga      180
tgttagggct cagggaagaa aagtcagaag accaggacct ccagggcctc aaggacaaac      240
ccctcaagtt taaaaggtg aagaaagata agaaagaaga gaaagagggc aagcatgagc      300
ccgtgcagcc atcagcccac cactctgctg agcccgcaga ggcaggcaaa gcagagacat      360
cagaagggtc aggctccgcc ccggctgtgc cggaagcttc tgcctccccc aaacagcggc      420
gctccatcat ccgtgaccgg ggacccatgt atgatgaccc caccctgcct gaaggctgga      480
cacggaagct taagcaaagg aaatctggcc gctctgctgg gaagtatgat gtgtatttga      540
```

-continued

| | | |
|---|---|---|
| taggcgccca gggaaaagcc tttcgctcta aagtggagtt gattgcgtac ttcgaaaagg | 600 |
| taggcgacac atccctggac cctaatgatt ttgacttcac ggtaactggg agagggagcc | 660 |
| cctcccggcg agagcagaaa ccacctaaga agcccaaatc tcccaaagct ccaggaactg | 720 |
| gcagaggccg gggacgcccc aaagggagcg gcaccacgag acccaaggcg gccacgtcag | 780 |
| agggtgtgca ggtgaaaagg gtcctggaga aagtcctgg gaagctcctt gtcaagatgc | 840 |
| cttttcaaac ttcgccaggg ggcaaggctg agggggggtgg ggccaccaca tccacccagg | 900 |
| tcatggtgat caaacgcccc ggcaggaagc gaaaagctga ggccgaccct caggccattc | 960 |
| ccaagaaacg gggccgaaag ccggggagtg tggtggcagc cgctgccgcc gaggccaaaa | 1020 |
| agaaagccgt gaaggagtct tctatccgat ctgtgcagga gaccgtactc cccatcaaga | 1080 |
| agcgcaagac ccgggagacg gtcagcatcg aggtcaagga agtggtgaag cccctgctgg | 1140 |
| tgtccaccct cggtgagaag agcgggaaag gactgaagac ctgtaagagc cctgggcgga | 1200 |
| aaagcaagga gagcagcccc aagggggcgca gcagcagcgc ctcctcaccc cccaagaagg | 1260 |
| agcaccacca ccatcaccac cactcagagt ccccaaaggc ccccgtgcca ctgctcccac | 1320 |
| ccctgccccc acctccacct gagcccgaga gctccgagga cccaccagc cccctgagc | 1380 |
| cccaggactt gagcagcagc gtctgcaaag aggagaagat gcccagagga ggctcactgg | 1440 |
| agagcgacgg ctgccccaag gagccagcta agactcagcc cgcggttgcc accgccgcca | 1500 |
| cggccgcaga aaagtacaaa caccgagggg agggagagcg caaagacatt gtttcatcct | 1560 |
| ccatgccaag gccaaacaga gaggagcctg tggacagccg gacgccgtg accgagagag | 1620 |
| ttagctgact ttacacggag cggattgcaa agcaaaccaa caagaataaa ggcagctgtt | 1680 |
| gtctcttctc cttatgggta gggctctgac aaagcttccc gattaactga aataaaaaat | 1740 |
| atttttttt ctttcagtaa acttagagtt tcgtggcttc agggtgggag tagttggagc | 1800 |
| attggggatg ttttcttac cgacaagcac agtcaggttg aagacctaac cagggccaga | 1860 |
| agtagctttg cacttttcta aactaggctc cttcaacaag gcttgctgca gatactactg | 1920 |
| accagacaag ctgttgacca ggcacctccc ctcccgccca aacctttccc ccatgtggtc | 1980 |
| gttagagaca gagcgacaga gcagttgaga ggacactccc gttttcggtg ccatcagtgc | 2040 |
| cccgtctaca gctcccccag ctcccccac ctccccact cccaaccacg ttgggacagg | 2100 |
| gaggtgtgag gcaggagaga cagttggatt ctttagagaa gatggatatg accagtggct | 2160 |
| atggcctgtg cgatcccacc cgtggtggct caagtctggc cccacaccag ccccaatcca | 2220 |
| aaactggcaa ggacgcttca caggacagga aagtggcacc tgtctgctcc agctctggca | 2280 |
| tggctaggag gggggagtcc cttgaactac tgggtgtaga ctggcctgaa ccacaggaga | 2340 |
| ggatggccca gggtgaggtg gcatggtcca ttctcaaggg acgtcctcca acgggtggcg | 2400 |
| ctagaggcca tggaggcagt aggacaaggt gcaggcaggc tggcctgggg tcaggccggg | 2460 |
| cagagcacag cggggtgaga gggattccta atcactcaga gcagtctgtg acttagtgga | 2520 |
| caggggaggg ggcaaagggg gaggagaaga aaatgttctt ccagttactt tccaattctc | 2580 |
| ctttagggac agcttagaat tatttgcact attgagtctt catgttccca cttcaaaaca | 2640 |
| aacagatgct ctgagagcaa actggcttga attggtgaca tttagtccct caagccacca | 2700 |
| gatgtgacag tgttgagaac tacctggatt tgtatatata cctgcgcttg ttttaaagtg | 2760 |
| ggctcagcac atagggttcc cacgaagctc cgaaactcta agtgtttgct gcaattttat | 2820 |
| aaggacttcc tgattggttt ctcttctccc cttccatttc tgccttttgt tcatttcatc | 2880 |
| cttttcacttc tttcccttcc tccgtcctcc tccttcctag ttcatcccctt ctcttccagg | 2940 |

-continued

```
cagccgcggt gcccaaccac acttgtcggc tccagtcccc agaactctgc ctgcccttttg   3000 tcctcctgct gccagtacca gccccaccct gttttgagcc ctgaggaggc cttgggctct   3060
gctgagtccg acctggcctg tctgtgaaga gcaagagagc agcaaggtct tgctctccta   3120
ggtagccccc tcttccctgg taagaaaaag caaaaggcat ttcccaccct gaacaacgag   3180
ccttttcacc cttctactct agagaagtgg actggaggag ctgggcccga tttggtagtt   3240
gaggaaagca cagaggcctc ctgtggcctg ccagtcatcg agtggcccaa caggggctcc   3300
atgccagccg accttgacct cactcagaag tccagagtct agcgtagtgc agcagggcag   3360
tagcggtacc aatgcagaac tcccaagacc cgagctggga ccagtacctg ggtccccagc   3420
ccttcctctg ctcccccttt tccctcggag ttcttcttga atggcaatgt tttgcttttg   3480
ctcgatgcag acaggggggcc agaacaccac acatttcact gtctgtctgg tccatagctg   3540
tggtgtaggg gcttagaggc atgggcttgc tgtgggtttt taattgatca gtttttcatgt   3600 gggatcccat ctttttaacc tctgttcagg aagtccttat ctagctgcat atcttcatca   3660
tattggtata tcctttttctg tgtttacaga gatgtctctt atatctaaat ctgtccaact   3720
gagaagtacc ttatcaaagt agcaaatgag acagcagtct tatgcttcca gaaacaccca   3780
caggcatgtc ccatgtgagc tgctgccatg aactgtcaag tgtgtgttgt cttgtgtatt   3840
tcagttattg tccctggctt ccttactatg gtgtaatcat gaaggagtga aacatcatag   3900
aaactgtcta gcacttcctt gccagtcttt agtgatcagg aaccatagtt gacagttcca   3960
atcagtagct taagaaaaaa ccgtgtttgt ctcttctgga atggttagaa gtgagggagt   4020
ttgccccgtt ctgttttgtag agtctcatag ttggactttc tagcatatat gtgtccatttt   4080 ccttatgctg taaaagcaag tcctgcaacc aaactcccat cagcccaatc cctgatccct   4140
gatcccttcc acctgctctg ctgatgaccc cccagcttc acttctgact cttccccagg   4200
aagggaaggg gggtcagaag agagggtgag tcctccagaa ctcttcctcc aaggacagaa   4260
ggctcctgcc cccatagtgg cctcgaactc ctggcactac caaggacac ttatccacga   4320 gagcgcagca tccgaccagg ttgtcactga aagatgttt attttggtca gttgggtttt   4380
tatgtattat acttagtcaa atgtaatgtg gcttctggaa tcattgtcca gagctgcttc   4440
cccgtcacct gggcgtcatc tggtcctggt aagaggagtg cgtggcccac caggccccc   4500 tgtcacccat gacagttcat tcagggccga tggggcagtc gtggttggga acacagcatt   4560
tcaagcgtca ctttatttca ttcgggcccc acctgcagct ccctcaaaga ggcagttgcc   4620
cagcctcttt cccttccagt ttattccaga gctgccagtg gggcctgagg ctccttaggg   4680
ttttctctct atttccccct ttcttcctca ttccctcgtc tttcccaaag gcatcacgag   4740
tcagtcgcct ttcagcaggc agccttggcg gtttatcgcc ctggcaggca ggggccctgc   4800
agctctcatg ctgcccctgc cttggggtca ggttgacagg aggttggagg gaaagcctta   4860
agctgcagga ttctcaccag ctgtgtccgg cccagttttg gggtgtgacc tcaatttcaa   4920
ttttgtctgt acttgaacat tatgaagatg ggggcctctt tcagtgaatt tgtgaacagc   4980
agaattgacc gacagctttc cagtacccat ggggctaggt cattaaggcc acatccacag   5040
tctcccccac ccttgttcca gttgttagtt actacctcct ctcctgacaa tactgtatgt   5100
cgtcgagctc cccccaggtc tacccctccc ggccctgcct gctggtgggc ttgtcatagc   5160
cagtgggatt gccggtcttg acagctcagt gagctggaga tacttggtca cagccaggcg   5220
ctagcacagc tcccttctgt tgatgctgta ttcccatatc aaaagacaca ggggacaccc   5280
```

-continued

```
agaaacgcca catcccccaa tccatcagtg ccaaactagc caacggcccc agcttctcag      5340
ctcgctggat ggcggaagct gctactcgtg agcgccagtg cgggtgcaga caatcttctg      5400
ttgggtggca tcattccagg cccgaagcat gaacagtgca cctgggacag ggagcagccc      5460
caaattgtca cctgcttctc tgcccagctt ttcattgctg tgacagtgat ggcgaaagag      5520
ggtaataacc agacacaaac tgccaagttg gtgtggagaaa ggagtttctt tagctgacag      5580
aatctctgaa ttttaaatca cttagtaagc ggctcaagcc caggagggag cagagggata      5640
cgagcggagt cccctgcgcg ggaccatctg gaattggttt agcccaagtg gagcctgaca      5700
gccagaactc tgtgtccccc gtctaaccac agctccttt ccagagcatt ccagtcaggc       5760
tctctgggct gactgggcca ggggaggtta caggtaccag ttcttaaga agatctttgg       5820 gcatatacat ttttagcctg tgtcattgcc ccaaatggat tcctgtttca agttcacacc     5880
tgcagattct aggacctgtg tcctagactt cagggagtca gctgtttcta gagttcctac      5940
catggagtgg gtctggagga cctgcccggt ggggggcag agccctgctc cctccgggtc       6000
ttcctactct tctctctgct ctgacgggat ttgttgattc tctccatttt ggtgtcttc      6060 tcttttagat attgtatcaa tctttagaaa aggcatagtc tacttgttat aaatcgttag      6120
gatactgcct cccccaggt ctaaaattac atattagagg ggaaaagctg aacactgaag       6180
tcagttctca acaatttaga aggaaaacct agaaaacatt tggcagaaaa ttacatttcg      6240
atgtttttga atgaatacga gcaagctttt acaacagtgc tgatctaaaa atacttagca     6300
cttggcctga gatgcctggt gagcattaca ggcaagggga atctggaggt agccgacctg      6360
aggacatggc ttctgaacct gtcttttggg agtggtatgg aaggtggagc gttcaccagt     6420
gacctggaag gcccagcacc accctccttc ccactcttct catcttgaca gagcctgccc      6480
cagcgctgac gtgtcaggaa acacccagg gaactaggaa ggcacttctg cctgaggggc     6540
agcctgcctt gcccactcct gctctgctcg cctcggatca gctgagcctt ctgagctggc     6600
ctctcactgc ctcccaagg ccccctgcct gccctgtcag gaggcagaag gaagcaggtg     6660
tgagggcagt gcaaggaggg agcacaaccc ccagctcccg ctccgggctc cgacttgtgc     6720
acaggcagag cccagaccct ggaggaaatc ctacctttga attcaagaac atttggggaa      6780
tttggaaatc tctttgcccc caaaccccca ttctgtccta cctttaatca ggtcctgctc      6840
agcagtgaga gcagatgagg tgaaaaggcc aagaggtttg gctcctgccc actgatagcc      6900
cctctccccg cagtgtttgt gtgtcaagtg gcaaagctgt tcttcctggt gaccctgatt      6960
atatccagta acacatagac tgtgcgcata ggcctgcttt gtctcctcta tcctgggctt     7020
ttgttttgct ttttagtttt gcttttagtt ttctgtcccc ttttatttaa cgcaccgact     7080
agacacacaa agcagttgaa ttttatata tatatctgta tattgcacaa ttataaactc      7140
attttgcttg tggctccaca cacacaaaaa aagacctgtt aaaattatac ctgttgctta     7200
attacaatat ttctgataac catagcatag gacaagggaa aataaaaaaa gaaaaaaaag     7260
aaaaaaaaac gacaaatctg tctgctggtc acttcttctg tccaagcaga ttcgtggtct     7320
tttcctcgct tctttcaagg gctttcctgt gccaggtgaa ggaggctcca ggcagcaccc     7380
aggttttgca ctcttgttc tcccgtgctt gtgaaagagg tcccaaggtt ctgggtgcag      7440
gagcgctccc ttgacctgct gaagtccgga acgtagtcgg cacagcctgg tcgccttcca     7500
cctctgggag ctggagtcca ctggggtggc ctgactcccc cagtcccctt cccgtgacct    7560
ggtcagggtg agcccatgtg gagtcagcct cgcaggcctc cctgccagta gggtccgagt     7620
gtgtttcatc cttcccactc tgtcgagcct gggggctgga gcggagacgg gaggcctggc     7680
```

```
ctgtctcgga acctgtgagc tgcaccaggt agaacgccag ggaccccaga atcatgtgcg    7740
tcagtccaag gggtcccctc caggagtagt gaagactcca gaaatgtccc tttcttctcc    7800
cccatcctac gagtaattgc atttgctttt gtaattctta atgagcaata tctgctagag    7860
agtttagctg taacagttct ttttgatcat cttttttaa taattagaaa caccaaaaaa     7920
atccagaaac ttgttcttcc aaagcagaga gcattataat caccagggcc aaaagcttcc    7980
ctccctgctg tcattgcttc ttctgaggcc tgaatccaaa agaaaaacag cataggccc     8040 tttcagtggc cgggctaccc gtgagccctt cggaggacca gggctgggc agcctctggg     8100 cccacatccg gggccagctc cggcgtgtgt tcagtgttag cagtgggtca tgatgctctt    8160
tcccacccag cctgggatag gggcagagga ggcgaggagg ccgttgccgc tgatgtttgg    8220
ccgtgaacag gtgggtgtct gcgtgcgtcc acgtgcgtgt tttctgactg acatgaaatc    8280
gacgcccgag ttagcctcac ccggtgacct ctagccctgc ccggatggag cggggcccac    8340
ccggttcagt gtttctgggg agctggacag tggagtgcaa aaggcttgca gaacttgaag    8400
cctgctcctt cccttgctac cacggcctcc tttccgtttg atttgtcact gcttcaatca    8460
ataacagccg ctccagagtc agtagtcaat gaatatatga ccaaatatca ccaggactgt    8520
tactcaatgt gtgccgagcc cttgcccatg ctgggctccc gtgtatctgg acactgtaac    8580
gtgtgctgtg tttgctcccc ttccccttcc ttctttgccc tttacttgtc tttctggggt    8640
ttttctgttt gggtttggtt tggttttat ttctccttt gtgttccaaa catgaggttc      8700
tctctactgg tcctcttaac tgtggtgttg aggcttatat ttgtgtaatt tttggtgggt    8760
gaaaggaatt ttgctaagta aatctcttct gtgtttgaac tgaagtctgt attgtaacta    8820
tgtttaaagt aattgttcca gagacaaata tttctagaca cttttctt acaaacaaaa      8880 gcattcggag ggagggggat ggtgactgag atgagagggg agagctgaac agatgacccc    8940
tgcccagatc agccagaagc cacccaaagc agtggagccc aggagtccca ctccaagcca    9000
gcaagccgaa tagctgatgt gttgccactt tccaagtcac tgcaaaacca ggttttgttc    9060
cgcccagtgg attcttgttt tgcttcccct ccccccgaga ttattaccac catcccgtgc    9120
ttttaaggaa aggcaagatt gatgtttcct tgaggggagc caggagggga tgtgtgtgtg    9180
cagagctgaa gagctgggga gaatgggct gggcccaccc aagcaggagg ctgggacgct     9240
ctgctgtggg cacaggtcag gctaatgttg gcagatgcag ctcttcctgg acaggccagg    9300
tggtgggcat tctctctcca aggtgtgccc cgtgggcatt actgtttaag acacttccgt    9360
cacatcccac cccatcctcc agggctcaac actgtgacat ctctattccc caccctcccc    9420
ttcccagggc aataaaatga ccatggaggg ggcttgcact ctcttggctg tcacccgatc    9480
gccagcaaaa cttagatgtg agaaaacccc ttcccattcc atggcgaaaa catctcctta    9540
gaaaagccat taccctcatt aggcatggtt ttgggctccc aaaacacctg acagcccctc    9600
cctcctctga gaggcggaga gtgctgactg tagtgaccat tgcatgccgg gtgcagcatc    9660
tggaagagct aggcagggtg tctgcccct cctgagttga agtcatgctc ccctgtgcca     9720 gcccagagc cgagagctat ggacagcatt gccagtaaca caggccaccc tgtgcagaag     9780
ggagctggct ccagcctgga aacctgtctg aggttgggag aggtgcactt ggggcacagg    9840
gagaggccgg gacacactta gctggagatg tctctaaaag ccctgtatcg tattcacctt    9900 cagttttgt gttttgggac aattacttta gaaataagt aggtcgtttt aaaaacaaaa      9960
attattgatt gcttttttgt agtgttcaga aaaaggttc tttgtgtata gccaaatgac    10020
```

-continued

| | | | | |
|---|---|---|---|---|
| tgaaagcact | gatatattta | aaaacaaaag | gcaatttatt | aaggaaattt | gtaccatttc | 10080 |
| agtaaacctg | tctgaatgta | cctgtatacg | tttcaaaaac | acccccccc | cactgaatcc | 10140 |
| ctgtaaccta | tttattatat | aaagagtttg | ccttataaat | tt | | 10182 |

<210> SEQ ID NO 29
<211> LENGTH: 10087
<212> TYPE: DNA
<213> ORGANISM: Mouse

<400> SEQUENCE: 29

| | | | | | |
|---|---|---|---|---|---|
| accttgcttc | tgtagaccag | ctccaacagg | attccatggt | agctgggatg | ttagggctca | 60 |
| gggaggaaaa | gtcagaagac | caggatctcc | agggcctcag | agacaagcca | ctgaagttta | 120 |
| agaaggcgaa | gaaagacaag | aaggaggaca | agaaggcaa | gcatgagcca | ctacaacctt | 180 |
| cagcccacca | ttctgcagag | ccagcagagg | caggcaaagc | agaaacatca | gaaagctcag | 240 |
| gctctgcccc | agcagtgcca | gaagcctcgg | cttcccccaa | acagcggcgc | tccattatcc | 300 |
| gtgaccgggg | acctatgtat | gatgacccca | ccttgcctga | aggttggaca | cgaaagctta | 360 |
| aacaaaggaa | gtctggccga | tctgctggaa | agtatgatgt | atatttgatc | aatccccagg | 420 |
| gaaaagcttt | tcgctctaaa | gtagaattga | ttgcatactt | tgaaaaggtg | ggagacacct | 480 |
| ccttggaccc | taatgatttt | gacttcacgg | taactgggag | agggagcccc | tccaggagag | 540 |
| agcagaaacc | acctaagaag | cccaaatctc | ccaaagctcc | aggaactggc | agggtcggg | 600 |
| gacgccccaa | agggagcggc | actggagac | caaaggcagc | agcatcagaa | ggtgttcagg | 660 |
| tgaaagggt | cctggagaag | agccctggga | aacttgttgt | caagatgcct | ttccaagcat | 720 |
| cgcctggggg | taagggtgag | ggaggtgggg | ctaccacatc | tgcccaggtc | atggtgatca | 780 |
| aacgccctgg | cagaaagcga | aaagctgaag | ctgaccccca | ggccattcct | aagaaacggg | 840 |
| gtagaaagcc | tgggagtgtg | gtggcagctg | ctgcagctga | ggccaaaaag | aaagccgtga | 900 |
| aggagtcttc | catacggtct | gtgcatgaga | ctgtgctccc | catcaagaag | cgcaagaccc | 960 |
| gggagacggt | cagcatcgag | gtcaaggaag | tggtgaagcc | cctgctggtg | tccacccttg | 1020 |
| gtgagaaaag | cgggaaggga | ctgaagacct | gcaagagccc | tgggcgtaaa | agcaaggaga | 1080 |
| gcagccccaa | gggcgcagc | agcagtgcct | cctccccacc | taagaaggag | caccatcatc | 1140 |
| accaccatca | ctcagagtcc | acaaaggccc | ccatgccact | gctcccatcc | ccaccccac | 1200 |
| ctgagcctga | gagctctgag | gaccccatca | gccccctga | gcctcaggac | ttgagcagca | 1260 |
| gcatctgcaa | agaagagaag | atgccccgag | gaggctcact | ggaaagcgat | ggctgcccca | 1320 |
| aggagccagc | taagactcag | cctatggtcg | ccaccactac | cacagttgca | gaaaagtaca | 1380 |
| aacaccgagg | ggagggagag | cgcaaagaca | ttgtttcatc | ttccatgcca | aggccaaaca | 1440 |
| gagaggagcc | tgtggacagc | cggacgcccg | tgaccgagag | agttagctga | ctttacatag | 1500 |
| agcggattgc | aaagcaaacc | aacaagaata | aaggcagctg | ttgtctcttc | tccttatggg | 1560 |
| tagggctctg | acaaagcttc | ccgattaact | gaaataaaaa | atattttttt | ttctttcagt | 1620 |
| aaacttagag | tttcgtggct | tcggggtggg | agtagttgga | gcattgggat | gtttttctta | 1680 |
| ccgacaagca | cagtcaggtt | gaagacctaa | ccagggccag | aagtagcttt | gcacttttct | 1740 |
| aaactaggct | ccttcaacaa | ggcttgctgc | agatactact | gaccagacaa | gctgttgacc | 1800 |
| aggcactccc | cccaacaata | tcctccctct | tccccccccc | caccccgcc | ccgtgtgctc | 1860 |
| gttagggcaa | ttgagaggac | actcccattt | ttggtgccat | tgatgccctg | tccataatag | 1920 |
| cttccctgac | ttttacacca | ccccaactcc | caatctgaag | gactgggagg | tgtgatgcag | 1980 |

```
gagaaactat gggactcttg ggagaagact atggagttgg ccagtgatta aggcccagta    2040
attccaactg tggtagcaca gatctggctc cacatcaacc caatccaaaa ctgacaagga    2100
tattttgcaa aaaagaaag tggcacctgt ctgatccagc tctgacatgg ctagaggtga    2160
gtcctaaact gatggcttat aaactagcct gagccacaga agagtatggc ccagagtgaa    2220
gtgtcatcat ctgttcacaa ggcatgctcc cctagaagat aatgctaaag aggtgccatg    2280
gaggcagcag gacaaagtac aggcaggcta ggtggagtca agccaggcct agtgccacag    2340
aacaagagag cagtctgact agtaattaag agggaagaaa ggaaaatatt cttccaatta    2400
ctttccagtt ctcctttagg gacagcttag aattatttgc actattgagt cttcatgttc    2460
ccacttcaaa acaaacagat gctctgaaag caaactggct tgaaatggtg acactgtccc    2520
acaagccacc agacatggca gtgttcagaa ctacctgtat ctgtatatac ctgcgcttgt    2580
tttaaagtgg gctcagcaca taggattccc aagaagctcc gaaactctaa gtgtttgctg    2640
caattttata aggacttcct gattgctttc tctctcgtcc ttccatttct tccttccttc    2700
cattttatgc tttcatttct tccctagct tctagttgtt cttctgttc caggcagctg    2760 cagtgctgaa ccacatggtt acctaacagc agtcagctgc agcctaggagg ttcttcctgc    2820 cctttaactt cccattgcca gtgccaggta tcatatttaa ccttgagcaa gagctgggct    2880
cttttgagcc ctccctaacc tctgtgaaga agaacaagaa ggtaggaagc tcttgctctt    2940
gctaagaaaa atgtcaaaag gctttcagac cttaaacaat gagcctttc acctttact    3000 ctagaaaagt ggactagaaa atctgggtca cattgggtag ctgaaggaga tacagaggcc    3060
cctatggcct gccagagtcg ttgcatggcc aacaggggc tccatgccca ctacccttga    3120
ccctactcag aaatctaatg tcatacttag tgtgggcagg ggacctgtca ggacagatgc    3180
agacctaagc agggagtgac accagggccc ttggcccttc ttctgacaaa catacacatc    3240
ccaagtcttt ttctagtgga attcttaacc tcttgctcac tggggactgg gaagcatcag    3300
cacatcccat atttcaaact ctgctccata agtacagtgg tgaattttat agacttgact    3360
ttgctgtggg gttttaattg gtcagtttta atttgggatc ccaaagttt aacctccatt    3420 caggaagtcc ttatctagct gcatatcttc atcatattgg tatatccttt tctgtgttta    3480
cagagatgtc tcatatctat cgaaatctgt ctgagaagta ccttatcaaa gtagcaaatg    3540
agacagcagt cttatgcttc cagaaacacc cacaggcacg tcccatgtga gctgctgcca    3600
tgaactgtcg agtgtgtatt gtcttgtgta ttttcgttaa cgttccccag cttccttcct    3660
gcggtgtaat catggaagag tgaaacatca tagaaatcgt ctagcacttc ctggccagtc    3720
cttagtgatc aggaaccgta gttgacagtt ccaattgata gcttaagata aaaccatgtt    3780
tgtctcttat ggaatggtta gaactaagtg agagatcttg ccccattctg tttgccgaat    3840
catagttgga cttttagtgt atttgtatcc atttccttgt gctataaaag caaaccctgc    3900
aaccagcttt ctgtcaggca gtccttttgc ctgctctgct tttgatcctc ttagtcttgc    3960
ttctggttcc tccctggaga gggaggaggg gtcagaagag gaattctgga ggatccagga    4020
tatgtccttc tgaactcctg cttcttccag tgacaaaagg cccctactgc cccaccccaa    4080
cctgccccat gcactcctct aggacacctt tccatacttt tcacaacacc tagccaggtt    4140
gacaccaagt tgtttattgt ggtctgcttg gaatttacc tgttaggctt acttagtcca    4200
atcaaatgga ctccaagttg ggtatccctc atctttggaa gacaacctag gctgattaga    4260
tatttacttt tgggattgca gcactttggg tgccgttttt cttttacttg ggttttatct    4320
```

-continued

```
gcagctccct caccaccacc accacccccc acttacctgt atgtagaact gatttcaaaa      4380
ctgcaggtgg tggtaactgc agcttcttag ggttttcttc acttcttgct tctttcccca      4440
ttccctcatc cacaaataag ggcatcacaa gtcagtctcc tttaagcagg cagctttggt      4500
ggggtttttc ccctggaagc cagggaccct gtcaggctgc ctctgccttg tggtcaggtt      4560
gacaggaggt tggagggaaa agccttaagt catgggattc tcaccagctg tgtctggctc      4620
agacctggaa tgtgaccttt attttgttgt atttgaacat tgtaaagtgt gggtggtacc      4680
ttaaactgaa tatgtgaaga atccagaaac tgaccaacag ctttcagata cctggggcta      4740
ggtcactaag gtcacatcca gtcttcccta ccctgttcta gttgttagct actacctctc      4800
ccagatagat tgctgtatat cctccaacta tgatcatcct ggcccaagct tgcctgttct      4860
tgagtctgtc ttaaccagtg aactgctgc ccttggtgtg cagtgagttg aggactcttg       4920
gtcacagcca ggctctagta gtacagctcc tttctgctgg tgctgtattt ccatatcaaa      4980
aggcacaggg gagatctaga aatgccatct cccccagtcc atcagtgcca aacaagccca      5040
tgatcccagc atgggtacag acaactctgt tcagtgctat cacaacagac tagaggccat      5100
gaacattgga cgtgggaacc agagcaaccc gaattgctgc tgctttattc agctttccgt      5160
tgctctgaca atgataaaac aaggcagtaa cttaaaacag actgccaggt ttggcagaga      5220
aaggaaattc cttagctgac agcacctctg gattttaaat aggttgtaat aagtggctca      5280
aacccatcca ggaaaaagca aaagggttag aactgaccag atgagaccag cctgatttca      5340
tgcagcccaa atggagtcca gctgtctgaa ctctgcagca cttctctact acagtctcct      5400
agagcattcc agccaggctc ttcaggctga ggagacatca caggtgccag ttcttcaaga      5460
agacttttgt gcatcagttc atagcctata tctttgccca agattgtaga ttcaggttaa      5520
cactacagat tctagggcag atgactgaga ctcagaaaaa aagcccctgt ggactgtggt      5580
atagcgaagt acaaaaactg aagggggcta ggcagatgc cgcatgcctc atgccagagc       5640
caagccctct gctccatcca catccttttc tggctccttc ttcctgctct ctgcttcagt      5700
gaaccagccc cactctgaag agatttgttg attctctcca tttttatgtc tttctctttt      5760
aggtactata tagaaaaggc ttagtctaat tgttataaat tgctagaata ctgcctcccc      5820
cagggtctaa aaatatatgc taaaggggaa aacttgaaca ctgaaaccag ttctgaacaa      5880
tttagaagga aaaccttgaa aacatttaac aaaaaattat attttaatgt ttatgaataa      5940
gaggaggctt tgaaaaaat gttgatctat aaatacttac tttaggcctg aggtgtctaa       6000
tgagtgaact gagcaatggg aactcaaggc tgaagcctcc tgcatcagag gaggtagaac      6060
caggagcctc ttgagatttg aggtgtttta gcattggaaa gccactcttt gggtagctgg      6120
ccccagaaac tacttctgac cttgtcattt ggaatggagg ttagtggtct gccagatgcc      6180
aaagctgcat gagaccagct cttggtttat caatttgaac actcagtaac ctagaaggcc      6240
cagcacaaag tgtctgctct cttcttaact gagcctgccc cagcactact gcacaaatta      6300
gggagggtct acttcctaca gagcatccct ccctgggccc cctcccatcc tttgtactct      6360
acctacctga ccttcaggat cttggcacat acgaaatggc tgtgtagcaa gcactttggc      6420 atgcctcct aaacttaccc cagagcctct ccctgcctcc ttaagccagt ctgcctgtct       6480
tctggggagg tgttagagcc catagaatgg agaggagaaa gaaagagga agaggcaggc       6540 aggtagtaaa aaggctctgg gaggaaagac agctcctag gctttgcaca agcaggactc       6600
agccccttgt gggaactaag tgccatcttg gagtttaaga acatttggac aagttgcaaa      6660
tgacctttgc tccttgctcc tctcaccttt tatgggccc tgcttagcac tgaaagcaaa       6720
```

```
tgcgctgaaa aggcaaagag gtttggctcc tgcccactga tagtcctttc cctgcagtgt    6780
ttgtgtgtca agtggcaaag ctgttcttcc tggtgactct gattagatcc agtaacttaa    6840
gagatttgta tgcataggtc tgctttgact cttctattct gggcttttga tttgttttc    6900 agttttgctt ttagttttcc tattttatt ttatgcacca actagacaca caaagcagtt    6960
gaatttatat atatatatat atatatatat ctgtatattt cacaattata aactcatttt    7020
gcttgtgacg ccacacacac acaaaaagaa aaaccttta aaattatacc tgttgcttaa    7080
ttacaatatt tctgataacc atagagtagg acaagggaaa aaatttaaaa agaaaaaaaa    7140
aaaaagaaaa aacacatctg tctgctggtc acttcttcaa tccaagcaga tctgtgatct    7200
ttcctcgcgt ctttcaaaga cttccctgtg ctaagtgaag gaagctccag gctgcaccca    7260
ggttttgtgc tttgtttctc ctctgttgtg aaaggggccc caagattctg ggtacaggac    7320
agttcatttc agcatggggt caggagacaa gagcactccc tttacatgct gacgtacaga    7380
acttagtggg aatagcctag tccccacctc tagggatggg gagctagcat gcatggggt    7440 gacccaactc cctccaccct tccctggcca ggaagagcct gtgtacagta agtctgacaa    7500
gctttcccca gttagcaggg ctcagagcat ttaaaaaccc tccaaacttt gctgagtcta    7560
gggactagag agaagataga agatttggtc tatctccaag gtgtgtaagc tgtaccaggt    7620
agaatgccag ggaccccaga accacatcca acagcccaat gggtctcctc cagaaagtag    7680
tgaagactcc agaaacatcc ctttctcttc tccctgctcc catgagtaac tgcatttgct    7740
tttgtaatcc ttaatgagca ttatctgcta aaaaaaaaa attagctgta acagttcttt    7800
ttgcaaaagg atcattctta aataattaaa acacccccc ccccaaaaaa aagtccagaa    7860
ccttgttctt ccaaagcaga gagcattata atcagggcca aaatctgtcc cacacctcta    7920
ccccatctcc tcatgattgc tgcttctaag gccagaatac agcaaagata tttgtaggcc    7980
cttggggtga ctgggctacc cttggagctc ttggaagatg ggctgggaa gcctctgaga    8040 ccctatccta gggccttgct ctagggagta atcagtatta gtagagtgtc acaacattat    8100
tccccagccg gcatgagatg ggggcagaag aagccaaagg gttgtctcca ctgctactta    8160
cttggccact gacaggtagg tgaccatgta tgtccatatg catgttttat ggctgatgtg    8220
agatcagcac ccaagttagc ttcacctggt gacctctaac cctgcctgga tggagcaggc    8280
cacctggttc aatgtttctg ggcagctgga caatggagtg caaaaggctt acagaacttg    8340
aagccttttc cttactttgc tagcacggcc tccttttcca tttgatttgt cactgcttca    8400
gtcaataaca gccgctccag agtcagtagt tgatgaatat atgaccaaat atcaccagga    8460
ctgttactca acgtgtgccg agcccttcc ttgtgctggg ctccctgtgt acctggacac    8520
tgtaatgtgt gctgtgtttg ctctccttcc tcttccttcc ttgcccttc cttgtctttc    8580 tggggttttt ctgttgggtt tggtttggtt ttattttcc ttttgtgttc caaacatgag    8640
tccccatcta ctggtcctct ttaactgtgg tgttgaggct tctatttgtg taattttgg    8700 tgggtgaaag gaactttgct aagtaaatct cttctgtgtt tgaaatgaag tctgtattgt    8760
aactatgttt aaagtaattg ttccagagac aaatgcttct aggtacattt tcattacaaa    8820
caaagcattt gaagggaggg aagtggtgaa taagacaaga ggggcaatct gaattgatcc    8880
ctgcccagat cagccagaag ctaccaaaag ttaagcactg gttttccatt ccaagtcaag    8940
agactgaagc tgatgttttg ccattttcaa agtcaaagca aaaccagctt ttccaccccaa    9000 tggattcttt gcttctcctt cccagattat tactactgct gtaataatct aggagtgcca    9060
```

-continued

```
ggagggaaag gagtattaac acagagctgt gctcactgag tatggaaagg cttggtctga      9120
gttttcagga ggatgaccca ctgtggacat ggggagaaga cagaagataa attagccgct      9180
cttggcctaa gatacctctt aatagataag tcaaggccat ggacattatt gtctacaagg      9240
catgtttcaa agacatgacc agtcaggaca cttctgtcat actccatgtt gcccctagt       9300 acacagtact aatctgatat ctctgttccc gccatgcctg ggggataaaa tgatagcaga      9360
gactcctttc cttcaatgtg atctaattcc caacaaaatc tgggcctgag ataccacctg      9420
tttctatggc aaacatcctc agtaaagtgt tattctcatt gcagattgtt ccagcctaat      9480
gtaagaggaa cagagcagtg ttcccttgga gcctcatgtg acagttcta cctgtagtga       9540 ccagttggct atagtagtta ttagctggaa caaccagaca gggtacatgc ccctccaaa       9600 atccatgttg tactcccctc tgccagccag ggggggtgag atctgtagaa tagtgcagcc      9660
agtgacaagc caccttgtgt ttgtcaccag ctcaaaaact catctaaggt tgggagcagg      9720
cagacaaggc agagagaaag atccaggaca gacctagctg ggctggaggg gtcttgaaaa      9780
gccctctgtc gtattcacct tcagtttttg tgctttggga caattacttt agaaaataag      9840
taggtcgttt taaaaacaaa atattgattg cttttttgta gtgttcaaaa caaaggttc       9900 tttgtgtata gccaaatgac tgaaagcact gatatattta aaacaaaag gcaatttatt       9960 aaggaaattt gtaccatttc agtaaacctg tctgaatgta cctgtatacg tttcaaaaac      10020 acacccact gaaccctgt aacctattta ttatataaag agtttgcctt ataaatttac       10080
ataaaaa                                                               10087

<210> SEQ ID NO 30
<211> LENGTH: 1451
<212> TYPE: DNA
<213> ORGANISM: Mouse

<400> SEQUENCE: 30
atggtagctg ggatgttagg gctcagggag gaaaagtcag aagaccagga tctccagggc        60
ctcagagaca agccactgaa gtttaagaag gcgaagaaag acaagaagga ggacaaagaa       120
ggcaagcatg agccactaca accttcagcc caccattctg cagagccagc agaggcaggc       180
aaagcagaaa catcagaaag ctcaggctct gccccagcag tgccagaagc ctcggcttcc       240
cccaaacagc ggcgctccat tatccgtgac cggggaccta tgtatgatga ccccaccttg       300
cctgaaggtt ggacacgaaa gcttaaacaa aggaagtctg gccgatctgc tggaaagtat       360
gatgtatatt tgatcaatcc ccagggaaaa gcttttcgct ctaaagtaga attgattgca       420
actttgaaaa ggtgggagac acctccttgg ccctaatga ttttgacttc acggtaactg        480
ggagagggag cccctccagg agagagcaga aaccacctaa gaagcccaaa tctcccaaag       540
ctccaggaac tggcagggt cggggacgcc ccaaagggag cggcactggg agaccaaagg       600
cagcagcatc agaaggtgtt caggtgaaaa gggtcctgga aagagccct gggaaacttg        660 ttgtcaagat gcctttccaa gcatcgcctg ggggtaaggg tgagggaggt ggggctacca      720
catctgccca ggtcatggtg atcaaacgcc ctggcagaaa gcgaaaagct gaagctgacc      780
cccaggccat tcctaagaaa cggggtagaa agcctgggg tgtggtggca gctgctgcag       840
ctgaggccaa aaagaaagcc gtgaaggagt cttccatacg gtctgtgcat gagactgtgc      900
tccccatcaa gaagcgcaag acccgggaga cggtcagcat cgaggtcaag gaagtggtga      960 agccctgct ggtgtccacc cttggtgaga aaagcggaa gggactgaag acctgcaaga       1020
gccctgggcg taaaagcaag gagagcagcc ccaaggggcg cagcagcagt gcctcctccc      1080
```

-continued

| | |
|---|---|
| cacctaagaa ggagcaccat catcaccacc atcactcaga gtccacaaag gcccccatgc | 1140 |
| cactgctccc atccccaccc ccacctgagc ctgagagctc tgaggacccc atcagccccc | 1200 |
| ctgagcctca ggacttgagc agcagcatct gcaaagaaga gaagatgccc cgaggaggct | 1260 |
| cactggaaag cgatggctgc cccaaggagc cagctaagac tcagcctatg gtcgccacca | 1320 |
| ctaccacagt tgcagaaaag tacaaacacc gaggggaggg agagcgcaaa gacattgttt | 1380 |
| catcttccat gccaaggcca aacagagagg agcctgtgga cagccggacg cccgtgaccg | 1440 |
| agagagttag c | 1451 |

<210> SEQ ID NO 31
<211> LENGTH: 842
<212> TYPE: DNA
<213> ORGANISM: Human

<400> SEQUENCE: 31

| | |
|---|---|
| ttgctgcaga tactactgac cagacaagct gttgaccagg cacctcccct cccgcccaaa | 60 |
| cctttccccc atgtggtcgt tagagacaga gcgacagagc agttgagagg cactcccgt | 120 |
| tttcggtgcc atcagtgccc cgtctacagc tcccccagct ccccccacct ccccactcc | 180 |
| caaccacgtt gggacaggga ggtgtgaggc aggagagaca gttggattct ttagagaaga | 240 |
| tggatatgac cagtggctat ggcctgtgcg atcccacccg tggtggctca agtctggccc | 300 |
| cacaccagcc ccaatccaaa actggcaagg acgcttcaca ggacaggaaa gtggcacctg | 360 |
| tctgctccag ctctggcatg ctaggaggg gggagtccct tgaactactg ggtgtagact | 420 |
| ggcctgaacc acaggagagg atggcccagg gtgaggtggc atggtccatt ctcaagggac | 480 |
| gtcctccaac gggtggcgct agaggccatg gaggcagtag acaaggtgc aggcaggctg | 540 |
| gcctggggtc aggccgggca gagcacacgc gggtgagagg gattcctaat cactcagagc | 600 |
| agtctgtgac ttagtggaca ggggagggg caaaggggga ggagaagaaa atgttcttcc | 660 |
| agttactttc caattctcct ttagggacag cttagaatta tttgcactat tgagtcttca | 720 |
| tgttcccact tcaaaacaaa cagatgctct gagagcaaac tggcttgaat tggtgacatt | 780 |
| tagtccctca agccaccaga tgtgacagtg ttgagaacta cctggatttg tatatatacc | 840 |
| tg | 842 |

<210> SEQ ID NO 32
<211> LENGTH: 813
<212> TYPE: DNA
<213> ORGANISM: Rat

<400> SEQUENCE: 32

| | |
|---|---|
| ttgctgcaga tactactgac cagacaagct gttgaccagg cactcccac aacaacaacc | 60 |
| ccctccctcc tcaccccacc cctatcccct gtgtgctcat tagagagggc aattgagagg | 120 |
| acactcccat ttttggtgcc actgatgccc tgtccatagc ttccctgact tttacaccac | 180 |
| cccaactccc aatctgaggg actgggaggt gtgacgcagg agaaactata taggactctt | 240 |
| gggagaagac tatagagttg caagtgatt gcgcccagt aattccaact gtggtagcac | 300 |
| aagtctggct ccacaccaac ccaatccaaa actgacaagg acattttgca aaaatgaaa | 360 |
| gtggcatttg tctgatccag ctctggcatg ctagagatg agtcttaaac tgttggctta | 420 |
| taaactggcc tgagcaacag aagaggatgg cccagagtaa agtgtcatca tctgttcaca | 480 |
| aggcatgctc ccctagaagt tcatgctaaa gaagtgccat ggaggcagca ggacaaagta | 540 |

-continued

| | | |
|---|---|---|
| caggctaggt ggagtcaagc caggcctagt gccacagagc aagagagcag tctctgacta | 600 |
| gtagttaagg gggaagaaag aaaaatattc ttccaattgc tttccagttc tcctttaggg | 660 |
| acagcttaga attatttgca ctattgagtc ttcatgttcc cacttcaaaa caaatagatg | 720 |
| ctctgaaagc aaactggctt gaaatggtga cactgtccca caagccacca gacaatggca | 780 |
| gtgttcagaa ctacctgtat atgtatatac ctg | 813 |

<210> SEQ ID NO 33
<211> LENGTH: 846
<212> TYPE: DNA
<213> ORGANISM: Orangutan

<400> SEQUENCE: 33

| | |
|---|---|
| ttgctgcaga tactactgac cagacaagct gttgaccagg cacctcccct cccgcccaaa | 60 |
| cctttccccc atgtggtcgt tagagacaga gcagttgaga ggacactccc gttttcggtg | 120 |
| ccatcagtgc cccgtctgca gctcccccag ctcccccac ctcccccact cccaaccacg | 180 |
| ttgggacagg gaggtgtgag gcaggagaga cagttggatt cttcgagaa gatggatatg | 240 |
| accagtggcc atggcctgtg cgatcccacc cgtggcggct caagtctggc cccacaccag | 300 |
| ccccaatcca aaactggcaa ggacgcttca caggacagga aagtggcacc tgtctgctcc | 360 |
| agctctggca tggctaggag ggagtcgtcc cttgaactac tgggtgtaga ctggcctgaa | 420 |
| ccacaggaga ggatgcccca gggtgaggtg gcatggtcca ttctcaaggg acgtcctcca | 480 |
| acgggtggcg ctagaaaggc catggaggca gtaggacaag gcgcaggcag gctggcccgg | 540 |
| ggtcaggccg ggcagggcac agcggggtga gagggattcc taatcactca gagcagtgtg | 600 |
| tgactggtag ttagggactc agtggacagg ggaggggcga gggggcagga aagaaaatg | 660 |
| ttcttccagt tactttccaa ttctccttta gggacagctt agaattattt gcactattga | 720 |
| gtcttcatgt tcccacttca aaacaaacga tgctctgaga gcaaactggc ttgaattggt | 780 |
| gacatttagt ccctcaagcc accagatgtg agtgttgaga actacctgga tttgtatata | 840 |
| tacctg | 846 |

<210> SEQ ID NO 34
<211> LENGTH: 806
<212> TYPE: DNA
<213> ORGANISM: Mouse

<400> SEQUENCE: 34

| | |
|---|---|
| ttgctgcaga tactactgac cagacaagct gttgaccagg cactccccc aacaatatcc | 60 |
| tccctcttcc ccccccccac ccccgccccg tgtgctcgtt agggcaattg agaggacact | 120 |
| cccattttg gtgccattga tgccctgtcc ataatagctt ccctgacttt tacaccaccc | 180 |
| caactcccaa tctgaaggac tgggaggtgt gatgcaggag aaactatggg actcttggga | 240 |
| gaagactatg gagttggcca gtgattaagg cccagtaatt ccaactgtgg tagcacagat | 300 |
| ctggctccac atcaacccaa tccaaaactg acaaggatat tttgcaaaaa agaaagtgg | 360 |
| cacctgtctg atccagctct gacatggcta gaggtgagtc ctaaactgat ggcttataaa | 420 |
| ctagcctgag ccacagaaga gtatggccca gagtgaagtg tcatcatctg ttcacaaggc | 480 |
| atgctcccct agaagataat gctaaagagg tgccatggag gcagcaggac aaagtacagg | 540 |
| caggctaggt ggagtcaagc caggcctagt gccacagaac aagagagcag tctgactagt | 600 |
| aattaagagg gaagaaagga aaatattctt ccaattactt tccagttctc ctttagggac | 660 |
| agcttagaat tatttgcact attgagtctt catgttccca cttcaaaaca aacagatgct | 720 |

-continued

```
ctgaaagcaa actggcttga aatggtgaca ctgtcccaca agccaccaga catggcagtg      780
ttcagaacta cctgtatctg tatata                                          806

<210> SEQ ID NO 35
<211> LENGTH: 9480
<212> TYPE: DNA
<213> ORGANISM: Mouse

<400> SEQUENCE: 35
aggaccccat cagccccct gagcctcagg acttgagcag cagcatctgc aaagaagaga       60
agatgccccg aggaggctca ctggaaagcg atggctgccc caaggagcca gctaagactc     120
agcctatggt cgccaccact accacagttg cagaaaagta caaacaccga ggggagggag     180
agcgcaaaga cattgtttca tcttccatgc caaggccaaa cagagaggag cctgtggaca     240
gccggacgcc cgtgaccgag agagttagct gactttacat agagcggatt gcaaagcaaa     300
ccaacaagaa taaaggcagc tgttgtctct tctccttatg ggtagggctc tgacaaagct     360
tcccgattaa ctgaaataaa aaatatttt ttttctttca gtaaacttag agtttcgtgg      420
cttcggggtg ggagtagttg gagcattggg atgtttttct taccgacaag cacagtcagg     480
ttgaagaccc aaccagggcc agaagtagct ttgcactttt ctaaactagg ctccttcaac     540
aaggcttgct gcagatacta ctgaccagac aagctgttga ccaggcactc cccccaacaa     600
tatcctccct cttccccccc cccacccccg ccccgtgtgc tcgttagggc aattgagagg     660
acactcccat ttttggtgcc attgatgccc tgtccataat agcttccctg acttttacac     720 cacccccaact cccaatctga aggactggga ggtgtgatgc aggagaaact atgggactct     780
tgggagaaga ctatggagtt ggccagtgat taaggcccag taattccaac tgtggtagca     840
cagatctggc tccacatcaa cccaatccaa aactgacaag gatattttgc aaaaaaagaa     900
agtggcacct gtctgatcca gctctgacat ggctagaggt gagtcctaaa ctgatggctt     960
ataaactagc ctgagccaca gaagagtatg cccagagtg aagtgtcatc atctgttcac     1020
aaggcatgct cccctagaag ataatgctaa agaggtgcca tggaggcagc aggacaaagt     1080
acaggcaggc taggtggagt caagccaggc ctagtccac agaacaagag agcagtctga     1140
ctagtaatta agagggaaga aggaaaata ttcttccaat tactttccag ttctcctta      1200 gggacagctt agaattattt gcactattga gtcttcatgt tcccacttca aaacaaacag     1260
atgctctgaa agcaaactgg cttgaaatgg tgacactgtc ccacaagcca ccagacatgg     1320
cagtgttcag aactacctgt atctgtatat acctgcgctt gttttaaagt gggctcagca     1380
cataggattc ccaagaagct ccgaaactct aagtgtttgc tgcaattta taaggacttc      1440 ctgattgctt tctctctcgt ccttccattt ctccttcct tccatttcat gctttcattt      1500
cttcccctag cttctagttg tttcttctgt tccaggcagc tgcagtgctg aaccacatgg     1560
ttacctaaca gcagtcagct gcagccctag gattcttcct gcccttaac ttcccattgc      1620 cagtgccagg tatcatattt aaccttgagc aagagctggg ctcttttgag ccctccctaa     1680
cctctgtgaa gaagaacaag aaggtaggaa gctcttgctc ttgctaagaa aaatgtcaaa    1740
aggctttcag accttaaaca atgagccttt tcaccttta ctctagaaaa gtggactaga     1800
aaatctgggt cacattgggt agctgaagga gatacagagg cccctatggc ctgccagagt     1860
cgttgcatgg cccaacaggg gctccatgcc cactaccctt gacccactc agaaatctaa     1920 tgtcatactt agtgtgggca ggggacctgt caggacagat gcagacctaa gcagggagtg     1980
```

-continued

```
acaccagggc ccttggccct tcttctgaca aacatacaca tcccaagtct ttttctagtg      2040
gaattcttaa cctcttgctc actggggact gggaagcatc agcacatccc atatttcaaa      2100
ctctgctcca taagtacagt ggtgaatttt atagacttga ctttgctgtg ggttttaat       2160 tggtcagttt taatttggga tcccaaagtt ttaacctcca ttcaggaagt ccttatctag      2220
ctgcatatct tcatcatatt ggtatatcct tttctgtgtt tacagagatg tctcatatct      2280
atcgaaatct gtctgagaag taccttatca aagtagcaaa tgagacagca gtcttatgct      2340
tccagaaaca cccacaggca cgtcccatgt gagctgctgc catgaactgt cgagtgtgta      2400
ttgtcttgtg tattttcgtt aacgttcccc agcttccttc ctgcggtgta atcatggaag      2460
agtgaaacat catagaaatc gtctagcact tcctggccag tccttagtga tcaggaaccg      2520
tagttgacag ttccaattga tagcttaaga taaaaccatg tttgtctctt atggaatggt      2580
tagaactaag tgagagatct tgccccattc tgtttgccga atcatagttg gactttagt       2640 gtatttgtat ccatttcctt gtgctataaa agcaaaccct gcaaccagct ttctgtcagg      2700
cagtcctttt gcctgctctg cttttgatcc tcttagtctt gcttctggtt cctccctgga      2760
gagggaggag gggtcagaag aggaattctg gaggatccag gatatgtcct tctgaactcc      2820
tgcttcttcc agtgacaaaa ggcccctact gccccacccc aacctgcccc atgcactcct      2880
ctaggacacc tttccatact tttcacaaca cctagccagg ttgacaccaa gttgtttatt      2940
gtggtctgct tggaattta cctgttaggc ttacttagtc caatcaaatg gactccaagt       3000
tgggtatccc tcatctttgg aagacaacct aggctgatta gatatttact tttgggattg      3060
cagcactttg ggtgccgttt ttcttttact tgggttttat ctgcagctcc ctcaccacca      3120
ccaccacccc ccacttacct gtatgtagaa ctgatttcaa aactgcaggt ggtggtaact      3180
gcagcttctt agggttttct tcacttcttg cttctttccc cattccctca tccacaaata      3240
agggcatcac aagtcagtct cctttaagca ggcagctttg gtgggtttt tccctggaa        3300 gccagggacc ctgtcaggct gcctctgcct tgtggtcagg ttgacaggag gttggaggga     3360
aaagccttaa gtcatgggat tctcaccagc tgtgtctggc tcagacctgg aatgtgacct      3420
ttattttgtt gtatttgaac attgtaaagt gtgggtggta ccttaaactg aatatgtgaa      3480
gaatccagaa actgaccaac agctttcaga tacctgggc taggtcacta aggtcacatc       3540
cagtcttccc taccctgttc tagttgttag ctactacctc tcccagatag attgctgtat      3600
atcctccaac tatgatcatc ctggcccaag cttgcctgtt cttgagtctg tcttaaccag      3660
tggaactgct gcccttggtg tgcagtgagt tgaggactct tggtcacagc caggctctag      3720
tagtacagct cctttctgct ggtgctgtat ttccatatca aaaggcacag gggagatcta      3780
gaaatgccat ctcccccagt ccatcagtgc caaacaagcc catgatccca gcatgggtac      3840
agacaactct gttcagtgct atcacaacag actagaggcc atgaacattg gacgtgggaa      3900
ccagagcaac ccgaattgct gctgctttat tcagctttcc gttgctctga caatgataaa      3960
acaaggcagt aacttaaaac agactgccag gtttggcaga gaaaggaaat tccttagctg      4020
acagcacctc tggattttaa ataggttgta ataagtggct caaacccatc caggaaaaag      4080
caaaagggtt agaactgacc agatgagacc agcctgattt catgcagccc aaatggagtc      4140
cagctgtctg aactctgcag cacttctcta ctacagtctc ctagagcatt ccagccaggc      4200
tcttcaggct gaggagacat cacaggtgcc agttcttcaa gaagacttt gtgcatcagt       4260 tcatagccta tatctttgcc caagattgta gattcaggtt aacactacag attctagggc      4320
agatgactga gactcagaaa aaagccccct gtggactgtg gtatagcgaa gtacaaaaac      4380
```

```
tgaaggggc  tagggcagat  gccgcatgcc  tcatgccaga  gccaagccct  ctgctccatc   4440
cacatccttt  tctggctcct  tcttcctgct  ctctgcttca  gtgaaccagc  cccactctga   4500
agagatttgt  tgattctctc  cattttatg   tctttctctt  ttaggtacta  tatagaaaag   4560
gcttagtcta  attgttataa  attgctagaa  tactgcctcc  cccagggtct  aaaatatat   4620
gctaaggggg  aaacttgaa   cactgaaacc  agttctgaac  aatttagaag  gaaaaccttg   4680
aaaacattta  acaaaaaatt  atattttaat  gtttatgaat  aagaggaggc  ttttgaaaaa   4740
atgttgatct  ataaatactt  actttaggcc  tgaggtgtct  aatgagtgaa  ctgagcaatg   4800
ggaactcaag  gctgaagcct  cctgcatcag  aggaggtaga  accaggagcc  tcttgagatt   4860
tgaggtgttt  tagcattgga  aagccactct  ttgggtagct  ggcccagaa   actacttctg   4920
accttgtcat  ttggaatgga  ggttagtggt  ctgccagatg  ccaaagctgc  atgagaccag   4980
ctcttggttt  atcaatttga  acactcagta  acctagaagg  cccagcacaa  agtgtctgct   5040
ctcttcttaa  ctgagcctgc  cccagcacta  ctgcacaaat  tagggagggt  ctacttccta   5100
cagagcatcc  ctccctgggc  cccctcccat  cctttgtact  ctacctacct  gaccttcagg   5160
atcttggcac  atacgaaatg  gctgtgtagc  aagcactttg  gcatgccctc  ctaaacttac   5220
cccagagcct  ctccctgcct  ccttaagcca  gtctgcctgt  cttctgggga  ggtgttagag   5280
cccatagaat  ggagaggaga  aagaaaagag  gaagaggcag  gcaggtagta  aaaaggctct   5340
gggaggaaag  acagcctcct  aggctttgca  caagcaggac  tcagccccctt  gtgggaacta   5400
agtgccatct  tggagtttaa  gaacatttgg  acaagttgca  aatgaccttt  gctccttgct   5460
cctctcacct  tttatggggc  cctgcttagc  actgaaagca  aatgcgctga  aaaggcaaag   5520
aggtttggct  cctgcccact  gatagtcctt  tccctgcagt  gtttgtgtgt  caagtggcaa   5580
agctgttctt  cctggtgact  ctgattagat  ccagtaactt  aagagatttg  tatgcatagg   5640
tctgctttga  ctcttctatt  ctgggctttt  gatttgtttt  tcagttttgc  ttttagtttt   5700
cctatttta   ttttatgcac  caactagaca  cacaaagcag  ttgaatttat  atatatat   5760
atatatatat  atctgtatat  ttcacaatta  taaactcatt  ttgcttgtga  cgccacacac   5820
acacaaaaag  aaaacccttt  taaaattata  cctgttgctt  aattacaata  tttctgataa   5880
ccatagagta  ggacaaggga  aaaatttaa   aaagaaaaaa  aaaaaaagaa  aaacacatc   5940
tgtctgctgg  tcacttcttc  aatccaagca  gatctgtgat  cttcctcgc   gtctttcaaa   6000
gacttccctg  tgctaagtga  aggaagctcc  aggctgcacc  caggttttgt  gctttgtttc   6060
tcctctgttg  tgaaggggc   cccaagattc  tgggtacagg  acagttcatt  tcagcatggg   6120
gtcaggagac  aagagcactc  cctttacatg  ctgacgtaca  gaacttagtg  ggaatagcct   6180
agtccccacc  tctagggatg  gggagctagc  atgcatgggg  gtgacccaac  tccctccacc   6240
tttccctggc  caggaagagc  ctgtgtacag  taagtctgac  aagctttccc  cagttagcag   6300
ggctcagagc  atttaaaaac  cctccaaact  ttgctgagtc  tagggactag  agaagata    6360
gaagatttgg  tctatctcca  aggtgtgtaa  gctgtaccag  gtagaatgcc  agggacccca   6420
gaaccacatc  caacagccca  atgggtctcc  tccagaaagt  agtgaagact  ccagaaacat   6480
cccttctct   tctccctgct  cccatgagta  actgcatttg  cttttgtaat  ccttaatgag   6540
cattatctgc  taaaaaaaaa  aaattagctg  taacagttct  ttttgcaaaa  ggatcattct   6600
taaataatta  aaaacacccc  ccccccaaaa  aaagtccag   aaccttgttc  ttccaaagca   6660
gagagcatta  taatcagggc  caaaatctgt  cccacacctc  taccccatct  cctcatgatt   6720
```

```
gctgcttcta aggccagaat acagcaaaga tatttgtagg ccctttgggt gactgggcta    6780
cccttggagc tcttggaaga tgggctgggg aagcctctga gaccctatcc tagggccttg    6840
ctctagggag taatcagtat tagtagagtg tcacaacatt attccccagc cggcatgaga    6900
tgggggcaga agaagccaaa gggttgtctc cactgctact tacttggcca ctgacaggta    6960
ggtgaccatg tatgtccata tgcatgtttt atggctgatg tgagatcagc acccaagtta    7020
gcttcacctg gtgacctcta accctgcctg gatggagcag gccacctggt tcaatgtttc    7080
tgggcagctg acaatggag tgcaaaaggc ttacagaact tgaagccttt ccttactttt     7140
gctagcacgg cctccttttc catttgattt gtcactgctt cagtcaataa cagccgctcc    7200
agagtcagta gttgatgaat atatgaccaa atatcaccag gactgttact caacgtgtgc    7260
cgagcccttt ccttgtgctg ggctccctgt gtacctggac actgtaatgt gtgctgtgtt    7320
tgctctcctt cctcttcctt ccttgccctt tccttgtctt tctggggttt ttctgttggg    7380
tttggtttgg ttttattttt ccttttgtgt tccaaacatg aggttttctc tactggtcct    7440
ctttaactgt ggtgttgagg cttctatttg tgtaattttt ggtgggtgaa aggaactttg    7500
ctaagtaaat ctcttctgtg tttgaaatga agtctgtatt gtaactatgt ttaaagtaat    7560
tgttccagag acaaatgctt ctaggtacat tttcattaca aacaaagcat ttgaagggag    7620
ggaagtggtg aataagacaa gagggcaat ctgaattgat ccctgcccag atcagccaga     7680
agctaccaaa agttaagcac tggttttcca ttccaagtca agagactgaa gctgatgttt    7740
tgccattttc aaagtcaaag caaaaccagc ttttccaccc aatggattct ttgcttctcc    7800
ttcccagatt attactactg ctgtaataat ctaggagtgc caggagggaa aggagtatta    7860
acacagagct gtgctcactg agtatggaaa ggcttggtct gagttttcag gaggatgacc    7920
cactgtggac atggggagaa acagaagat aaattagccg ctccctgcct aagatacctc     7980
ttaatagata agtcaaggcc atggacatta ttgtctacaa ggcatgtttc aaagacatga    8040
ccagtcagga cacttctgtc atactccatg ttgcccccta gtacacagta ctaatctgat    8100
atctctgttc ccgccatgcc tgggggataa aatgatagca gagactcctt tccttcaatg    8160
tgatctaatt cccaacaaaa tctgggcctg agataccacc tgtttctatg caaacatcc     8220
tcagtaaagt gttattctca ttgcagattg ttccagccta atgtaagagg aacagagcag    8280
tgttcccttg gagcctcatg tggacagttc tacctgtagt gaccagttgg ctatagtagt    8340
tattagctgg aacaaccaga cagggtacat gcccctcca aaatccatgt tgtactcccc     8400
tctgccagcc aggggggtg agatctgtag aatagtgcag ccagtgacaa gccaccttgt     8460
gtttgtcacc agctcaaaaa ctcatctaag gttgggagca ggcagacaag gcagagagaa    8520
agatccagga cagacctagc tgggctggag gggtcttgaa aagccctctg tcgtattcac    8580
cttcagtttt tgtgctttgg gacaattact ttagaaaata gtaggtcgt tttaaaaaca     8640
aaatattgat tgctttttg tagtgttcaa acaaaaggt tctttgtgta tagccaaatg      8700
actgaaagca ctgatatatt taaaaacaaa aggcaattta ttaaggaaat ttgtaccatt    8760
tcagtaaacc tgtctgaatg tacctgtata cgtttcaaaa acacacccca ctgaaccct     8820
gtaacctatt tattatataa agagtttgcc ttataaattt acataaaaat gtccgtttgt    8880
gtcttttgtt gtaaaatcaa gtggttttc ataaggttct tttactattt gaaagatgg      8940
gcagcacgcg gtttcatttt atttttgtaa gttttttaat acatgtgaaa gcaaagaata    9000
ctcagcatgc ctttctaagt gatgcgtttg cacctttgt tgggaagtac tgtatcctgt     9060
gctgttagca ttctcgataa atctctctgt gaaagtgact caaggtctgg gctttcatta    9120
```

```
taagtcacca gtccctcca gctcacctga cagcatgata tgtttgattc agctatccct    9180 gaacccagt agcctctctc aggataggtg tgggagggta gggaagccta tttcatatac    9240
tggcatcctc cttagtttgc tctgtgtcaa tatttttcaa gcatactaca ccagcattcg    9300
acaggaaggc ctgacacaag tgtgcctaga gcatagcttc cctctcctga ccagtgtggc    9360 agggcagct gctaggtcct ggtgtgccat agtgttaaca ctttcctccc aactatgagg    9420
aactgcccaa agggagtcct tgtgtcactg gtttcctgta agaatatgag ccttctgcag    9480
```

<210> SEQ ID NO 36
<211> LENGTH: 790
<212> TYPE: DNA
<213> ORGANISM: Kangaroo

<400> SEQUENCE: 36

```
ttgctgcata tactactgac cagacaagct gtttatcagg cttttaggg tacaccagca      60 cctgccctcc attcatccct gttgggagag ggatggtgta ctggttgtca ctagagacct    120
aacagagtag ggttagtggg agcttacatt ttcagtgcca ttaacattct agtccaaggt    180
cttaaattat tatgttgagg ggttttttt ccctgaggg ggccggggg tggggggagg      240 gttgattaga ttccttagga aagagggttg agacagacag cagagcactg agcagttggc    300
actaaaggag accttgacta ggggccaggt ggcatcatct aatcccaagg ggctccaagt    360
gagtattagg gtgggggaag acattataga aggaatagaa acaggatagc tcagcctaaa    420
gaagagcggt taaaacccta cccaccagga gttgacttga aagaggcccc tatggaggaa    480
tccccaacca ccaaaagcaa tcttgagctg cagctgcttc atttagtgga ccttgtgtat    540
atctgggtgt gtatgcacat agatagacag tgagaaagaa aactgttctt ccagttcttt    600
tccagtgcta ctagcttagg gacaggttag aactgtctgc acaattgtgt gatcattccc    660
attcccactt caaaacaaac tgactgagat gttcaacaga aaactggctt caatgggtaa    720
catgcccttg ccacttactt aagacactgg tgtgatgggg ttttgaactc cctatatttg    780
taggtatctg                                                            790
```

<210> SEQ ID NO 37
<211> LENGTH: 842
<212> TYPE: DNA
<213> ORGANISM: Chimpanzee

<400> SEQUENCE: 37

```
ttgctgcaga tactactgac cagacaagct gttgaccagg cacctcccct cccgcccaaa     60
cctttccccc atgtggtcgt tagagacaga gcgacagagc agttgagagg acactcccgt    120
tttcggtgcc atcagtgccc cgtctacagc tcccccagct ccccccacct ccccactcc    180 caaccacgtt gggacaggga ggtgtgaggc aggagagaca gttggattct ttagagaaga    240
tggatatgac cagtggctat ggcctgtgtg atcccacccg tggtggctca agtctggccc    300
cacaccagcc ccaatccaaa actggcaagg acgcttcaca ggacaggaaa gtggcacctg    360
tctgctccag ctctggcatg ctaggaggg gggagtccct tgaactactg ggtgtagact    420
ggcctgaacc acaggagagg atggcccagg gtgaggtggc gtggtccatt ctcaagggac    480
gtcctccaac gggtggcgct agaggccatg gaggcagtag acaaggcgc aggcaggctg    540 gcccggggtc aggccgggca gagcacacg gggtgagagg gattcctaat cactcagagc    600
agtctgtgac ttagtggaca ggggaggggg caaaggggga ggagaagaaa atgttcttcc    660
```

```
agttactttc caattctcct ttagggacag cttagaatta tttgcactat tgagtcttca    720
tgttcccact tcaaaacaaa cagatgctct gagagcaaac tggcttgaat tggtgacatt    780
tagtccctca agccaccaga tgtgacagtg ttgagaacta cctggatttg tatatatacc    840
tg                                                                   842
```

<210> SEQ ID NO 38
<211> LENGTH: 841
<212> TYPE: DNA
<213> ORGANISM: Rhesus monkey

<400> SEQUENCE: 38

```
ttgctgcaga tactactgac cagacaagct gttgaccagg cacctcccct cccgcccaaa     60
cctttccccc atgtggtcgt tagagacaga gcagttgaga ggacactccc gttttcggtg    120
ccatcagtgc cccgtctacc actccccag ctcccccac ctcccccact cccaaccacg      180
ttgggacagg gaggtgtgag gcaggagaga cagttggatt ctttagagat ggatgtgacc    240
agtggctatg gcccgtgcga tcccacccgt ggcggctcaa atctggcccc accccagccc    300
caatccaaaa ctggcaagga cgcttcacag gacaggaaag tggcacctgt ctgttccggc    360
atggctagga gggagttgtc ccttgaacta ctgggtgtag actggcctaa atcacaggag    420
aggatggccc agggtgaggt ggcatggtcc attctcaagg gacgtcctcc agttggtggc    480
actagagagg ccatggaggc agtaggacaa ggcacaggca ggctggccca gggtcaggcc    540
gggccgaaca cagcggggtg agagggattc ctcgtctcag agcagtctgt gaccggtagt    600
tagggactta gtggacaggg aaggggcaaa ggggagagg aagaaaatgt tcttccagtt     660
actttccaat tctactcctt tagggacagc ttagaattat ttgcactatt gagtcttcat    720
gttcccactt caaaacaaac agatgctctg agagcaaact ggcttgaatt ggtgacgttt    780
agtccctcag gccaccagat gtgatggtgt tgagaactac tggatatgt atatatacct     840 g                                                                    841
```

<210> SEQ ID NO 39
<211> LENGTH: 803
<212> TYPE: DNA
<213> ORGANISM: Hamster

<400> SEQUENCE: 39

```
ttgctgcaga tactactgac cagacaagct gttgaccagg caccccccca atactccccc     60
aatgtgctca ttagagatag cagttgagag gacactccca ttttggtgc cctgtccata    120 gcttccctga ctcttccacc accccaactc ccaatctgag ggaccgggag gtgcgaggca    180
ggaaaaatat tggattcttt agagaagact agaggtgacc agtgactgtg cccagtaat    240 tagaactgtg gtggcacaag tctggccccca catccaccca atccaaaact gataaggata    300
ttttgaaaaa caggaaagca gtacctgtct gatccagctc tggtataggt aggagtgagt    360
cctgaactgc tggattacag actggcttga gccacagaag atgatggacc agagtaaagt    420
atcatcacct gctcacaagg catgcttcac tagagaataa ttctaaagag gtgccatgga    480
ggcagcagga caaggcacaa gcagtctggg tgggggtcaa gccagaccta gtgccacaga    540
acaagagagc aatctgtgac tagtagttag ggactttgtg gatgggacaa ggggcatggg    600
ggaagaaatg aaaatattct tccaattact ttccagttct cctttaggga cagcttagaa    660
ttatttgcac tattgagtct tcatgttccc acttaaaaac aaacagatgc tctgaaagca    720
aactggcttg aaatggtgac actttgtccc acaagccacc aaatgtggca gtgtttagaa    780
```
ctacctggat ctgtatatac ctg          803

<210> SEQ ID NO 40
<211> LENGTH: 2559
<212> TYPE: DNA
<213> ORGANISM: Human

<400> SEQUENCE: 40

| | | | | |
|---|---|---|---|---|
| gcgggccgag | gagccgggcg | caatggagcg | gaagaggtgg | gagtgcccgg | cgctcccgca | 60 |
| gggctgggag | agggaagaag | tgcccagaag | gtcggggctg | tcggccggcc | acagggatgt | 120 |
| cttttactat | agcccgagcg | ggaagaagtt | ccgcagcaag | ccgcagctgg | cgcgctacct | 180 |
| gggcggctcc | atggacctga | gcaccttcga | cttccgcacg | gcaagatgc | tgatgagcaa | 240 |
| gatgaacaag | agccgccagc | gcgtgcgcta | cgactcctcc | aaccaggtca | agggcaagcc | 300 |
| cgacctgaac | acgcgcctgc | ccgtgcgcca | gacgcgtcc | atcttcaagc | agccggtgac | 360 |
| caagattacc | aaccacccca | gcaacaaggt | caagagcgac | ccgcagaagg | cggtggacca | 420 |
| gccgcgccag | ctcttctggg | agaagaagct | gagcggcctg | aacgccttcg | acattgctga | 480 |
| ggagctggtc | aagaccatgg | acctccccaa | gggcctgcag | ggggtgggac | ctggctgcac | 540 |
| ggatgagacg | ctgctgtcgg | ccatcgccag | cgccctgcac | actagcacca | tgcccatcac | 600 |
| gggacagctc | tcggccgccg | tggagaagaa | ccccggcgta | tggctcaaca | ccacgcagcc | 660 |
| cctgtgcaaa | gccttcatgg | tgaccgacga | ggacatcagg | aagcaggaag | agctggtgca | 720 |
| gcaggtgcgg | aagcggctgg | aggaggcgct | gatggccgac | atgctggcgc | acgtggagga | 780 |
| gctggcccgt | gacggggagg | cgccgctgga | caaggcctgc | gctgaggacg | acgacgagga | 840 |
| agacgaggag | gaggaggagg | aggagcccga | cccggacccg | gagatggagc | acgtctaggg | 900 |
| caggtgctgc | ggggccacgg | gggctccctg | gagtcgggtc | ctggcagtgg | ggactgcctg | 960 |
| gtgaacacag | atgtgcttgg | gatgacgggt | gcctcccaag | agcttcccat | ctccctagaa | 1020 |
| gagcccaagc | gtccccgtcc | cgtggagtcg | ctaaagccag | ccctccctgt | cctttccaga | 1080 |
| ggccctgccg | agagccgtg | ctgcctgctg | gagccgcctg | cagacgcggt | cctcggcccc | 1140 |
| acgtgaacca | ggctcggcgg | cgaagcccag | ccttggagac | acccaggagg | aaggccgtgc | 1200 |
| tcctggctcc | ctcctcggcc | cgtccccact | tcccggggcc | tcggggcaca | cagctggggc | 1260 |
| tgccccacc | cgaaagaccc | tccacgctcg | tcctctacag | agtccggctt | cgggaagtgc | 1320 |
| cgggtgctcc | tgggccctgc | ctggctccct | acgacctttg | ggctcgaggc | cagctcctcc | 1380 |
| ccatgcccgc | tgtcccagct | ccttgagact | ggagagcagc | cagcaggtgc | ccggcagctc | 1440 |
| ggcgccacgg | cttgctgaca | gctgggaggg | tttctcggtc | tggaggcgta | gttttgaaac | 1500 |
| tcacatcacc | cactgtgcag | cgtgaggacg | ggactctggt | ctgctgtggg | gggcatgcag | 1560 |
| gacggcgcca | ctctctgccc | tgccatgcgg | ctggtggtgc | cacagagcct | caccgtgcct | 1620 |
| gagtggcatg | cccaggaggc | cgctctcctt | cagtaaatgt | aacacagtcg | aggcacgtca | 1680 |
| tcgggcagcc | ttccctgtgt | gccaacgcca | gccttcgctt | ctgaaaacca | aactccagcc | 1740 |
| gctgccagtc | gggacttggt | cgcccggcgc | tgccagaatg | ctccactgcc | agccggcccc | 1800 |
| cctgcctcgg | tttcccttct | gtttagtggc | gacacaggca | cccagctttg | gggtggtgct | 1860 |
| gacgctccca | ggggtgccag | gagccactgg | gacagggtga | ggctcccaga | cgctcctcga | 1920 |
| ggtgcccagc | tctccaggga | gcttctggcc | caaggccgtc | tgagggatct | gctccttaac | 1980 |
| cccccagtgc | cttggcgagg | gcaggttcca | agccacagac | gcctgccccg | agtggactct | 2040 |

```
gcggccagtc cctggtgccc tcctggccct gctgcccagt gagggctcct acgggtgggt    2100
tcattggcct gggcccagcg agcccccacc tgcattgacc ttaggcccat agagagggcc    2160
tgtcccggtg ctgccccagc caggatctgg tcgctgcccc aggggactg atgggcagag     2220 tcgcccctgt ggctggactg tgaccatccc tgatgggcc tgaccgcggg agctgaggaa     2280
gcgccgctcc accgtctgcc ctccaaggac ccgcatggag gcagtgggct ggcagcttcc    2340
tgctgctccc tgtcagagtc aaagcacaaa tcctcaggac gggctcaagg gccagggcag    2400
ccgagggaag ctccaggtgg ggaccacgtc ttcctgaggt tggtgcccac tggctgggac    2460
cctttgcagt ggggtggcct cccctctgtc tgcctggtgg agggagccgt gggcgtgggg    2520
acgtgactga ataaagccac catgggtgga tgtgcttgg                           2559
```

<210> SEQ ID NO 41
<211> LENGTH: 2792
<212> TYPE: DNA
<213> ORGANISM: Human

<400> SEQUENCE: 41

```
gggggcgtgg ccccgagaag gcggagacaa gatggccgcc catagcgctt ggaggaccta     60
agaggcggtg gccggggcca cgcccgggc aggaggccg ctctgtgcgc gcccgctcta      120
tgatgcttgc gcgcgtcccc cgcgcgccgc gctgcgggcg gggcgggtct ccgggattcc    180
aagggctcgg ttacggaaga agcgcagcgc cggctgggga gggggctgga tgcgcgcgca    240
cccgggggga ggccgctgct gcccggagca ggaggagggg gagagtgcgg cggcggcag     300 cggcgctggc ggcgactccg ccatagagca gggggggccag ggcagcgcgc tcgccccgtc   360
cccggtgagc ggcgtgcgca gggaaggcgc tcggggcggc ggccgtggcc ggggcggtg    420 gaagcaggcg gcccggggcg gcggcgtctg tggccgtggc cggggccggg gccgtggccg    480
gggacgggga cggggccggg gccggggccg cggccgtccc ccgagtggcg gcagcggcct    540
tggcggcgac ggcggcggct gcggcggcgg cggcagcggt ggcggcggcg ccccccggcg    600
ggagccggtc cctttcccgt cggggagcgc ggggccgggg cccaggggac cccgggccac    660
ggagagcggg aagaggatgg attgcccggc cctccccccc ggatggaaga aggaggaagt    720
gatccgaaaa tctgggctaa gtgctggcaa gagcgatgtc tactacttca gtccaagtgg    780
taagaagttc agaagcaagc ctcagttggc aaggtacctg ggaaatactg ttgatctcag    840
cagttttgac ttcagaactg gaaagatgat gcctagtaaa ttacagaaga caaacagag     900 actgcgaaac gatcctctca atcaaaataa gctgcgctgg aacactcatc gtcctgcacc    960
atggcatgcg ctttcaagac tctgcttgct catacgctgt ttgctctgct tggaatgtgc   1020 ttacccccctt cccccttcatc tggtgaactc ctactcatcc aagacccagc ttcattgtct  1080
ccatctctgg gaagcctgcc ctgcatactc caggcagaac caatcctttc ctccataagg   1140
gtaaaccaga cttgaataca acattgccaa ttagacaaac agcatcaatt tcaaacaac    1200 cggtaaccaa agtcacaaat catcctagta ataaagtgaa atcagaccca caacgaatga   1260
atgaacagcc acgtcagctt ttctgggaga agaggctaca aggacttagt gcatcagatg   1320
taacagaaca aattataaaa accatggaac tacccaaagg tcttcaagga gttggtccag   1380
gtagcaatga tgagacccctt ttatctgctg ttgccagtgc tttgcacaca agctctgcgc  1440
caatcacagg gcaagtctcc gctgctgtgg aaaagaaccc tgctgtttgg cttaacacat   1500 ctcaaccct ctgcaaagct tttattgtca cagatgaaga catcaggaaa caggaagagc    1560
gagtacagca agtacgcaag aaattggaag aagcactgat ggcagacatc ttgtcgcgag   1620
```

```
ctgctgatac agaagagatg gatattgaaa tggacagtgg agatgaagcc taagaatatg    1680
atcaggtaac tttcgaccga cttteecca gagaaaatte ctagaaattg aacaaaaatg    1740
tttccactgg cttttgcctg taagaaaaaa aatgtacccg agcacataga gcttttaat    1800 agcactaacc aatgccttt tagatgtatt tttgatgtat atatctatta ttcaaaaat    1860 catgtttatt ttgagtccta ggacttaaaa ttagtcttt gtaatatcaa gcaggaccct   1920
aagatgaagc tgagcttttg atgccaggtg caatctactg gaaatgtagc acttacgtaa    1980
aacatttgtt tcccccacag ttttaataag aacagatcag gaattctaaa taaatttccc    2040
agttaaagat tattgtgact tcactgtata taaacatatt tttatacttt attgaaaggg    2100
gacacctgta cattcttcca tcatcactgt aaagacaaat aaatgattat attcacagac    2160
tgattggaat tcttctgtt gaaaagcaca cacaataaag accccctcgt tagccttcct    2220
ctgatttaca ttcaactctg atccctgggc cttaggttg acatggaggt ggaggaagat    2280
agcgcatata tttgcagtat gaactattgc ctctggacgt tgtgagaatt gtgctttcac    2340
cagaatttct aagaatttct gctaaatatc acctagcatg tgtaattttt ttccttgcc    2400 tgtgacttgg acttttgata gttctataag aataaggctt tttcttccct tgggcatgag    2460
tcagatacac aaggacccctt caggtgttac tagaaggcgt ccatgtttat tgtttttaa    2520 agaatgtttg gcactctcta acgtccacta gcttactgag ttatcaggtg caggtcagac    2580
tcttggctac agtgagaggc agcttctagg cagagttgct taatgaaagg gtttgtaata    2640
ctttacaaac cattacctgt acctggcctg gcctccaaaa tattaacatt cttttctgt    2700 tgaaactcgc gagtgtaact ttcataccac ttgaatttat tgatatttaa ttatgaaaac    2760
tagcattaca ttattaaacg atttctaaaa tc                                 2792

<210> SEQ ID NO 42
<211> LENGTH: 2655
<212> TYPE: DNA
<213> ORGANISM: Human

<400> SEQUENCE: 42
gcggccgcgg aggaggagga aggggaggag ggcgaggcgg gaggtgcagg agggaccctc    60
gccatgggtc cacgggccta gagtggcgga agataccggc ctggtgccaa actggctact   120
gctgcttcct gtggcctcca tggctgagga ctggctggac tgcccggccc tgggccctgg   180
ctggaagcgc cgcgaagtct ttcgcaagtc aggggccacc tgtggacgct cagacaccta   240
ttaccagagc cccacaggag acaggatccg aagcaaagtt gagctgactc gatacctggg   300
ccctgcgtgt gatctcaccc tcttcgactt caaacaaggc atcttgtgct atccagcccc   360
caaggcccat cccgtggcgg ttgccagcaa gaagcgaaag aagccttcaa ggccagccaa    420
gactcggaaa cgtcaggttg gaccccagag tggtgaggtc aggaaggagg ccccgaggga    480
tgagaccaag gctgacactg acacagcccc agcttcattc cctgctcctg ggtgctgtga    540
gaactgtgga atcagcttct cagggatgga cacccaaagg cagcggctca aaacgttgtg    600
caaagactgt cgagcacaga gaattgcctt caaccgggaa cagagaatgt ttaagcgtgt    660
gggctgtggg gagtgtcag cctgccaggt aacagagac tgtggggcct gctccacctg    720
cctcctgcag ctgccccatg atgtggcatc ggggctgttc tgcaagtgtg aacggagacg    780
ctgcctccgg attgtggaaa ggagccgagg gtgtggagta tgccggggct gtcagaccca    840
agaggattgt ggccattgcc ccatctgcct tcgccctccc cgccctggtc tcaggcgcca    900
```

-continued

```
gtggaaatgt gtccagcgac gttgcctacg gggtaaacat gcccgccgca agggaggctg    960
tgactccaag atggctgcca ggcggcgccc cggagcccag ccactgcctc caccaccccc    1020
atcacagtcc ccagagccca cagagccgca ccccagagcc ctggccccct cgccacctgc    1080
cgagttcatc tattactgtg tagacgagga cgagctaaag cggctgctgc ccagtgtctg    1140
gtcagagtct gaggatgggg caggatcgcc cccaccttac cgtcgtcgaa agaggcccag    1200
ctctgcccga cggcaccatc ttggccctac cttgaagccc accttggcta cacgcacagc    1260
ccaaccagac catacccagg ctccaacgaa gcaggaagca ggtggtggct ttgtgctgcc    1320
cccgcctggc actgaccttg tgttttacg ggaaggcgca agcagtcctg tgcaggtgcc    1380
gggccctgtt gcagcttcca cagaagccct gttgcaggga gtagacccag gcctgccttc    1440
tgtgaagcaa gagccacctg acccagagga ggacaaggag gagaacaagg atgattctgc    1500
ctccaaattg gccccagagg aagaggcagg aggggctggc acaccgtga tcacggagat    1560 tttcagcctg ggtggaaccc gcttccgaga tacagcagtc tggttgccaa ggtccaaaga    1620
ccttaaaaaa cctggagcta gaaagcagta gactggaggc ttctacagac tgtaggattc    1680
aagtctgcag ggcaggcact cgggaaggga agatggatgt aaagtgtggg agaccgagga    1740
cacagtggag cccacgagca cgagctgaaa cccacgagga tggcctggaa cccatgtcag    1800
tctctcacca cctccagctt cgatgatgtg ggtgtcctgc agaagaagct ggtgcccttc    1860
ctcacagagt taaatatgca tctggcccag gaattagaga agctgaaagg atgatcctgg    1920
ggaaggtgga gcagctgcag gcctggctgc aggcctgact actgcccaca caacgaggt    1980 gatctagcag atacatggca acgtgtgaac tgcaacaacg cctggtgccc cagcaccaac    2040
cttccaagtg taaaaacaat gtgctgctgc ttcacttccg ccctccggtt atcaagcaaa    2100
atgtctcttg tggcccatct tactggaaga gagttccggg aaacatagcc tcaccaaggt    2160
gacacattac aaagccaccc taccatgaat ccgctcccaa gggtctcact gctcacctga    2220
ggataactca atataactat gttgctgaaa atgcaaagct gaagaccatg gatttcatgg    2280
tgattccagc aagtacagag attctatgaa gcccacccga aaaaaacttg ctggtcctgg    2340
ctatttttgt gtcatttatt caagtattga gaacctggcc tgtggtaggc actgtactta    2400
atactaggat acagaaatgc aaaagatacg gcccatgcaa tttattaaa tgcatcaata    2460 tgtattacaa atggtgaatg gatttccaac tttatcatgg aatttaatgc tgaatatata    2520
gaattcagaa aattgttggg aggacagccc ttttgtgaac cttgtttggg gcacagtagg    2580
aattggaaat aatttagttt ctatctctaa gctgttctat tttaaaatta tttttaaatt    2640
tttattgtcc cactt                                                     2655
```

<210> SEQ ID NO 43
<211> LENGTH: 2815
<212> TYPE: DNA
<213> ORGANISM: Human

<400> SEQUENCE: 43

```
gcggccgcgg aggaggagga aggggaggag ggcgaggcgg gaggtgcagg agggaccctc      60
gccatgggtc cacgggccta gagtggcgga agataccggc ctggtgccaa actggctact     120
gctgcttcct gtggcctcca tggctgagga ctggctggac tgcccggccc tgggccctgg     180
ctggaagcgc cgcgaagtct ttcgcaagtc aggggccacc tgtggacgct cagacaccta     240
ttaccagagc cccacaggag acaggatccg aagcaaagtt gagctgactc gatacctggg     300
ccctgcgtgt gatctcaccc tcttcgactt caaacaaggc atcttgtgct atccagcccc     360
```

```
caaggcccat cccgtggcgg ttgccagcaa gaagcgaaag aagccttcaa ggccagccaa      420
gactcggaaa cgtcaggttg acccccagag tggtgaggtc aggaaggagg ccccgaggga      480
tgagaccaag gctgacactg acacagcccc agcttcattc cctgctcctg ggtgctgtga      540
gaactgtgga atcagcttct caggggatgg cacccaaagg cagcggctca aaacgttgtg      600
caaagactgt cgagcacaga gaattgcctt caaccgggaa cagagaatgt ttaagagccg      660
agggtgtgga gtatgccggg gctgtcagac ccaagaggat tgtggccatt gccccatctg      720
ccttcgccct ccccgccctg gtctcaggcg ccagtggaaa tgtgtccagc gacgttgcct      780
acggggtaaa catgcccgcc gcaagggagg ctgtgactcc aagatggctg ccaggcggcg      840
ccccggagcc cagccactgc ctccaccacc cccatcacag tccccagagc ccacagagcc      900
gcacccagag gccctggccc cctcgccacc tgccgagttc atctattact gtgtagacga      960
ggacgagcta cagccctaca cgaaccgccg cagaaccgc aagtgcgggg cctgtgcagc     1020
ctgcctacgg cggatggact gtggccgctg cgacttctgc tgcgacaagc ccaaattcgg     1080
gggcagcaac cagaagcgcc agaagtgtcg ttggcgccaa tgcctgcagt ttgccatgaa     1140
gcggctgctg cccagtgtct ggtcagagtc tgaggatggg gcaggatcgc ccccaccttta     1200 ccgtcgtcga agaggcccca gctctgcccg acggcaccat cttggcccta ccttgaagcc     1260
caccttggct acacgcacag cccaaccaga ccatacccag gctccaacga agcaggaagc     1320
aggtggtggc tttgtgctgc cccgcctgg cactgacctt tgtttttac gggaaggcgc      1380 aagcagtcct gtgcaggtgc cgggccctgt tgcagcttcc acagaagccc tgttgcagga     1440
ggcccagtgc tctggcctga gttgggttgt ggccttaccc caggtgaagc aagagaaggc     1500
ggatacccag gacgagtgga caccaggcac agctgtcctg acttctcccg tattggtgcc     1560
tggctgccct agcaaggcag tagacccagg cctgccttct gtgaagcaag agccacctga     1620
cccagaggag gacaaggagg agaacaagga tgattctgcc tccaaattgg ccccagagga     1680
agaggcagga ggggctggca cacccgtgat cacggagatt ttcagcctgg gtggaacccg     1740
cttccgagat acagcagtct ggttgccaag gtccaaagac cttaaaaaac ctggagctag     1800
aaagcagtag actggaggct tctacagact gtaggattca agtctgcagg gcaggcactc     1860
gggaagggaa gatggatgta aagtgtggga gaccgaggac acagtggagc ccacgagcac     1920
gagctggaac ccacgaggat ggcctggaac ccatgtcagt ctctcaccac ctccagcttc     1980
gatgatgtgg gtgtcctgca gaagaagctg gtgcccttcc tcacagagtt aaatatgcat     2040
ctggcccagg aattagagaa gctgaaagga tgatcctggg gaaggtggag cagctgcagg     2100
cctggctgca ggcctgacta ctgcccacac caacgaggta atctagcaga tacatggcaa     2160
cgtgtgaact gcaacaacgc ctggtgcccc agcaccaacc ttccaagtgt aaaaacaatg     2220
tgctgctgct tcacttccgc cctccggtta tcaagcaaaa tgtctcttgt ggcccatctt     2280
actggaagag agttccggga aacatagcct caccaaggtg acacattaca agccaccct      2340 accatgaatc cgctcccaag ggtctcactg ctcacctgag gataactcaa tataactatg     2400
ttgctgaaaa tgcaaagctg aagaccatgg atttcatggt gattccagca agtacagaga     2460
ttctatgaag cccacccaga aaaaacttgc tggtcctggc tatttttgtg tcatttattc     2520
aagtattgag aacctggcct gtggtaggca ctgtacttaa tactaggata cagaaatgca     2580
aaagatacgg cccatgcaat tttattaaat gcatcaatat gtattacaaa tggtgaatgg     2640
atttccaact ttatcatgga atttaatgct gaatatatag aattcagaaa attgtttggga     2700
```

-continued

| | |
|---|---|
| ggacagccct tttgtgaacc ttgtttgggg cacagtagga attggaaata atttagtttc | 2760 |
| tatctctaag ctgttctatt ttaaaattat ttttaaattt ttattgtccc actta | 2815 |

<210> SEQ ID NO 44
<211> LENGTH: 2961
<212> TYPE: DNA
<213> ORGANISM: Human

<400> SEQUENCE: 44

| | |
|---|---|
| gcggccgcgg aggaggagga aggggaggag ggcgaggcgg gaggtgcagg agggaccctc | 60 |
| gccatgggtc cacgggccta gagtggcgga agataccggc ctggtgccaa actggctact | 120 |
| gctgcttcct gtggcctcca tggctgagga ctggctggac tgcccggccc tgggccctgg | 180 |
| ctggaagcgc cgcgaagtct tcgcaagtc aggggccacc tgtggacgct cagacaccta | 240 |
| ttaccagagc cccacaggag acaggatccg aagcaaagtt gagctgactc gatacctggg | 300 |
| ccctgcgtgt gatctcaccc tcttcgactt caaacaaggc atcttgtgct atccagcccc | 360 |
| caaggcccat cccgtggcgg ttgccagcaa gaagcgaaag aagccttcaa ggccagccaa | 420 |
| gactcggaaa cgtcaggttg acccccagag tggtgaggtc aggaaggagg ccccgaggga | 480 |
| tgagaccaag gctgacactg acacagcccc agcttcattc cctgctcctg ggtgctgtga | 540 |
| gaactgtgga atcagcttct caggggatgg cacccaaagg cagcggctca aaacgttgtg | 600 |
| caaagactgt cgagcacaga gaattgcctt caaccgggaa cagagaatgt ttaagcgtgt | 660 |
| gggctgtggg gagtgtgcag cctgccaggt aacagagaca tgtggggcct gctccacctg | 720 |
| cctcctgcag ctgccccatg atgtggcatc ggggctgttc tgcaagtgtg aacggagacg | 780 |
| ctgcctccgg attgtggaaa ggagccgagg gtgtggagta tgccgggct gtcagaccca | 840 |
| agaggattgt ggccattgcc ccatctgcct tcgccctccc cgccctggtc tcaggcgcca | 900 |
| gtggaaatgt gtccagcgac gttgcctacg ggtaaacat gcccgccgca agggaggctg | 960 |
| tgactccaag atggctgcca ggcggcgccc cggagcccag ccactgcctc caccaccccc | 1020 |
| atcacagtcc ccagagccca cagagccgca ccccagagcc ctggcccct cgccacctgc | 1080 |
| cgagttcatc tattactgtg tagacgagga cgagctacag ccctacacga accgccggca | 1140 |
| gaaccgcaag tgcgggggcct gtgcagcctg cctacgcgg atggactgtg gccgctgcga | 1200 |
| cttctgctgc gacaagccca aattcggggg cagcaaccag aagcgccaga agtgtcgttg | 1260 |
| gcgccaatgc ctgcagtttg ccatgaagcg gctgctgccc agtgtctggt cagagtctga | 1320 |
| ggatggggca ggatcgcccc caccttaccg tcgtcgaaag aggcccagct ctgcccgacg | 1380 |
| gcaccatctt ggcctacct tgaagcccac cttggctaca cgcacagccc aaccagacca | 1440 |
| tacccaggct ccaacgaagc aggaagcagg tggtggcttt gtgctgcccc cgcctggcac | 1500 |
| tgaccttgtg tttttacggg aaggcgcaag cagtcctgtg caggtgccgg gcctgttgc | 1560 |
| agcttccaca gaagccctgt tgcaggaggc ccagtgctct ggcctgagtt gggttgtggc | 1620 |
| cttaccccag gtgaagcaag agaaggcgga tacccaggac gagtggacac caggcacagc | 1680 |
| tgtcctgact tctcccgtat tggtgcctgg ctgccctagc aaggcagtag acccaggcct | 1740 |
| gccttctgtg aagcaagagc cacctgaccc agaggaggac aaggaggaga acaaggatga | 1800 |
| ttctgcctcc aaaattggcc cagaggaaga ggcaggaggg gctggacacac ccgtgatcac | 1860 |
| ggagattttc agcctgggtg aacccgcctt ccgagataca gcagtctggt tgccaaggtc | 1920 |
| caaagacctt aaaaaacctg gagctagaaa gcagtagact ggaggcttct acagactgta | 1980 |
| ggattcaagt ctgcagggca ggcactcggg aagggaagat ggatgtaaag tgtgggagac | 2040 |

```
cgaggacaca gtggagccca cgagcacgag ctggaaccca cgaggatggc ctggaaccca    2100
tgtcagtctc tcaccacctc cagcttcgat gatgtgggtg tcctgcagaa gaagctggtg    2160
cccttcctca cagagttaaa tatgcatctg gcccaggaat tagagaagct gaaaggatga    2220
tcctggggaa ggtggagcag ctgcaggcct ggctgcaggc ctgactactg cccacaccaa    2280
cgaggtgatc tagcagatac atggcaacgt gtgaactgca caacgcctg gtgccccagc    2340 accaaccttc caagtgtaaa acaatgtgc tgctgcttca cttccgccct ccggttatca    2400
agcaaaatgt ctcttgtggc ccatcttact ggaagagagt tccgggaaac atagcctcac    2460
caaggtgaca cattacaaag ccaccctacc atgaatccgc tcccaagggt ctcactgctc    2520
acctgaggat aactcaatat aactatgttg ctgaaaatgc aaagctgaag accatggatt    2580
tcatggtgat ccagcaagt acagagattc tatgaagccc acccagaaaa aacttgctgg    2640
tcctggctat ttttgtgtca tttattcaag tattgagaac ctggcctgtg gtaggcactg    2700
tacttaatac taggatacag aaatgcaaaa gatacggccc atgcaatttt attaaatgca    2760
tcaatatgta ttacaaatgg tgaatggatt tccaacttta tcatgaatt taatgctgaa    2820 tatatagaat tcagaaaatt gttgggagga cagcccttt gtgaaccttg tttggggcac    2880
agtaggaatt ggaaataatt tagtttctat ctctaagctg ttctattta aaattatttt    2940 taaattttta ttgtcccact t                                              2961

<210> SEQ ID NO 45
<211> LENGTH: 1900
<212> TYPE: DNA
<213> ORGANISM: Human

<400> SEQUENCE: 45
gcggccgcgg aggaggagga aggggaggag ggcgaggcgg gaggtgcagg agggaccctc      60
gccatgggtc cacgggccta gagtggcgga agataccggc ctggtgccaa actggctact     120
gctgcttcct gtggcctcca tggctgagga ctggctggac tgcccggccc tgggccctgg     180
ctggaagcgc cgcgaagtct ttcgcaagtc aggggccacc tgtggacgct cagacaccta     240
ttaccagagc cccacaggag acaggatccg aagcaaagtt gagctgactc gatacctggg     300
ccctgcgtgt gatctcaccc tcttcgactt caaacaaggc atcttgtgct atccagcccc     360 caagcccat cccgtggcgg ttgccagcaa gaagcgaaag aagccttcaa ggccagccaa     420
gactcggaaa cgtcaggttg accccagag tggtgaggtc aggaaggagg ccccgaggga     480
tgagaccaag gctgacactg acacagcccc agcttcattc cctgctcctg ggtgctgtga     540
gaactgtgga atcagcttct cagggatgga cacccaaagg cagcggctca aaacgttgtg     600
caaagactgt cgagcacaga gaattgcctt caaccgggaa cagagaatgt ttaagcgtgt     660
gggctgtggg gagtgtgcag cctgccaggt aacagaagac tgtggggcct gctccacctg     720
cctcctgcag ctgccccatg atgtggcatc ggggctgttc tgcaagtgtg aacggagacg     780
ctgcctccgg attgtggaaa ggagccgagg tgtggagta gccgggct gtcagaccca     840 agaggattgt ggccattgcc ccatctgcct tcgccctccc cgccctggtc tcaggcgcca     900
gtggaaatgt gtccagcgac gttgcctacg gggtaaacat gcccgccgca agggaggctg     960
tgactccaag atggctgcca ggcggcgccc cggagcccag ccactgcctc caccacccc    1020 atcacagtcc ccagagccca cagagccgca gccctacacg aaccgccggc agaaccgcaa    1080
gtgcggggcc tgtgcagcct gcctacggcg gatggactgt ggccgctgcg acttctgctg    1140
```

| | |
|---|---|
| cgacaagccc aaattcgggg gcagcaacca gaagcgccag aagtgtcgtt ggcgccaatg | 1200 |
| cctgcagttt gccatgaagc ggctgctgcc cagtgtctgg tcagagtctg aggatggggc | 1260 |
| aggatcgccc ccaccttacc gtcgtcgaaa gaggcccagc tctgcccgac ggcaccatct | 1320 |
| tggccctacc ttgaagccca ccttggctac acgcacagcc caaccagacc atacccaggc | 1380 |
| tccaacgaag caggaagcag gtggtggctt tgtgctgccc ccgcctggca ctgaccttgt | 1440 |
| gtttttacgg gaaggcgcaa gcagtcctgt gcaggtgccg ggccctgttg cagcttccac | 1500 |
| agaagccctg ttgcaggcag tagacccagg cctgccttct gtgaagcaag agccacctga | 1560 |
| cccagaggag gacaaggagg agaacaagga tgattctgcc tccaaattgg ccccagagga | 1620 |
| agaggcagga ggggctggca cacccgtgat cacggagatt ttcagcctgg gtggaacccg | 1680 |
| cttccgagat acagcagtct ggttgccaag tctgcagggc aggcactcgg aagggaaga | 1740 |
| tggatgtaaa gtgtgggaga ccgaggacac agtggagccc acgagcacga gctggaaccc | 1800 |
| acgaggatgg cctggaaccc atgtcagtct ctcaccacct ccagcttcga tgatgtgggt | 1860 |
| gtcctgcaga gaagctggt gcccttcctc acagagttaa | 1900 |

<210> SEQ ID NO 46
<211> LENGTH: 2792
<212> TYPE: DNA
<213> ORGANISM: Human

<400> SEQUENCE: 46

| | |
|---|---|
| gcggccgcgg aggaggagga aggggaggag ggcgaggcgg gaggtgcagg agggaccctc | 60 |
| gccatgggtc cacgggccta gagtggcgga agataccggc ctggtgccaa actggctact | 120 |
| gctgcttcct gtggcctcca ggctgaggac tggctggact gcccggccct gggccctggc | 180 |
| tggaagcgcc gcgaagtctt tcgcaagtca ggggccacct gtggacgctc agacacctat | 240 |
| taccagagcc ccacaggaga caggatccga agcaaagttg agctgactcg ataccctggggc | 300 |
| cctgcgtgtg atctcaccct cttcgacttc aaacaaggca tcttgtgcta tccagccccc | 360 |
| aaggcccatc ccgtggcggt tgccagcaag aagcgaaaga agccttcaag gccagccaag | 420 |
| actcggaaac gtcaggttgg accccagagt ggtgaggtca ggaaggaggc cccgagggat | 480 |
| gagaccaagc tgacactga cacagcccca gcttcattcc ctgctcctgg gtgctgtgag | 540 |
| aactgtggaa tcagcttctc aggggatggc acccaaaggc agcggctcaa acgttgtgc | 600 |
| aaagactgtc gagcacagag aattgccttc aaccgggaac agagaatgtt taagcgtgtg | 660 |
| ggctgtgggg agtgtgcagc ctgccaggta acagaagact gtggggcctg ctccacctgc | 720 |
| ctcctgcagc tgccccatga tgtggcatcg ggctgttct gcaagtgtga acggagacgc | 780 |
| tgcctccgga ttgtggaaag gagccgaggg tgtggagtat gccggggctg tcagacccaa | 840 |
| gaggattgtg gccattgccc catctgcctt cgccctcccc gccctggtct caggcgccag | 900 |
| tggaaatgtg tccagcgacg ttgcctacgg ggtaaacatg cccgccgcaa gggaggctgt | 960 |
| gactccaaga tggctgccag gcggcgcccc ggagcccagc cactgcctcc accacccca | 1020 |
| tcacagtccc cagagcccac agagccgcac cccagagccc tggcccctc gccacctgcc | 1080 |
| gagttcatct attactgtgt agacgaggac gagctacagc ggctgctgcc cagtgtctgg | 1140 |
| tcagagtctg aggatggggc aggatcgccc ccaccttacc gtcgtcgaaa gaggcccagc | 1200 |
| tctgcccgac ggcaccatct tggccctacc ttgaagccca ccttggctac acgcacagcc | 1260 |
| caaccagacc atacccaggc tccaacgaag caggaagcag gtggtggctt tgtgctgccc | 1320 |
| ccgcctggca ctgaccttgt gtttttacgg gaaggcgcaa gcagtcctgt gcaggtgccg | 1380 |

-continued

```
ggccctgttg cagcttccac agaagccctg ttgcaggagg cccagtgctc tggcctgagt      1440
tgggttgtgg ccttacccca ggtgaagcaa gagaaggcgg atacccagga cgagtggaca      1500
ccaggcacag ctgtcctgac ttctcccgta ttggtgcctg gctgccctag caaggcagta      1560
gacccaggcc tgccttctgt gaagcaagag ccacctgacc cagaggagga caaggaggag      1620
aacaaggatg attctgcctc caaattggcc ccagaggaag aggcaggagg ggctggcaca      1680
cccgtgatca cggagatttt cagcctgggt ggaacccgct tccgagatac agcagtctgg      1740
ttgccaaggt ccaaagacct taaaaaacct ggagctagaa agcagtagac tggaggcttc      1800
tacagactgt aggattcaag tctgcagggc aggcactcgg aagggaaga tggatgtaaa       1860 gtgtgggaga ccgaggacac agtggagccc acgagcacga gctggaaccc acgaggatgg      1920
cctggaaccc atgtcagtct ctcaccacct ccagcttcga tgatgtgggt gtcctgcaga      1980
agaagctggt gccttcctc acagagttaa atatgcatct ggcccaggaa ttagagaagc       2040
tgaaaggatg atcctgggga aggtggagca gctgcaggcc tggctgcagg cctgactact      2100
gcccacacca acgaggtgat ctagcagata catggcaacg tgtgaactgc aacaacgcct      2160
ggtgccccag caccaacctt ccaagtgtaa aaacaatgtg ctgctgcttc acttccgccc      2220
tccggttatc aagcaaaatg tctcttgtgg cccatcttac tggaagagag ttccgggaaa      2280
catagcctca ccaaggtgac acattacaaa gccaccctac catgaatccg ctcccaaggg      2340
tctcactgct cacctgagga taactcaata taactatgtt gctgaaaatg caaagctgaa      2400
gaccatggat ttcatggtga ttccagcaag tacagagatt ctatgaagcc cacccagaaa      2460
aaacttgctg gtcctggcta tttttgtgtc atttattcaa gtattgagaa cctggcctgt      2520
ggtaggcact gtacttaata ctaggataca gaaatgcaaa agatacggcc catgcaattt      2580
tattaaatgc atcaatatgt attacaaatg gtgaatggat ttccaacttt atcatggaat      2640
ttaatgctga atatatagaa ttcagaaaat tgtttgggagg acagcccttt tgtgaaccct      2700
gtttggggca cagtaggaat tggaaataat ttagtttcta tctctaagct gttctatttt      2760
aaaattattt ttaaattttt attgtcccac tt                                    2792
```

<210> SEQ ID NO 47
<211> LENGTH: 2470
<212> TYPE: DNA
<213> ORGANISM: Human

<400> SEQUENCE: 47

```
ggcggctgta gccgaggggg cggccggaaa gcagcggcgg cgtctgggc gctttcgcaa       60 cattcagacc tcggttgcag cccggtgccg tgagctgaag aggtttcaca tcttactccg      120
ccccacaccc tgggcgttgc ggcgctgggc tcgttgctgc agccggaccc tgctcgatgg      180
gcacgactgg gctggagagt ctgagtctgg gggaccgcgg agctgccccc accgtcacct      240
ctagtgagcg cctagtccca gacccgccga atgacctccg caaagaagat gttgctatgg      300
aattggaaag agtgggagaa gatgaggaac aaatgatgat aaaagaagc agtgaatgta       360 atcccttgct acaagaaccc atcgcttctg ctcagtttgg tgctactgca ggaacagaat      420
gccgtaagtc tgtcccatgt ggatgggaaa gagttgtgaa gcaaaggtta tttgggaaga      480
cagcaggaag atttgatgtg tactttatca gcccacaagg actgaagttc agatccaaaa      540
gttcacttgc taattatctt cacaaaaatg gagagacttc tcttaagcca gaagattttg      600
attttactgt actttctaaa aggggtatca agtcaagata taaagactgc agcatggcag      660
```

-continued

```
ccctgacatc ccatctacaa aaccaaagta acaattcaaa ctggaacctc aggacccgaa    720
gcaagtgcaa aaggatgtgt tttatgccgc caagtagtag ttcagagttg caggagagca    780
gaggactctc taactttact tccactcatt tgcttttgaa agaagatgag ggtgttgatg    840
atgttaactt cagaaaggtt agaaagccca aggaaaggt gactatttg aaaggaatcc     900 caattaagaa aactaaaaaa ggatgtagga agagctgttc aggttttgtt caaagtgata    960
gcaaaagaga atctgtgtgt aataaagcag atgctgaaag tgaacctgtt gcacaaaaaa   1020
gtcagcttga tagaactgtc tgcatttctg atgctggagc atgtggtgag accctcagtg   1080
tgaccagtga agaaaacagc cttgtaaaaa aaaagaaag atcattgagt tcaggatcaa    1140 attttgttc tgaacaaaaa acttctggca tcataaacaa attttgttca gccaaagact    1200
cagaacacaa cgagaagtat gaggatacct ttttagaatc tgaagaaatc ggaacaaaag   1260
tagaagttgt ggaaaggaaa gaacatttgc atactgacat tttaaaacgt ggctctgaaa   1320
tggacaacaa ctgctcacca accaggaaag acttcactgg tgagaaaata tttcaagaag   1380
ataccatccc acgaacacag atagaaagaa ggaaaacaag cctgtatttt ccagcaaat    1440 ataacaaaga agctcttagc cccccacgac gtaaagcctt taagaaatgg acacctcctc   1500
ggtcaccttt taatctcgtt caagaaacac ttttcatga tccatggaag cttctcatcg    1560
ctactatatt tctcaatcgg acctcaggca aaatggcaat acctgtgctt tggaagtttc   1620
tggagaagta tccttcagct gaggtagcaa gaaccgcaga ctggagagat gtgtcagaac   1680
ttcttaaacc tcttggtctc tacgatcttc gggcaaaaac cattgtcaag ttctcagatg   1740
aatacctgac aaagcagtgg aagtatccaa ttgagcttca tgggattggt aaatatggca   1800
acgactctta ccgaattttt tgtgtcaatg agtggaagca ggtgcaccct gaagaccaca   1860
aattaaataa atatcatgac tggctttggg aaaatcatga aaaattaagt ctatcttaaa   1920
ctctgcagct ttcaagctca tctgttatgc atagctttgc acttcaaaaa agcttaatta   1980
agtacaacca accacctttc cagccataga gattttaatt agcccaacta gaagcctagt   2040
gtgtgtgctt tcttaatgtg tgtgccaatg gtggatcttt gctactgaat gtgtttgaac   2100
atgttttgag atttttttaa aataaattat tatttgacaa caatccaaaa aaaatacggc   2160
ttttccaatg atgaaatata atcagaagat gaaaatagt tttaaactat caataataca   2220
aagcaaattt ctatcagcct tgctaaagct aggggcccac taaatatttt tatcggctag   2280
gcgtggtggt gcatgcctgt aatctcggaa ggctgaggca ggaggatcat ttgagctcat   2340
gagggcccag gaggtcaagg cttcagtgag ccatgatcat gccactgcac tccagtctgg   2400
atgacagaga gagaccctgt ctcaaaaaat atatatttaa aaaataaaaa taaaagctga   2460
ccccaaagac                                                          2470
```

<210> SEQ ID NO 48
<211> LENGTH: 291
<212> TYPE: PRT
<213> ORGANISM: Human

<400> SEQUENCE: 48

```
Met Glu Arg Lys Arg Trp Glu Cys Pro Ala Leu Pro Gln Gly Trp Glu
1               5                   10                  15

Arg Glu Glu Val Pro Arg Arg Ser Gly Leu Ser Ala Gly His Arg Asp
            20                  25                  30

Val Phe Tyr Tyr Ser Pro Ser Gly Lys Lys Phe Arg Ser Lys Pro Gln
        35                  40                  45
```

```
Leu Ala Arg Tyr Leu Gly Gly Ser Met Asp Leu Ser Thr Phe Asp Phe
     50                  55                  60

Arg Thr Gly Lys Met Leu Met Ser Lys Met Asn Lys Ser Arg Gln Arg
 65                  70                  75                  80

Val Arg Tyr Asp Ser Ser Asn Gln Val Lys Gly Lys Pro Asp Leu Asn
                 85                  90                  95

Thr Ala Leu Pro Val Arg Gln Thr Ala Ser Ile Phe Lys Gln Pro Val
            100                 105                 110

Thr Lys Ile Thr Asn His Pro Ser Asn Lys Val Lys Ser Asp Pro Gln
        115                 120                 125

Lys Ala Val Asp Gln Pro Arg Gln Leu Phe Trp Glu Lys Lys Leu Ser
    130                 135                 140

Gly Leu Asn Ala Phe Asp Ile Ala Glu Glu Leu Val Lys Thr Met Asp
145                 150                 155                 160

Leu Pro Lys Gly Leu Gln Gly Val Gly Pro Gly Cys Thr Asp Glu Thr
                165                 170                 175

Leu Leu Ser Ala Ile Ala Ser Ala Leu His Thr Ser Thr Met Pro Ile
            180                 185                 190

Thr Gly Gln Leu Ser Ala Ala Val Glu Lys Asn Pro Gly Val Trp Leu
        195                 200                 205

Asn Thr Thr Gln Pro Leu Cys Lys Ala Phe Met Val Thr Asp Glu Asp
    210                 215                 220

Ile Arg Lys Gln Glu Glu Leu Val Gln Gln Val Arg Lys Arg Leu Glu
225                 230                 235                 240

Glu Ala Leu Met Ala Asp Met Leu Ala His Val Glu Glu Leu Ala Arg
                245                 250                 255

Asp Gly Glu Ala Pro Leu Asp Lys Ala Cys Ala Glu Asp Asp Asp Glu
            260                 265                 270

Glu Asp Glu Glu Glu Glu Glu Glu Pro Asp Pro Asp Pro Glu Met
        275                 280                 285

Glu His Val
    290

<210> SEQ ID NO 49
<211> LENGTH: 302
<212> TYPE: PRT
<213> ORGANISM: Human

<400> SEQUENCE: 49

Met Arg Ala His Pro Gly Gly Arg Cys Cys Pro Glu Gln Glu Glu
 1               5                  10                  15

Gly Glu Ser Ala Ala Gly Gly Ser Gly Ala Gly Asp Ser Ala Ile
                 20                  25                  30

Glu Gln Gly Gly Gln Ser Ala Leu Ala Pro Ser Pro Val Ser Gly
             35                  40                  45

Val Arg Arg Glu Gly Ala Arg Gly Gly Arg Gly Arg Trp
     50                  55                  60

Lys Gln Ala Gly Arg Gly Gly Val Cys Arg Gly Arg Gly Arg
 65                  70                  75                  80

Gly Arg Gly Arg Gly Arg Gly Arg Gly Arg Gly Arg
                 85                  90                  95

Pro Pro Ser Gly Gly Ser Gly Leu Gly Gly Asp Gly Gly Cys Gly
            100                 105                 110

Gly Gly Gly Ser Gly Gly Gly Ala Pro Arg Arg Glu Pro Val Pro
        115                 120                 125
```

```
Phe Pro Ser Gly Ser Ala Gly Pro Gly Pro Arg Gly Pro Arg Ala Thr
    130                 135                 140

Glu Ser Gly Lys Arg Met Asp Cys Pro Ala Leu Pro Pro Gly Trp Lys
145                 150                 155                 160

Lys Glu Glu Val Ile Arg Lys Ser Gly Leu Ser Ala Gly Lys Ser Asp
                165                 170                 175

Val Tyr Tyr Phe Ser Pro Ser Gly Lys Lys Phe Arg Ser Lys Pro Gln
                180                 185                 190

Leu Ala Arg Tyr Leu Gly Asn Thr Val Asp Leu Ser Ser Phe Asp Phe
            195                 200                 205

Arg Thr Gly Lys Met Met Pro Ser Lys Leu Gln Lys Asn Lys Gln Arg
210                 215                 220

Leu Arg Asn Asp Pro Leu Asn Gln Asn Lys Leu Arg Trp Asn Thr His
225                 230                 235                 240

Arg Pro Ala Pro Trp His Ala Leu Ser Arg Leu Cys Leu Leu Ile Arg
                245                 250                 255

Cys Leu Leu Cys Leu Glu Cys Ala Tyr Pro Leu Pro Leu His Leu Val
                260                 265                 270

Asn Ser Tyr Ser Ser Lys Thr Gln Leu His Cys Leu His Leu Trp Glu
            275                 280                 285

Ala Cys Pro Ala Tyr Ser Arg Gln Asn Gln Ser Phe Pro Pro
290                 295                 300

<210> SEQ ID NO 50
<211> LENGTH: 503
<212> TYPE: PRT
<213> ORGANISM: Human

<400> SEQUENCE: 50

Met Ala Glu Asp Trp Leu Asp Cys Pro Ala Leu Gly Pro Gly Trp Lys
1               5                   10                  15

Arg Arg Glu Val Phe Arg Lys Ser Gly Ala Thr Cys Gly Arg Ser Asp
                20                  25                  30

Thr Tyr Tyr Gln Ser Pro Thr Gly Asp Arg Ile Arg Ser Lys Val Glu
            35                  40                  45

Leu Thr Arg Tyr Leu Gly Pro Ala Cys Asp Leu Thr Leu Phe Asp Phe
50                  55                  60

Lys Gln Gly Ile Leu Cys Tyr Pro Ala Pro Lys Ala His Pro Val Ala
65                  70                  75                  80

Val Ala Ser Lys Lys Arg Lys Lys Pro Ser Arg Pro Ala Lys Thr Arg
                85                  90                  95

Lys Arg Gln Val Gly Pro Gln Ser Gly Glu Val Arg Lys Glu Ala Pro
                100                 105                 110

Arg Asp Glu Thr Lys Ala Asp Thr Asp Thr Ala Pro Ala Ser Phe Pro
            115                 120                 125

Ala Pro Gly Cys Cys Glu Asn Cys Gly Ile Ser Phe Ser Gly Asp Gly
130                 135                 140

Thr Gln Arg Gln Arg Leu Lys Thr Leu Cys Lys Asp Cys Arg Ala Gln
145                 150                 155                 160

Arg Ile Ala Phe Asn Arg Glu Gln Arg Met Phe Lys Arg Val Gly Cys
                165                 170                 175

Gly Glu Cys Ala Ala Cys Gln Val Thr Glu Asp Cys Gly Ala Cys Ser
            180                 185                 190

Thr Cys Leu Leu Gln Leu Pro His Asp Val Ala Ser Gly Leu Phe Cys
```

-continued

```
                    195                 200                 205
Lys Cys Glu Arg Arg Cys Leu Arg Ile Val Glu Arg Ser Arg Gly
            210                 215                 220

Cys Gly Val Cys Arg Gly Cys Gln Thr Gln Glu Asp Cys Gly His Cys
225                 230                 235                 240

Pro Ile Cys Leu Arg Pro Pro Arg Pro Gly Leu Arg Arg Gln Trp Lys
                245                 250                 255

Cys Val Gln Arg Arg Cys Leu Arg Gly Lys His Ala Arg Arg Lys Gly
            260                 265                 270

Gly Cys Asp Ser Lys Met Ala Ala Arg Arg Pro Gly Ala Gln Pro
            275                 280                 285

Leu Pro Pro Pro Pro Ser Gln Ser Pro Glu Pro Thr Glu Pro His
    290                 295                 300

Pro Arg Ala Leu Ala Pro Ser Pro Ala Glu Phe Ile Tyr Tyr Cys
305                 310                 315                 320

Val Asp Glu Asp Glu Leu Lys Arg Leu Leu Pro Ser Val Trp Ser Glu
                325                 330                 335

Ser Glu Asp Gly Ala Gly Ser Pro Pro Tyr Arg Arg Arg Lys Arg
            340                 345                 350

Pro Ser Ser Ala Arg Arg His His Leu Gly Pro Thr Leu Lys Pro Thr
            355                 360                 365

Leu Ala Thr Arg Thr Ala Gln Pro Asp His Thr Gln Ala Pro Thr Lys
    370                 375                 380

Gln Glu Ala Gly Gly Gly Phe Val Leu Pro Pro Gly Thr Asp Leu
385                 390                 395                 400

Val Phe Leu Arg Glu Gly Ala Ser Ser Pro Val Gln Val Pro Gly Pro
                405                 410                 415

Val Ala Ala Ser Thr Glu Ala Leu Leu Gln Ala Val Asp Pro Gly Leu
            420                 425                 430

Pro Ser Val Lys Gln Glu Pro Pro Asp Pro Glu Glu Asp Lys Glu Glu
            435                 440                 445

Asn Lys Asp Asp Ser Ala Ser Lys Leu Ala Pro Glu Glu Glu Ala Gly
    450                 455                 460

Gly Ala Gly Thr Pro Val Ile Thr Glu Ile Phe Ser Leu Gly Gly Thr
465                 470                 475                 480

Arg Phe Arg Asp Thr Ala Val Trp Leu Pro Arg Ser Lys Asp Leu Lys
                485                 490                 495

Lys Pro Gly Ala Arg Lys Gln
            500

<210> SEQ ID NO 51
<211> LENGTH: 556
<212> TYPE: PRT
<213> ORGANISM: Human

<400> SEQUENCE: 51

Met Ala Glu Asp Trp Leu Asp Cys Pro Ala Leu Gly Pro Gly Trp Lys
1               5                   10                  15

Arg Arg Glu Val Phe Arg Lys Ser Gly Ala Thr Cys Gly Arg Ser Asp
                20                  25                  30

Thr Tyr Tyr Gln Ser Pro Thr Gly Asp Arg Ile Arg Ser Lys Val Glu
            35                  40                  45

Leu Thr Arg Tyr Leu Gly Pro Ala Cys Asp Leu Thr Leu Phe Asp Phe
    50                  55                  60
```

-continued

```
Lys Gln Gly Ile Leu Cys Tyr Pro Ala Pro Lys Ala His Pro Val Ala
 65                  70                  75                  80

Val Ala Ser Lys Lys Arg Lys Lys Pro Ser Arg Pro Ala Lys Thr Arg
                 85                  90                  95

Lys Arg Gln Val Gly Pro Gln Ser Gly Glu Val Arg Lys Glu Ala Pro
            100                 105                 110

Arg Asp Glu Thr Lys Ala Asp Thr Asp Thr Ala Pro Ala Ser Phe Pro
            115                 120                 125

Ala Pro Gly Cys Cys Glu Asn Cys Gly Ile Ser Phe Ser Gly Asp Gly
130                 135                 140

Thr Gln Arg Gln Arg Leu Lys Thr Leu Cys Lys Asp Cys Arg Ala Gln
145                 150                 155                 160

Arg Ile Ala Phe Asn Arg Glu Gln Arg Met Phe Lys Ser Arg Gly Cys
                165                 170                 175

Gly Val Cys Arg Gly Cys Gln Thr Gln Glu Asp Cys Gly His Cys Pro
            180                 185                 190

Ile Cys Leu Arg Pro Pro Arg Pro Gly Leu Arg Arg Gln Trp Lys Cys
            195                 200                 205

Val Gln Arg Arg Cys Leu Arg Gly Lys His Ala Arg Arg Lys Gly Gly
        210                 215                 220

Cys Asp Ser Lys Met Ala Ala Arg Arg Pro Gly Ala Gln Pro Leu
225                 230                 235                 240

Pro Pro Pro Pro Ser Gln Ser Pro Glu Pro Thr Glu Pro His Pro
                245                 250                 255

Arg Ala Leu Ala Pro Ser Pro Ala Glu Phe Ile Tyr Tyr Cys Val
            260                 265                 270

Asp Glu Asp Glu Leu Gln Pro Tyr Thr Asn Arg Arg Gln Asn Arg Lys
            275                 280                 285

Cys Gly Ala Cys Ala Ala Cys Leu Arg Arg Met Asp Cys Gly Arg Cys
        290                 295                 300

Asp Phe Cys Cys Asp Lys Pro Lys Phe Gly Gly Ser Asn Gln Lys Arg
305                 310                 315                 320

Gln Lys Cys Arg Trp Arg Gln Cys Leu Gln Phe Ala Met Lys Arg Leu
                325                 330                 335

Leu Pro Ser Val Trp Ser Glu Ser Glu Asp Gly Ala Gly Ser Pro Pro
            340                 345                 350

Pro Tyr Arg Arg Arg Lys Arg Pro Ser Ser Ala Arg His His Leu
            355                 360                 365

Gly Pro Thr Leu Lys Pro Thr Leu Ala Thr Arg Thr Ala Gln Pro Asp
370                 375                 380

His Thr Gln Ala Pro Thr Lys Gln Glu Ala Gly Gly Phe Val Leu
385                 390                 395                 400

Pro Pro Pro Gly Thr Asp Leu Val Phe Leu Arg Glu Gly Ala Ser Ser
                405                 410                 415

Pro Val Gln Val Pro Gly Pro Val Ala Ala Ser Thr Glu Ala Leu Leu
            420                 425                 430

Gln Glu Ala Gln Cys Ser Gly Leu Ser Trp Val Val Ala Leu Pro Gln
        435                 440                 445

Val Lys Gln Glu Lys Ala Asp Thr Gln Asp Glu Trp Thr Pro Gly Thr
    450                 455                 460

Ala Val Leu Thr Ser Pro Val Leu Val Pro Gly Cys Pro Ser Lys Ala
465                 470                 475                 480

Val Asp Pro Gly Leu Pro Ser Val Lys Gln Glu Pro Pro Asp Pro Glu
```

-continued

```
                485                 490                 495
Glu Asp Lys Glu Glu Asn Lys Asp Asp Ser Ala Ser Lys Leu Ala Pro
                500                 505                 510
Glu Glu Glu Ala Gly Gly Ala Gly Thr Pro Val Ile Thr Glu Ile Phe
            515                 520                 525
Ser Leu Gly Gly Thr Arg Phe Arg Asp Thr Ala Val Trp Leu Pro Arg
        530                 535                 540
Ser Lys Asp Leu Lys Lys Pro Gly Ala Arg Lys Gln
545                 550                 555
```

<210> SEQ ID NO 52
<211> LENGTH: 605
<212> TYPE: PRT
<213> ORGANISM: Human

<400> SEQUENCE: 52

```
Met Ala Glu Asp Trp Leu Asp Cys Pro Ala Leu Gly Pro Gly Trp Lys
1               5                   10                  15
Arg Arg Glu Val Phe Arg Lys Ser Gly Ala Thr Cys Gly Arg Ser Asp
                20                  25                  30
Thr Tyr Tyr Gln Ser Pro Thr Gly Asp Arg Ile Arg Ser Lys Val Glu
            35                  40                  45
Leu Thr Arg Tyr Leu Gly Pro Ala Cys Asp Leu Thr Leu Phe Asp Phe
        50                  55                  60
Lys Gln Gly Ile Leu Cys Tyr Pro Ala Pro Lys Ala His Pro Val Ala
65                  70                  75                  80
Val Ala Ser Lys Lys Arg Lys Lys Pro Ser Arg Pro Ala Lys Thr Arg
                85                  90                  95
Lys Arg Gln Val Gly Pro Gln Ser Gly Glu Val Arg Lys Glu Ala Pro
                100                 105                 110
Arg Asp Glu Thr Lys Ala Asp Thr Asp Thr Ala Pro Ala Ser Phe Pro
            115                 120                 125
Ala Pro Gly Cys Cys Glu Asn Cys Gly Ile Ser Phe Ser Gly Asp Gly
        130                 135                 140
Thr Gln Arg Gln Arg Leu Lys Thr Leu Cys Lys Asp Cys Arg Ala Gln
145                 150                 155                 160
Arg Ile Ala Phe Asn Arg Glu Gln Arg Met Phe Lys Arg Val Gly Cys
                165                 170                 175
Gly Glu Cys Ala Ala Cys Gln Val Thr Glu Asp Cys Gly Ala Cys Ser
                180                 185                 190
Thr Cys Leu Leu Gln Leu Pro His Asp Val Ala Ser Gly Leu Phe Cys
            195                 200                 205
Lys Cys Glu Arg Arg Cys Leu Arg Ile Val Glu Arg Ser Arg Gly
        210                 215                 220
Cys Gly Val Cys Arg Gly Cys Gln Thr Gln Glu Asp Cys Gly His Cys
225                 230                 235                 240
Pro Ile Cys Leu Arg Pro Pro Arg Pro Gly Leu Arg Arg Gln Trp Lys
                245                 250                 255
Cys Val Gln Arg Arg Cys Leu Arg Gly Lys His Ala Arg Arg Lys Gly
                260                 265                 270
Gly Cys Asp Ser Lys Met Ala Ala Arg Arg Arg Pro Gly Ala Gln Pro
            275                 280                 285
Leu Pro Pro Pro Pro Ser Gln Ser Pro Glu Pro Thr Glu Pro His
        290                 295                 300
```

-continued

```
Pro Arg Ala Leu Ala Pro Ser Pro Pro Ala Glu Phe Ile Tyr Tyr Cys
305                 310                 315                 320

Val Asp Glu Asp Glu Leu Gln Pro Tyr Thr Asn Arg Arg Gln Asn Arg
                325                 330                 335

Lys Cys Gly Ala Cys Ala Ala Cys Leu Arg Arg Met Asp Cys Gly Arg
            340                 345                 350

Cys Asp Phe Cys Cys Asp Lys Pro Lys Phe Gly Ser Asn Gln Lys
        355                 360                 365

Arg Gln Lys Cys Arg Trp Arg Gln Cys Leu Gln Phe Ala Met Lys Arg
    370                 375                 380

Leu Leu Pro Ser Val Trp Ser Glu Ser Glu Asp Gly Ala Gly Ser Pro
385                 390                 395                 400

Pro Pro Tyr Arg Arg Lys Arg Pro Ser Ala Arg Arg His His
                405                 410                 415

Leu Gly Pro Thr Leu Lys Pro Thr Leu Ala Thr Arg Thr Ala Gln Pro
                420                 425                 430

Asp His Thr Gln Ala Pro Thr Lys Gln Glu Ala Gly Gly Phe Val
        435                 440                 445

Leu Pro Pro Gly Thr Asp Leu Val Phe Leu Arg Glu Gly Ala Ser
450                 455                 460

Ser Pro Val Gln Val Pro Gly Pro Val Ala Ala Ser Thr Glu Ala Leu
465                 470                 475                 480

Leu Gln Glu Ala Gln Cys Ser Gly Leu Ser Trp Val Ala Leu Pro
            485                 490                 495

Gln Val Lys Gln Glu Lys Ala Asp Thr Gln Asp Glu Trp Thr Pro Gly
                500                 505                 510

Thr Ala Val Leu Thr Ser Pro Val Leu Val Pro Gly Cys Pro Ser Lys
            515                 520                 525

Ala Val Asp Pro Gly Leu Pro Ser Val Lys Gln Glu Pro Pro Asp Pro
530                 535                 540

Glu Glu Asp Lys Glu Glu Asn Lys Asp Asp Ser Ala Ser Lys Leu Ala
545                 550                 555                 560

Pro Glu Glu Glu Ala Gly Gly Ala Gly Thr Pro Val Ile Thr Glu Ile
                565                 570                 575

Phe Ser Leu Gly Gly Thr Arg Phe Arg Asp Thr Ala Val Trp Leu Pro
            580                 585                 590

Arg Ser Lys Asp Leu Lys Lys Pro Gly Ala Arg Lys Gln
            595                 600                 605

<210> SEQ ID NO 53
<211> LENGTH: 586
<212> TYPE: PRT
<213> ORGANISM: Human

<400> SEQUENCE: 53

Met Ala Glu Asp Trp Leu Asp Cys Pro Ala Leu Gly Pro Gly Trp Lys
1               5                   10                  15

Arg Arg Glu Val Phe Arg Lys Ser Gly Ala Thr Cys Gly Arg Ser Asp
                20                  25                  30

Thr Tyr Tyr Gln Ser Pro Thr Gly Asp Arg Ile Arg Ser Lys Val Glu
            35                  40                  45

Leu Thr Arg Tyr Leu Gly Pro Ala Cys Asp Leu Thr Leu Phe Asp Phe
        50                  55                  60

Lys Gln Gly Ile Leu Cys Tyr Pro Ala Pro Lys Ala His Pro Val Ala
65                  70                  75                  80
```

```
Val Ala Ser Lys Lys Arg Lys Lys Pro Ser Arg Pro Ala Lys Thr Arg
                85                  90                  95
Lys Arg Gln Val Gly Pro Gln Ser Gly Glu Val Arg Lys Glu Ala Pro
            100                 105                 110
Arg Asp Glu Thr Lys Ala Asp Thr Asp Thr Ala Pro Ala Ser Phe Pro
        115                 120                 125
Ala Pro Gly Cys Cys Glu Asn Cys Gly Ile Ser Phe Ser Gly Asp Gly
    130                 135                 140
Thr Gln Arg Gln Arg Leu Lys Thr Leu Cys Lys Asp Cys Arg Ala Gln
145                 150                 155                 160
Arg Ile Ala Phe Asn Arg Glu Gln Arg Met Phe Lys Arg Val Gly Cys
                165                 170                 175
Gly Glu Cys Ala Ala Cys Gln Val Thr Glu Asp Cys Gly Ala Cys Ser
            180                 185                 190
Thr Cys Leu Leu Gln Leu Pro His Asp Val Ala Ser Gly Leu Phe Cys
        195                 200                 205
Lys Cys Glu Arg Arg Arg Cys Leu Arg Ile Val Glu Arg Ser Arg Gly
    210                 215                 220
Cys Gly Val Cys Arg Gly Cys Gln Thr Gln Glu Asp Cys Gly His Cys
225                 230                 235                 240
Pro Ile Cys Leu Arg Pro Pro Arg Pro Gly Leu Arg Arg Gln Trp Lys
                245                 250                 255
Cys Val Gln Arg Arg Cys Leu Arg Gly Lys His Ala Arg Arg Lys Gly
            260                 265                 270
Gly Cys Asp Ser Lys Met Ala Ala Arg Arg Pro Gly Ala Gln Pro
        275                 280                 285
Leu Pro Pro Pro Pro Ser Gln Ser Pro Glu Pro Thr Glu Pro Gln
290                 295                 300
Pro Tyr Thr Asn Arg Arg Gln Asn Arg Lys Cys Gly Ala Cys Ala Ala
305                 310                 315                 320
Cys Leu Arg Arg Met Asp Cys Gly Arg Cys Asp Phe Cys Cys Asp Lys
                325                 330                 335
Pro Lys Phe Gly Gly Ser Asn Gln Lys Arg Gln Lys Cys Arg Trp Arg
            340                 345                 350
Gln Cys Leu Gln Phe Ala Met Lys Arg Leu Leu Pro Ser Val Trp Ser
        355                 360                 365
Glu Ser Glu Asp Gly Ala Gly Ser Pro Pro Tyr Arg Arg Arg Lys
    370                 375                 380
Arg Pro Ser Ser Ala Arg Arg His His Leu Gly Pro Thr Leu Lys Pro
385                 390                 395                 400
Thr Leu Ala Thr Arg Thr Ala Gln Pro Asp His Thr Gln Ala Pro Thr
                405                 410                 415
Lys Gln Glu Ala Gly Gly Phe Val Leu Pro Pro Gly Thr Asp
            420                 425                 430
Leu Val Phe Leu Arg Glu Gly Ala Ser Ser Pro Val Gln Val Pro Gly
        435                 440                 445
Pro Val Ala Ala Ser Thr Glu Ala Leu Leu Gln Ala Val Asp Pro Gly
    450                 455                 460
Leu Pro Ser Val Lys Gln Glu Pro Pro Asp Pro Glu Asp Lys Glu
465                 470                 475                 480
Glu Asn Lys Asp Asp Ser Ala Ser Lys Leu Ala Pro Glu Glu Ala
                485                 490                 495
```

-continued

Gly Gly Ala Gly Thr Pro Val Ile Thr Glu Ile Phe Ser Leu Gly Gly
                500                 505                 510

Thr Arg Phe Arg Asp Thr Ala Val Trp Leu Pro Ser Leu Gln Gly Arg
            515                 520                 525

His Ser Gly Arg Glu Asp Gly Cys Lys Val Trp Glu Thr Glu Asp Thr
        530                 535                 540

Val Glu Pro Thr Ser Thr Ser Trp Asn Pro Arg Gly Trp Pro Gly Thr
545                 550                 555                 560

His Val Ser Leu Ser Pro Pro Ala Ser Met Met Trp Val Ser Cys
                565                 570                 575

Arg Arg Ser Trp Cys Pro Ser Ser Gln Ser
                580                 585

<210> SEQ ID NO 54
<211> LENGTH: 549
<212> TYPE: PRT
<213> ORGANISM: Human

<400> SEQUENCE: 54

Met Ala Glu Asp Trp Leu Asp Cys Pro Ala Leu Gly Pro Gly Trp Lys
1               5                   10                  15

Arg Arg Glu Val Phe Arg Lys Ser Gly Ala Thr Cys Gly Arg Ser Asp
            20                  25                  30

Thr Tyr Tyr Gln Ser Pro Thr Gly Asp Arg Ile Arg Ser Lys Val Glu
        35                  40                  45

Leu Thr Arg Tyr Leu Gly Pro Ala Cys Asp Leu Thr Leu Phe Asp Phe
    50                  55                  60

Lys Gln Gly Ile Leu Cys Tyr Pro Ala Pro Lys Ala His Pro Val Ala
65                  70                  75                  80

Val Ala Ser Lys Lys Arg Lys Lys Pro Ser Arg Pro Ala Lys Thr Arg
                85                  90                  95

Lys Arg Gln Val Gly Pro Gln Ser Gly Glu Val Arg Lys Glu Ala Pro
            100                 105                 110

Arg Asp Glu Thr Lys Ala Asp Thr Asp Thr Ala Pro Ala Ser Phe Pro
        115                 120                 125

Ala Pro Gly Cys Cys Glu Asn Cys Gly Ile Ser Phe Ser Gly Asp Gly
    130                 135                 140

Thr Gln Arg Gln Arg Leu Lys Thr Leu Cys Lys Asp Cys Arg Ala Gln
145                 150                 155                 160

Arg Ile Ala Phe Asn Arg Glu Gln Arg Met Phe Lys Arg Val Gly Cys
                165                 170                 175

Gly Glu Cys Ala Ala Cys Gln Val Thr Glu Asp Cys Gly Ala Cys Ser
            180                 185                 190

Thr Cys Leu Leu Gln Leu Pro His Asp Val Ala Ser Gly Leu Phe Cys
        195                 200                 205

Lys Cys Glu Arg Arg Cys Leu Arg Ile Val Glu Arg Ser Arg Gly
    210                 215                 220

Cys Gly Val Cys Arg Gly Cys Gln Thr Gln Glu Asp Cys Gly His Cys
225                 230                 235                 240

Pro Ile Cys Leu Arg Pro Pro Arg Pro Gly Leu Arg Arg Gln Trp Lys
                245                 250                 255

Cys Val Gln Arg Arg Cys Leu Arg Gly Lys His Ala Arg Arg Lys Gly
            260                 265                 270

Gly Cys Asp Ser Lys Met Ala Ala Arg Arg Arg Pro Gly Ala Gln Pro
        275                 280                 285

-continued

```
Leu Pro Pro Pro Pro Ser Gln Ser Pro Glu Pro Thr Glu Pro His
    290                 295                 300

Pro Arg Ala Leu Ala Pro Ser Pro Ala Glu Phe Ile Tyr Tyr Cys
305                 310                 315                 320

Val Asp Glu Asp Glu Leu Gln Arg Leu Leu Pro Ser Val Trp Ser Glu
                325                 330                 335

Ser Glu Asp Gly Ala Gly Ser Pro Pro Tyr Arg Arg Lys Arg
                340                 345                 350

Pro Ser Ser Ala Arg Arg His His Leu Gly Pro Thr Leu Lys Pro Thr
            355                 360                 365

Leu Ala Thr Arg Thr Ala Gln Pro Asp His Thr Gln Ala Pro Thr Lys
    370                 375                 380

Gln Glu Ala Gly Gly Gly Phe Val Leu Pro Pro Gly Thr Asp Leu
385                 390                 395                 400

Val Phe Leu Arg Glu Gly Ala Ser Ser Pro Val Gln Val Pro Gly Pro
                405                 410                 415

Val Ala Ala Ser Thr Glu Ala Leu Leu Gln Glu Ala Gln Cys Ser Gly
                420                 425                 430

Leu Ser Trp Val Val Ala Leu Pro Gln Val Lys Gln Glu Lys Ala Asp
            435                 440                 445

Thr Gln Asp Glu Trp Thr Pro Gly Thr Ala Val Leu Thr Ser Pro Val
    450                 455                 460

Leu Val Pro Gly Cys Pro Ser Lys Ala Val Asp Pro Gly Leu Pro Ser
465                 470                 475                 480

Val Lys Gln Glu Pro Pro Asp Pro Glu Glu Asp Lys Glu Glu Asn Lys
                485                 490                 495

Asp Asp Ser Ala Ser Lys Leu Ala Pro Glu Glu Glu Ala Gly Gly Ala
                500                 505                 510

Gly Thr Pro Val Ile Thr Glu Ile Phe Ser Leu Gly Gly Thr Arg Phe
            515                 520                 525

Arg Asp Thr Ala Val Trp Leu Pro Arg Ser Lys Asp Leu Lys Lys Pro
    530                 535                 540

Gly Ala Arg Lys Gln
545

<210> SEQ ID NO 55
<211> LENGTH: 486
<212> TYPE: PRT
<213> ORGANISM: Human

<400> SEQUENCE: 55

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
                20                  25                  30

Lys Asp Lys Lys Glu Glu Lys Glu Gly Lys His Glu Pro Val Gln Pro
            35                  40                  45

Ser Ala His His Ser Ala Glu Pro Ala Glu Ala Gly Lys Ala Glu Thr
    50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
```

-continued

```
                   100                 105                 110
    Ser Gly Arg Ser Ala Gly Lys Tyr Asp Val Tyr Leu Ile Asn Pro Gln
                   115                 120                 125
    Gly Lys Ala Phe Arg Ser Lys Val Glu Leu Ile Ala Tyr Phe Glu Lys
                   130                 135                 140
    Val Gly Asp Thr Ser Leu Asp Pro Asn Asp Phe Asp Phe Thr Val Thr
    145                 150                 155                 160
    Gly Arg Gly Ser Pro Ser Arg Arg Glu Gln Lys Pro Pro Lys Lys Pro
                        165                 170                 175
    Lys Ser Pro Lys Ala Pro Gly Thr Gly Arg Gly Arg Gly Arg Pro Lys
                    180                 185                 190
    Gly Ser Gly Thr Thr Arg Pro Lys Ala Ala Thr Ser Glu Gly Val Gln
                195                 200                 205
    Val Lys Arg Val Leu Glu Lys Ser Pro Gly Lys Leu Leu Val Lys Met
    210                 215                 220
    Pro Phe Gln Thr Ser Pro Gly Gly Lys Ala Glu Gly Gly Ala Thr
    225                 230                 235                 240
    Thr Ser Thr Gln Val Met Val Ile Lys Arg Pro Gly Arg Lys Arg Lys
                        245                 250                 255
    Ala Glu Ala Asp Pro Gln Ala Ile Pro Lys Lys Arg Gly Arg Lys Pro
                    260                 265                 270
    Gly Ser Val Val Ala Ala Ala Ala Glu Ala Lys Lys Lys Ala Val
                275                 280                 285
    Lys Glu Ser Ser Ile Arg Ser Val Gln Glu Thr Val Leu Pro Ile Lys
        290                 295                 300
    Lys Arg Lys Thr Arg Glu Thr Val Ser Ile Glu Val Lys Glu Val Val
    305                 310                 315                 320
    Lys Pro Leu Leu Val Ser Thr Leu Gly Glu Lys Ser Gly Lys Gly Leu
                        325                 330                 335
    Lys Thr Cys Lys Ser Pro Gly Arg Lys Ser Lys Glu Ser Ser Pro Lys
                    340                 345                 350
    Gly Arg Ser Ser Ser Ala Ser Ser Pro Lys Lys Glu His His His
                355                 360                 365
    His His His His Ser Glu Ser Pro Lys Ala Pro Val Pro Leu Leu Pro
        370                 375                 380
    Pro Leu Pro Pro Pro Pro Glu Pro Glu Ser Ser Glu Asp Pro Thr
    385                 390                 395                 400
    Ser Pro Pro Glu Pro Gln Asp Leu Ser Ser Ser Val Cys Lys Glu Glu
                        405                 410                 415
    Lys Met Pro Arg Gly Gly Ser Leu Glu Ser Asp Gly Cys Pro Lys Glu
                    420                 425                 430
    Pro Ala Lys Thr Gln Pro Ala Val Ala Thr Ala Ala Thr Ala Ala Glu
                435                 440                 445
    Lys Tyr Lys His Arg Gly Glu Gly Glu Arg Lys Asp Ile Val Ser Ser
        450                 455                 460
    Ser Met Pro Arg Pro Asn Arg Glu Glu Pro Val Asp Ser Arg Thr Pro
    465                 470                 475                 480
    Val Thr Glu Arg Val Ser
                        485

<210> SEQ ID NO 56
<211> LENGTH: 580
<212> TYPE: PRT
<213> ORGANISM: Human
```

```
<400> SEQUENCE: 56

Met Gly Thr Thr Gly Leu Glu Ser Leu Ser Leu Gly Asp Arg Gly Ala
1               5                   10                  15

Ala Pro Thr Val Thr Ser Ser Glu Arg Leu Val Pro Asp Pro Pro Asn
            20                  25                  30

Asp Leu Arg Lys Glu Asp Val Ala Met Glu Leu Glu Arg Val Gly Glu
        35                  40                  45

Asp Glu Glu Gln Met Met Ile Lys Arg Ser Ser Glu Cys Asn Pro Leu
    50                  55                  60

Leu Gln Glu Pro Ile Ala Ser Ala Gln Phe Gly Ala Thr Ala Gly Thr
65                  70                  75                  80

Glu Cys Arg Lys Ser Val Pro Cys Gly Trp Glu Arg Val Val Lys Gln
                85                  90                  95

Arg Leu Phe Gly Lys Thr Ala Gly Arg Phe Asp Val Tyr Phe Ile Ser
            100                 105                 110

Pro Gln Gly Leu Lys Phe Arg Ser Lys Ser Ser Leu Ala Asn Tyr Leu
        115                 120                 125

His Lys Asn Gly Glu Thr Ser Leu Lys Pro Glu Asp Phe Asp Phe Thr
    130                 135                 140

Val Leu Ser Lys Arg Gly Ile Lys Ser Arg Tyr Lys Asp Cys Ser Met
145                 150                 155                 160

Ala Ala Leu Thr Ser His Leu Gln Asn Gln Ser Asn Asn Ser Asn Trp
                165                 170                 175

Asn Leu Arg Thr Arg Ser Lys Cys Lys Lys Asp Val Phe Met Pro Pro
            180                 185                 190

Ser Ser Ser Ser Glu Leu Gln Glu Ser Arg Gly Leu Ser Asn Phe Thr
        195                 200                 205

Ser Thr His Leu Leu Leu Lys Glu Asp Glu Gly Val Asp Asp Val Asn
    210                 215                 220

Phe Arg Lys Val Arg Lys Pro Lys Gly Lys Val Thr Ile Leu Lys Gly
225                 230                 235                 240

Ile Pro Ile Lys Lys Thr Lys Lys Gly Cys Arg Lys Ser Cys Ser Gly
                245                 250                 255

Phe Val Gln Ser Asp Ser Lys Arg Glu Ser Val Cys Asn Lys Ala Asp
            260                 265                 270

Ala Glu Ser Glu Pro Val Ala Gln Lys Ser Gln Leu Asp Arg Thr Val
        275                 280                 285

Cys Ile Ser Asp Ala Gly Ala Cys Gly Glu Thr Leu Ser Val Thr Ser
    290                 295                 300

Glu Glu Asn Ser Leu Val Lys Lys Lys Glu Arg Ser Leu Ser Ser Gly
305                 310                 315                 320

Ser Asn Phe Cys Ser Glu Gln Lys Thr Ser Gly Ile Ile Asn Lys Phe
                325                 330                 335

Cys Ser Ala Lys Asp Ser Glu His Asn Glu Lys Tyr Glu Asp Thr Phe
            340                 345                 350

Leu Glu Ser Glu Glu Ile Gly Thr Lys Val Glu Val Glu Arg Lys
        355                 360                 365

Glu His Leu His Thr Asp Ile Leu Lys Arg Gly Ser Glu Met Asp Asn
    370                 375                 380

Asn Cys Ser Pro Thr Arg Lys Asp Phe Thr Gly Glu Lys Ile Phe Gln
385                 390                 395                 400

Glu Asp Thr Ile Pro Arg Thr Gln Ile Glu Arg Arg Lys Thr Ser Leu
```

-continued

```
                    405                 410                 415
Tyr Phe Ser Ser Lys Tyr Asn Lys Glu Ala Leu Ser Pro Pro Arg Arg
                420                 425                 430

Lys Ala Phe Lys Lys Trp Thr Pro Pro Arg Ser Pro Phe Asn Leu Val
            435                 440                 445

Gln Glu Thr Leu Phe His Asp Pro Trp Lys Leu Leu Ile Ala Thr Ile
        450                 455                 460

Phe Leu Asn Arg Thr Ser Gly Lys Met Ala Ile Pro Val Leu Trp Lys
465                 470                 475                 480

Phe Leu Glu Lys Tyr Pro Ser Ala Glu Val Ala Arg Thr Ala Asp Trp
                485                 490                 495

Arg Asp Val Ser Glu Leu Leu Lys Pro Leu Gly Leu Tyr Asp Leu Arg
            500                 505                 510

Ala Lys Thr Ile Val Lys Phe Ser Asp Glu Tyr Leu Thr Lys Gln Trp
        515                 520                 525

Lys Tyr Pro Ile Glu Leu His Gly Ile Gly Lys Tyr Gly Asn Asp Ser
    530                 535                 540

Tyr Arg Ile Phe Cys Val Asn Glu Trp Lys Gln Val His Pro Glu Asp
545                 550                 555                 560

His Lys Leu Asn Lys Tyr His Asp Trp Leu Trp Glu Asn His Glu Lys
                565                 570                 575

Leu Ser Leu Ser
            580

<210> SEQ ID NO 57
<211> LENGTH: 411
<212> TYPE: PRT
<213> ORGANISM: Human

<400> SEQUENCE: 57

Met Arg Ala His Pro Gly Gly Arg Cys Cys Pro Glu Gln Glu Glu
1               5                   10                  15

Gly Glu Ser Ala Ala Gly Gly Ser Gly Ala Gly Gly Asp Ser Ala Ile
                20                  25                  30

Glu Gln Gly Gly Gln Gly Ser Ala Leu Ala Pro Ser Pro Val Ser Gly
            35                  40                  45

Val Arg Arg Glu Gly Ala Arg Gly Gly Arg Gly Arg Gly Arg Trp
    50                  55                  60

Lys Gln Ala Gly Arg Gly Gly Val Cys Gly Arg Gly Arg Gly Arg
65                  70                  75                  80

Gly Arg Gly Arg Gly Arg Gly Arg Gly Arg Gly Arg Gly Arg Gly Arg
                85                  90                  95

Pro Pro Ser Gly Gly Ser Gly Leu Gly Gly Asp Gly Gly Cys Gly
            100                 105                 110

Gly Gly Gly Ser Gly Gly Gly Ala Pro Arg Arg Glu Pro Val Pro
        115                 120                 125

Phe Pro Ser Gly Ser Ala Gly Pro Gly Pro Arg Gly Pro Arg Ala Thr
    130                 135                 140

Glu Ser Gly Lys Arg Met Asp Cys Pro Ala Leu Pro Pro Gly Trp Lys
145                 150                 155                 160

Lys Glu Glu Val Ile Arg Lys Ser Gly Leu Ser Ala Gly Lys Ser Asp
                165                 170                 175

Val Tyr Tyr Phe Ser Pro Ser Gly Lys Lys Phe Arg Ser Lys Pro Gln
            180                 185                 190
```

```
Leu Ala Arg Tyr Leu Gly Asn Thr Val Asp Leu Ser Ser Phe Asp Phe
            195                 200                 205

Arg Thr Gly Lys Met Met Pro Ser Lys Leu Gln Lys Asn Lys Gln Arg
    210                 215                 220

Leu Arg Asn Asp Pro Leu Asn Gln Asn Lys Gly Lys Pro Asp Leu Asn
225                 230                 235                 240

Thr Thr Leu Pro Ile Arg Gln Thr Ala Ser Ile Phe Lys Gln Pro Val
                245                 250                 255

Thr Lys Val Thr Asn His Pro Ser Asn Lys Val Lys Ser Asp Pro Gln
            260                 265                 270

Arg Met Asn Glu Gln Pro Arg Gln Leu Phe Trp Glu Lys Arg Leu Gln
        275                 280                 285

Gly Leu Ser Ala Ser Asp Val Thr Glu Gln Ile Ile Lys Thr Met Glu
    290                 295                 300

Leu Pro Lys Gly Leu Gln Gly Val Gly Pro Gly Ser Asn Asp Glu Thr
305                 310                 315                 320

Leu Leu Ser Ala Val Ala Ser Ala Leu His Thr Ser Ser Ala Pro Ile
                325                 330                 335

Thr Gly Gln Val Ser Ala Ala Val Glu Lys Asn Pro Ala Val Trp Leu
            340                 345                 350

Asn Thr Ser Gln Pro Leu Cys Lys Ala Phe Ile Val Thr Asp Glu Asp
        355                 360                 365

Ile Arg Lys Gln Glu Glu Arg Val Gln Gln Val Arg Lys Lys Leu Glu
    370                 375                 380

Glu Ala Leu Met Ala Asp Ile Leu Ser Arg Ala Ala Asp Thr Glu Glu
385                 390                 395                 400

Met Asp Ile Glu Met Asp Ser Gly Asp Glu Ala
                405                 410

<210> SEQ ID NO 58
<211> LENGTH: 484
<212> TYPE: PRT
<213> ORGANISM: Human

<400> SEQUENCE: 58

Met Val Ala Gly Met Leu Gly Leu Arg Glu Glu Lys Ser Glu Asp Gln
1               5                   10                  15

Asp Leu Gln Gly Leu Arg Asp Lys Pro Leu Lys Phe Lys Lys Ala Lys
            20                  25                  30

Lys Asp Lys Lys Glu Asp Lys Glu Gly Lys His Glu Pro Leu Gln Pro
        35                  40                  45

Ser Ala His His Ser Ala Glu Pro Ala Glu Ala Gly Lys Ala Glu Thr
    50                  55                  60

Ser Glu Ser Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
        115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160
```

```
Gly Arg Gly Ser Pro Ser Arg Glu Gln Lys Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Gly Arg Pro Lys Ala Ala Ser Glu Gly Val Gln
        195                 200                 205

Val Lys Arg Val Leu Glu Lys Ser Pro Gly Lys Leu Val Val Lys Met
    210                 215                 220

Pro Phe Gln Ala Ser Pro Gly Gly Lys Gly Glu Gly Gly Gly Ala Thr
225                 230                 235                 240

Thr Ser Ala Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
                260                 265                 270

Gly Ser Val Val Ala Ala Ala Ala Glu Ala Lys Lys Lys Ala Val
            275                 280                 285

Lys Glu Ser Ser Ile Arg Ser Val His Glu Thr Val Leu Pro Ile Lys
                290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Lys Glu Ser Ser Pro Lys
                340                 345                 350

Gly Arg Ser Ser Ser Ala Ser Ser Pro Pro Lys Lys Glu His His His
            355                 360                 365

His His His His Ser Glu Ser Thr Lys Ala Pro Met Pro Leu Leu Pro
        370                 375                 380

Ser Pro Pro Pro Glu Pro Glu Ser Ser Glu Asp Pro Ile Ser Pro
385                 390                 395                 400

Pro Glu Pro Gln Asp Leu Ser Ser Ile Cys Lys Glu Glu Lys Met
                405                 410                 415

Pro Arg Gly Gly Ser Leu Glu Ser Asp Gly Cys Pro Lys Glu Pro Ala
            420                 425                 430

Lys Thr Gln Pro Met Val Ala Thr Thr Thr Val Ala Glu Lys Tyr
            435                 440                 445

Lys His Arg Gly Glu Gly Glu Arg Lys Asp Ile Val Ser Ser Ser Met
        450                 455                 460

Pro Arg Pro Asn Arg Glu Glu Pro Val Asp Ser Arg Thr Pro Val Thr
465                 470                 475                 480

Glu Arg Val Ser

<210> SEQ ID NO 59
<211> LENGTH: 486
<212> TYPE: PRT
<213> ORGANISM: Human

<400> SEQUENCE: 59

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
            20                  25                  30

Lys Asp Lys Lys Glu Glu Lys Glu Gly Lys His Glu Pro Val Gln Pro
        35                  40                  45
```

-continued

```
Ser Ala His His Ser Ala Glu Pro Ala Glu Ala Gly Lys Ala Glu Thr
    50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
        115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
        195                 200                 205

Val Lys Arg Val Leu Glu Lys Ser Pro Gly Lys Leu Leu Val Lys Met
210                 215                 220

Pro Phe Gln Thr Ser Pro Gly Gly Lys Ala Glu Gly Gly Gly Ala Thr
225                 230                 235                 240

Thr Ser Thr Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
            260                 265                 270

Gly Ser Val Val Ala Ala Ala Ala Glu Ala Lys Lys Lys Ala Val
        275                 280                 285

Lys Glu Ser Ser Ile Arg Ser Val Gln Glu Thr Val Leu Pro Ile Lys
    290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Lys Glu Ser Ser Pro Lys
            340                 345                 350

Gly Arg Ser Ser Ser Ala Ser Ser Pro Pro Lys Lys Glu His His His
        355                 360                 365

His His His Ser Glu Ser Pro Lys Ala Pro Val Pro Leu Leu Pro
    370                 375                 380

Pro Leu Pro Pro Pro Pro Glu Pro Glu Ser Ser Glu Asp Pro Thr
385                 390                 395                 400

Ser Pro Pro Glu Pro Gln Asp Leu Ser Ser Ser Val Cys Lys Glu Glu
                405                 410                 415

Lys Met Pro Arg Gly Gly Ser Leu Glu Ser Asp Gly Cys Pro Lys Glu
            420                 425                 430

Pro Ala Lys Thr Gln Pro Ala Val Ala Thr Ala Ala Thr Ala Ala Glu
        435                 440                 445

Lys Tyr Lys His Arg Gly Glu Gly Glu Arg Lys Asp Ile Val Ser Ser
    450                 455                 460
```

```
Ser Met Pro Arg Pro Asn Arg Glu Glu Pro Val Asp Ser Arg Thr Pro
465                 470                 475                 480

Val Thr Glu Arg Val Ser
                485

<210> SEQ ID NO 60
<211> LENGTH: 486
<212> TYPE: PRT
<213> ORGANISM: Human

<400> SEQUENCE: 60

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
                20                  25                  30

Lys Asp Lys Lys Glu Glu Lys Glu Gly Lys His Glu Pro Val Gln Pro
            35                  40                  45

Ser Ala His His Ser Ala Glu Pro Ala Glu Ala Gly Lys Ala Glu Thr
    50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
                100                 105                 110

Ser Gly Arg Ser Ala Gly Lys Tyr Asp Val Tyr Leu Ile Asn Pro Gln
            115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
                180                 185                 190

Gly Ser Gly Thr Thr Arg Pro Lys Ala Ala Thr Ser Glu Gly Val Gln
            195                 200                 205

Val Lys Arg Val Leu Glu Lys Ser Pro Gly Lys Leu Leu Val Lys Met
    210                 215                 220

Pro Phe Gln Thr Ser Pro Gly Gly Lys Ala Glu Gly Gly Gly Ala Thr
225                 230                 235                 240

Thr Ser Thr Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
                260                 265                 270

Gly Ser Val Val Ala Ala Ala Ala Glu Ala Lys Lys Lys Ala Val
            275                 280                 285

Lys Glu Ser Ser Ile Arg Ser Val Gln Glu Thr Val Leu Pro Ile Lys
    290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Lys Glu Ser Ser Pro Lys
                340                 345                 350
```

```
Gly Arg Ser Ser Ser Ala Ser Ser Pro Pro Lys Glu His His His
            355                 360                 365

His His His His Ser Glu Ser Pro Lys Ala Pro Val Pro Leu Leu Pro
        370                 375                 380

Pro Leu Pro Pro Pro Pro Glu Pro Glu Ser Ser Glu Asp Pro Thr
385                 390                 395                 400

Ser Pro Pro Glu Pro Gln Asp Leu Ser Ser Ser Val Cys Lys Glu Glu
                405                 410                 415

Lys Met Pro Arg Gly Gly Ser Leu Glu Ser Asp Gly Cys Pro Lys Glu
                420                 425                 430

Pro Ala Lys Thr Gln Pro Ala Val Ala Thr Ala Ala Thr Ala Ala Glu
            435                 440                 445

Lys Tyr Lys His Arg Gly Glu Gly Glu Arg Lys Asp Ile Val Ser Ser
        450                 455                 460

Ser Met Pro Arg Pro Asn Arg Glu Glu Pro Val Asp Ser Arg Thr Pro
465                 470                 475                 480

Val Thr Glu Arg Val Ser
                485

<210> SEQ ID NO 61
<211> LENGTH: 484
<212> TYPE: PRT
<213> ORGANISM: Mouse

<400> SEQUENCE: 61

Met Val Ala Gly Met Leu Gly Leu Arg Glu Glu Lys Ser Glu Asp Gln
1               5                   10                  15

Asp Leu Gln Gly Leu Arg Asp Lys Pro Leu Lys Phe Lys Lys Ala Lys
                20                  25                  30

Lys Asp Lys Lys Glu Asp Lys Glu Gly Lys His Glu Pro Leu Gln Pro
            35                  40                  45

Ser Ala His His Ser Ala Glu Pro Ala Glu Ala Gly Lys Ala Glu Thr
        50                  55                  60

Ser Glu Ser Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
                100                 105                 110

Ser Gly Arg Ser Ala Gly Lys Tyr Asp Val Tyr Leu Ile Asn Pro Gln
            115                 120                 125

Gly Lys Ala Phe Arg Ser Lys Val Glu Leu Ile Ala Tyr Phe Glu Lys
        130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
                180                 185                 190

Gly Ser Gly Thr Gly Arg Pro Lys Ala Ala Ala Ser Glu Gly Val Gln
            195                 200                 205

Val Lys Arg Val Leu Glu Lys Ser Pro Gly Lys Leu Val Val Lys Met
        210                 215                 220

Pro Phe Gln Ala Ser Pro Gly Gly Lys Gly Glu Gly Gly Gly Ala Thr
```

-continued

```
                225                 230                 235                 240
Thr Ser Ala Gln Val Met Val Ile Lys Arg Pro Gly Arg Lys Arg Lys
                245                 250                 255
Ala Glu Ala Asp Pro Gln Ala Ile Pro Lys Arg Gly Arg Lys Pro
            260                 265                 270
Gly Ser Val Val Ala Ala Ala Ala Glu Ala Lys Lys Lys Ala Val
            275                 280                 285
Lys Glu Ser Ser Ile Arg Ser Val His Glu Thr Val Leu Pro Ile Lys
            290                 295                 300
Lys Arg Lys Thr Arg Glu Thr Val Ser Ile Glu Val Lys Glu Val Val
305                 310                 315                 320
Lys Pro Leu Leu Val Ser Thr Leu Gly Glu Lys Ser Lys Gly Leu
                325                 330                 335
Lys Thr Cys Lys Ser Pro Gly Arg Lys Ser Lys Glu Ser Ser Pro Lys
            340                 345                 350
Gly Arg Ser Ser Ser Ala Ser Ser Pro Pro Lys Lys Glu His His His
            355                 360                 365
His His His His Ser Glu Ser Thr Lys Ala Pro Met Pro Leu Leu Pro
            370                 375                 380
Ser Pro Pro Pro Glu Pro Glu Ser Ser Glu Asp Pro Ile Ser Pro
385                 390                 395                 400
Pro Glu Pro Gln Asp Leu Ser Ser Ile Cys Lys Glu Glu Lys Met
                405                 410                 415
Pro Arg Gly Gly Ser Leu Glu Ser Asp Gly Cys Pro Lys Glu Pro Ala
            420                 425                 430
Lys Thr Gln Pro Met Val Ala Thr Thr Thr Val Ala Glu Lys Tyr
                435                 440                 445
Lys His Arg Gly Glu Gly Glu Arg Lys Asp Ile Val Ser Ser Ser Met
            450                 455                 460
Pro Arg Pro Asn Arg Glu Glu Pro Val Asp Ser Arg Thr Pro Val Thr
465                 470                 475                 480
Glu Arg Val Ser

<210> SEQ ID NO 62
<211> LENGTH: 486
<212> TYPE: PRT
<213> ORGANISM: human

<400> SEQUENCE: 62

Met Val Ala Gly Met Leu Gly Leu Arg Glu Glu Lys Ser Glu Asp Gln
1               5                   10                  15
Asp Leu Gln Gly Leu Lys Asp Lys Pro Leu Lys Phe Lys Lys Val Lys
                20                  25                  30
Lys Asp Lys Lys Glu Glu Lys Glu Gly Lys His Glu Pro Val Gln Pro
            35                  40                  45
Ser Ala His His Ser Ala Glu Pro Ala Glu Ala Gly Lys Ala Glu Thr
        50                  55                  60
Ser Glu Gly Ser Gly Ser Ala Pro Ala Val Pro Glu Ala Ser Ala Ser
65                  70                  75                  80
Pro Lys Gln Arg Arg Ser Ile Ile Arg Asp Arg Gly Pro Met Tyr Asp
                85                  90                  95
Asp Pro Thr Leu Pro Glu Gly Trp Thr Arg Lys Leu Lys Gln Arg Lys
                100                 105                 110
Ser Gly Arg Ser Ala Gly Lys Tyr Asp Val Tyr Leu Ile Asn Pro Gln
```

```
            115                 120                 125
Gly Lys Ala Phe Arg Ser Lys Val Glu Leu Ile Ala Tyr Phe Glu Lys
        130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
                195                 200                 205

Val Lys Arg Val Leu Glu Lys Ser Pro Gly Lys Leu Leu Val Lys Met
        210                 215                 220

Pro Phe Gln Thr Ser Pro Gly Gly Lys Ala Glu Gly Gly Gly Ala Thr
225                 230                 235                 240

Thr Ser Thr Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
            260                 265                 270

Gly Ser Val Val Ala Ala Ala Ala Glu Ala Lys Lys Lys Ala Val
                275                 280                 285

Lys Glu Ser Ser Ile Arg Ser Val Gln Glu Thr Val Leu Pro Ile Lys
        290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Lys Glu Ser Ser Pro Lys
            340                 345                 350

Gly Arg Ser Ser Ser Ala Ser Ser Pro Pro Lys Lys Glu His His His
                355                 360                 365

His His His Ser Glu Ser Pro Lys Ala Pro Val Pro Leu Leu Pro
        370                 375                 380

Pro Leu Pro Pro Pro Pro Glu Pro Glu Ser Ser Glu Asp Pro Thr
385                 390                 395                 400

Ser Pro Pro Glu Pro Gln Asp Leu Ser Ser Val Cys Lys Glu Glu
                405                 410                 415

Lys Met Pro Arg Gly Gly Ser Leu Glu Ser Asp Gly Cys Pro Lys Glu
            420                 425                 430

Pro Ala Lys Thr Gln Pro Ala Val Ala Thr Ala Ala Thr Ala Ala Glu
        435                 440                 445

Lys Tyr Lys His Arg Gly Glu Gly Glu Arg Lys Asp Ile Val Ser Ser
        450                 455                 460

Ser Met Pro Arg Pro Asn Arg Glu Glu Pro Val Asp Ser Arg Thr Pro
465                 470                 475                 480

Val Thr Glu Arg Val Ser
                485

<210> SEQ ID NO 63
<211> LENGTH: 477
<212> TYPE: PRT
<213> ORGANISM: Human

<400> SEQUENCE: 63
```

-continued

```
Glu Glu Lys Ser Glu Asp Gln Asp Leu Gln Gly Leu Lys Asp Lys Pro
1               5                   10                  15
Leu Lys Phe Lys Lys Val Lys Lys Asp Lys Lys Glu Glu Lys Glu Gly
            20                  25                  30
Lys His Glu Pro Val Gln Pro Ser Ala His His Ser Ala Glu Pro Ala
            35                  40                  45
Glu Ala Gly Lys Ala Glu Thr Ser Glu Gly Ser Gly Ser Ala Pro Ala
50                      55                  60
Val Pro Glu Ala Ser Ala Ser Pro Lys Gln Arg Arg Ser Ile Ile Arg
65                  70                  75                  80
Asp Arg Gly Pro Met Tyr Asp Asp Pro Thr Leu Pro Glu Gly Trp Thr
                85                  90                  95
Arg Lys Leu Lys Gln Arg Lys Ser Gly Arg Ser Ala Gly Lys Tyr Asp
            100                 105                 110
Val Tyr Leu Ile Asn Pro Gln Gly Lys Ala Phe Arg Ser Lys Val Glu
        115                 120                 125
Leu Ile Ala Tyr Phe Glu Lys Val Gly Asp Thr Ser Leu Asp Pro Asn
    130                 135                 140
Asp Phe Asp Phe Thr Val Thr Gly Arg Gly Ser Pro Ser Arg Arg Glu
145                 150                 155                 160
Gln Lys Pro Pro Lys Lys Pro Lys Ser Pro Lys Ala Pro Gly Thr Gly
                165                 170                 175
Arg Gly Arg Gly Arg Pro Lys Gly Ser Gly Thr Thr Arg Pro Lys Ala
            180                 185                 190
Ala Thr Ser Glu Gly Val Gln Val Lys Arg Val Leu Glu Lys Ser Pro
        195                 200                 205
Gly Lys Leu Leu Val Lys Met Pro Phe Gln Thr Ser Pro Gly Gly Lys
    210                 215                 220
Ala Glu Gly Gly Gly Ala Thr Thr Ser Thr Gln Val Met Val Ile Lys
225                 230                 235                 240
Arg Pro Gly Arg Lys Arg Lys Ala Glu Ala Asp Pro Gln Ala Ile Pro
                245                 250                 255
Lys Lys Arg Gly Arg Lys Pro Gly Ser Val Val Ala Ala Ala Ala Ala
            260                 265                 270
Glu Ala Lys Lys Lys Ala Val Lys Glu Ser Ser Ile Arg Ser Val Gln
        275                 280                 285
Glu Thr Val Leu Pro Ile Lys Lys Arg Lys Thr Arg Glu Thr Val Ser
    290                 295                 300
Ile Glu Val Lys Glu Val Val Lys Pro Leu Leu Val Ser Thr Leu Gly
305                 310                 315                 320
Glu Lys Ser Gly Lys Gly Leu Lys Thr Cys Lys Ser Pro Gly Arg Lys
                325                 330                 335
Ser Lys Glu Ser Ser Pro Lys Gly Arg Ser Ser Ser Ala Ser Ser Pro
            340                 345                 350
Pro Lys Lys Glu His His His His His His Ser Glu Ser Pro Lys
        355                 360                 365
Ala Pro Val Pro Leu Leu Pro Pro Leu Pro Pro Pro Pro Pro Glu Pro
    370                 375                 380
Glu Ser Ser Glu Asp Pro Thr Ser Pro Pro Glu Pro Gln Asp Leu Ser
385                 390                 395                 400
Ser Ser Val Cys Lys Glu Glu Lys Met Pro Arg Gly Gly Ser Leu Glu
                405                 410                 415
Ser Asp Gly Cys Pro Lys Glu Pro Ala Lys Thr Gln Pro Ala Val Ala
```

```
                    420                 425                 430
Thr Ala Ala Thr Ala Ala Glu Lys Tyr Lys His Arg Gly Glu Gly Glu
            435                 440                 445
Arg Lys Asp Ile Val Ser Ser Met Pro Arg Pro Asn Arg Glu Glu
    450                 455                 460
Pro Val Asp Ser Arg Thr Pro Val Thr Glu Arg Val Ser
465                 470                 475

<210> SEQ ID NO 64
<211> LENGTH: 92
<212> TYPE: PRT
<213> ORGANISM: Human
<220> FEATURE:
<221> NAME/KEY: MISC_FEATURE
<222> LOCATION: (1)..(92)
<223> OTHER INFORMATION: X is unknown

<400> SEQUENCE: 64

Xaa Ser Ala Ser Pro Lys Gln Arg Arg Ser Ile Ile Arg Asp Arg Gly
1               5                   10                  15
Pro Met Tyr Asp Asp Pro Thr Leu Pro Glu Gly Trp Thr Arg Lys Leu
            20                  25                  30
Lys Gln Arg Lys Ser Gly Arg Ser Ala Gly Lys Tyr Asp Val Tyr Leu
        35                  40                  45
Ile Asn Pro Gln Gly Lys Ala Phe Arg Ser Lys Val Glu Leu Ile Ala
    50                  55                  60
Tyr Phe Glu Lys Val Gly Asp Thr Ser Leu Asp Pro Asn Asp Phe Asp
65                  70                  75                  80
Phe Thr Val Thr Gly Arg Gly Ser Gly Ser Gly Cys
                85                  90

<210> SEQ ID NO 65
<211> LENGTH: 486
<212> TYPE: PRT
<213> ORGANISM: Human

<400> SEQUENCE: 65

Met Val Ala Gly Met Leu Gly Leu Arg Glu Glu Lys Ser Glu Asp Gln
1               5                   10                  15
Asp Leu Gln Gly Leu Lys Asp Lys Pro Leu Lys Phe Lys Lys Val Lys
            20                  25                  30
Lys Asp Lys Lys Glu Glu Lys Glu Gly Lys His Glu Pro Val Gln Pro
        35                  40                  45
Ser Ala His His Ser Ala Glu Pro Ala Glu Ala Gly Lys Ala Glu Thr
    50                  55                  60
Ser Glu Gly Ser Gly Ser Ala Pro Ala Val Pro Glu Ala Ser Ala Ser
65                  70                  75                  80
Pro Lys Gln Arg Arg Ser Ile Ile Arg Asp Arg Gly Pro Met Tyr Asp
                85                  90                  95
Asp Pro Thr Leu Pro Glu Gly Trp Thr Arg Lys Leu Lys Gln Arg Lys
            100                 105                 110
Ser Gly Arg Ser Ala Gly Lys Tyr Asp Val Tyr Leu Ile Asn Pro Gln
        115                 120                 125
Gly Lys Ala Phe Arg Ser Lys Val Glu Leu Ile Ala Tyr Phe Glu Lys
    130                 135                 140
Val Gly Asp Thr Ser Leu Asp Pro Asn Asp Phe Asp Phe Thr Val Thr
145                 150                 155                 160
```

```
Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
            195                 200                 205

Val Lys Arg Val Leu Glu Lys Ser Pro Gly Lys Leu Leu Val Lys Met
    210                 215                 220

Pro Phe Gln Thr Ser Pro Gly Lys Ala Glu Gly Gly Gly Ala Thr
225                 230                 235                 240

Thr Ser Thr Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
                260                 265                 270

Gly Ser Val Val Ala Ala Ala Ala Glu Ala Lys Lys Lys Ala Val
            275                 280                 285

Lys Glu Ser Ser Ile Arg Ser Val Gln Glu Thr Val Leu Pro Ile Lys
    290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Glu Ser Pro Lys
                340                 345                 350

Gly Arg Ser Ser Ser Ala Ser Ser Pro Pro Lys Lys Glu His His His
            355                 360                 365

His His His Ser Glu Ser Pro Lys Ala Pro Val Pro Leu Leu Pro
    370                 375                 380

Pro Leu Pro Pro Pro Pro Glu Pro Glu Ser Ser Glu Asp Pro Thr
385                 390                 395                 400

Ser Pro Pro Glu Pro Gln Asp Leu Ser Ser Ser Val Cys Lys Glu Glu
                405                 410                 415

Lys Met Pro Arg Gly Gly Ser Leu Glu Ser Asp Gly Cys Pro Lys Glu
                420                 425                 430

Pro Ala Lys Thr Gln Pro Ala Val Ala Thr Ala Ala Thr Ala Ala Glu
            435                 440                 445

Lys Tyr Lys His Arg Gly Glu Gly Glu Arg Lys Asp Ile Val Ser Ser
    450                 455                 460

Ser Met Pro Arg Pro Asn Arg Glu Glu Pro Val Asp Ser Arg Thr Pro
465                 470                 475                 480

Val Thr Glu Arg Val Ser
                485

<210> SEQ ID NO 66
<211> LENGTH: 492
<212> TYPE: PRT
<213> ORGANISM: Rat

<400> SEQUENCE: 66

Met Val Ala Gly Met Leu Gly Leu Arg Lys Glu Lys Ser Glu Asp Gln
1               5                   10                  15

Asp Leu Gln Gly Leu Lys Glu Lys Pro Leu Lys Phe Lys Lys Val Lys
            20                  25                  30

Lys Asp Lys Lys Glu Asp Lys Glu Gly Lys His Glu Pro Leu Gln Pro
        35                  40                  45
```

-continued

```
Ser Ala His His Ser Ala Glu Pro Ala Glu Ala Gly Lys Ala Glu Thr
 50                  55                  60
Ser Glu Ser Ser Gly Ser Ala Pro Ala Val Pro Glu Ala Ser Ala Ser
65                  70                  75                  80
Pro Lys Gln Arg Arg Ser Ile Ile Arg Asp Arg Gly Pro Met Tyr Asp
                 85                  90                  95
Asp Pro Thr Leu Pro Glu Gly Trp Thr Arg Lys Leu Lys Gln Arg Lys
            100                 105                 110
Ser Gly Arg Ser Ala Gly Lys Tyr Asp Val Tyr Leu Ile Asn Pro Gln
            115                 120                 125
Gly Lys Ala Phe Arg Ser Lys Val Glu Leu Ile Ala Tyr Phe Glu Lys
130                 135                 140
Val Gly Asp Thr Ser Leu Asp Pro Asn Asp Phe Asp Phe Thr Val Thr
145                 150                 155                 160
Gly Arg Gly Ser Pro Ser Arg Arg Glu Gln Lys Pro Pro Lys Lys Pro
                165                 170                 175
Lys Ser Pro Lys Ala Pro Gly Thr Gly Arg Gly Arg Gly Arg Pro Lys
            180                 185                 190
Gly Ser Gly Thr Gly Arg Pro Lys Ala Ala Ser Glu Gly Val Gln
            195                 200                 205
Val Lys Arg Val Leu Glu Lys Ser Pro Gly Lys Leu Leu Val Lys Met
210                 215                 220
Pro Phe Gln Ala Ser Pro Gly Gly Lys Gly Glu Gly Gly Gly Ala Thr
225                 230                 235                 240
Thr Ser Ala Gln Val Met Val Ile Lys Arg Pro Gly Arg Lys Arg Lys
                245                 250                 255
Ala Glu Ala Asp Pro Gln Ala Ile Pro Lys Lys Arg Gly Arg Lys Pro
            260                 265                 270
Gly Ser Val Val Ala Ala Ala Ala Glu Ala Lys Lys Lys Ala Val
            275                 280                 285
Lys Glu Ser Ser Ile Arg Ser Val Gln Glu Thr Val Leu Pro Ile Lys
290                 295                 300
Lys Arg Lys Thr Arg Glu Thr Val Ser Ile Glu Val Lys Glu Val Val
305                 310                 315                 320
Lys Pro Leu Leu Val Ser Thr Leu Gly Glu Lys Ser Gly Lys Gly Leu
                325                 330                 335
Lys Thr Cys Lys Ser Pro Gly Arg Lys Ser Lys Glu Ser Ser Pro Lys
            340                 345                 350
Gly Arg Ser Ser Ser Ala Ser Ser Pro Pro Lys Lys Glu His His His
            355                 360                 365
His His His His Ala Glu Ser Pro Lys Ala Pro Met Pro Leu Leu Pro
            370                 375                 380
Pro Pro Pro Pro Pro Glu Pro Gln Ser Ser Glu Asp Pro Ile Ser Pro
385                 390                 395                 400
Pro Glu Pro Gln Asp Leu Ser Ser Ile Cys Lys Glu Glu Lys Met
                405                 410                 415
Pro Arg Ala Gly Ser Leu Glu Ser Asp Gly Cys Pro Lys Glu Pro Ala
            420                 425                 430
Lys Thr Gln Pro Met Val Ala Ala Ala Thr Thr Thr Thr Thr
            435                 440                 445
Thr Thr Thr Val Ala Glu Lys Tyr Lys His Arg Gly Glu Gly Glu Arg
450                 455                 460
```

```
Lys Asp Ile Val Ser Ser Met Pro Arg Pro Asn Arg Glu Glu Pro
465                 470                 475                 480

Val Asp Ser Arg Thr Pro Val Thr Glu Arg Val Ser
                485                 490

<210> SEQ ID NO 67
<211> LENGTH: 484
<212> TYPE: PRT
<213> ORGANISM: Mouse

<400> SEQUENCE: 67

Met Val Ala Gly Met Leu Gly Leu Arg Glu Glu Lys Ser Glu Asp Gln
1               5                   10                  15

Asp Leu Gln Gly Leu Arg Asp Lys Pro Leu Lys Phe Lys Lys Ala Lys
            20                  25                  30

Lys Asp Lys Lys Glu Asp Lys Glu Gly Lys His Glu Pro Leu Gln Pro
        35                  40                  45

Ser Ala His His Ser Ala Glu Pro Ala Glu Ala Gly Lys Ala Glu Thr
    50                  55                  60

Ser Glu Ser Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
        115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Gly Arg Pro Lys Ala Ala Ser Glu Gly Val Gln
        195                 200                 205

Val Lys Arg Val Leu Glu Lys Ser Pro Gly Lys Leu Val Val Lys Met
210                 215                 220

Pro Phe Gln Ala Ser Pro Gly Gly Lys Gly Glu Gly Gly Gly Ala Thr
225                 230                 235                 240

Thr Ser Ala Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
            260                 265                 270

Gly Ser Val Val Ala Ala Ala Ala Glu Ala Lys Lys Lys Ala Val
        275                 280                 285

Lys Glu Ser Ser Ile Arg Ser Val His Glu Thr Val Leu Pro Ile Lys
    290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Lys Glu Ser Ser Pro Lys
            340                 345                 350
```

```
Gly Arg Ser Ser Ala Ser Ser Pro Pro Lys Lys Glu His His His
        355                 360                 365

His His His His Ser Glu Ser Thr Lys Ala Pro Met Pro Leu Leu Pro
        370                 375                 380

Ser Pro Pro Pro Glu Pro Glu Ser Ser Glu Asp Pro Ile Ser Pro
385                 390                 395                 400

Pro Glu Pro Gln Asp Leu Ser Ser Ser Ile Cys Lys Glu Glu Lys Met
                405                 410                 415

Pro Arg Gly Gly Ser Leu Glu Ser Asp Gly Cys Pro Lys Glu Pro Ala
            420                 425                 430

Lys Thr Gln Pro Met Val Ala Thr Thr Thr Val Ala Glu Lys Tyr
        435                 440                 445

Lys His Arg Gly Glu Gly Glu Arg Lys Asp Ile Val Ser Ser Ser Met
        450                 455                 460

Pro Arg Pro Asn Arg Glu Glu Pro Val Asp Ser Arg Thr Pro Val Thr
465                 470                 475                 480

Glu Arg Val Ser

<210> SEQ ID NO 68
<211> LENGTH: 486
<212> TYPE: PRT
<213> ORGANISM: Human

<400> SEQUENCE: 68

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
                20                  25                  30

Lys Asp Lys Lys Glu Glu Lys Glu Gly Lys His Glu Pro Val Gln Pro
            35                  40                  45

Ser Ala His His Ser Ala Glu Pro Ala Glu Ala Gly Lys Ala Glu Thr
        50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
                100                 105                 110

Ser Gly Arg Ser Ala Gly Lys Tyr Asp Val Tyr Leu Ile Asn Pro Gln
            115                 120                 125

Gly Lys Ala Phe Arg Ser Lys Val Glu Leu Ile Ala Tyr Phe Glu Lys
        130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
        195                 200                 205

Val Lys Arg Val Leu Glu Lys Ser Pro Gly Lys Leu Leu Val Lys Met
        210                 215                 220

Pro Phe Gln Thr Ser Pro Gly Gly Lys Ala Glu Gly Gly Gly Ala Thr
225                 230                 235                 240
```

```
Thr Ser Thr Gln Val Met Val Ile Lys Arg Pro Gly Arg Lys Arg Lys
            245                 250                 255

Ala Glu Ala Asp Pro Gln Ala Ile Pro Lys Lys Arg Gly Arg Lys Pro
            260                 265                 270

Gly Ser Val Val Ala Ala Ala Ala Glu Ala Lys Lys Lys Lys Ala Val
            275                 280                 285

Lys Glu Ser Ser Ile Arg Ser Val Gln Glu Thr Val Leu Pro Ile Lys
            290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
            325                 330                 335

Lys Thr Cys Lys Ser Pro Gly Arg Lys Ser Lys Glu Ser Ser Pro Lys
            340                 345                 350

Gly Arg Ser Ser Ser Ala Ser Ser Pro Pro Lys Lys Glu His His His
            355                 360                 365

His His His His Ser Glu Ser Pro Lys Ala Pro Val Pro Leu Leu Pro
            370                 375                 380

Pro Leu Pro Pro Pro Pro Glu Pro Glu Ser Ser Glu Asp Pro Thr
385                 390                 395                 400

Ser Pro Pro Glu Pro Gln Asp Leu Ser Ser Ser Val Cys Lys Glu Glu
            405                 410                 415

Lys Met Pro Arg Gly Gly Ser Leu Glu Ser Asp Gly Cys Pro Lys Glu
            420                 425                 430

Pro Ala Lys Thr Gln Pro Ala Val Ala Thr Ala Thr Ala Ala Glu
            435                 440                 445

Lys Tyr Lys His Arg Gly Glu Gly Glu Arg Lys Asp Ile Val Ser Ser
            450                 455                 460

Ser Met Pro Arg Pro Asn Arg Glu Glu Pro Val Asp Ser Arg Thr Pro
465                 470                 475                 480

Val Thr Glu Arg Val Ser
            485

<210> SEQ ID NO 69
<211> LENGTH: 467
<212> TYPE: PRT
<213> ORGANISM: Frog

<400> SEQUENCE: 69

Met Ala Ala Pro Ser Gly Glu Glu Arg Leu Glu Glu Lys Ser Glu
1               5                   10                  15

Asp Gln Asp Leu Gln Gly Gln Lys Asp Lys Pro Lys Leu Arg Lys
            20                  25                  30

Val Lys Lys Asp Lys Lys Asp Glu Glu Lys Gln Glu Pro Phe His
            35                  40                  45

Ser Ser Glu His Gln Pro Gly Glu Pro Ala Asp Glu Gly Lys Ala Asp
    50                  55                  60

Met Ser Glu Ser Ala Glu Glu Asn Leu Ala Val Pro Glu Ser Ser Ala
65                  70                  75                  80

Ser Pro Lys Gln Arg Arg Ser Val Ile Arg Asp Arg Gly Pro Met Tyr
            85                  90                  95

Glu Asp Pro Thr Leu Pro Glu Gly Trp Thr Arg Lys Leu Lys Gln Arg
            100                 105                 110

Lys Ser Gly Arg Ser Ala Gly Lys Phe Asp Val Tyr Leu Ile Asn Pro
```

```
                115                 120                 125
Asn Gly Lys Ala Phe Arg Ser Lys Val Glu Leu Ile Ala Tyr Phe Gln
        130                 135                 140

Lys Val Gly Asp Thr Ser Leu Asp Pro Asn Asp Phe Asp Phe Thr Val
145                 150                 155                 160

Thr Gly Arg Gly Ser Pro Ser Arg Arg Glu Gln Lys Gln Pro Lys Lys
                165                 170                 175

Pro Lys Ala Pro Lys Ser Ser Val Ser Gly Arg Gly Arg Gly Arg Pro
        180                 185                 190

Lys Gly Ser Ile Lys Lys Val Lys Pro Val Lys Ser Glu Gly Val
        195                 200                 205

Gln Val Lys Arg Val Ile Glu Lys Ser Pro Gly Lys Leu Leu Val Lys
        210                 215                 220

Met Pro Tyr Ser Gly Thr Lys Glu Ala Ser Asp Ala Thr Thr Ser Gln
225                 230                 235                 240

Gln Val Leu Val Ile Lys Arg Gly Arg Lys Arg Lys Ser Glu Thr
                245                 250                 255

Asp Pro Ser Ala Ala Pro Lys Lys Arg Gly Arg Lys Pro Ser Asn Val
        260                 265                 270

Ser Leu Ala Ala Ala Ala Glu Ala Lys Lys Ala Ile Lys
        275                 280                 285

Glu Ser Ser Ile Lys Pro Leu Leu Glu Thr Val Leu Pro Ile Lys Lys
        290                 295                 300

Arg Lys Thr Arg Glu Thr Ile Ser Val Asp Val Lys Asp Thr Ile Lys
305                 310                 315                 320

Pro Glu Pro Leu Thr Pro Val Ile Glu Lys Val Met Lys Gly Gln Asn
                325                 330                 335

Pro Ala Lys Ser Pro Glu Ser Arg Ser Thr Glu Gly Ser Pro Lys Ile
                340                 345                 350

Lys Thr Gly Leu Pro Lys Lys Glu Leu Gln Gln His His His His
        355                 360                 365

His His His His His His His Ser Glu Ser Lys Ala Ser Ala Thr
        370                 375                 380

Ser Pro Glu Pro Glu Thr Ser Lys Asp Asn Ile Gly Val Gln Glu Pro
385                 390                 395                 400

Gln Asp Leu Ser Val Lys Met Cys Lys Glu Lys Leu Pro Glu Ser
                405                 410                 415

Asp Gly Cys Ala Gln Glu Pro Ala Lys Thr Gln Pro Ala Asp Lys Cys
        420                 425                 430

Arg Asn Arg Ala Glu Gly Glu Arg Lys Asp Ile Val Ser Ser Val Pro
        435                 440                 445

Arg Pro Thr Arg Glu Glu Pro Val Asp Thr Arg Thr Thr Val Thr Glu
        450                 455                 460

Arg Val Ser
465

<210> SEQ ID NO 70
<211> LENGTH: 467
<212> TYPE: PRT
<213> ORGANISM: Frog

<400> SEQUENCE: 70

Met Ala Ala Ala Pro Ser Gly Glu Glu Arg Leu Glu Glu Lys Ser Glu
1               5                   10                  15
```

-continued

```
Asp Gln Asp Leu Gln Gly Gln Lys Asp Lys Pro Pro Lys Leu Arg Lys
            20                  25                  30

Val Lys Lys Asp Lys Lys Asp Glu Glu Glu Lys Gln Glu Pro Phe His
        35                  40                  45

Ser Ser Glu His Gln Pro Gly Glu Pro Ala Asp Glu Gly Lys Ala Asp
    50                  55                  60

Met Ser Glu Ser Ala Glu Glu Asn Leu Ala Val Pro Glu Ser Ser Ala
65                  70                  75                  80

Ser Pro Lys Gln Arg Arg Ser Val Ile Arg Asp Arg Gly Pro Met Tyr
                85                  90                  95

Glu Asp Pro Thr Leu Pro Glu Gly Trp Thr Arg Lys Leu Lys Gln Arg
            100                 105                 110

Lys Ser Gly Arg Ser Ala Gly Lys Phe Asp Val Tyr Leu Ile Asn Pro
        115                 120                 125

Asn Gly Lys Ala Phe Arg Ser Lys Val Glu Leu Ile Ala Tyr Phe Gln
    130                 135                 140

Lys Val Gly Asp Thr Ser Leu Asp Pro Asn Asp Phe Asp Phe Thr Val
145                 150                 155                 160

Thr Gly Arg Gly Ser Pro Ser Arg Arg Glu Gln Lys Gln Pro Lys Lys
                165                 170                 175

Pro Lys Ala Pro Lys Ser Ser Val Ser Gly Arg Gly Arg Gly Arg Pro
            180                 185                 190

Lys Gly Ser Ile Lys Lys Val Lys Pro Val Lys Ser Glu Gly Val
                195                 200                 205

Gln Val Lys Arg Val Ile Glu Lys Ser Pro Gly Lys Leu Leu Val Lys
        210                 215                 220

Met Pro Tyr Ser Gly Thr Lys Glu Ala Ser Asp Ala Thr Thr Ser Gln
225                 230                 235                 240

Gln Val Leu Val Ile Lys Arg Gly Gly Arg Lys Arg Lys Ser Glu Thr
                245                 250                 255

Asp Pro Ser Ala Ala Pro Lys Lys Arg Gly Arg Lys Pro Ser Asn Val
            260                 265                 270

Ser Leu Ala Ala Ala Ala Glu Ala Ala Lys Lys Ala Ile Lys
        275                 280                 285

Glu Ser Ser Ile Lys Pro Leu Leu Glu Thr Val Leu Pro Ile Lys Lys
    290                 295                 300

Arg Lys Thr Arg Glu Thr Ile Ser Val Asp Val Lys Asp Thr Ile Lys
305                 310                 315                 320

Pro Glu Pro Leu Thr Pro Val Ile Glu Lys Val Met Lys Gly Gln Asn
                325                 330                 335

Pro Ala Lys Ser Pro Glu Ser Arg Ser Thr Glu Gly Ser Pro Lys Ile
            340                 345                 350

Lys Thr Gly Leu Pro Lys Lys Glu Leu Gln Gln His His His His
        355                 360                 365

His His His His His His His Ser Glu Ser Lys Ala Ser Ala Thr
    370                 375                 380

Ser Pro Glu Pro Glu Thr Ser Lys Asp Asn Ile Gly Val Gln Glu Pro
385                 390                 395                 400

Gln Asp Leu Ser Val Lys Met Cys Lys Glu Glu Lys Leu Pro Glu Ser
                405                 410                 415

Asp Gly Cys Ala Gln Glu Pro Ala Lys Thr Gln Pro Ala Asp Lys Cys
            420                 425                 430

Arg Asn Arg Ala Glu Gly Glu Arg Lys Asp Ile Val Ser Ser Val Pro
```

Arg Pro Thr Arg Glu Glu Pro Val Asp Thr Arg Thr Thr Val Thr Glu
          450                 455                 460

Arg Val Ser
465

<210> SEQ ID NO 71
<211> LENGTH: 484
<212> TYPE: PRT
<213> ORGANISM: Mouse

<400> SEQUENCE: 71

Met Val Ala Gly Met Leu Gly Leu Arg Glu Glu Lys Ser Glu Asp Gln
1               5                   10                  15

Asp Leu Gln Gly Leu Arg Asp Lys Pro Leu Lys Phe Lys Lys Ala Lys
            20                  25                  30

Lys Asp Lys Lys Glu Asp Lys Glu Gly Lys His Glu Pro Leu Gln Pro
        35                  40                  45

Ser Ala His His Ser Ala Glu Pro Ala Glu Ala Gly Lys Ala Glu Thr
    50                  55                  60

Ser Glu Ser Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
        115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Gly Arg Pro Lys Ala Ala Ala Ser Glu Gly Val Gln
        195                 200                 205

Val Lys Arg Val Leu Glu Lys Ser Pro Gly Lys Leu Val Val Lys Met
    210                 215                 220

Pro Phe Gln Ala Ser Pro Gly Gly Lys Gly Glu Gly Gly Gly Ala Thr
225                 230                 235                 240

Thr Ser Ala Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
            260                 265                 270

Gly Ser Val Val Ala Ala Ala Ala Glu Ala Lys Lys Lys Ala Val
        275                 280                 285

Lys Glu Ser Ser Ile Arg Ser Val His Glu Thr Val Leu Pro Ile Lys
    290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

```
Lys Thr Cys Lys Ser Pro Gly Arg Lys Ser Lys Glu Ser Ser Pro Lys
            340                 345                 350

Gly Arg Ser Ser Ser Ala Ser Ser Pro Pro Lys Lys Glu His His His
            355                 360                 365

His His His His Ser Glu Ser Thr Lys Ala Pro Met Pro Leu Leu Pro
            370                 375                 380

Ser Pro Pro Pro Glu Pro Glu Ser Ser Glu Asp Pro Ile Ser Pro
385                 390                 395                 400

Pro Glu Pro Gln Asp Leu Ser Ser Ser Ile Cys Lys Glu Glu Lys Met
                405                 410                 415

Pro Arg Gly Gly Ser Leu Glu Ser Asp Gly Cys Pro Lys Glu Pro Ala
            420                 425                 430

Lys Thr Gln Pro Met Val Ala Thr Thr Thr Val Ala Glu Lys Tyr
            435                 440                 445

Lys His Arg Gly Glu Gly Glu Arg Lys Asp Ile Val Ser Ser Ser Met
            450                 455                 460

Pro Arg Pro Asn Arg Glu Glu Pro Val Asp Ser Arg Thr Pro Val Thr
465                 470                 475                 480

Glu Arg Val Ser

<210> SEQ ID NO 72
<211> LENGTH: 486
<212> TYPE: PRT
<213> ORGANISM: Human

<400> SEQUENCE: 72

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
                20                  25                  30

Lys Asp Lys Lys Glu Glu Lys Glu Gly Lys His Glu Pro Val Gln Pro
            35                  40                  45

Ser Ala His His Ser Ala Glu Pro Ala Glu Ala Gly Lys Ala Glu Thr
    50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
        115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
        195                 200                 205

Val Lys Arg Val Leu Glu Lys Ser Pro Gly Lys Leu Leu Val Lys Met
210                 215                 220
```

```
Pro Phe Gln Thr Ser Pro Gly Gly Lys Ala Glu Gly Gly Ala Thr
225                 230                 235                 240

Thr Ser Thr Gln Val Met Val Ile Lys Arg Pro Gly Arg Lys Arg Lys
            245                 250                 255

Ala Glu Ala Asp Pro Gln Ala Ile Pro Lys Lys Arg Gly Arg Lys Pro
            260                 265                 270

Gly Ser Val Val Ala Ala Ala Ala Glu Ala Lys Lys Lys Ala Val
                275                 280                 285

Lys Glu Ser Ser Ile Arg Ser Val Gln Glu Thr Val Leu Pro Ile Lys
        290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Lys Glu Ser Ser Pro Lys
                340                 345                 350

Gly Arg Ser Ser Ser Ala Ser Ser Pro Pro Lys Lys Glu His His His
                355                 360                 365

His His His Ser Glu Ser Pro Lys Ala Pro Val Pro Leu Leu Pro
        370                 375                 380

Pro Leu Pro Pro Pro Pro Glu Pro Glu Ser Ser Glu Asp Pro Thr
385                 390                 395                 400

Ser Pro Pro Glu Pro Gln Asp Leu Ser Ser Val Cys Lys Glu Glu
                405                 410                 415

Lys Met Pro Arg Gly Gly Ser Leu Glu Ser Asp Gly Cys Pro Lys Glu
                420                 425                 430

Pro Ala Lys Thr Gln Pro Ala Val Ala Thr Ala Ala Thr Ala Ala Glu
            435                 440                 445

Lys Tyr Lys His Arg Gly Glu Gly Glu Arg Lys Asp Ile Val Ser Ser
        450                 455                 460

Ser Met Pro Arg Pro Asn Arg Glu Glu Pro Val Asp Ser Arg Thr Pro
465                 470                 475                 480

Val Thr Glu Arg Val Ser
                485

<210> SEQ ID NO 73
<211> LENGTH: 486
<212> TYPE: PRT
<213> ORGANISM: Human

<400> SEQUENCE: 73

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
            20                  25                  30

Lys Asp Lys Lys Glu Glu Lys Glu Gly Lys His Glu Pro Val Gln Pro
        35                  40                  45

Ser Ala His His Ser Ala Glu Pro Ala Glu Ala Gly Lys Ala Glu Thr
    50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
                100                 105                 110
```

-continued

```
Ser Gly Arg Ser Ala Gly Lys Tyr Asp Val Tyr Leu Ile Asn Pro Gln
            115                 120                 125
Gly Lys Ala Phe Arg Ser Lys Val Glu Leu Ile Ala Tyr Phe Glu Lys
        130                 135                 140
Val Gly Asp Thr Ser Leu Asp Pro Asn Asp Phe Asp Phe Thr Val Thr
145                 150                 155                 160
Gly Arg Gly Ser Pro Ser Arg Arg Glu Gln Lys Pro Pro Lys Lys Pro
                165                 170                 175
Lys Ser Pro Lys Ala Pro Gly Thr Gly Arg Gly Arg Gly Arg Pro Lys
            180                 185                 190
Gly Ser Gly Thr Thr Arg Pro Lys Ala Ala Thr Ser Glu Gly Val Gln
        195                 200                 205
Val Lys Arg Val Leu Glu Lys Ser Pro Gly Lys Leu Leu Val Lys Met
210                 215                 220
Pro Phe Gln Thr Ser Pro Gly Gly Lys Ala Glu Gly Gly Gly Ala Thr
225                 230                 235                 240
Thr Ser Thr Gln Val Met Val Ile Lys Arg Pro Gly Arg Lys Arg Lys
                245                 250                 255
Ala Glu Ala Asp Pro Gln Ala Ile Pro Lys Lys Arg Gly Arg Lys Pro
            260                 265                 270
Gly Ser Val Val Ala Ala Ala Ala Glu Ala Lys Lys Lys Ala Val
        275                 280                 285
Lys Glu Ser Ser Ile Arg Ser Val Gln Glu Thr Val Leu Pro Ile Lys
290                 295                 300
Lys Arg Lys Thr Arg Glu Thr Val Ser Ile Glu Val Lys Glu Val Val
305                 310                 315                 320
Lys Pro Leu Leu Val Ser Thr Leu Gly Glu Lys Ser Gly Lys Gly Leu
                325                 330                 335
Lys Thr Cys Lys Ser Pro Gly Arg Lys Ser Lys Glu Ser Ser Pro Lys
            340                 345                 350
Gly Arg Ser Ser Ser Ala Ser Ser Pro Pro Lys Lys Glu His His His
        355                 360                 365
His His His His Ser Glu Ser Pro Lys Ala Pro Val Pro Leu Leu Pro
370                 375                 380
Pro Leu Pro Pro Pro Pro Glu Pro Glu Ser Ser Glu Asp Pro Thr
385                 390                 395                 400
Ser Pro Pro Glu Pro Gln Asp Leu Ser Ser Ser Val Cys Lys Glu Glu
                405                 410                 415
Lys Met Pro Arg Gly Gly Ser Leu Glu Ser Asp Gly Cys Pro Lys Glu
            420                 425                 430
Pro Ala Lys Thr Gln Pro Ala Val Ala Thr Ala Ala Thr Ala Ala Glu
        435                 440                 445
Lys Tyr Lys His Arg Gly Glu Gly Glu Arg Lys Asp Ile Val Ser Ser
450                 455                 460
Ser Met Pro Arg Pro Asn Arg Glu Glu Pro Val Asp Ser Arg Thr Pro
465                 470                 475                 480
Val Thr Glu Arg Val Ser
                485

<210> SEQ ID NO 74
<211> LENGTH: 486
<212> TYPE: PRT
<213> ORGANISM: Human
```

```
<400> SEQUENCE: 74

Met Val Ala Gly Met Leu Gly Leu Arg Glu Glu Lys Ser Glu Asp Gln
1               5                   10                  15
Asp Leu Gln Gly Leu Lys Asp Lys Pro Leu Lys Phe Lys Lys Val Lys
                20                  25                  30
Lys Asp Lys Lys Glu Lys Glu Gly Lys His Glu Pro Val Gln Pro
            35                  40                  45
Ser Ala His His Ser Ala Glu Pro Ala Glu Ala Gly Lys Ala Glu Thr
        50                  55                  60
Ser Glu Gly Ser Gly Ser Ala Pro Ala Val Pro Glu Ala Ser Ala Ser
65                  70                  75                  80
Pro Lys Gln Arg Arg Ser Ile Ile Arg Asp Arg Gly Pro Met Tyr Asp
                    85                  90                  95
Asp Pro Thr Leu Pro Glu Gly Trp Thr Arg Lys Leu Lys Gln Arg Lys
                100                 105                 110
Ser Gly Arg Ser Ala Gly Lys Tyr Asp Val Tyr Leu Ile Asn Pro Gln
            115                 120                 125
Gly Lys Ala Phe Arg Ser Lys Val Glu Leu Ile Ala Tyr Phe Glu Lys
        130                 135                 140
Val Gly Asp Thr Ser Leu Asp Pro Asn Asp Phe Asp Phe Thr Val Thr
145                 150                 155                 160
Gly Arg Gly Ser Pro Ser Arg Arg Glu Gln Lys Pro Pro Lys Lys Pro
                    165                 170                 175
Lys Ser Pro Lys Ala Pro Gly Thr Gly Arg Gly Arg Gly Arg Pro Lys
                180                 185                 190
Gly Ser Gly Thr Thr Arg Pro Lys Ala Ala Thr Ser Glu Gly Val Gln
            195                 200                 205
Val Lys Arg Val Leu Glu Lys Ser Pro Gly Lys Leu Leu Val Lys Met
210                 215                 220
Pro Phe Gln Thr Ser Pro Gly Gly Lys Ala Glu Gly Gly Ala Thr
225                 230                 235                 240
Thr Ser Thr Gln Val Met Val Ile Lys Arg Pro Gly Arg Lys Arg Lys
                    245                 250                 255
Ala Glu Ala Asp Pro Gln Ala Ile Pro Lys Lys Arg Gly Arg Lys Pro
                260                 265                 270
Gly Ser Val Val Ala Ala Ala Ala Glu Ala Lys Lys Lys Ala Val
            275                 280                 285
Lys Gly Ser Ser Ile Arg Ser Val Gln Glu Thr Val Leu Pro Ile Lys
290                 295                 300
Lys Arg Lys Thr Arg Glu Thr Val Ser Ile Glu Val Lys Glu Val Val
305                 310                 315                 320
Lys Pro Leu Leu Val Ser Thr Leu Gly Glu Lys Ser Gly Lys Gly Leu
                325                 330                 335
Lys Thr Cys Lys Ser Pro Gly Arg Lys Ser Lys Glu Ser Ser Pro Lys
            340                 345                 350
Gly Arg Ser Ser Ala Ser Ser Pro Lys Lys Glu His His His
        355                 360                 365
His His His His Ser Glu Ser Pro Lys Ala Pro Val Pro Leu Leu Pro
        370                 375                 380
Pro Leu Pro Pro Pro Pro Glu Pro Glu Ser Ser Glu Asp Pro Thr
385                 390                 395                 400
Ser Pro Pro Glu Pro Gln Asp Leu Ser Ser Ser Val Cys Lys Glu Glu
                405                 410                 415
```

-continued

Lys Met Pro Arg Gly Gly Ser Leu Glu Ser Asp Gly Cys Pro Lys Glu
            420                 425                 430

Pro Ala Lys Thr Gln Pro Ala Val Ala Thr Ala Ala Thr Ala Ala Glu
            435                 440                 445

Lys Tyr Lys His Arg Gly Glu Gly Glu Arg Lys Asp Ile Val Ser Ser
            450                 455                 460

Ser Met Pro Arg Pro Asn Arg Glu Glu Pro Val Asp Ser Arg Thr Pro
465                 470                 475                 480

Val Thr Glu Arg Val Ser
                485

<210> SEQ ID NO 75
<211> LENGTH: 476
<212> TYPE: PRT
<213> ORGANISM: Human

<400> SEQUENCE: 75

Glu Glu Lys Ser Glu Asp Gln Asp Leu Gln Gly Leu Lys Asp Lys Pro
1               5                   10                  15

Leu Lys Phe Lys Lys Val Lys Lys Asp Lys Lys Glu Glu Lys Glu Gly
            20                  25                  30

Lys His Glu Pro Val Gln Pro Ser Ala His Ser Ala Glu Pro Ala
            35                  40                  45

Glu Ala Gly Lys Ala Glu Thr Ser Glu Gly Ser Gly Ser Ala Arg Leu
50                  55                  60

Cys Glu Ala Ser Ala Ser Pro Lys Gln Arg Arg Ser Ile Ile Arg Asp
65                  70                  75                  80

Arg Gly Pro Met Tyr Asp Asp Pro Thr Leu Pro Glu Gly Trp Thr Arg
            85                  90                  95

Lys Leu Lys Gln Arg Lys Ser Gly Arg Ser Ala Gly Lys Tyr Asp Val
            100                 105                 110

Tyr Leu Ile Asn Pro Gln Gly Lys Ala Phe Arg Ser Lys Val Glu Leu
            115                 120                 125

Ile Ala Tyr Phe Glu Lys Val Gly Asp Thr Ser Leu Asp Pro Asn Asp
130                 135                 140

Phe Asp Phe Thr Val Thr Gly Arg Gly Ser Pro Ser Arg Arg Glu Gln
145                 150                 155                 160

Lys Pro Pro Lys Lys Pro Lys Ser Pro Lys Ala Pro Gly Thr Gly Arg
            165                 170                 175

Gly Arg Gly Arg Pro Lys Gly Ser Gly Thr Thr Arg Pro Lys Ala Ala
            180                 185                 190

Thr Ser Glu Gly Val Gln Val Lys Arg Val Leu Glu Lys Ser Pro Gly
            195                 200                 205

Lys Leu Leu Val Lys Met Pro Phe Gln Thr Ser Pro Gly Gly Lys Ala
            210                 215                 220

Glu Gly Gly Gly Ala Thr Thr Ser Thr Gln Val Met Val Ile Lys Arg
225                 230                 235                 240

Pro Gly Arg Lys Arg Lys Ala Glu Ala Asp Pro Gln Ala Ile Pro Lys
            245                 250                 255

Lys Arg Gly Arg Lys Pro Gly Ser Val Val Ala Ala Ala Ala Glu
            260                 265                 270

Ala Lys Lys Lys Ala Val Lys Glu Ser Ser Ile Arg Ser Val Gln Glu
            275                 280                 285

Thr Val Leu Pro Ile Lys Lys Arg Lys Thr Arg Glu Thr Val Ser Ile

-continued

```
            290                 295                 300
Glu Val Lys Glu Val Val Lys Pro Leu Leu Val Ser Thr Leu Gly Glu
305                 310                 315                 320

Lys Ser Gly Lys Gly Leu Lys Thr Cys Lys Ser Pro Gly Arg Lys Ser
                325                 330                 335

Lys Glu Ser Ser Pro Lys Gly Arg Ser Ser Ala Ser Ser Pro Pro
            340                 345                 350

Lys Lys Glu His His His His His His Ser Glu Ser Pro Lys Ala
            355                 360                 365

Pro Val Pro Leu Leu Pro Pro Leu Pro Pro Pro Pro Glu Pro Glu
        370                 375                 380

Ser Ser Glu Asp Pro Thr Ser Pro Pro Glu Pro Gln Asp Leu Ser Ser
385                 390                 395                 400

Ser Val Cys Lys Glu Glu Lys Met Pro Arg Gly Gly Ser Leu Glu Ser
                405                 410                 415

Asp Gly Cys Pro Lys Glu Pro Ala Lys Thr Gln Pro Ala Val Ala Thr
                420                 425                 430

Ala Ala Thr Ala Ala Glu Lys Tyr Lys His Arg Gly Glu Gly Glu Arg
            435                 440                 445

Lys Asp Ile Val Ser Ser Met Pro Arg Pro Asn Arg Glu Glu Pro
        450                 455                 460

Val Asp Ser Arg Thr Pro Val Thr Glu Arg Val Ser
465                 470                 475
```

<210> SEQ ID NO 76
<211> LENGTH: 23
<212> TYPE: DNA
<213> ORGANISM: Artificial Sequence
<220> FEATURE:
<223> OTHER INFORMATION: Primer

<400> SEQUENCE: 76
taagctggga aatagcctag tac                                              23

<210> SEQ ID NO 77
<211> LENGTH: 23
<212> TYPE: DNA
<213> ORGANISM: Artificial Sequence
<220> FEATURE:
<223> OTHER INFORMATION: Primer

<400> SEQUENCE: 77
ttatatggca cagtttggca cag                                              23

<210> SEQ ID NO 78
<211> LENGTH: 23
<212> TYPE: DNA
<213> ORGANISM: Artificial Sequence
<220> FEATURE:
<223> OTHER INFORMATION: Primer

<400> SEQUENCE: 78
aggacatcaa gatctgagtg tat                                              23

<210> SEQ ID NO 79
<211> LENGTH: 20
<212> TYPE: DNA
<213> ORGANISM: Artificial Sequence
<220> FEATURE:
<223> OTHER INFORMATION: Primer -continued

<400> SEQUENCE: 79
ggtcatttca agcacacctg                                               20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
cgagtgagtg gctttggtga                                               20

<210> SEQ ID NO 81
<211> LENGTH: 19
<212> TYPE: DNA
<213> ORGANISM: Artificial Sequence
<220> FEATURE:
<223> OTHER INFORMATION: Primer

<400> SEQUENCE: 81
cgctctgccc tatctctga                                                19

<210> SEQ ID NO 82
<211> LENGTH: 23
<212> TYPE: DNA
<213> ORGANISM: Artificial Sequence
<220> FEATURE:
<223> OTHER INFORMATION: Primer

<400> SEQUENCE: 82
acagatcgga tagaagactc ctt                                           23

<210> SEQ ID NO 83
<211> LENGTH: 21
<212> TYPE: DNA
<213> ORGANISM: Artificial Sequence
<220> FEATURE:
<223> OTHER INFORMATION: Primer

<400> SEQUENCE: 83
ggcaggaagc gaaaagctga g                                             21

<210> SEQ ID NO 84
<211> LENGTH: 22
<212> TYPE: DNA
<213> ORGANISM: Artificial Sequence
<220> FEATURE:
<223> OTHER INFORMATION: Primer

<400> SEQUENCE: 84
tgagtggtgg tgatggtggt gg                                            22

<210> SEQ ID NO 85
<211> LENGTH: 23
<212> TYPE: DNA
<213> ORGANISM: Artificial Sequence
<220> FEATURE:
<223> OTHER INFORMATION: Primer

<400> SEQUENCE: 85
ggaaaggact gaagacctgt aag                                           23

<210> SEQ ID NO 86
<211> LENGTH: 20

```
<212> TYPE: DNA
<213> ORGANISM: Artificial Sequence
<220> FEATURE:
<223> OTHER INFORMATION: Primer

<400> SEQUENCE: 86
ctccctcccc tcggtgtttg                                              20

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
ggagaagatg cccagaggag                                              20

<210> SEQ ID NO 88
<211> LENGTH: 21
<212> TYPE: DNA
<213> ORGANISM: Artificial Sequence
<220> FEATURE:
<223> OTHER INFORMATION: Primer

<400> SEQUENCE: 88
cggtaagaaa aacatcccca a                                            21

<210> SEQ ID NO 89
<211> LENGTH: 18
<212> TYPE: DNA
<213> ORGANISM: Artificial Sequence
<220> FEATURE:
<223> OTHER INFORMATION: Primer

<400> SEQUENCE: 89
tgtaaaacga cggccagt                                                18

<210> SEQ ID NO 90
<211> LENGTH: 18
<212> TYPE: DNA
<213> ORGANISM: Artificial Sequence
<220> FEATURE:
<223> OTHER INFORMATION: Primer

<400> SEQUENCE: 90
caggaaacag ctatgacc                                                18

<210> SEQ ID NO 91
<211> LENGTH: 25
<212> TYPE: DNA
<213> ORGANISM: Artificial Sequence
<220> FEATURE:
<223> OTHER INFORMATION: Primer

<400> SEQUENCE: 91
ctaaaaaaaa aaaaggaag gttac                                         25

<210> SEQ ID NO 92
<211> LENGTH: 18
<212> TYPE: DNA
<213> ORGANISM: Artificial Sequence
<220> FEATURE:
<223> OTHER INFORMATION: Primer

<400> SEQUENCE: 92
```
agccctgggc ggaaaagc                                              18

<210> SEQ ID NO 93
<211> LENGTH: 18
<212> TYPE: DNA
<213> ORGANISM: Artificial Sequence
<220> FEATURE:
<223> OTHER INFORMATION: Primer

<400> SEQUENCE: 93
tacttttctg cggccgtg                                              18

<210> SEQ ID NO 94
<211> LENGTH: 11
<212> TYPE: DNA
<213> ORGANISM: Human

<400> SEQUENCE: 94
agagcaaaag g                                                     11

<210> SEQ ID NO 95
<211> LENGTH: 11
<212> TYPE: DNA
<213> ORGANISM: Human

<400> SEQUENCE: 95
agagcgaaag g                                                     11

<210> SEQ ID NO 96
<211> LENGTH: 11
<212> TYPE: DNA
<213> ORGANISM: Human

<400> SEQUENCE: 96
tgattctgac t                                                     11

<210> SEQ ID NO 97
<211> LENGTH: 11
<212> TYPE: DNA
<213> ORGANISM: Human

<400> SEQUENCE: 97
tgattttgac t                                                     11

<210> SEQ ID NO 98
<211> LENGTH: 11
<212> TYPE: DNA
<213> ORGANISM: Human

<400> SEQUENCE: 98
cttcatggta a                                                     11

<210> SEQ ID NO 99
<211> LENGTH: 11
<212> TYPE: DNA
<213> ORGANISM: Human

<400> SEQUENCE: 99
cttcacggta a                                                     11

<210> SEQ ID NO 100
<211> LENGTH: 11
<212> TYPE: DNA
<213> ORGANISM: Human

<400> SEQUENCE: 100
ggaagtgaaa a                                                                          11

<210> SEQ ID NO 101
<211> LENGTH: 11
<212> TYPE: DNA
<213> ORGANISM: Human

<400> SEQUENCE: 101
ggaagcgaaa a                                                                          11

<210> SEQ ID NO 102
<211> LENGTH: 12
<212> TYPE: DNA
<213> ORGANISM: Human

<400> SEQUENCE: 102
gtgttgcagg tg                                                                         12

<210> SEQ ID NO 103
<211> LENGTH: 12
<212> TYPE: DNA
<213> ORGANISM: Human

<400> SEQUENCE: 103
gtgtgcaggt ga                                                                         12

<210> SEQ ID NO 104
<211> LENGTH: 11
<212> TYPE: DNA
<213> ORGANISM: Human

<400> SEQUENCE: 104
agagcgaaag g                                                                          11

<210> SEQ ID NO 105
<211> LENGTH: 11
<212> TYPE: DNA
<213> ORGANISM: Human

<400> SEQUENCE: 105
tgattttgac t                                                                          11

<210> SEQ ID NO 106
<211> LENGTH: 11
<212> TYPE: DNA
<213> ORGANISM: Human

<400> SEQUENCE: 106
cttcacggta a                                                                          11

<210> SEQ ID NO 107
<211> LENGTH: 11
<212> TYPE: DNA
<213> ORGANISM: Human

<400> SEQUENCE: 107
ggaagcgaaa a                                                                          11

<210> SEQ ID NO 108
<211> LENGTH: 11
<212> TYPE: DNA

```
<213> ORGANISM: Human

<400> SEQUENCE: 108
gtgtgcaggt g                                                         11

<210> SEQ ID NO 109
<211> LENGTH: 11
<212> TYPE: DNA
<213> ORGANISM: Human

<400> SEQUENCE: 109
ggacatggaa g                                                         11

<210> SEQ ID NO 110
<211> LENGTH: 11
<212> TYPE: DNA
<213> ORGANISM: Human

<400> SEQUENCE: 110
ggacacggaa g                                                         11

<210> SEQ ID NO 111
<211> LENGTH: 11
<212> TYPE: DNA
<213> ORGANISM: Human

<400> SEQUENCE: 111
ggacacggaa g                                                         11

<210> SEQ ID NO 112
<211> LENGTH: 345
<212> TYPE: PRT
<213> ORGANISM: Chicken

<400> SEQUENCE: 112
```

Met Ala Ala Ala Ala Ala Ala Ala Gly Gly Glu Glu Arg Leu Glu
1               5                   10                  15

Glu Gln Ala Asp Glu Gly Val Ala Gly Leu Lys Glu Arg Pro Pro Lys
            20                  25                  30

Ala Lys Lys Gly Arg Lys Glu Arg Arg Glu Asp Pro Glu Ala Glu Ala
        35                  40                  45

Glu Ala Glu Pro Ser Gly Ala Glu Pro Ala Glu Ala Gly Lys Ala Asp
    50                  55                  60

Gly Ser Gly Gly Thr Ala Ala Pro Ala Val Pro Glu Ala Ser Ala
65                  70                  75                  80

Ser Pro Lys Gln Arg Arg Ser Ile Ile Arg Asp Arg Gly Pro Met Tyr
                85                  90                  95

Asp Asp Pro Thr Leu Pro Glu Gly Trp Thr Arg Lys Leu Lys Gln Arg
            100                 105                 110

Lys Ser Gly Arg Ser Ala Gly Lys Tyr Asp Val Tyr Leu Ile Asn Pro
        115                 120                 125

Gln Gly Lys Ala Phe Arg Ser Lys Val Glu Leu Ile Ala Tyr Phe Glu
    130                 135                 140

Lys Val Gly Asp Thr Ser Leu Asp Pro Asn Asp Phe Asp Phe Thr Val
145                 150                 155                 160

Thr Gly Arg Gly Ser Pro Ser Arg Arg Glu Gln Arg Pro Pro Lys Lys
                165                 170                 175

Ala Lys Ser Pro Lys Ser Pro Gly Ser Gly Arg Gly Arg Gly Arg Pro
            180                 185                 190

-continued

```
Lys Gly Ser Gly Gly Gly Gly Gly Gly Gly Gly Gly Gly
        195                 200                 205

Gly Gly Gly Gly Arg Val Gly Gly Gly Gly Gly Arg Val Arg Ala
    210                 215                 220

Ala Ala Glu Arg Gly Gly Arg Leu Leu Val Lys Met Pro Phe Ala
225                 230                 235                 240

Gly Gly Gly Ala Pro Ala Ser Pro Pro Ala Pro Thr Pro Leu Pro
                245                 250                 255

Pro Ser Ala Ala His Pro Pro Pro Thr Ala Pro Pro Ala Thr His Gly
                260                 265                 270

Gln Gly Leu Gly Gly Val Lys Arg Pro Gly Arg Lys Arg Lys Ala
    275                 280                 285

Glu Ala Asp Ser Arg Ser Val Pro Lys Lys Arg Gly Arg Lys Pro Gly
    290                 295                 300

Gly Gly Gly Gly Gly Gly Gly Gly Gly Gly Gly Gly Gly Gly Gly
305                 310                 315                 320

Val Gly Gly Gly Gly Gly Gly Val Arg Gly Gly Gly Gly Gly Arg
                325                 330                 335

Gly Gly Phe Val Arg Ala Pro Pro Pro
            340                 345

<210> SEQ ID NO 113
<211> LENGTH: 12
<212> TYPE: DNA
<213> ORGANISM: Human
<220> FEATURE:
<221> NAME/KEY: misc_feature
<222> LOCATION: (1)..(12)
<223> OTHER INFORMATION: N is a pyrimidine

<400> SEQUENCE: 113
tggacangga ag                                                              12

<210> SEQ ID NO 114
<211> LENGTH: 14
<212> TYPE: DNA
<213> ORGANISM: Human
<220> FEATURE:
<221> NAME/KEY: misc_feature
<222> LOCATION: (1)..(14)
<223> OTHER INFORMATION: N is a C or A

<400> SEQUENCE: 114
cctcctnacc cccc                                                            14
```